(12) United States Patent
Zhang et al.

(10) Patent No.: US 11,274,342 B2
(45) Date of Patent: Mar. 15, 2022

(54) SYSTEMS AND METHODS FOR SEQUENCING T CELL RECEPTORS AND USES THEREOF

(71) Applicant: Regeneron Pharmaceuticals, Inc., Tarrytown, NY (US)

(72) Inventors: Wen Zhang, Tarrytown, NY (US); Bei Wang, Tarrytown, NY (US); Namita Gupta, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 850 days.

(21) Appl. No.: 15/838,203

(22) Filed: Dec. 11, 2017

(65) Prior Publication Data

US 2018/0201991 A1 Jul. 19, 2018

Related U.S. Application Data

(60) Provisional application No. 62/508,667, filed on May 19, 2017, provisional application No. 62/432,525, filed on Dec. 9, 2016.

(51) Int. Cl.
*C12Q 1/6869* (2018.01)
*A61K 35/17* (2015.01)
(Continued)

(52) U.S. Cl.
CPC ............ *C12Q 1/6869* (2013.01); *A61K 35/17* (2013.01); *C07K 16/2818* (2013.01);
(Continued)

(58) Field of Classification Search
CPC ............ G01N 33/505; G01N 2800/52; G01N 33/57484; G01N 2333/7051; G16B 25/00;
G16B 20/00; G16B 30/10; G16B 30/00; G16B 20/20; G16B 25/10; G16B 40/00; G16B 40/10; G16B 40/20; C40B 30/04; C40B 40/06; G16H 50/30; C12Q 2535/122; C12Q 1/6809; C12Q 2600/106; C12Q 1/6846; C12Q 2521/107; A61P 37/04; A61P 37/02; A61P 37/00; A61P 37/06; A61K 35/17; A61K 2039/545; A61K 39/39; C12N 15/1072; C12N 15/1093; C12N 15/1075; C12N 15/1034; C12N 15/1065; C12N 15/1096; C12N 5/0636; C12N 15/85; C12N 15/1089; C12N 2320/31;
(Continued)

(56) References Cited

U.S. PATENT DOCUMENTS 6,984,720 B1  1/2006  Korman et al.
7,034,121 B2  4/2006  Carreno et al.
(Continued)

OTHER PUBLICATIONS

Freeman et al. Profiling the T-cell receptor beta-chain repertoire by massively parallel sequencing. 2009 Genome Research. 19:1817-1824. (Year: 2009).*

(Continued)

*Primary Examiner* — Mary K Zeman
(74) *Attorney, Agent, or Firm* — Ballard Spahr LLP

(57) ABSTRACT

Disclosed herein are methods and systems that can reconstruct, extract, and/or analyze TCR sequences using short reads. The methods and systems can be applied to both single cell and bulk sequencing data.

20 Claims, 78 Drawing Sheets

Specification includes a Sequence Listing.

(51) Int. Cl.
| | |
|---|---|
| C07K 16/28 | (2006.01) |
| G16B 20/00 | (2019.01) |
| C12Q 1/6886 | (2018.01) |
| C12Q 1/6883 | (2018.01) |
| G16B 20/20 | (2019.01) |
| A61K 39/00 | (2006.01) |

(52) U.S. Cl.
CPC ........ *C07K 16/2878* (2013.01); *C12Q 1/6883* (2013.01); *C12Q 1/6886* (2013.01); *G16B 20/00* (2019.02); *G16B 20/20* (2019.02); *A61K 2039/505* (2013.01); *C12Q 2600/106* (2013.01); *C12Q 2600/118* (2013.01); *C12Q 2600/158* (2013.01)

(58) Field of Classification Search
CPC .......... C07K 14/7051; C07K 14/70596; C07K 14/705; C07K 2317/565; C07K 16/00; C07K 16/28; C07K 16/2866; C07K 16/2896
See application file for complete search history.

(56) References Cited

U.S. PATENT DOCUMENTS

| 7,605,238 | B2 | 10/2009 | Korman et al. |
|---|---|---|---|
| 2015/0203579 | A1 | 7/2015 | Papadopoulos et al. |
| 2015/0203580 | A1 | 7/2015 | Papadopoulos et al. |
| 2016/0310584 | A1* | 10/2016 | Fritsch ........... A61K 39/001156 |
| 2017/0101472 | A1 | 4/2017 | Ullman et al. |
| 2017/0355774 | A1 | 12/2017 | Delfino et al. |

OTHER PUBLICATIONS

Freeman, J. D et al. Profiling the T cell receptor beta chain repertoire by massively parallel sequencing. 2009 Genome Research 19:1817-1824 (Year: 2009).*
Li et al. (Li, B et al. Landscape of tumor-infiltrating T cell repertoire of human cancers. (Jul. 2016) Nature Genetics V 48:7 p. 725, and some supplemental material). (Year: 2016).*
Gongora-Castillo et al. Bioinformatics challenges in de novo transcriptome assembly using short read sequences in the absence of a reference genome sequence. 2013 Nat Prod Rep vol. 30:490. (Year: 2013).*
Brueffer et al. TopHat-Recondition: a post-processor for TopHat unaligned reads. (May 4, 2016) BMC Bioinformatics 17:199. (Year: 2016).*
Hansen, Kasper et al. biases in Illumina transcriptome sequencing caused by random hexamer priming. (Apr. 2010) Nucleic Acids Research vol. 38, No. 12: e131. (Year: 2010).*
Glusman, G. Comparative genomics of the human and mouse T cell receptor loci. 2001 Cell 15:337. (Year: 2001).*
Ryan et al. Successful immunotherapy induces previously unidentified allergen specific CD4+ T cell subsets. (Jan. 2016) PNAS e1286-1295 and supplemental information. (Year: 2016).*
U.S. Appl. No. 62/537,753, filed Jul. 27, 2017, Unknown.
Alamyar, E et al., IMGT® Tools for the Nucleotide Analysis of Immunoglobulin (IG) and T Cell Receptor (TR) V-(D)-J Repertoires, Polymorphisms, and IG Mutations: IMGT/V-Quest and IMGT/High V-Quest for NGS. Methods Mol Biol. 2012; 882:569-604.
Grabherr, M.G. et al., Full-length Transcriptome Assembly from RNA-Seq Data without a Reference Genome. Nat Biotechnol. 2011; 29(7):644-52.
Gupta, N.T. et al., Hierarchical Clustering Can Identify B Cell Clones with High Confidence in Ig Repertoire Sequencing Data. J Immunol. 2017; 198(6):2489-99.
Trapnell, C. et al., TopHat: Discovering Splice Junctions with RNA-Seq. Bioinformatics. 2009; 25(9):1105-11.
Warren, R.L. et al., Profiling Model T-cell Metagenomes with Short Reads. Bioinformatics. 2009; 25:458-64.
Yang, X et al., TCRklass: a New K-String-Based Algorithm for Human and Mouse TCR Repertoire Characterization. J Immunol. 2015; 194:446-54.
U.S. Appl. No. 62/432,525, filed Dec. 9, 2016, Wen Zhang et al. (Regeneron Pharmaceuticals, Inc.).
U.S. Appl. No. 62/508,667, filed May 19, 2017, Wen Zhang et al. (Regeneron Pharmaceuticals, Inc.).
PCT/US2017/065649, filed Dec. 11, 2017, Wen Zhang et al. (Regeneron Pharmaceuticals, Inc.).
Haas, B. et al.: "De novo transcript sequence reconstruction from RNA-seq using the Trinity platform for reference generation and analysis", Nature Protocols, vol. 8, No. 8, pp. 1494-1512, (2013).
Hansen, K., et al.: "Biases in Illumina transcriptome sequencing caused by random hexamer priming", Nucleic Acids Research, vol. 38, No. 12, pp. e131-e131, (2010).
Li, B. et al.: "Landscape of tumor-infiltrating T cell repertoire of human cancers", Nature Genetics., vol. 48, No. 7, pp. 725-732, (2016).
Mose, L., et al.: "Assembly-based inference of B-cell receptor repertoires from short read RNA sequencing data with V'DJer", Bioinformatics., vol. 32, No. 24, pp. 3729-3734, (2016).
Picelli, S.: "Single-cell RNA-sequencing: The future of genome biology is now", RNA Biology, vol. 14, No. 5, , pp. 637-650, (2016).
International Search Report and Written Opinion were dated Mar. 20, 2018 by the International Searching Authority for Application No. PCT/US2017/065649, which was filed on Dec. 11, 2017, (Applicant-Regeneron Pharmaceuticals, Inc.) ( pages).
Office Action dated Jun. 19, 2020 by the Korean Patent Office for Application No. 10-2019-7016302, which was filed on Dec. 11, 2017, (Applicant-Regeneron Pharmaceuticals, Inc.) (3 pages).
Office Action dated Aug. 11, 2020 by the Japanese Patent Office for Application No. 2019-531078, which was filed on Dec. 11, 2017, (Applicant-Regeneron Pharmaceuticals, Inc.) (2 pages).
Office Action dated Jul. 23, 2020 by the European Patent Office for Application No. 17829775, which was filed on Dec. 11, 2017, (Applicant-Regeneron Pharmaceuticals, Inc.) (7 pages).
Office Action dated Jul. 3, 2020 by the Canadian Patent Office for Application No. 3,040,924, which was filed on Dec. 11, 2017, (Applicant-Regeneron Pharmaceuticals, Inc.) (4 pages).
Office Action dated Feb. 10, 2020 by the Australian Patent Office for Application No. 2017371498, which was filed on Dec. 11, 2017, (Applicant-Regeneron Pharmaceuticals, Inc.) (3 pages).
Office Action dated Aug. 26, 2020 by the Singaporean Patent Office for Application No. 11201903612P, which was filed on Dec. 11, 2017, (Applicant-Regeneron Pharmaceuticals, Inc.) (6 pages).
Office Action dated Jul. 20, 2021 by the European Patent Office for Application No. 17829775, which was filed on Dec. 11, 2017, (Applicant-Regeneron Pharmaceuticals, Inc.) (4 pages).
Office Action dated May 18, 2021 by the Canadian Patent Office for Application No. 3,040,924, which was filed on Dec. 11, 2017, (Applicant-Regeneron Pharmaceuticals, Inc.) (4 pages).

* cited by examiner

| Sample ID | Description | Species | Sample type | MiTCR | TCRKlass | rpsTCR | Input reads (passed QC>=25) |
|---|---|---|---|---|---|---|---|
| Renca | kidney tumor cell line | mouse | negative control | 23 | 0 | 0 | 44,906,248 |
| B16F1 | melanoma tumor cell line | mouse | negative control | 76 | 0 | 0 | 39,305,839 |
| Colon26 | Colon tumor cell line | mouse | negative control | 22 | 1 | 0 | 39,233,756 |
| MC38 | colon tumor cell line | mouse | negative control | 99 | 1 | 0 | 48,661,267 |
| T-ALL_neg1 | Spleen from Rag1/2 KO mouse | mouse | negative control | 17 | 1 | 0 | 39,068,155 |
| T-ALL_neg2 | Spleen from Rag1/2 KO mouse | mouse | negative control | 51 | 0 | 0 | 39,469,692 |
| NeuProgCell | Neural progenitor cell line | human | negative control | 123 | 0 | 0 | 37,684,399 |
| LHCN-M2 | Skeletal myoblast cell line | human | negative control | 77 | 0 | 0 | 36,639,557 |

| TCR type | Total | CDR3 detected by our pipeline | Detection rate of our pipeline | Detection rate reported by Han A. et al. |
|---|---|---|---|---|
| TRB-CDR3 | 1,379 | 1,186 | 86.0% | 92% |
| TRA-CDR3 | 1,379 | 1,078 | 78.2% | 87% |
| TRA&B-CDR3 | 1,379 | 1,009 | 73.1% | 82% |

| Treatment | Pathway | p Value |
|---|---|---|
| Anti-PD1 + Anti-GITR | Adpative immune response | 1.50E-08 |
| | Cell cycle | 5.80E-07 |
| | Metabolism of lipids and lipoproteins | 3.00E-04 |
| Anti-PD1 | Lymphocyte activation | 2.30E-05 |
| | Gene targets for miR-124u (T cell activation) | 1.80E-05 |
| | Jak-STAT signaling pathway | 3.00E-04 |
| Anti-GITR | Glucose metabolism | 8.20E-10 |
| | Protein metabolism | 7.50E-08 |
| | The citric acid cycle and respiratory electron transport | 3.90E-06 |

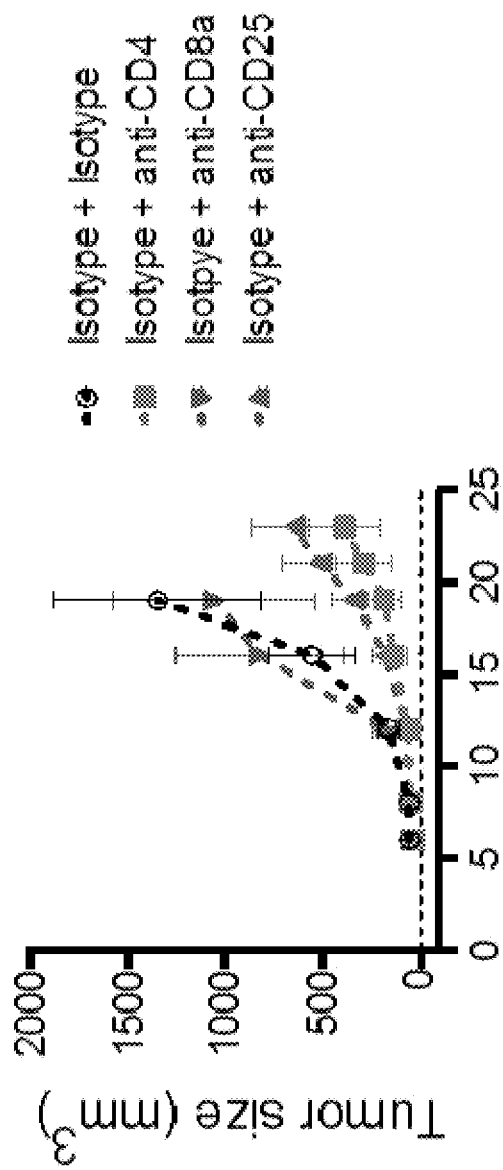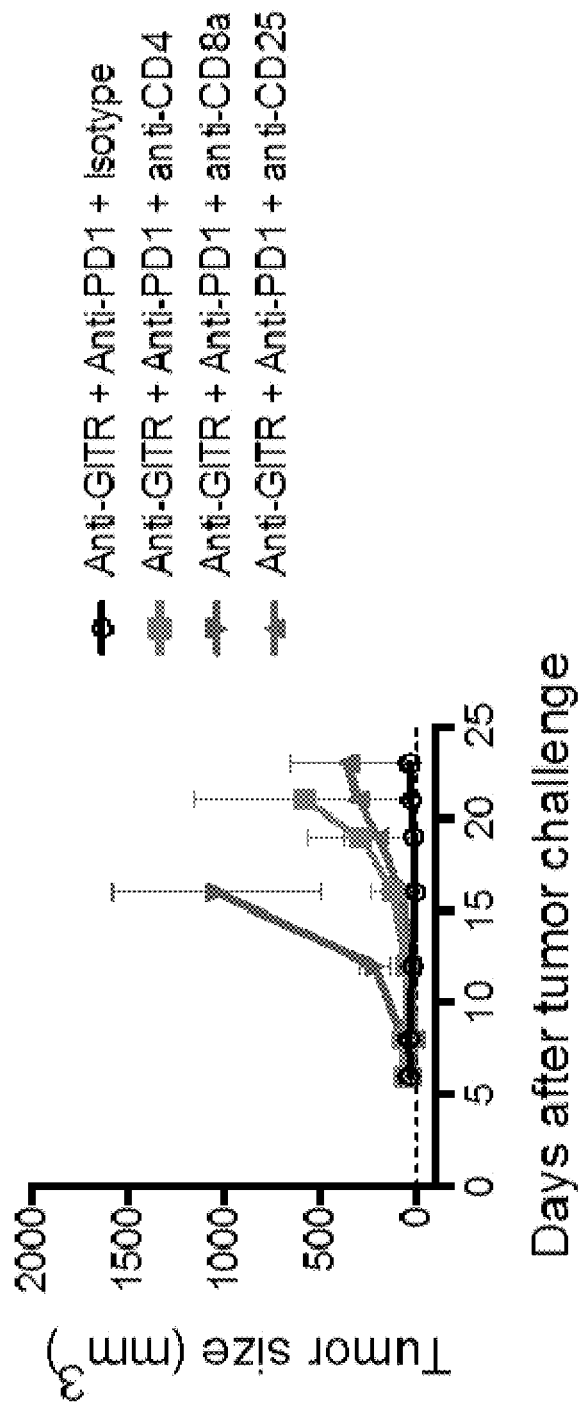
FIG. 16D

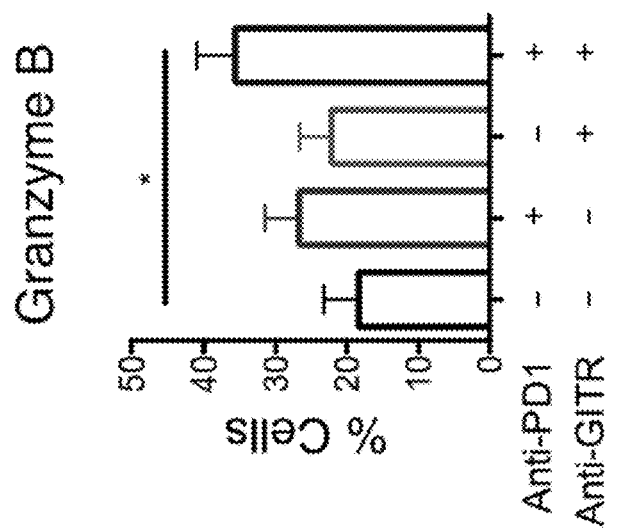
FIG. 16G FIG. 16H
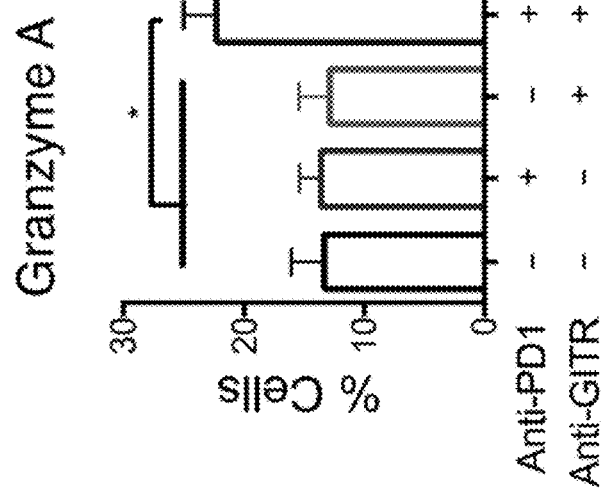
FIG. 16I
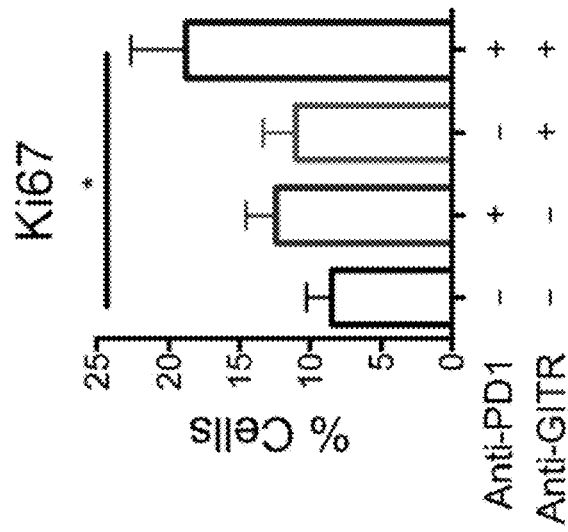

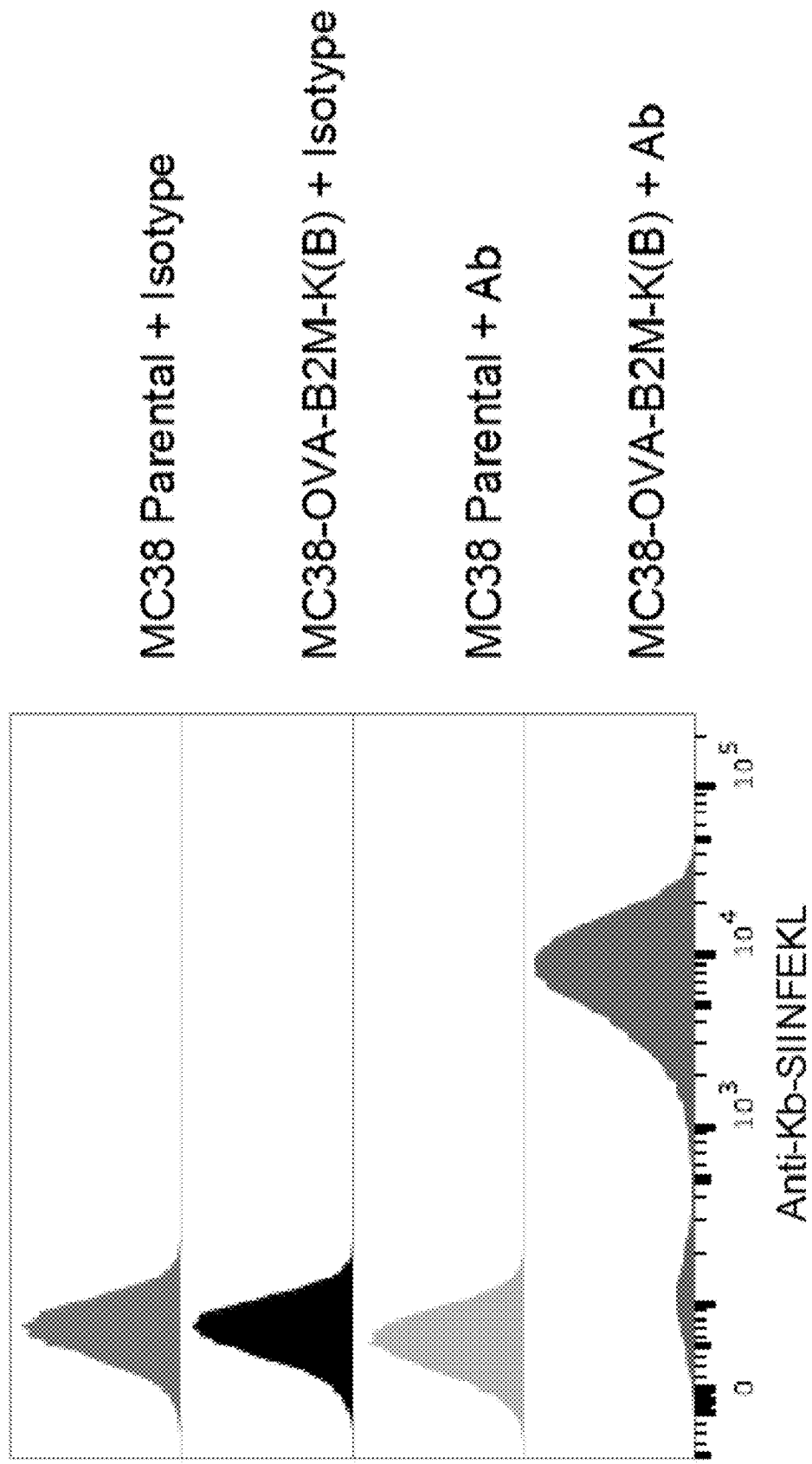

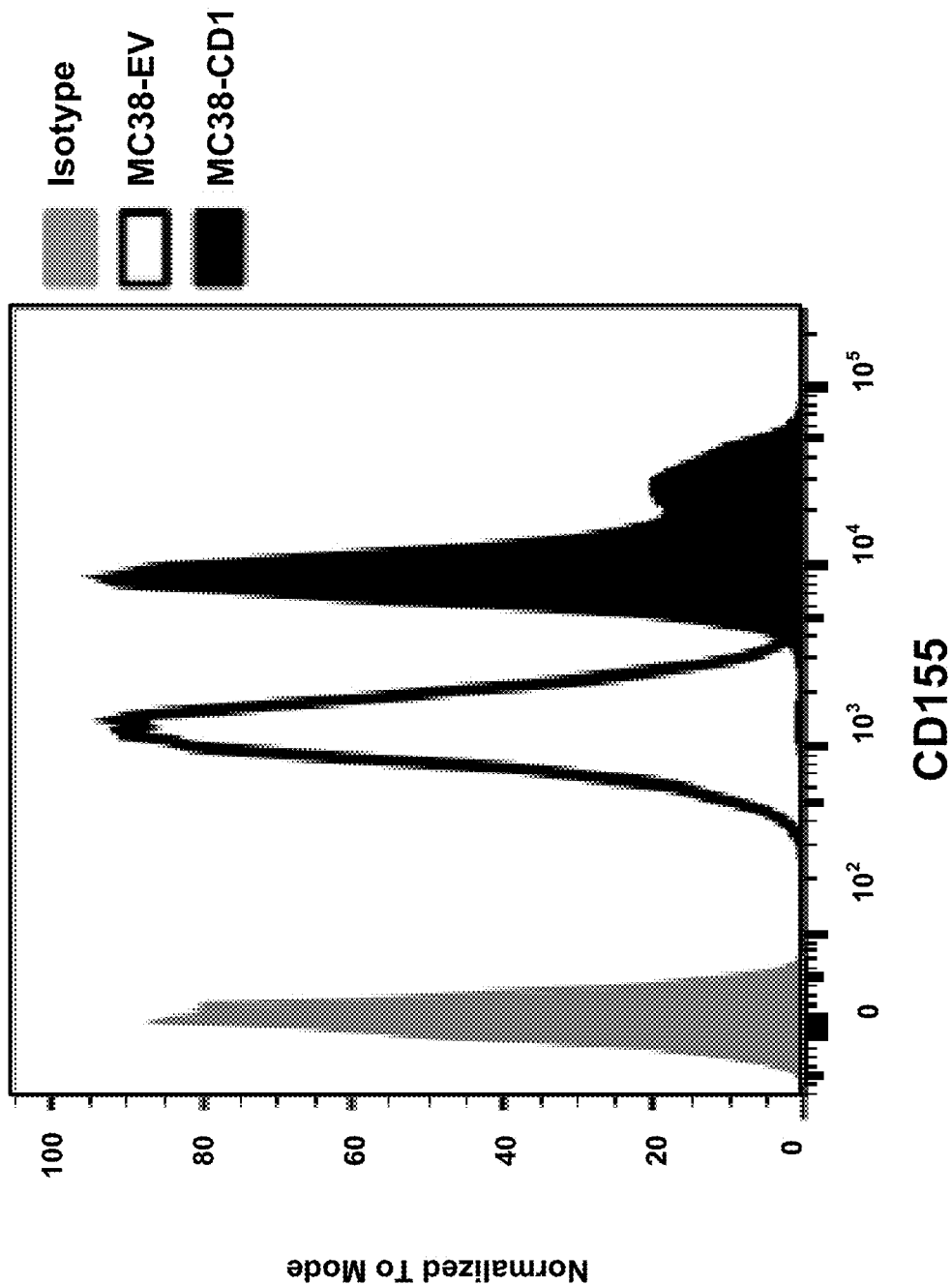

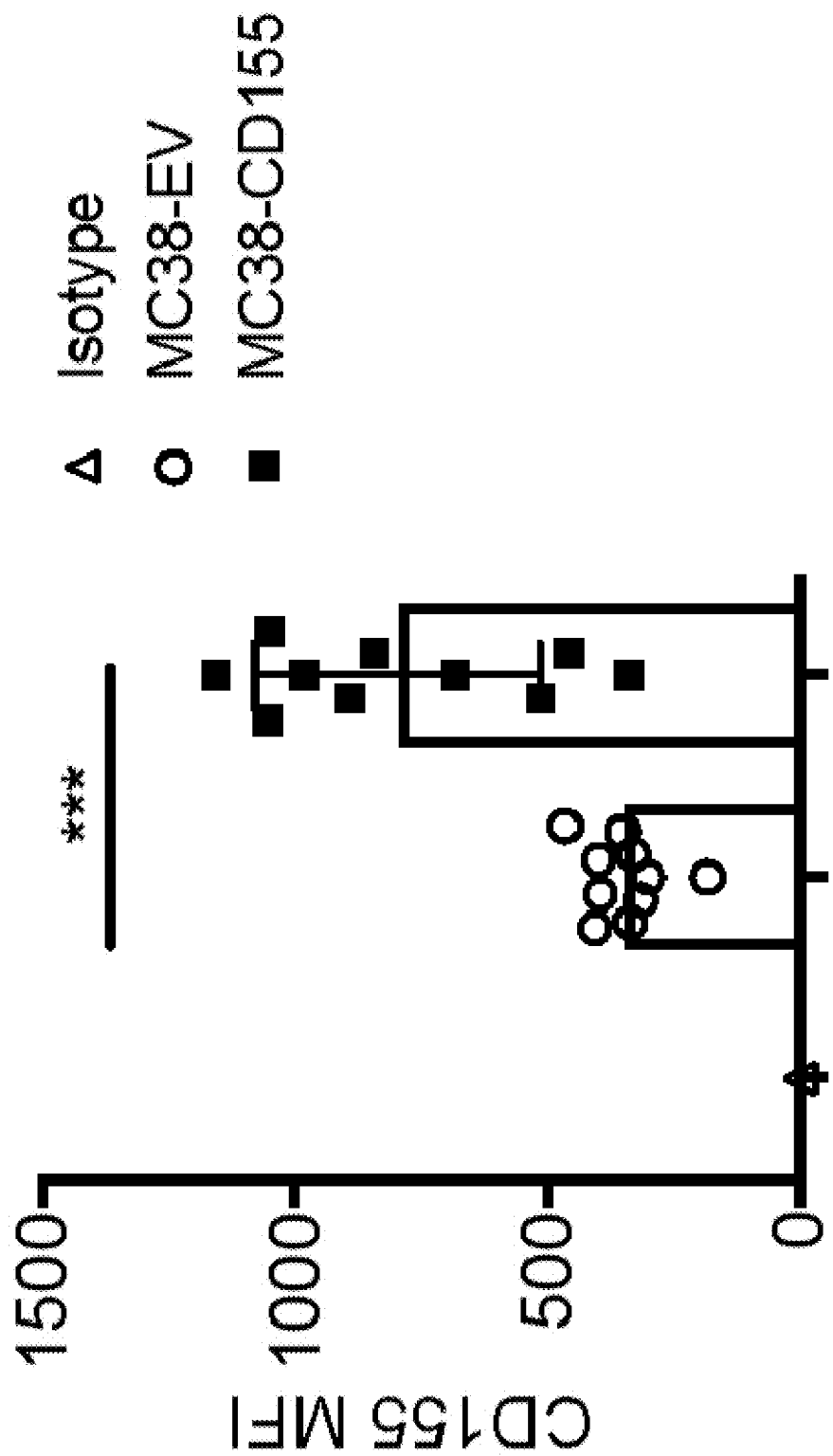

| | | |
|---|---|---|
| RT primers | TCRα | 5' – GCAGGTGAAGCTTGTGTCTGGTTGCT – 3' (SEQ ID NO:25) |
| | TCRβ | 5' – CGAGGGTAGCCTTTTGTTTGTTTGC – 3' (SEQ ID NO:26) |
| 1st round PCR primers | TCRα | 5' – ACACTCTTTCCCTACACGACGCTCTTCCGATCT TCAAAGTCGGGTGAACAGGCAGAG – 3' (SEQ ID NO:27) |
| | TCRβ | 5' – ACACTCTTTCCCTACACGACGCTCTTCCGATCT GACCTTGGGTGGAGTCACATTTCTC – 3' (SEQ ID NO:28) |
| | PE2-PIIA | 5' – GTGACTGGAGTTCAGACGTGTGCTCTTCCGATCT AAGCAGTGGTATCAACGCAGAGT – 3' (SEQ ID NO:29) |
| 2nd round PCR Primers | Forward | 5' – AATGATACGGCGACCACCGAGATCTACACXXXXXX ACACTCTTTCCCTACACGACGCTCTTCCGATCT– 3' (SEQ ID NO:30) |
| | Reverse | 5' – CAAGCAGAAGACGGCATACGAGATXXXXXX GTGACTGGAGTTCAGACGTGTGCTCTTCCGATCT– 3' (SEQ ID NO:31) |

| Sample ID | Species | Sample type | MiTCR | TCRklass | rpsTCR pipeline | Input reads (passed QC>=25) |
|---|---|---|---|---|---|---|
| M620343 | mouse | negative control | 23 | 0 | 0 | 44,906,248 |
| M620295 | mouse | negative control | 76 | 0 | 0 | 39,305,839 |
| M620279 | mouse | negative control | 22 | 1 | 0 | 39,233,756 |
| M620274 | mouse | negative control | 99 | 1 | 0 | 48,661,267 |
| M620272 | mouse | negative control | 5 | 0 | 0 | 32,426,335 |
| M620270 | mouse | negative control | 22 | 0 | 0 | 46,609,234 |
| T-ALL_neg1-40M | mouse | negative control | 17 | 1 | 0 | 39,068,155 |
| T-ALL_neg2-40M | mouse | negative control | 51 | 0 | 0 | 39,469,692 |
| NeuProgCell-40M | human | negative control | 123 | 0 | 0 | 37,684,399 |
| LHCN-M2-40M | human | negative control | 77 | 0 | 0 | 36,639,557 |
| VI-next-mouse-T cell | mouse | positive control | 128,956 | 137,156 | 135,980 | 169,009 |

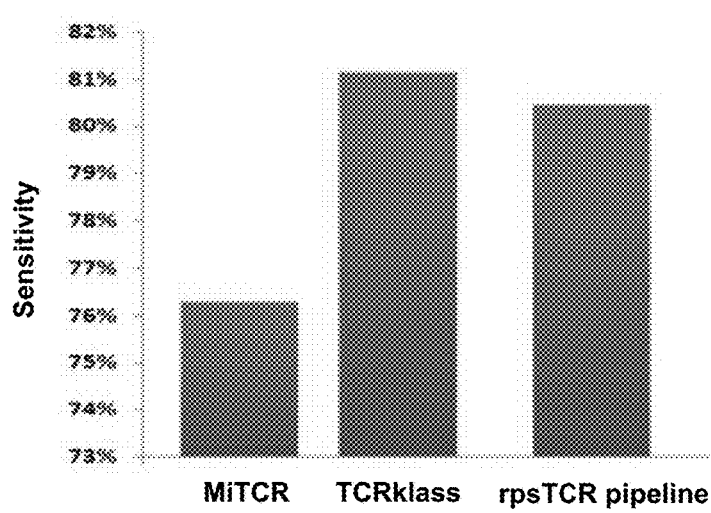

FIG. 28

| | CDR3 | VI-next | | | MP-50bp-500M | | |
|---|---|---|---|---|---|---|---|
| | | MiTCR | TCRklass | rpsTCR | MiTCR | TCRklass | rpsTCR |
| Top CDR3s found by MiTCR | CATSNYLGYF | 0 | 0 | 0 | 63 | 0 | 0 |
| | CARHYF | 0 | 0 | 0 | 63 | 0 | 0 |
| | CAFFYWLF | 0 | 0 | 0 | 62 | 0 | 0 |
| | CGAGSFQHF | 0 | 0 | 0 | 39 | 0 | 0 |
| | CARDRSIF | 0 | 0 | 0 | 21 | 0 | 0 |
| | CARGRRITIF | 0 | 0 | 0 | 15 | 0 | 0 |
| | CARHDLYYF | 0 | 0 | 0 | 15 | 0 | 0 |
| | CARHGIF | 0 | 0 | 0 | 15 | 0 | 0 |
| | CAKDRGTIF | 0 | 0 | 0 | 14 | 0 | 0 |
| | CARGPRGIF | 0 | 0 | 0 | 13 | 0 | 0 |

| | CDR3 | VI-next | | | MP-50bp-500M | | |
|---|---|---|---|---|---|---|---|
| | | MiTCR | TCRklass | rpsTCR | MiTCR | TCRklass | rpsTCR |
| Top CDR3s found by TCRklass | CASSPDADTQYF | 0 | 0 | 0 | 3 | 3 | 0 |
| | CGAGTTETLYF | 27 | 27 | 27 | 3 | 2 | 2 |
| | CASSDVRDTEVFF | 178 | 174 | 174 | 2 | 2 | 0 |
| | CASSDLGEDTQYF | 39 | 44 | 44 | 2 | 2 | 1 |
| | CTCSASAETLYF | 35 | 30 | 29 | 2 | 2 | 1 |
| | CASSQEARNYAEQFF | 21 | 21 | 21 | 2 | 2 | 0 |
| | CASSLGNYAEQFF | 8 | 8 | 8 | 2 | 2 | 1 |
| | CASGDRYAEQFF | 7 | 7 | 7 | 2 | 2 | 0 |
| | CASGDGGGNTLYF | 5 | 5 | 5 | 2 | 2 | 2 |
| | CASSVGGQDTQYF | 2 | 0 | 2 | 2 | 2 | 0 |

| | CDR3 | VI-next | | | MP-50bp-500M | | |
|---|---|---|---|---|---|---|---|
| | | MiTCR | TCRklass | rpsTCR | MiTCR | TCRklass | rpsTCR |
| Top CDR3s found by rps TCR pipeline | CASSSPGQGAREQYF | 1423 | 1383 | 1374 | 3 | 0 | 21 |
| | CTCSAGQKAETLYF | 805 | 788 | 773 | 1 | 1 | 9 |
| | CASSQDWGGDEQYF | 287 | 277 | 274 | 1 | 1 | 7 |
| | CASSPGQISNERLFF | 0 | 0 | 0 | 0 | 0 | 5 |
| | CTCSADWGAETLYF | 266 | 265 | 260 | 2 | 1 | 4 |
| | CASSPGQLQNTLYF | 103 | 102 | 102 | 0 | 0 | 4 |
| | CASSGRDRGLGNTLYF | 77 | 76 | 75 | 0 | 0 | 4 |
| | CAKTENSDYTF | 18 | 18 | 18 | 4 | 1 | 4 |
| | CASSVTGEGNTLYF | 18 | 18 | 18 | 0 | 0 | 4 |
| | CASRRHLSYEQYF | 8 | 8 | 8 | 3 | 0 | 4 |

FIG. 29

| CDR3 | VI-Next data (301bp) | | | |
|---|---|---|---|---|
| | Rank | MiTCR | TCRklass | rps TCR pipeline |
| CASSSPGQGAREQYF | 1 | 1423 | 1383 | 1374 |
| CTCSAGQKAETLYF | 2 | 805 | 788 | 773 |
| CTCSAERASAETLYF | 3 | 337 | 330 | 326 |
| CASSRDWGASAETLYF | 4 | 329 | 323 | 323 |
| CASSQDWGGDEQYF | 5 | 287 | 277 | 274 |
| CTCSADWGAETLYF | 6 | 266 | 265 | 260 |
| CASGDAPGTNSDYFT | 7 | 237 | 231 | 231 |
| CASSDGTGDYAEQFF | 8 | 224 | 217 | 217 |
| CASSDGGKANERLFF | 9 | 215 | 211 | 211 |
| CTCSADGRGNYAEQFF | 10 | 190 | 189 | 188 |

| CDR3 | MP-50BP-MiTCR | | | | |
|---|---|---|---|---|---|
| | 10M | 50m | 100m | 200m | 500m |
| CASSSPGQGAREQYF | 0 | 0 | 0 | 1 | 3(rank 15) |
| CTCSAGQKAETLYF | 0 | 0 | 0 | 0 | 1 |
| CTCSAERASAETLYF | 0 | 0 | 0 | 0 | 1 |
| CASSRDWGASAETLYF | 0 | 0 | 0 | 0 | 0 |
| CASSQDWGGDEQYF | 0 | 0 | 0 | 1 | 1 |
| CTCSADWGAETLYF | 0 | 0 | 0 | 0 | 2 |
| CASGDAPGTNSDYFT | 0 | 0 | 0 | 0 | 0 |
| CASSDGTGDYAEQFF | 0 | 0 | 0 | 1 | 1 |
| CASSDGGKANERLFF | 0 | 0 | 0 | 0 | 0 |
| CTCSADGRGNYAEQFF | 0 | 0 | 0 | 0 | 0 |

| CDR3 | MP-50bp-TCRklass | | | | |
|---|---|---|---|---|---|
| | 10M | 50m | 100m | 200m | 500m |
| CASSSPGQGAREQYF | 0 | 0 | 0 | 0 | 0 |
| CTCSAGQKAETLYF | 0 | 0 | 0 | 0 | 1 |
| CTCSAERASAETLYF | 0 | 0 | 0 | 0 | 0 |
| CASSRDWGASAETLYF | 0 | 0 | 0 | 0 | 0 |
| CASSQDWGGDEQYF | 0 | 0 | 0 | 1 | 1 |
| CTCSADWGAETLYF | 0 | 0 | 0 | 0 | 1 |
| CASGDAPGTNSDYFT | 0 | 0 | 0 | 0 | 0 |
| CASSDGTGDYAEQFF | 0 | 0 | 0 | 1 | 1 |
| CASSDGGKANERLFF | 0 | 0 | 0 | 0 | 0 |
| CTCSADGRGNYAEQFF | 0 | 0 | 0 | 0 | 0 |

| CDR3 | MP-50bp-rpsTCR pipeline | | | | |
|---|---|---|---|---|---|
| | 10M | 50m | 100m | 200m | 500m |
| CASSSPGQGAREQYF | 1 | 2 | 5(rank 1) | 9(rank 1) | 21(rank 1) |
| CTCSAGQKAETLYF | 0 | 0 | 3(rank 2) | 4(rank 2) | 9(rank 2) |
| CTCSAERASAETLYF | 0 | 0 | 0 | 1 | 1 |
| CASSRDWGASAETLYF | 0 | 0 | 0 | 0 | 1 |
| CASSQDWGGDEQYF | 0 | 0 | 0 | 2 | 7(rank 3) |
| CTCSADWGAETLYF | 0 | 0 | 1 | 1 | 4(rank 5) |
| CASGDAPGTNSDYFT | 0 | 0 | 0 | 2 | 2 |
| CASSDGTGDYAEQFF | 0 | 0 | 0 | 0 | 2 |
| CASSDGGKANERLFF | 0 | 0 | 0 | 0 | 0 |
| CTCSADGRGNYAEQFF | 0 | 0 | 0 | 0 | 0 |

FIG. 30

| | CDR3 | VI-next | | | MP-100bp-200M | | |
|---|---|---|---|---|---|---|---|
| | | MiTCR | TCRklass | rpsTCR | MiTCR | TCRklass | rpsTCR |
| Top CDR3s found by MiTCR | CATSNYLGYF | 0 | 0 | 0 | 106 | 0 | 0 |
| | CARHYF | 0 | 0 | 0 | 85 | 0 | 0 |
| | CAFFYWLF | 0 | 0 | 0 | 83 | 0 | 0 |
| | CGAGSFQHF | 0 | 0 | 0 | 60 | 0 | 0 |
| | CARGRRITIF | 0 | 0 | 0 | 49 | 0 | 0 |
| | CAKDGGVTIF | 0 | 0 | 0 | 33 | 0 | 0 |
| | CARDRSIF | 0 | 0 | 0 | 31 | 0 | 0 |
| | CARGPRGIF | 0 | 0 | 0 | 31 | 0 | 0 |
| | CARHDLYYF | 0 | 0 | 0 | 25 | 0 | 0 |
| | CASSFKDKRMQDVNF | 0 | 0 | 0 | 24 | 0 | 0 |

| | CDR3 | VI-next | | | MP-100bp-200M | | |
|---|---|---|---|---|---|---|---|
| | | MiTCR | TCRklass | rpsTCR | MiTCR | TCRklass | rpsTCR |
| Top CDR3s found by TCRklass | CASLQYF | 0 | 0 | 0 | 0 | 99 | 0 |
| | CASGGKKTSTAFF | 0 | 0 | 0 | 0 | 97 | 0 |
| | CASSSPGQGAREQYF | 1423 | 1383 | 1374 | 23 | 18 | 13 |
| | CASRRGIGNTLYF | 87 | 86 | 86 | 9 | 8 | 8 |
| | CTCSAGQKAETLYF | 805 | 788 | 773 | 8 | 5 | 7 |
| | CASRRHLSYEQYF | 8 | 8 | 8 | 6 | 5 | 6 |
| | CASGDAPGTNSDYTF | 237 | 231 | 231 | 6 | 4 | 4 |
| | CASSQDWGGDEQYF | 287 | 277 | 274 | 4 | 4 | 4 |
| | CASSGRDRGLGNTLYF | 77 | 76 | 75 | 4 | 4 | 4 |
| | CGARDRGSGNTLYF | 1 | 1 | 1 | 4 | 4 | 7 |

| | CDR3 | VI-next | | | MP-100bp-200M | | |
|---|---|---|---|---|---|---|---|
| | | MiTCR | TCRklass | rpsTCR | MiTCR | TCRklass | rpsTCR |
| Top CDR3s found by rps TCR pipeline | CASSSPGQGAREQYF | 1423 | 1383 | 1374 | 23 | 18 | 13 |
| | CASRRGIGNTLYF | 87 | 86 | 86 | 9 | 8 | 8 |
| | CTCSAGQKAETLYF | 805 | 788 | 773 | 8 | 5 | 7 |
| | CGARDRGSGNTLYF | 1 | 1 | 1 | 4 | 4 | 7 |
| | CASRRHLSYEQYF | 8 | 8 | 8 | 6 | 5 | 6 |
| | CASSQDPWGVEQYF | 2 | 2 | 2 | 3 | 3 | 5 |
| | CASGDAPGTNSDYTF | 237 | 231 | 231 | 6 | 4 | 4 |
| | CASSQDWGGDEQYF | 287 | 277 | 274 | 4 | 4 | 4 |
| | CASSGRDRGLGNTLYF | 77 | 76 | 75 | 4 | 4 | 4 |
| | CASSDHSSAETLYF | 78 | 77 | 77 | 3 | 3 | 4 |

| CDR3 | # of cells | Single cell sequencing (75bp) | | | Bulk RNA sequencing (80bp) | | |
|---|---|---|---|---|---|---|---|
| | | MiTCR | TCRklass | rpsTCR | MiTCR | TCRklass | rpsTCR |
| CASSPTGYNSPLYF | 4 | 495 | 465 | 982 | 242 | 302 | 512 |
| CASSQVQGSAETLYF | 5 | 142 | 138 | 646 | 200 | 185 | 394 |
| CASSGTGGNQDTQYF | 1 | 495 | 408 | 595 | 0 | 0 | 0 |
| CASGDAGTGNYAEQFF | 1 | 282 | 247 | 399 | 32 | 26 | 29 |
| CASSLRTGYNSPLYF | 3 | 206 | 202 | 294 | 123 | 141 | 114 |
| CASRLGGDQNTLYF | 3 | 292 | 151 | 291 | 82 | 58 | 131 |
| CASKTGGYEQYF | 1 | 297 | 140 | 285 | 154 | 93 | 75 |
| CASSEGDTLYF | 1 | 370 | 307 | 225 | 46 | 38 | 18 |
| CASSPGTFNQDTQYF | 3 | 113 | 78 | 195 | 45 | 23 | 36 |
| CASASWTGDEQYF | 1 | 110 | 89 | 144 | 0 | 0 | 0 |
| CASSLPGSQNTLYF | 1 | 98 | 61 | 140 | 0 | 0 | 0 |
| CASSRDWAQDTQYF | 2 | 127 | 81 | 128 | 141 | 125 | 169 |
| CASSDNWGAGEQYF | 1 | 161 | 107 | 99 | 5 | 5 | 2 |
| CASSSGTASDTQYF | 1 | 41 | 30 | 86 | 0 | 0 | 0 |
| CASSQTRDWGYEQYF | 1 | 33 | 17 | 75 | 28 | 18 | 70 |
| CTCSGGLGGLEQYF | 1 | 66 | 34 | 74 | 10 | 6 | 9 |
| CASSLGTGGIEQYF | 1 | 56 | 32 | 54 | 4 | 4 | 5 |
| CASSLSDSNQDTQYF | 1 | 52 | 47 | 50 | 0 | 0 | 0 |
| CASSERGGRDTQYF | 1 | 49 | 34 | 46 | 0 | 0 | 0 |
| CTCSAVREGNSPLYF | 1 | 41 | 34 | 46 | 6 | 3 | 4 |
| CASSLTGVSNERLFF | 1 | 74 | 63 | 42 | 0 | 0 | 0 |
| CASSRQLNSDYTF | 2 | 50 | 46 | 35 | 129 | 114 | 96 |
| CASSLRQGSNTEVFF | 1 | 34 | 32 | 34 | 40 | 28 | 20 |
| CASSQNRDISAETLYF | 1 | 22 | 23 | 34 | 77 | 76 | 117 |
| CASSWTANTEVFF | 1 | 72 | 42 | 30 | 0 | 0 | 0 |
| CASSLRDWGQDTQYF | 1 | 26 | 19 | 28 | 39 | 27 | 39 |
| CASSHWGGTTGQLYF | 1 | 28 | 27 | 21 | 0 | 0 | 0 |
| CASSYSKGSAETLYF | 1 | 17 | 17 | 17 | 0 | 0 | 0 |
| CAVSMINYNVLYF | 1 | 0 | 1 | 17 | 0 | 6 | 15 |
| CASSDGQYEQYF | 1 | 10 | 7 | 14 | 0 | 0 | 0 |
| CASSQRTGQNTLYF | 1 | 12 | 9 | 6 | 0 | 0 | 0 |
| CASSQEGPGQLYF | 1 | 8 | 7 | 5 | 39 | 35 | 27 |
| CASTGQGYNSPLYF | 1 | 0 | 1 | 1 | 0 | 0 | 0 |
| CGANSQIQLAVFF | 1 | 5 | 0 | 0 | 0 | 0 | 0 |
| CSFIYF | 1 | 4 | 0 | 0 | 5 | 0 | 0 |
| CAARGYNQGKLIF | 1 | 3 | 0 | 0 | 0 | 0 | 0 |

# SYSTEMS AND METHODS FOR SEQUENCING T CELL RECEPTORS AND USES THEREOF

CROSS REFERENCE TO RELATED APPLICATIONS

This application claims priority to U.S. Provisional Application No. 62/432,525, filed on Dec. 9, 2016, and U.S. Provisional Application No. 62/508,667, filed on May 19, 2017, the contents of each are incorporated by reference herein, in their entirety and for all purposes.

REFERENCE TO SEQUENCE LISTING

The Sequence Listing submitted Dec. 11, 2017 as a text file named "37595_0022U3_Sequence_Listing.txt," created on Dec. 11, 2017, and having a size of 312,651 bytes is hereby incorporated by reference pursuant to 37 C.F.R. § 1.52(e)(5).

FIELD

The disclosure relates generally to the field of bioinformatics. More particularly, the disclosure relates to systems and methods for sequencing T cell receptors (TCRs), identifying T cell clones in a population of cells and for bulk sequencing. The methods identify high-frequency T cell clones associated with tumor reactivity and patient survival.

BACKGROUND

Single or combination therapy with immune checkpoint inhibitors has shown significant therapeutic efficacy in cancer patients. However, the majority of patients either do not respond or only respond transiently, raising fundamental questions about the design of the next generation of immunotherapies. To overcome the immunosuppressive nature of the tumor microenvironment and promote durable responses, dual targeting of coinhibitory and costimulatory pathways inducing a stronger T cell activation, can be performed. In some scenarios, a combination of antibodies might synergistically enhance CD8$^+$ T cell effector function, for example by restoring a balance of homeostatic regulators, resulting in tumor rejection and long-term responses. T cell clonal expansion could provide a specific gene signature indicating the molecular mechanism of combination therapy. Existing TCR sequence analysis techniques are unable to accurately and reliable identify TCR sequences and clonal expansion based on short read sequencing data. These and other shortcomings are addressed by the methods and systems described herein.

SUMMARY

It is to be understood that both the following general description and the following detailed description are exemplary and explanatory only and are not restrictive. Provided are methods and systems for sequencing short reads of less than about 100 base pairs of RNA obtained from a T cell (and/or receiving sequence data indicative of the same), aligning the short reads with a reference sequence, wherein the reference sequence does not contain a TCR gene sequence, thereby generating a read set comprising mapped short reads and unmapped short reads, discarding mapped short reads from the read set, assembling the unmapped short reads remaining in the read set into one or more long reads, and generating one or more TCR sequences from the one or more long reads.

Disclosed are methods for sequencing a T cell receptor (TCR), comprising sequencing short reads of less than about 100 base pairs of RNA obtained from a T cell; aligning the short reads with a reference sequence, wherein the reference sequence does not contain a TCR gene sequence, thereby generating a read set comprising mapped short reads and unmapped short reads; discarding mapped short reads from the read set; assembling the unmapped short reads remaining in the read set into one or more long reads; translating the one or more long reads into corresponding amino acid sequences; fractioning TCR V region and TCR J region amino acid reference sequences into k-strings of about six amino acids, aligning the k-strings with the corresponding amino acid sequences from the translating step, detecting one or more conserved TCR. CDR3 residues in the k-strings that map to the corresponding amino acid sequences, scoring the level of conservation detected, and selecting corresponding amino acid sequences with a conservation score above a threshold conservation score, and detecting a candidate CDR3 region amino acid sequence in the selected corresponding amino acid sequences; identifying the nucleic acid sequence of the candidate CDR3 region amino acid sequences in the one or more long reads; aligning the nucleic acid sequence of the one or more long reads upstream of the candidate CDR3 region nucleic acid sequence with one or more TCR V gene reference sequences, scoring the degree of alignment, and identifying long reads above a threshold alignment score as comprising a candidate TCR V gene sequence; and aligning the nucleic acid sequence of the one or more long reads downstream of the candidate CDR3 region nucleic acid sequence with one or more TCR J gene reference sequences, scoring the degree of alignment, and identifying long reads above a threshold alignment score as comprising a candidate TCR J gene sequence, thereby generating a TCR sequence.

Disclosed are apparatuses comprising one or more processors; and a memory comprising processor executable instructions that, when executed by the one or more processors, cause the apparatus to receive sequence data comprising short reads of less than about 100 base pairs of RNA obtained from a T cell; align the short reads with a reference sequence, wherein the reference sequence does not contain a TCR gene sequence, thereby generating a read set comprising mapped short reads and unmapped short reads; discard mapped short reads from the read set; assemble the unmapped short reads remaining in the read set into one or more long reads; translate the one or more long reads into corresponding amino acid sequences; fraction TCR V region and TCR J region amino acid reference sequences into k-strings of about six amino acids, aligning the k-strings with the corresponding amino acid sequences from the translating step, detecting one or more conserved TCR CDR3 residues in the k-strings that map to the corresponding amino acid sequences, scoring the level of conservation detected, and selecting corresponding amino acid sequences with a conservation score above a threshold conservation score, and detecting a candidate CDR3 region amino acid sequence in the selected corresponding amino acid sequences; identify the nucleic acid sequence of the candidate CDR3 region amino acid sequences in the one or more long reads; align the nucleic acid sequence of the one or more long reads upstream of the candidate CDR3 region nucleic acid sequence with one or more TCR V gene reference sequences, scoring the degree of alignment, and identifying long reads above a threshold alignment score as comprising a candidate TCR V gene sequence; and align the nucleic acid sequence of the one or more long reads downstream of the candidate CDR3 region nucleic acid sequence with one or more TCR J gene reference sequences, scoring the degree of alignment, and identifying long reads above a threshold alignment score as comprising a candidate TCR J gene sequence, thereby generating a TCR sequence.

Disclosed are computer readable media, having computer executable instructions embodied thereon, configured for performing a method comprising sequencing short reads of less than about 100 base pairs of RNA obtained from a T cell; aligning the short reads with a reference sequence, wherein the reference sequence does not contain a TCR gene sequence, thereby generating a read set comprising mapped short reads and unmapped short reads; discarding mapped short reads from the read set; assembling the unmapped short reads remaining in the read set into one or more long reads; translating the one or more long reads into corresponding amino acid sequences; fractioning TCR V region and TCR J region amino acid reference sequences into k-strings of about six amino acids, aligning the k-strings with the corresponding amino acid sequences from the translating step, detecting one or more conserved TCR CDR3 residues in the k-strings that map to the corresponding amino acid sequences, scoring the level of conservation detected, and selecting corresponding amino acid sequences with a conservation score above a threshold conservation score, and detecting a candidate CDR3 region amino acid sequence in the selected corresponding amino acid sequences; identifying the nucleic acid sequence of the candidate CDR3 region amino acid sequences in the one or more long reads; aligning the nucleic acid sequence of the one or more long reads upstream of the candidate CDR3 region nucleic acid sequence with one or more TCR V gene reference sequences, scoring the degree of alignment, and identifying long reads above a threshold alignment score as comprising a candidate TCR V gene sequence; and aligning the nucleic acid sequence of the one or more long reads downstream of the candidate CDR3 region nucleic acid sequence with one or more TCR J gene reference sequences, scoring the degree of alignment, and identifying long reads above a threshold alignment score as comprising a candidate TCR J gene sequence, thereby generating a TCR sequence.

Disclosed are methods for sequencing a BCR, comprising sequencing short reads of less than about 100 base pairs of RNA obtained from a B cell; aligning the short reads with a reference sequence, wherein the reference sequence does not contain a BCR gene sequence, thereby generating a read set comprising mapped short reads and unmapped short reads; discarding mapped short reads from the read set; assembling the unmapped short reads remaining in the read set into one or more long reads; translating the one or more long reads into corresponding amino acid sequences; fractioning BCR V region and BCR J region amino acid reference sequences into k-strings of about six amino acids, aligning the k-strings with the corresponding amino acid sequences from the translating step, detecting one or more conserved BCR CDR3 residues in the k-strings that map to the corresponding amino acid sequences, scoring the level of conservation detected, and selecting corresponding amino acid sequences with a conservation score above a threshold conservation score, and detecting a candidate CDR3 region amino acid sequence in the selected corresponding amino acid sequences; identifying the nucleic acid sequence of the candidate CDR3 region amino acid sequences in the one or more long reads; aligning the nucleic acid sequence of the one or more long reads upstream of the candidate CDR3 region nucleic acid sequence with one or more BCR V gene reference sequences, scoring the degree of alignment, and identifying long reads above a threshold alignment score as comprising a candidate BCR V gene sequence; and aligning the nucleic acid sequence of the one or more long reads downstream of the candidate CDR3 region nucleic acid sequence with one or more BCR J gene reference sequences, scoring the degree of alignment, and identifying long reads above a threshold alignment score as comprising a candidate BCR J gene sequence, thereby generating a BCR sequence.

Disclosed are apparatuses comprising one or more processors; and a memory comprising processor executable instructions that, when executed by the one or more processors, cause the apparatus to receive sequence data comprising short reads of less than about 100 base pairs of RNA obtained from a B cell; align the short reads with a reference sequence, wherein the reference sequence does not contain a BCR gene sequence, thereby generating a read set comprising mapped short reads and unmapped short reads; discard mapped short reads from the read set; assemble the unmapped short reads remaining in the read set into one or more long reads; translate the one or more long reads into corresponding amino acid sequences; fraction BCR V region and BCR J region amino acid reference sequences into k-strings of about six amino acids, aligning the k-strings with the corresponding amino acid sequences from the translating step, detecting one or more conserved BCR CDR3 residues in the k-strings that map to the corresponding amino acid sequences, scoring the level of conservation detected, and selecting corresponding amino acid sequences with a conservation score above a threshold conservation score, and detecting a candidate CDR3 region amino acid sequence in the selected corresponding amino acid sequences; identify the nucleic acid sequence of the candidate CDR3 region amino acid sequences in the one or more long reads; align the nucleic acid sequence of the one or more long reads upstream of the candidate CDR3 region nucleic acid sequence with one or more BCR V gene reference sequences, scoring the degree of alignment, and identifying long reads above a threshold alignment score as comprising a candidate BCR V gene sequence; and align the nucleic acid sequence of the one or more long reads downstream of the candidate CDR3 region nucleic acid sequence with one or more TCR J gene reference sequences, scoring the degree of alignment, and identifying long reads above a threshold alignment score as comprising a candidate BCR J gene sequence, thereby generating a BCR sequence.

Disclosed are computer readable media, having computer executable instructions embodied thereon, configured for performing a method comprising sequencing short reads of less than about 100 base pairs of RNA obtained from a B cell; aligning the short reads with a reference sequence, wherein the reference sequence does not contain a BCR gene sequence, thereby generating a read set comprising mapped short reads and unmapped short reads; discarding mapped short reads from the read set; assembling the unmapped short reads remaining in the read set into one or more long reads; translating the one or more long reads into corresponding amino acid sequences; fractioning BCR V region and BCR J region amino acid reference sequences into k-strings of about six amino acids, aligning the k-strings with the corresponding amino acid sequences from the translating step, detecting one or more conserved BCR CDR3 residues in the k-strings that map to the corresponding amino acid sequences, scoring the level of conservation detected, and selecting corresponding amino acid sequences with a conservation score above a threshold conservation score, and detecting a candidate CDR3 region amino acid sequence in the selected corresponding amino acid sequences; identifying the nucleic acid sequence of the candidate CDR3 region amino acid sequences in the one or more long reads; aligning the nucleic acid sequence of the one or more long reads upstream of the candidate CDR3 region nucleic acid sequence with one or more BCR V gene reference sequences, scoring the degree of alignment, and identifying long reads above a threshold alignment score as comprising a candidate BCR V gene sequence; and aligning the nucleic acid sequence of the one or more long reads downstream of the candidate CDR3 region nucleic acid sequence with one or more BCR J gene reference sequences, scoring the degree of alignment, and identifying long reads above a threshold alignment score as comprising a candidate BCR J gene sequence, thereby generating a BCR sequence.

In some aspects of the disclosed methods, apparatuses, and computer readable media, the short reads are obtained from random-priming of RNA.

In some aspects of the disclosed methods, apparatuses, and computer readable media, the T cell is obtained from a human or mouse.

In some aspects of the disclosed methods, apparatuses, and computer readable media, the reference sequence comprises a human genome, a mouse genome, a human transcriptome, or a mouse transcriptome.

In some aspects of the disclosed methods, apparatuses, and computer readable media, discarding mapped short reads from the read set further comprises discarding unmapped short reads from the read set that are less than about 35 base pairs or that have a low sequence resolution.

In some aspects of the disclosed methods, apparatuses, and computer readable media, assembling the unmapped short reads remaining in the read set into one or more long reads comprises aligning the one or more unmapped short reads to one or more TCR sequences from a reference database of TCR sequences; and assembling, based on the alignment, the one or more unmapped short reads into long reads.

In some aspects, disclosed are methods, apparatuses, and computer readable media, further comprising appending a TCR C region nucleic acid sequence to the TCR sequence.

In some aspects, disclosed are methods, apparatuses, and computer readable media, further comprising, prior to sequencing the short reads of less than about 100 base pairs of RNA obtained from the T cell, administering an immunotherapy to a subject from which the T cell is obtained. In some aspects, the immunotherapy comprises a monotherapy or a combination therapy. In some aspects, the combination therapy comprises a costimulatory agonist and a coinhibitory antagonist.

In some aspects of the disclosed methods, apparatuses, and computer readable media, repeating all of the steps for a first plurality of T cells of a subject, wherein the T cells are collected prior to administration of a treatment; determining a number of occurrences of unique TCR sequences present in the first plurality of T cells; administering the treatment to the subject; repeating all of the steps for a second plurality of T cells of the subject, wherein the T cells are collected after the administration of the treatment; determining a number of occurrences of unique TCR sequences present in the second plurality of T cells; and determining, based on the numbers of occurrences of unique TCR sequences present in the first plurality of T cells and the second plurality of T cell, one or more unique TCR sequences that experienced clonal expansion.

In some aspects, disclosed are methods, apparatuses, and computer readable media, further comprising determining a T cell clonal expansion signature based on the one or more unique TCR sequences that experienced clonal expansion.

In some aspects, disclosed are methods, apparatuses, and computer readable media, further comprising querying a database of T cell clonal expansion signatures and corresponding treatment responses using the T cell clonal expansion signature; determining, based on the query, the subject's likelihood of responding to the treatment.

In some aspects, disclosed are methods, apparatuses, and computer readable media, further comprising the steps of determining the subject's response to the treatment; storing the T cell clonal expansion signature in a database; and associating the subject's response to the treatment with the T cell clonal expansion signature in the database.

In some aspects, disclosed are methods, apparatuses, and computer readable media, further comprising determining that the TCR sequence is present in a T cell clone that expands in response to a treatment; producing one or more T cells containing the TCR sequence; administering the one or more T cells to a subject; and administering the treatment to the subject.

In some aspects of the disclosed methods, apparatuses, and computer readable media, wherein sequencing short reads of less than about 100 base pairs of RNA obtained from a T cell comprises bulk sequencing of short reads of less than about 100 base pairs of RNA obtained from a plurality of T cells.

In some aspects, disclosed are methods, apparatuses, and computer readable media, further comprising performing the steps of aligning the short reads through the step of aligning the nucleic acid sequence of the one or more long reads downstream of the candidate CDR3 region nucleic acid sequence with one or more TCR J gene reference sequences, scoring the degree of alignment, and identifying long reads above a threshold alignment score as comprising a candidate TCR J gene sequence, thereby generating a TCR sequence for each of the plurality of T cells.

In some aspects of the disclosed methods, apparatuses, and computer readable media, performing steps of aligning the short reads through the step of aligning the nucleic acid sequence of the one or more long reads downstream of the candidate CDR3 region nucleic acid sequence with one or more TCR J gene reference sequences, scoring the degree of alignment, and identifying long reads above a threshold alignment score as comprising a candidate TCR J gene sequence, thereby generating a TCR sequence for each of the plurality of T cells comprising performing steps of aligning the short reads through the step of aligning the nucleic acid sequence of the one or more long reads downstream of the candidate CDR3 region nucleic acid sequence with one or more TCR J gene reference sequences, scoring the degree of alignment, and identifying long reads above a threshold alignment score as comprising a candidate TCR J gene sequence, thereby generating a TCR sequence comprises classifying at least a portion of one or more of steps of aligning the short reads through the step of aligning the nucleic acid sequence of the one or more long reads downstream of the candidate CDR3 region nucleic acid sequence with one or more TCR J gene reference sequences, scoring the degree of alignment, and identifying long reads above a threshold alignment score as comprising a candidate TCR J gene sequence, thereby generating a TCR sequence as a job; and distributing a workload for each job across a plurality of processors in parallel.

In some aspects of the disclosed methods, apparatuses, and computer readable media, the B cell is obtained from a human or mouse.

In some aspects of the disclosed methods, apparatuses, and computer readable media, assembling the unmapped short reads remaining in the read set into one or more long reads comprises aligning the one or more unmapped short reads to one or more BCR sequences from a reference database of BCR sequences; and assembling, based on the alignment, the one or more unmapped short reads into long reads.

In some aspects, disclosed are methods, apparatuses, and computer readable media, further comprising appending a BCR C region nucleic acid sequence to the BCR sequence.

In some aspects, disclosed are methods, apparatuses, and computer readable media, further comprising prior to sequencing the short reads of less than about 100 base pairs of RNA obtained from the B cell, administering an immunotherapy to a subject from which the B cell is obtained. In some aspects, the immunotherapy comprises a monotherapy or a combination therapy. In some aspects, the combination therapy comprises a costimulatory agonist and a coinhibitory antagonist.

In some aspects, disclosed are methods, apparatuses, and computer readable media, further comprising repeating all of the steps for a first plurality of B cells of a subject, wherein the B cells are collected prior to administration of a treatment; determining a number of occurrences of unique BCR sequences present in the first plurality of B cells; administering the treatment to the subject; repeating steps a-i for a second plurality of B cells of the subject, wherein the B cells are collected after the administration of the treatment; determining a number of occurrences of unique BCR sequences present in the second plurality of B cells; and determining, based on the numbers of occurrences of unique BCR sequences present in the first plurality of B cells and the second plurality of B cell, one or more unique BCR sequences that experienced clonal expansion.

In some aspects, disclosed are methods, apparatuses, and computer readable media, further comprising determining a B cell clonal expansion signature based on the one or more unique BCR sequences that experienced clonal expansion.

In some aspects, disclosed are methods, apparatuses, and computer readable media, further comprising querying a database of B cell clonal expansion signatures and corresponding treatment responses using the B cell clonal expansion signature; determining, based on the query, the subject's likelihood of responding to the treatment.

In some aspects, disclosed are methods, apparatuses, and computer readable media, further comprising determining the subject's response to the treatment; storing the B cell clonal expansion signature in a database; and associating the subject's response to the treatment with the B cell clonal expansion signature in the database.

In some aspects, disclosed are methods, apparatuses, and computer readable media, further comprising determining that the BCR sequence is present in a B cell clone that expands in response to a treatment; producing one or more B cells containing the BCR sequence; administering the one or more B cells to a subject; and administering the treatment to the subject.

In some aspects of the disclosed methods, apparatuses, and computer readable media, sequencing short reads of less than about 100 base pairs of RNA obtained from a B cell comprises bulk sequencing of short reads of less than about 100 base pairs of RNA obtained from a plurality of B cells.

In some aspects, disclosed are methods, apparatuses, and computer readable media, further comprising performing the steps of of aligning the short reads with a reference sequence through aligning the nucleic acid sequence of the one or more long reads downstream of the candidate CDR3 region nucleic acid sequence with one or more BCR J gene reference sequences, scoring the degree of alignment, and identifying long reads above a threshold alignment score as comprising a candidate BCR J gene sequence, thereby generating a BCR sequence for each of the plurality of B cells.

In some aspects of the disclosed methods, apparatuses, and computer readable media, performing the steps of aligning the short reads with a reference sequence through aligning the nucleic acid sequence of the one or more long reads downstream of the candidate CDR3 region nucleic acid sequence with one or more BCR J gene reference sequences, scoring the degree of alignment, and identifying long reads above a threshold alignment score as comprising a candidate BCR J gene sequence, thereby generating a BCR sequence for each of the plurality of B cells comprising performing the steps of aligning the short reads with a reference sequence through aligning the nucleic acid sequence of the one or more long reads downstream of the candidate CDR3 region nucleic acid sequence with one or more BCR J gene reference sequences, scoring the degree of alignment, and identifying long reads above a threshold alignment score as comprising a candidate BCR J gene sequence, thereby generating a BCR sequence comprises classifying at least a portion of one or more of the steps of aligning the short reads with a reference sequence through aligning the nucleic acid sequence of the one or more long reads downstream of the candidate CDR3 region nucleic acid sequence with one or more BCR J gene reference sequences, scoring the degree of alignment, and identifying long reads above a threshold alignment score as comprising a candidate BCR J gene sequence, thereby generating a BCR sequence as a job; and distributing a workload for each job across a plurality of processors in parallel.

Additional advantages will be set forth in part in the description which follows or may be learned by practice. The advantages will be realized and attained by means of the elements and combinations particularly pointed out in the appended claims.

BRIEF DESCRIPTION OF THE DRAWINGS

The accompanying drawings, which are incorporated in and constitute a part of this specification, illustrate embodiments and together with the description, serve to explain the principles of the methods and systems.

FIG. 2 depicts significant clonal expansion in intratumoral CD8+ T cells after treatment.

FIG. 13 is a table showing TCR-negative cancer or non-cancer cell lines were used as negative controls for MiTCR, TCRklass and rpsTCR pipeline—Negative controls: human and mouse non-T cell lines (2×100 bp).

FIG. 14 is a table showing the Comparison of TCR detection rate between TCR targeting sequencing and rpsTCR pipeline in single cell sequencing.

FIG. 15 is a table showing the pathways specifically upregulated in clonal expanded CD8+ T cells with antibody treatment on day 11.

FIGS. 16A-16J show that anti-GITR+anti-PD-1 combination synergistically rejects established tumors and reinvigorates dysfunctional T cells. 16a, MC38 tumor growth in wild-type C57BL/6 mice with anti-GITR and/or anti-PD-1 Ab treatment (day 6, 13). Results depict tumor growth curves of individual mice (cumulative data from two experiments, n=17 mice per group). Numbers on the top represent tumor-free mice over total number of mice in treatment group. 16b, Cumulative survival curves with indicated treatment. 16c, 16d, CD8+ T cell-dependent long-term tumor protection mediated by combination treatment. C57BL/6 mice were treated with anti-CD8, CD4 or anti-CD25 depletion antibody followed by therapy with anti-GITR+anti-PD-1 Ab or control Ab (see Method). c. Representative FACS plots showing depletion efficiency by different Abs. 16d. Average tumor growth curve upon treatment with different depletion Ab, showing one representative of two experiments (n=5 mice per group). 16e, 16f, Combination treatment increases intratumoral effector T cell/$T_{reg}$ ratio. 16e, Representative FACS plots showing tumor T cell subsets on day 11 (FoxP3 versus CD8, cells pre-gated on Live/single cells/CD45+/CD3+). 16f, Summary FACS result of intratumoral CD8+ T cell/$T_{reg}$ and CD4+ $T_{Eff}$ cell/$T_{reg}$ ratio on day 8 and 11 after tumor challenge. Data are representative of three independent experiments (n=6-7 mice per group). 16g-16i, Combination treatment reinvigorates intratumoral dysfunctional T cells. Tumors were harvested on day 11~12 after implantation, dissociated into single cell suspension restimulated with PMA/Ionomycin with the presence of BFA. Cells were fixed and permeabilized, followed by intracellular staining with Ki67 (16g), granzyme A (16h), and granzyme B (16i). Data shown are percentage of positive cells. (n=5-10 mice per group). 16j. Anti-GITR+anti-PD-1 synergistically rejects established mouse RENCA tumors. Balb/c mice were challenged with $1 \times 10^6$ RENCA tumor cells subcutaneously on day 0 and treated with anti-GITR (5 mg/kg) and or anti-PD-1 (5 mg/kg) Ab treatment on day 6, 13, and 20 after tumor implantation. Data shown are percentage of survival (n=10 mice per group). (*, $p<0.05$, , $p<0.01$, *, $p<0.001$, **, $p<0.0001$; 16b, 16j Log-rank test; 16f, 16g**, One-way ANOVA, Tukey's multiple comparison test).

Figure 17:
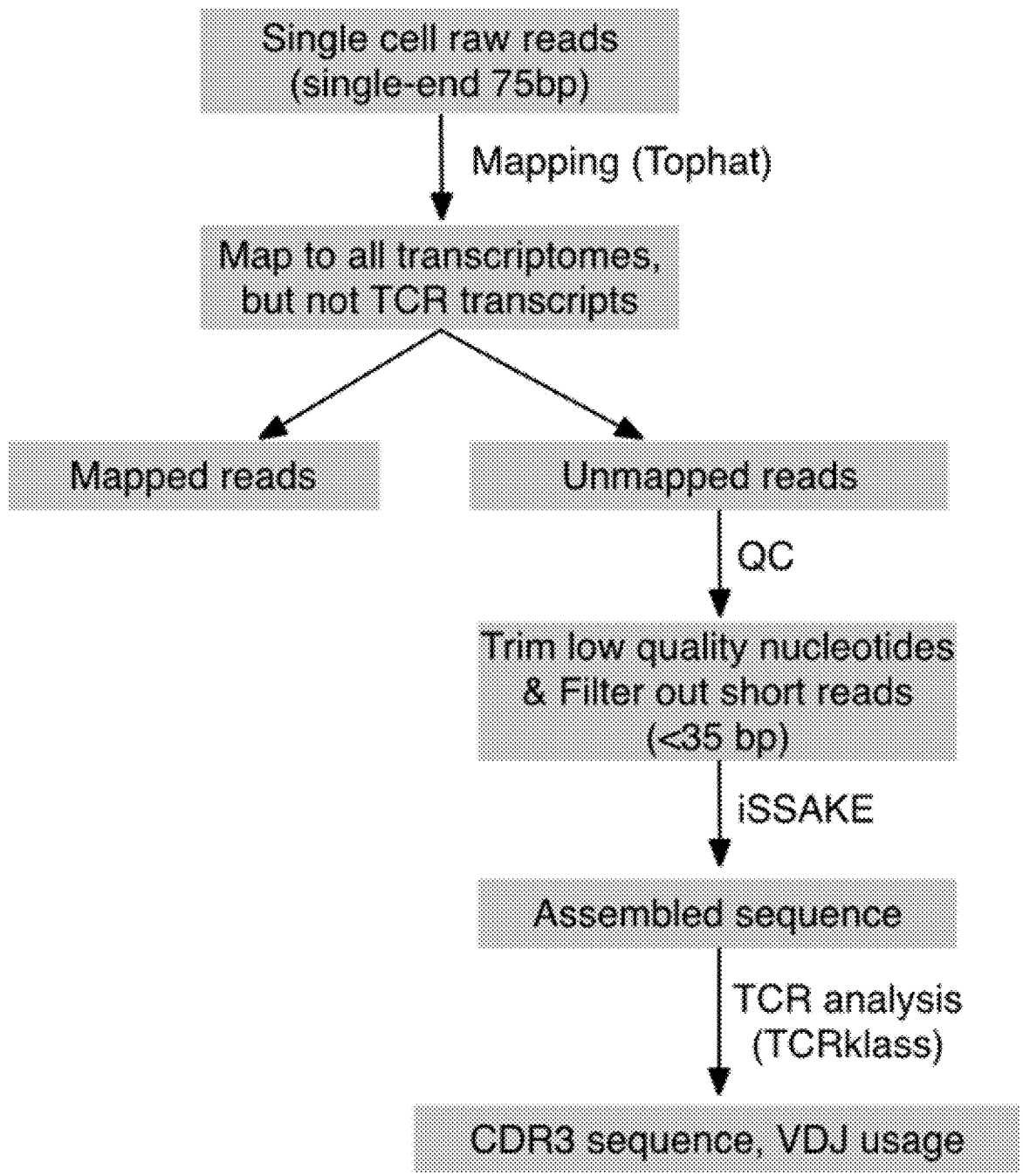

FIG. 17 shows an overview of rpsTCR pipeline. Schematic of rpsTCR pipeline, a bioinformatic pipeline for TCR repertoire analysis using random priming short RNA-seq data.

Figure 18:
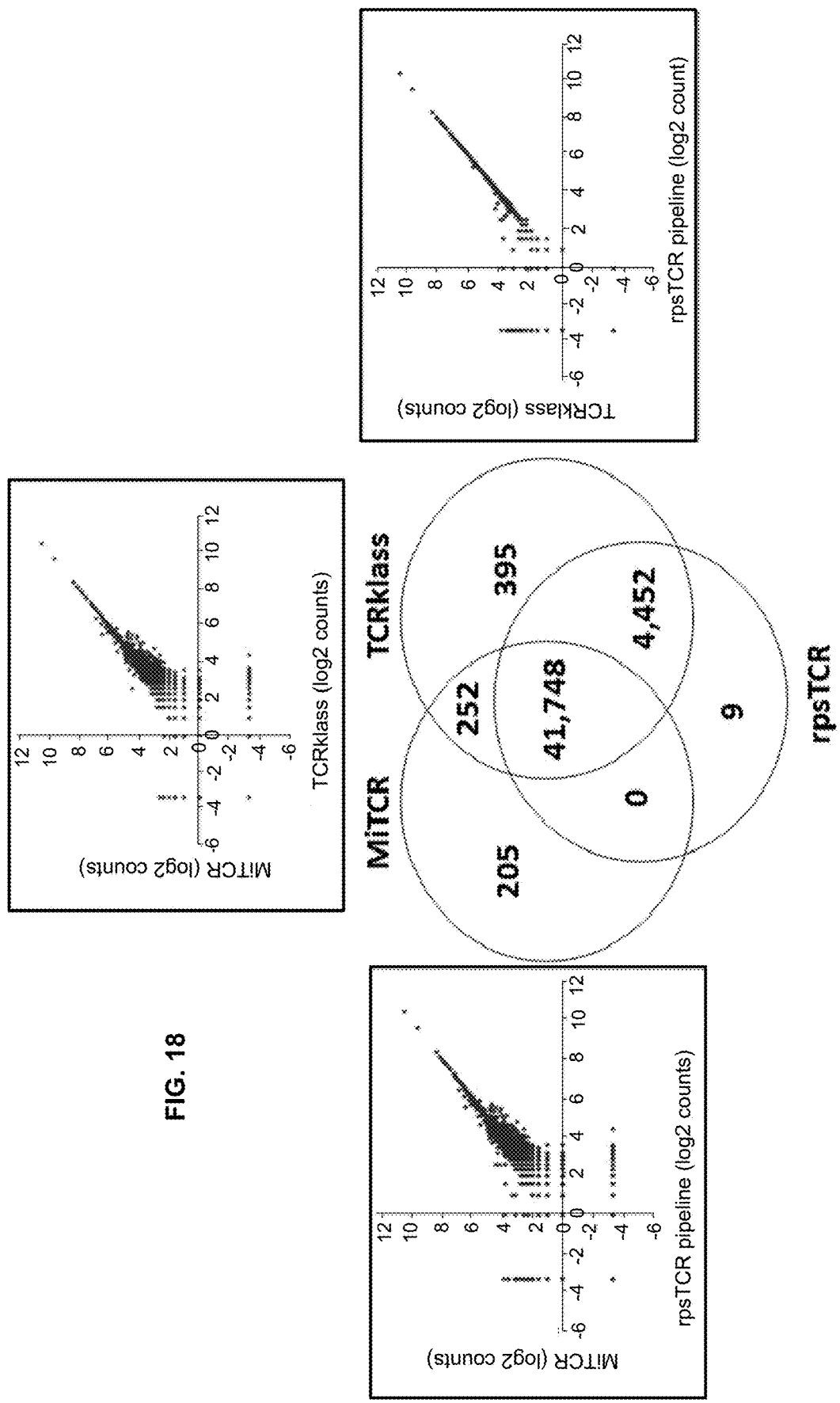

FIG. 18 shows rpsTCR pipeline platform validation using human and mouse primary blood cells. Targeted TCR-sect data from healthy human PBMC samples or mouse whole blood were used as a positive control to evaluate false positive or false negative rates comparing to TCRklass alone. Majority of unique CDR3 sequences were detected by the rpsTCR pipeline, MiTCR, and TCRklass, as indicated by the number in Venn diagram. The squared correlations ($R^2$) between the rpsTCR pipeline, MiTCR, and TCRklass were indicated in the figure.

Figure 19:
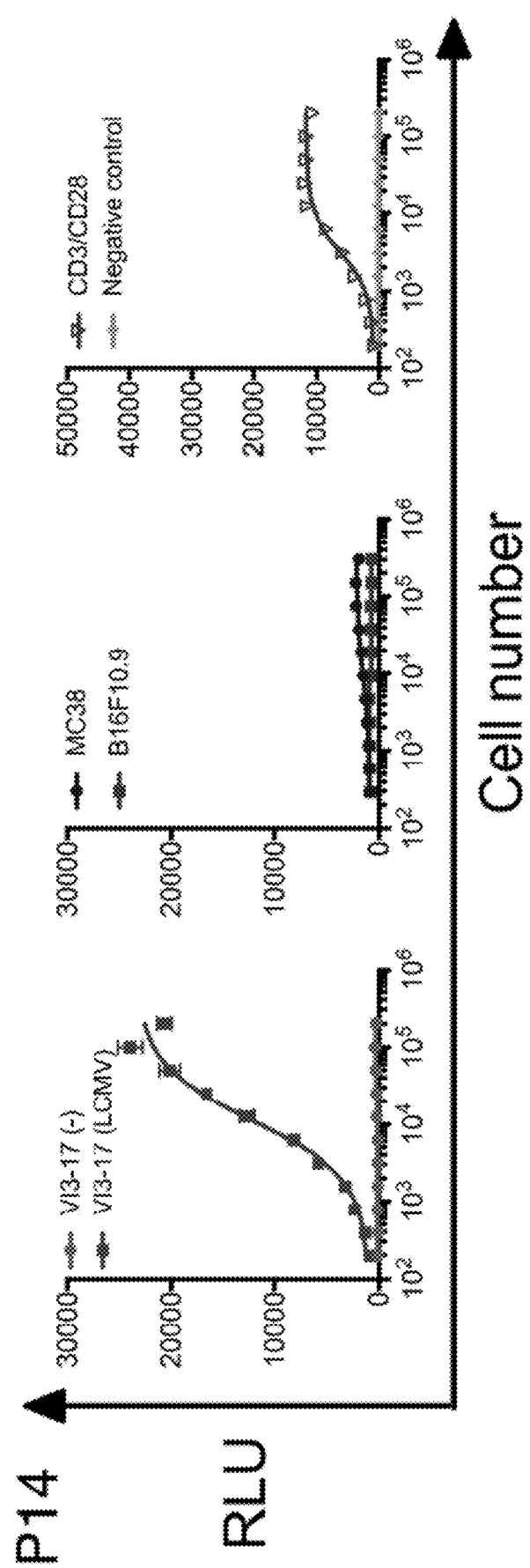

FIG. 19 shows TCRs from LCMV-specific T cell clones (P14) were used as positive control for the bioassay platform. P14 TCR engineered reporter cell line show specificity to LCMV infected cells but not to tumor cell lines. Anti-CD3 and CD28 stimulation was used as positive control for TCR complex signaling.

Figure 20:
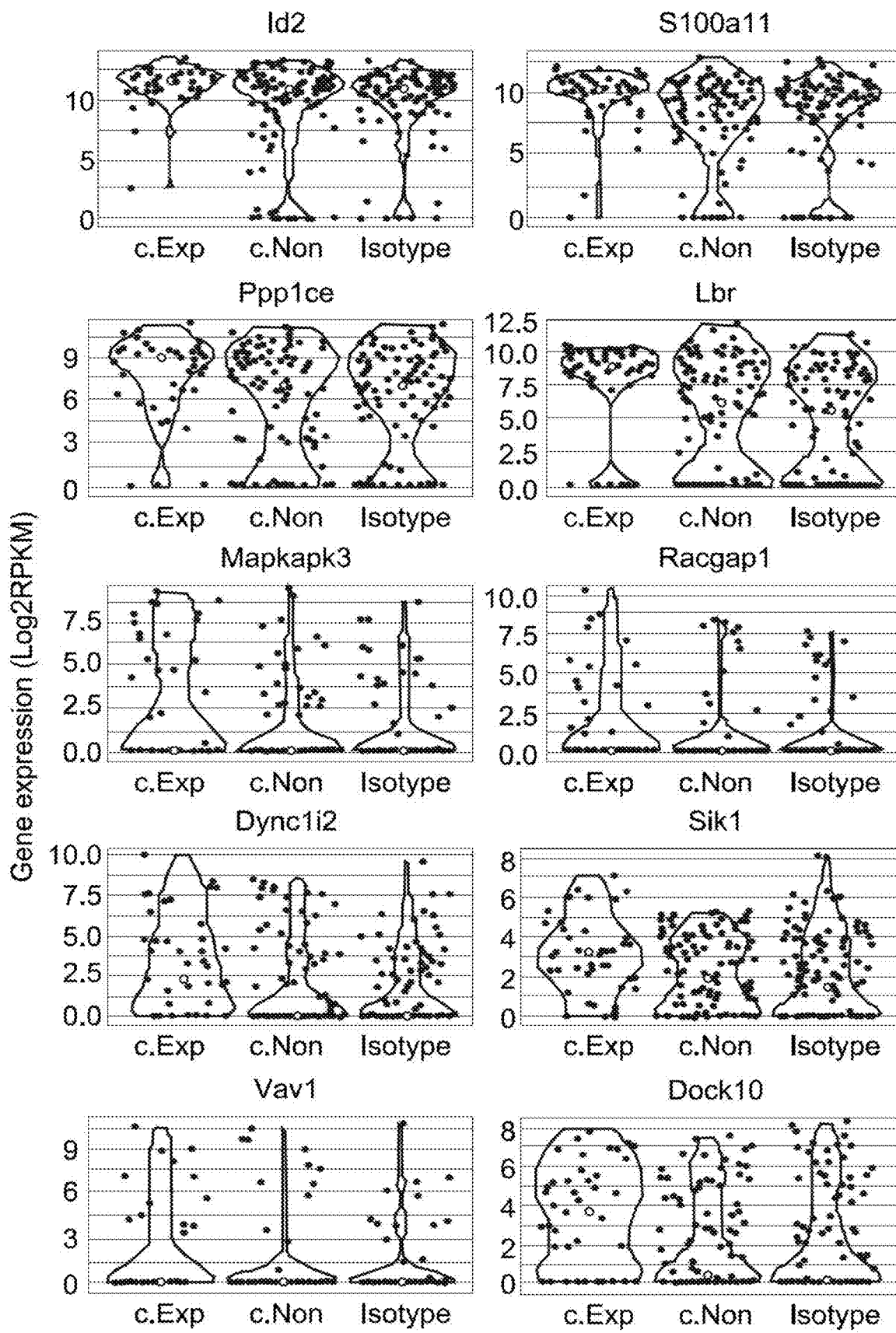
Figure 20:
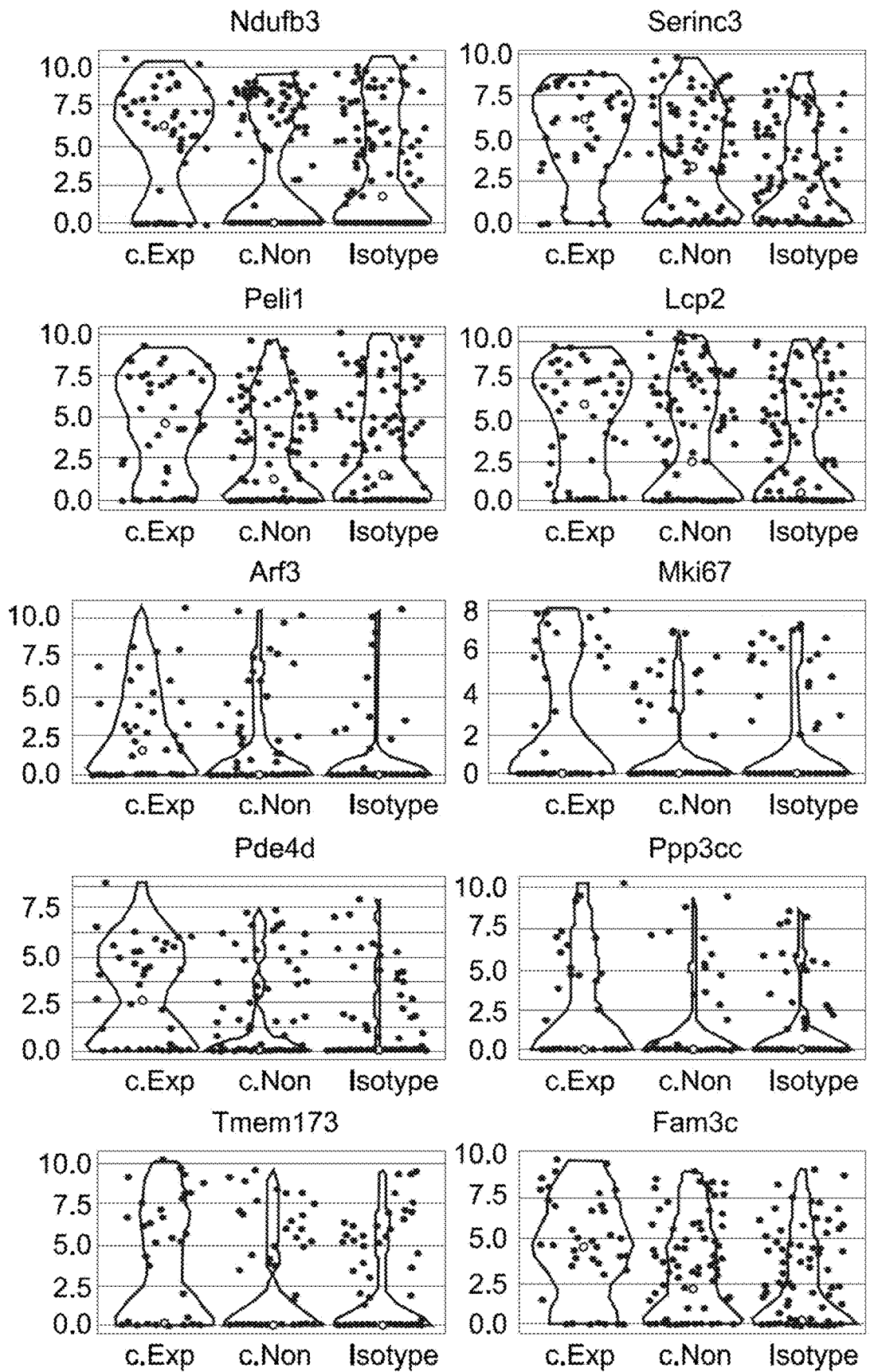
Figure 20:
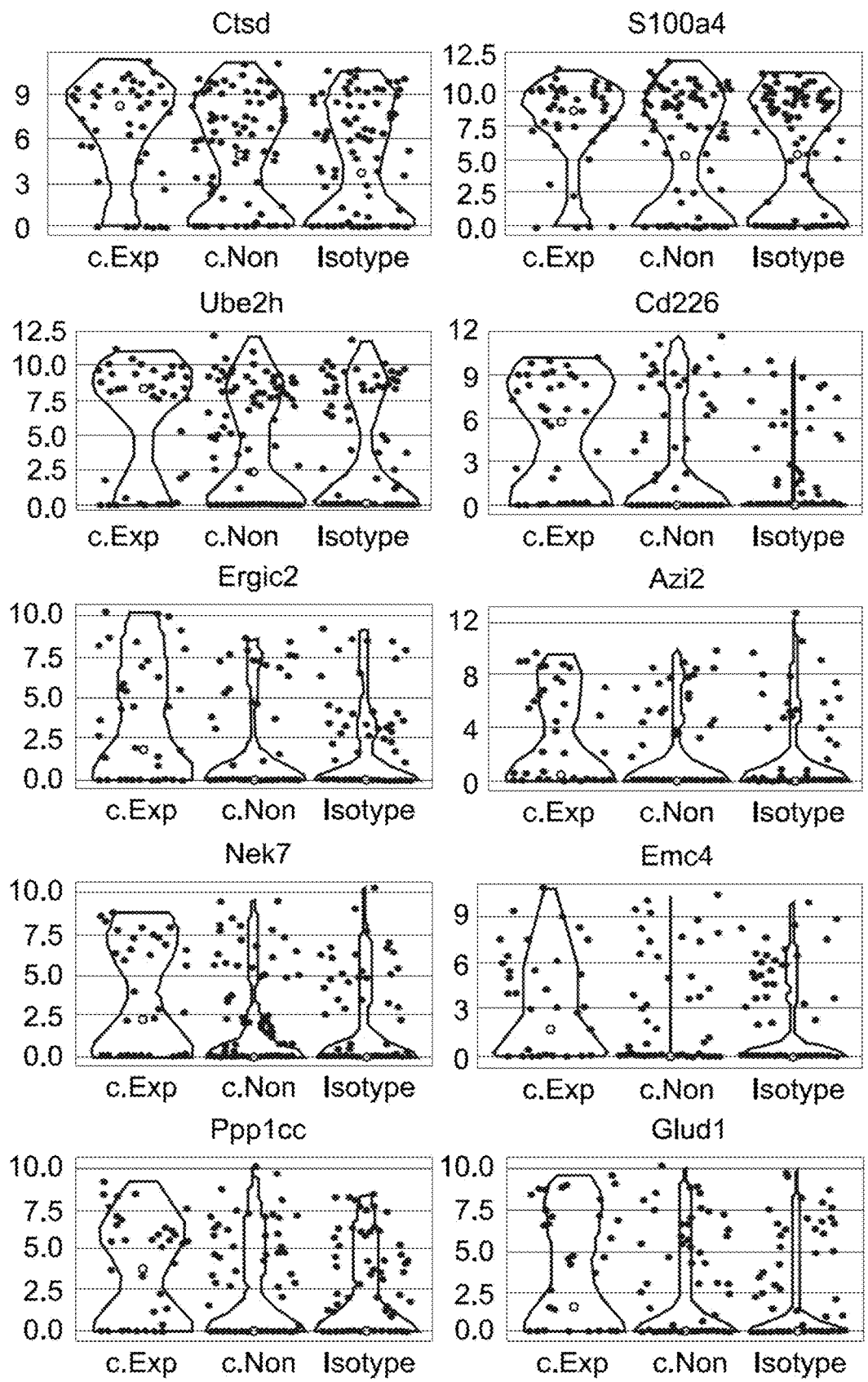

FIG. 20 shows a violin plot showing expression level of thirty genes significantly enriched in clonally expanded CD8+ T cells from combination treatment. Data shown are gene expression (Log 2 RPMK) in individual sequenced CD8+ T cells (cExp, combination treatment, clonal expanded T cell; cNon, combination treatment, non-expanded; Isotype, total CD8 from isotype treatment group).

Figure 21B:
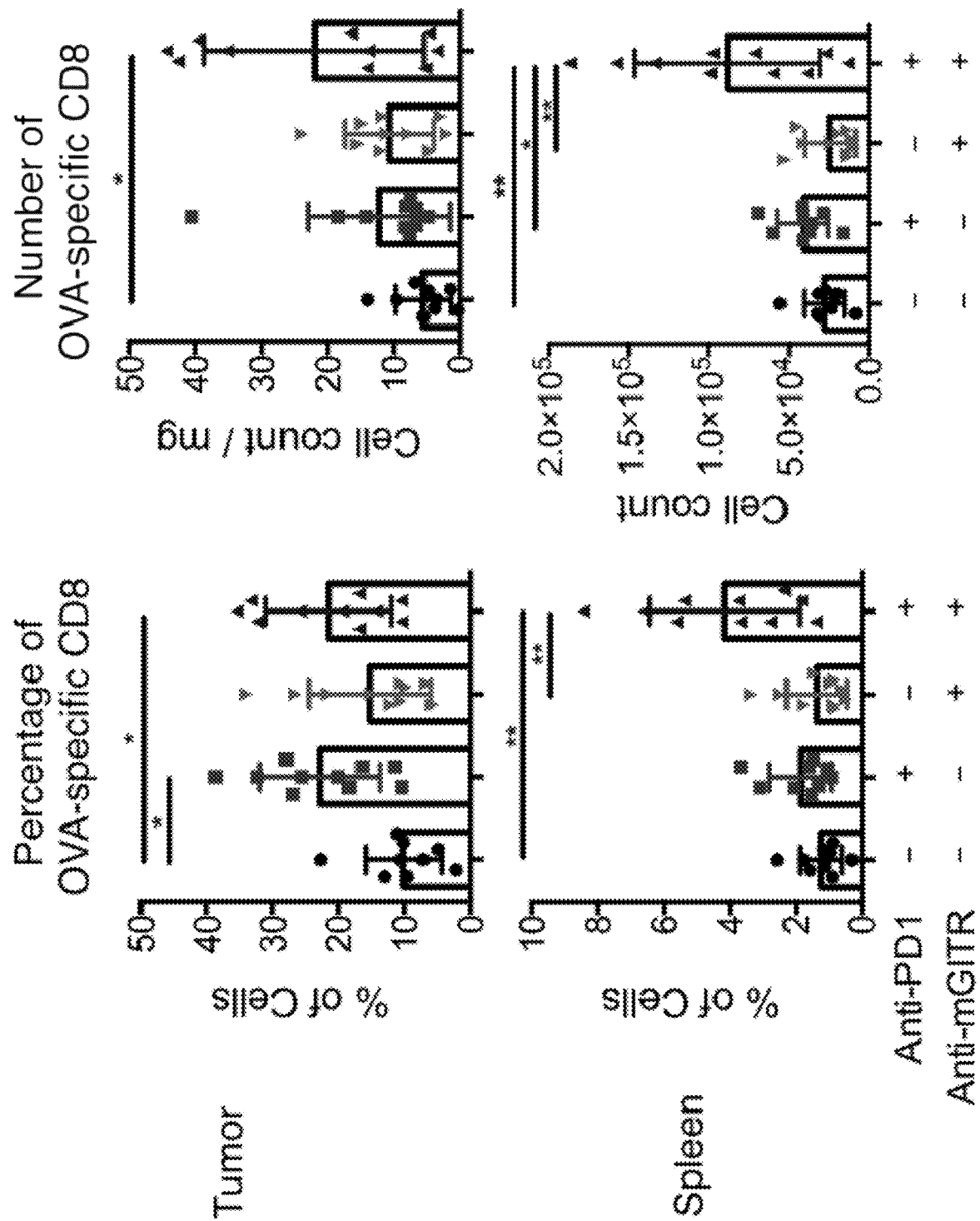
Figure 21C:
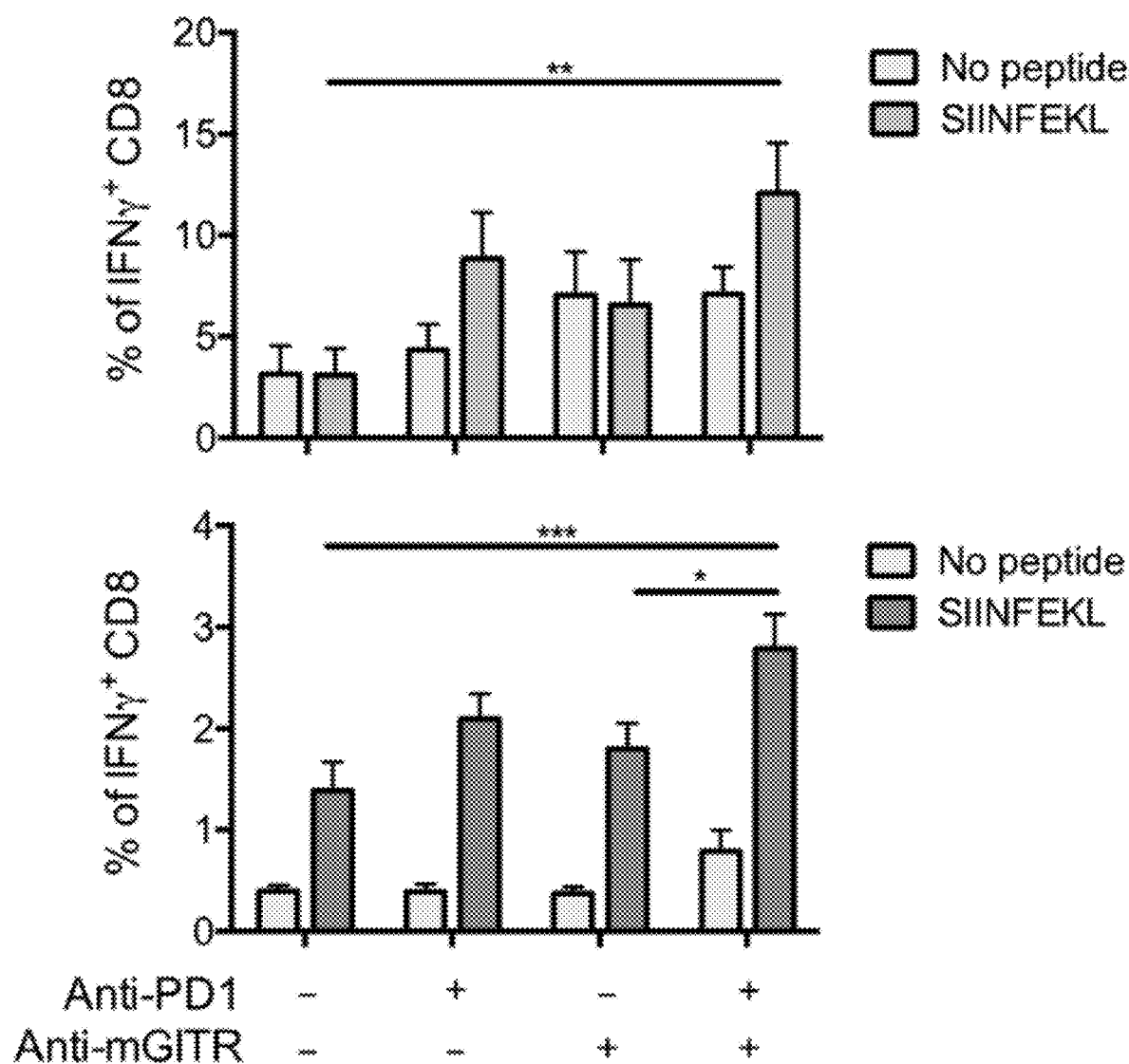

FIGS. 21A-21C show combination treatment expands tumor-antigen specific CD8+ T cells with effector function. a, Validation of surface expression of OVA peptide-Kb complex on MC38-OVA-$\beta_2$m-$K^b$ cells by FACS. MC38-OVA-$\beta_2$m-$K^b$ or empty vector control MC38 cells are stained with isotype or anti-Kb-SIINFEKL Ab. Representative histogram is shown. b, Frequency (left) and counts normalized to tumor weight (count/mg, right) of tumor and spleen OVA-specific CD8+ T cells from MC38-OVA-$\beta_2$m-$K^b$ bearing mice treated with anti-GITR and/or anti-PD-1 Ab. (Representative of two experiments, n=9-10 mice per group). c, Increase of OVA-specific recall response in spleen and tumor CD8+ T cells with combination treatment. Cells were restimulated with or without SIINFEKL peptide in the presence of BFA. Intracellular expression of IFNγ was analyzed by FACS. Data are representative of two experiments, n=9-10 mice per group, (*, $p<0.05$, , $p<0.01$, *, $p<0.001$, b, One-way ANOVA, c, Two-way ANOVA, Tukey's multiple comparison test).

FIGS. 22A-22D show TIGIT expression at single cell RNA level and FACS analysis of TIGIT/CD226 expression level on different T cell subsets. Cumulative distribution function (CDF) plots showing TIGIT RNA expression (a) and FACS analysis (b), representative of two experiments, n=9-10 mice per group) showing expression of TIGIT in total, clonally expanded (OVA-specific) or non-expanded (OVA-non-specific) CD8+ T cells. c. FACS analysis of TIGIT expression on spleen and tumor T cell subsets 8 days after MC38 wild type tumor implantation, percentage of TIGIT+ cells within each population are shown. d, FACS analysis of CD226 expression on spleen and tumor T cell subsets 11 days after MC38 wild type tumor implantation, percentage of CD226+ cells within each population are shown. Data are representative of two experiments, n=9-10 mice per group (*, $p<0.05$, , $p<0.01$, *, $p<0.001$, One-way ANOVA, Tukey's multiple comparison test).

FIGS. 23A-23F show CD226$^{-/-}$ mice show normal T cell development and homeostatic function. a, Targeting strategy. Coding exons 1 to 2 of mouse CD226 was replaced with self-deleting eGFP-Neo cassette (eGFP-polyA-hUb-EM7-neo-polyA-Prm-Crei-polyA), beginning just 3' to the start ATG in coding exon 1 to 13 bp before the 3' end of coding exon 2. The intron between coding exons 1-2 is also deleted. After cassette deletion, eGFP, polyA LoxP and cloning sites (1141 bp) remain. b, FACS validation of CD226 deletion on T cell subsets. c, FACS analysis of T cell development in thymus (Tconv, conventional T cells; DP, CD4/CD8 double positive; SP, single positive; DN, CD4/CD8 double negative). d, T cell subsets in spleen and blood analyzed by FACS. e, Inflammatory cytokine secretion upon TCR stimulation. Splenocytes from CD226$^{-/-}$ or wild type (WT) mice were stimulated ex vivo with anti-CD3+anti-CD28 Ab for 16 hours. Supernatant was collected for indicated cytokine release. f, Expression level of PD1 and GITR on spleen and blood T cell subsets from CD226$^{-/-}$ or WT mice. Data shown is Mean fluorescence intensity (MFI) (n=3 mice per group).

FIGS. 24A-24G show CD226 signaling pathway was required for enhanced tumor surveillance in TIGIT$^{-/-}$ mice. Wild type or TIGIT$^{-/-}$ mice were challenged with MC38 tumors, pre-treated with anti-CD226 or control IgG and either received isotype control (a) or anti-GITR+anti-PD-1 combination therapy (b). Data shown are average tumor growth curves representative of two experiments (n=4-5 mice per group). c, FACS validate over-expression of CD155 on engineered. MC38 tumor cells. d, Overexpressing CD155, a ligand for CD226/TIGIT, on MC38 tumor cells slows down tumor growth and synergizes with anti-GITR or anti-PD-1 Ab monotherapy (on day 3, 6, 10 and 13) in promoting tumor rejection and long-term survival. Data shown are average tumor growth curve (n=10 mice per group). e, Maintained over-expression of CD155 on engineered MC38 tumor cells in vivo. f, Overexpression of CD155 on MC38 tumor cells reduces free CD226 receptor on intratumoral, but not splenic, T cell subsets detected by FACS. g, Mice were challenged with MC38 control or CD155 overexpression cells. On day 9 after tumor challenge, tumor and spleen cells were analyzed by FACS for T cell activation. For IFNγ expression, cells were restimulated with PMA/ionomycin prior to intracellular staining (n=10 mice per group). (, $p<0.01$; *, $p<0.001$; ****, $p<0.0001$, One-way ANOVA, Tukey's multiple comparison test).

Figure 25:
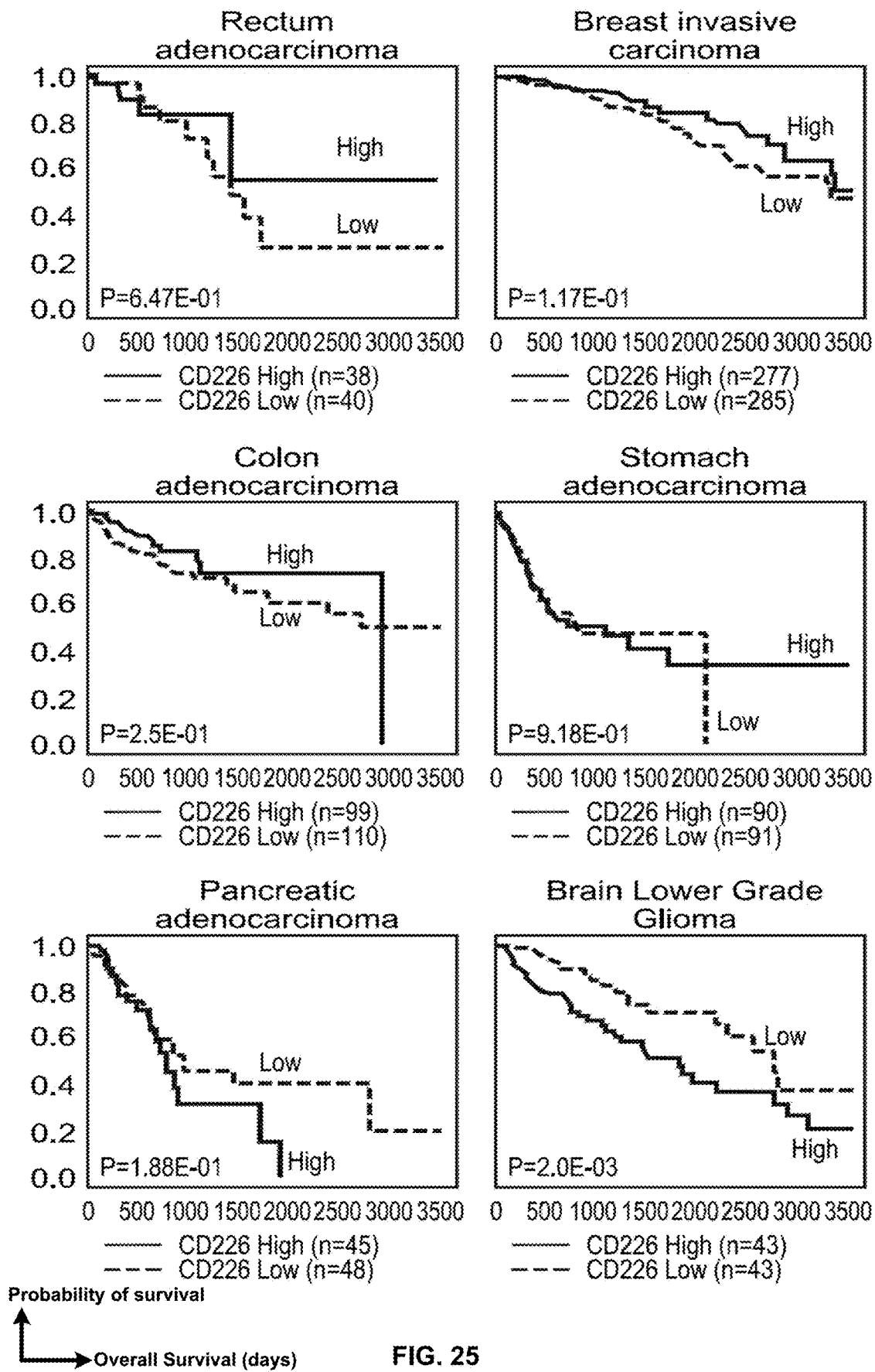
Figure 25:
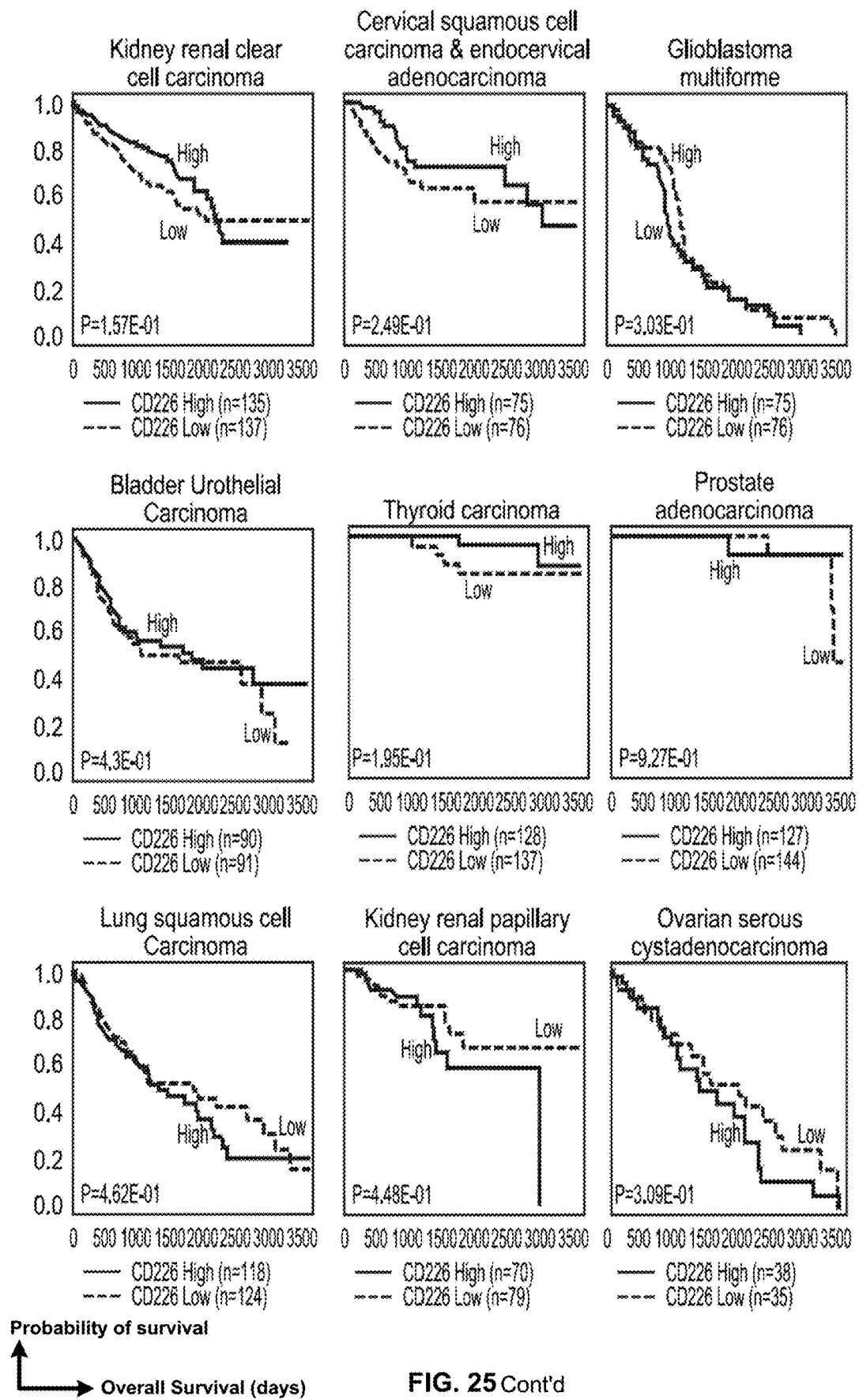

FIG. 25 shows the combination of local radiation with anti-GITR+anti-PD-1 Ab therapy shows efficacy against large established MC38 tumors. Mice bearing large established MC38 tumors were treated with 100 μg anti-GITR and/or anti-PD-1 Ab or isotype Abs (day 17, 20, 24 and 27) in combination with 0 or 8 Gy local radiation (day 18). a, Average tumor growth curve. b, Individual mouse tumor growth curves. Number of tumor-free mice is indicated in the top left panel. c, Survival curves from b. Data are representative of two experiments (n=5-6 mice per group), (*, p<0.05, **, p<0.01, Log-rank test).

FIG. 26 is a list of primers used in library preparation for TCRα/β repertoire sequencing.

FIG. 27 shows a comparison of three methods using positive and negative control data sets.

FIG. 28 shows the top CDR3s found by miTCR, TCRklass, and rpsTCR pipeline using 50 bp priming reads.

FIG. 29 shows the top CDR3s found in full VI-Next dataset using 50 bp priming reads.

FIG. 30 shows the top CDR3s found by miTCR, TCRklass, and rpsTCR pipeline using 100 bp priming reads.

Figure 31:
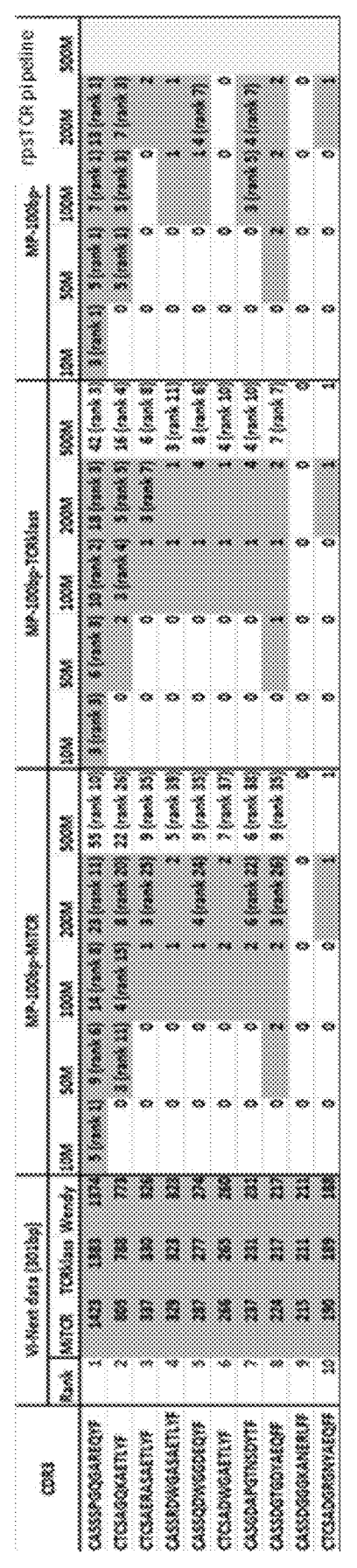

FIG. 31 shows the top CDR3s found in full VI-Next dataset using 100 bp priming reads.

FIG. 32 shows detection of CDR3 in both single cell sequencing and bulk RNA sequencing.

DETAILED DESCRIPTION

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

It has been observed in accordance with the disclosure that single or combination therapy with immune checkpoint inhibitors has shown significant therapeutic efficacy in cancer patients. However, the majority of patients either do not respond or only respond transiently, raising fundamental questions about the design of the next generation of immunotherapies. To overcome the immunosuppressive nature of the tumor microenvironment and promote durable responses, dual targeting of coinhibitory and costimulatory pathways inducing a stronger T cell activation, can be performed. In some scenarios, a combination of antibodies might synergistically enhance CD8$^+$ T cell effector function, for example by restoring a balance of homeostatic regulators, resulting in tumor rejection and long-term responses. Accurate measurement of clonal expansion as a result of treatment can provide a signature indicative of a subject's response to single or combination therapy. In one aspect, disclosed herein are methods and systems that can generate one or more TCR sequences from short reads obtained from sequencing one or more T cells of a subject. The methods and systems can determine clonal expansion based on the generation of the one or more TCR sequences to provide a signature indicative of subject response and/or potential response.

Disclosed are components that can be used to perform the disclosed methods and systems, also referred to as the "rpsTCR" pipeline. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Note that in various instances this detailed disclosure may refer to a given entity performing some action. It should be understood that this language may in some cases mean that a system (e.g., a computer) owned and/or controlled by the given entity is actually performing the action.

Figure 1:
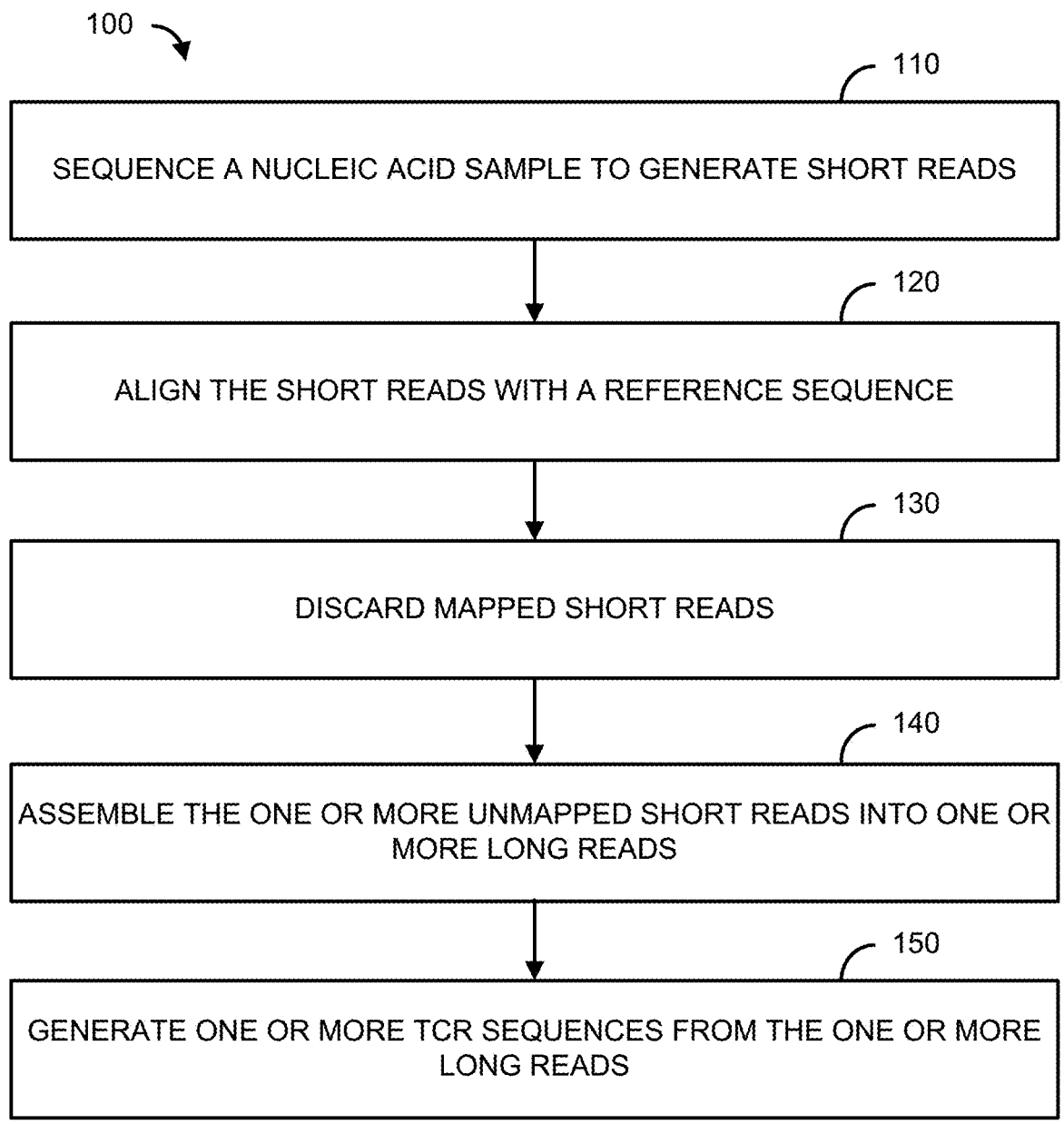
FIG. 1 is a flowchart illustrating a method of random sequencing short repeats and negative selection of unmapped reads to identify TCR CDR3 sequences.

In an aspect, illustrated in FIG. 1, disclosed is an rpsTCR method 100 for sequencing a T cell receptor (TCR). The steps of the method 100 can be performed in any order or simultaneously. The method 100 can comprise sequencing a nucleic acid sample to generate sequence data and/or receiving sequence data at 110. Sequencing the nucleic acid sample can comprise sequencing short reads of less than about 100 base pairs of RNA obtained from a T cell of a subject (e.g., single-end 75 base pair reads). The T cell can be obtained from a human or mouse. The T cell can be acquired and/or sequenced prior to, or after, administration of one or more treatments to the subject. The short reads can be obtained from random-priming of RNA. The random primers can be 4-40 nucleotides in length. In some instances, the random primers can be 4, 5, 6, 7, 8, 9, 10, 11, 12, 13, 14, 15, 16, 17, 18, 19 or 20 nucleotides in length. Sequencing the nucleic acid sample can generate sequence data that can be stored in a data structure. The data structure can comprise one or more nucleic acid sequences and/or a sample identifier.

In some embodiments, the sequence data can be obtained or received through any method. For example, the sequence data can be obtained directly, by performing a sequencing process on a sample. Alternatively, or additionally, the sequence data can be obtained indirectly, for example, from a third party, a database and/or a publication. In some embodiments, the sequence data are received at a computer system, for example, from a data storage device or from a separate computer system.

In some embodiments, the sequence data can comprise bulk sequence data. The term "bulk sequencing" or "next generation sequencing" or "massively parallel sequencing" refers to any high throughput sequencing technology that parallelizes the DNA and/or RNA sequencing process. For example, bulk sequencing methods are typically capable of producing more than one million polynucleic acid amplicons in a single assay. The terms "bulk sequencing," "massively parallel sequencing," and "next generation sequencing" refer only to general methods, not necessarily to the acquisition of greater than 1 million sequence tags in a single run. Any bulk sequencing method can be implemented in the disclosed methods and systems, such as reversible terminator chemistry (e.g., Illumina), pyrosequencing using polony emulsion droplets (e.g., Roche), ion semiconductor sequencing (IonTorrent), single molecule sequencing (e.g., Pacific Biosciences), massively parallel signature sequencing, etc.

In some embodiments, the sequence data can comprise a plurality of sequencing reads. In some embodiments, the sequencing reads have an average read length of no more than 35, 36, 37, 38, 39, 40, 45, 50, 55, 60, 65, 70, 75, 80, 85, 90, 95, 100, 125, 150, 175, 200, 250, 300, 400, 500, 600, 700, 800, 900 or 1000 nucleotides. In some embodiments, the sequencing reads have an average read length of at least 30, 31, 32, 33, 34, 35, 36, 37, 38, 39, 40, 45, 50, 55, 60, 65, 70, 75, 80, 85, 90, 95, 100, 125, 150, 175, 200 or 250 nucleotides. In some embodiments the coverage of the sequencing reads is no more than 100×, 90×, 80×, 70×, 60×, 50×, 40×, 30× or 20×. In some embodiments the coverage of the sequencing reads is at least 50×, 45×, 40×, 35×, 30×, 25×, 20×, 19×, 18×, 17×, 16×, 15×, 14×, 13×, 12×, 11× or 10×.

In some embodiments, the sequence data can be produced by any sequencing method known in the art. For example, in some embodiments the sequencing data are produced using chain termination sequencing, sequencing by ligation, sequencing by synthesis, pyrosequencing, ion semiconductor sequencing, single-molecule real-time sequencing, tag-based sequencing, dilute-'n'-go sequencing, and/or 454 sequencing.

In some embodiments, the sequence data are the result of a process whereby a nucleic acid amplification process is performed to amplify at least part of one or more genomic locus or transcript, followed by the sequencing of the resulting amplification product. Examples of nucleic acid amplification processes useful in the performance of methods disclosed herein include, but are not limited to, polymerase chain reaction (PCR), LATE-PCR, ligase chain reaction (LCR), strand displacement amplification (SDA), transcription mediated amplification (TMA), self-sustained sequence replication (3SR), Qβ replicase based amplification, nucleic acid sequence-based amplification (NASBA), repair chain reaction (RCR), boomerang DNA amplification (BDA) and/or rolling circle amplification (RCA).

In some embodiments, the method includes the step of performing a sequencing process on a sample. Any sample can be used, so long as the sample contains DNA and/or RNA capable of encoding a TCR. In some embodiments, the sample is from a perspective organ, cell or tissue donor. In some embodiments, the sample is from a perspective organ, cell or tissue recipient. The source of the sample may be, for example, solid tissue, as from a fresh, frozen and/or preserved organ, tissue sample, biopsy, or aspirate; blood or any blood constituents, serum, blood; bodily fluids such as cerebral spinal fluid, amniotic fluid, peritoneal fluid or interstitial fluid, urine, saliva, stool, tears; or cells from any time in gestation or development of the subject.

The method 100 can comprise aligning the short reads with a reference sequence at 120. The reference sequence can comprise a reference dataset of species-specific RNA sequences. The reference dataset can be stored in a data structure. The data structure can comprise one or more nucleic acid sequences and/or a identifiers. The reference sequence does not contain a TCR gene sequence (e.g., excludes reference sequences that correspond to gene loci of an adaptive immune cell receptor). The alignment thereby generates a read set comprised of mapped short reads and unmapped short reads. In an aspect, aligning the short reads with a reference sequence can comprise one or more techniques described in Trapnell C., et al. TopHat: discovering splice junctions with RNA-Seq, Bioinformatics (2009) 25 (9):1105-1111. Mapped short reads can be discarded at 130. A resulting data structure can be generated that comprises the unmapped short reads. The remaining steps of the method can be performed on the unmapped short reads which are normally discarded and not subjected to further analysis in the TCR context. Such filtering out of mapped short reads represents a departure from state of the art TCR analysis and results in downstream improvements in both accuracy and precision.

The method 100 can further comprise performing a quality control process on the one or more unmapped short reads. Performing the quality control process on the one or more unmapped short reads can comprise one or more of removing low quality nucleotides or removing very short reads. Removing very short reads can comprise removing any read less than 35 base pairs long.

In an aspect, the method 100 can assemble the one or more unmapped short reads into one or more long reads for further processing at 140. In an aspect, assembling the one or more unmapped short reads into one or more long reads for further processing can comprise aligning the one or more unmapped short reads to one or more TCR sequences from a reference database of TCR sequences and assembling the one or more unmapped short reads into long reads (candidate TCR sequences) based on the reference database of TCR sequences. In another aspect, assembling the one or more unmapped short reads into one or more long reads for further processing can comprise assembling the one or more unmapped reads into long reads (candidate TCR sequences) without the use of a reference database of TCR sequences.

In an aspect, assembling the one or more unmapped short reads into one or more long reads for further processing can comprise one or more techniques disclosed in Warren, R. L., B. H. Nelson, and R. A. Holt. 2009. Profiling model T-cell metagenomes with short reads. Bioinformatics 25: 458-464, incorporated herein by reference in its entirety (the iSSAKE platform). In an aspect, assembling the one or more unmapped short reads into one or more long reads for further processing can comprise aligning the one or more unmapped short reads against known, curated V genes of a desired adaptive immune cell receptor. The one or more unmapped short reads with best forward or reverse-complement alignment to 3' end of the V genes with unmatched nucleotides 3' of the V alignment can be labeled as seeds for de novo assembly. The one or more unmapped short reads fully aligning to receptor V genes or constant regions or possible junctions between J genes and constant regions can be discarded from future assembly.

Each seed sequence can be used to nucleate an assembly. For example, a subsequence length (k) can begin at the longest unassembled read length. Then the 3'-most subsequence of length k can be generated (k-mer). If the k-mer matches the 5' end bases of one or more forward or reverse-complement read(s) r, the matching read(s) r can be used to extend the assembly (if overhanging extension nucleotides do not agree across r, a majority rule can be used to build a consensus assembly sequence(s)). If there is no match and k is greater than the minimum subsequence length specified by the user, the matching can be repeated with a new k shorter by one base. If there is no match and k equals a minimum subsequence length specified by a user, assembly is complete. Assembly is complete when all seed sequences and resulting assembly sequences reach maximal extension (e.g., user defined). The steps above can be repeated with new assembly sequences. The result is a read set comprising one or more long reads.

In another aspect, an alternative approach for assembling the one or more unmapped short reads into one or more long reads for further processing can comprise one or more techniques disclosed in Grabherr M G, Haas B J, Yassour M, Levin J Z, Thompson D A, Amit I, et al. Full-length transcriptome assembly from RNA-Seq data without a reference genome. Nature biotechnology. 2011; 29(7):644-52, incorporated herein by reference in its entirety (the Trinity platform). Assembling the one or more unmapped short reads into one or more long reads for further processing can comprise a multi-step approach. The first step can comprise assembling the one or more unmapped short reads into unique sequences of transcripts using a greedy k-mer-based approach for transcript assembly, recovering a single (best) representative for a set of alternative variants that share k-mers (owing to alternative splicing, gene duplication or allelic variation). The k-mer-based approach can comprise constructing a dictionary of k-mer forward and reverse-complement subsequences from all candidate TCR sequences (by way of example, k=25). The most frequent k-mer in the dictionary can be selected to seed a contig assembly, excluding k-mers with low complexity or only observed once. The seed can be extended in either direction by finding the highest occurring k-mer with a k−1 overlap with the current assembly and concatenating its overhanging nucleotide to the growing assembly sequence. Once a k-mer has been used for extension, it can be removed from the dictionary. Seed extension can be repeated until the assembly cannot be further extended. Selection of most frequent k-mer and seed extension can be repeated with the next most frequent k-mer until the dictionary is exhausted.

The second step of the multi-step approach can comprise clustering related contigs that correspond to portions of alternatively spliced transcripts or otherwise unique portions of paralogous genes. A de Bruijn graph can then be constructed for each cluster of related contigs, each graph reflecting the complexity of overlaps between variants. Contigs can be clustered if there is an overlap of k−1 nucleotides between contigs and if there is a minimal number of reads that span the junction across both contigs with a (k−1)/2 nucleotide match on each side of the (k−1)-mer junction. Grouping can be repeated until no further contigs can be added to any group. A de Bruijn graph can be constructed for each group using a word size of k−1 to represent nodes and k to define the edges connecting the nodes. Each edge of the de Bruijn graph can comprise the number of k-mers in the original read set that support it. Each read can be assigned to the group with which it shares the largest number of k-mers and the regions within each read that contribute k-mers to the group can be determined.

The third step of the multi-step approach can comprise analyzing the paths taken by reads and read pairings in the context of the corresponding de Bruijn graph and outputting plausible transcript sequences, resolving alternatively spliced isoforms and transcripts derived from paralogous genes. Subsequent iteration between merging nodes and pruning edges can be implemented to identify paths that are supported by reads or read pairs and return these paths as long reads (candidate TCR sequences). Merging nodes can comprise merging consecutive nodes in linear paths in the de Bruijn graph to form nodes that represent longer sequences. Pruning edges can comprise pruning edges that represent minor deviations supported by comparatively few reads that likely correspond to sequencing errors. The third step can further comprise performing plausible path scoring, by identifying those paths in the de Bruijn graph that are supported by actual reads and read pairs, using a dynamic programming procedure that traverses potential paths in the graph while maintaining the reads (and pairs) that support them. Because reads and sequence fragments (paired reads) are typically much longer than k, they can resolve ambiguities and reduce the combinatorial number of paths to a much smaller number of actual transcripts, enumerated as linear sequences. The result is a read set comprising one or more long reads.

TCR sequence assembly can be carried out using one of several platforms such as, but not limited to, the iSSAKE platform and the Trinity platform. Table 1 shows that the Trinity platform and the iSSAKE platform were effectively equivalent for single cell sequencing as a component of the disclosed methods and systems, but the iSSAKE platform was superior at bulk sequencing. The iSSAKE platform utilizes seed sequences for TCRs which can improves performance of the rpsTCR pipeline with bulk assembly.

TABLE 1

| CDR3 | Single cells detected by ISSAKE | Single cells detected by Trinity | Counts in bulk by iSSAKE | Found in bulk by Trinity |
|---|---|---|---|---|
| CASSPTGYNSPLYF (SEQ ID NO: 293) | 4 | 4 | 116 | 1 |
| CASSQVQGSAETLYF (SEQ ID NO: 294) | 5 | 5 | 80 | 0 |
| CASSGTGGNQDTQYF (SEQ ID NO: 295) | 1 | 1 | 0 | 0 |
| CASGDAGTGNYAEQFF (SEQ ID NO: 296) | 1 | 1 | 19 | 1 |
| CASSLRTGYNSPLYF (SEQ ID NO: 297) | 3 | 3 | 41 | 1 |
| CASRLGGDQNTLYF (SEQ ID NO: 298) | 3 | 3 | 49 | 1 |
| CASKTGGYEQYF (SEQ ID NO: 299) | 1 | 1 | 37 | 0 |
| CASSEGDTLYF (SEQ ID NO: 300) | 1 | 1 | 13 | 0 |
| CASSPGTFNQDTQYF (SEQ ID NO: 301) | 3 | 3 | 16 | 0 |
| CASASWTGDEQYF (SEQ ID NO: 302) | 1 | 1 | 0 | 0 |
| CASSLPGSQNTLYF (SEQ ID NO: 303) | 1 | 1 | 0 | 0 |
| CASSRDWAQDTQYF (SEQ ID NO: 304) | 2 | 2 | 58 | 0 |
| CASSDNWGAGEQYF (SEQ ID NO: 305) | 1 | 1 | 1 | 1 |
| CASSSGTASDTQYF (SEQ ID NO: 306) | 1 | 1 | 0 | 0 |
| CASSQTRDWGYEQYF (SEQ ID NO: 307) | 1 | 1 | 33 | 0 |
| CTCSGGLGGLEQYF (SEQ ID NO: 308) | 1 | 1 | 5 | 1 |
| CASSLGTGGIEQYF (SEQ ID NO: 309) | 1 | 1 | 3 | 1 |
| CASSLSDSNQDTQYF (SEQ ID NO: 310) | 1 | 1 | 0 | 0 |
| CASSERGGRDTQYF (SEQ ID NO: 311) | 1 | 1 | 0 | 0 |
| CTCSAVREGNSPLYF (SEQ ID NO: 312) | 1 | 1 | 3 | 1 |
| CASSLTGVSNERLFF (SEQ ID NO: 313) | 1 | 1 | 0 | 0 |
| CASSRQLNSDYTF (SEQ ID NO: 314) | 2 | 2 | 39 | 1 |
| CASSLRQGSNTEVFF (SEQ ID NO: 315) | 1 | 1 | 15 | 1 |
| CASSQNRDISAETLYF (SEQ ID NO: 316) | 1 | 1 | 53 | 0 |
| CASSWTANTEVFF (SEQ ID NO: 317) | 1 | 1 | 0 | 0 |
| CASSLRDWGQDTQYF (SEQ ID NO: 318) | 1 | 1 | 22 | 0 |
| CASSHWGGTTGQLYF (SEQ ID NO: 319) | 1 | 1 | 0 | 0 |
| CASSYSKGSAETLYF (SEQ ID NO: 320) | 1 | 1 | 0 | 0 |
| CAVSMINYNVLYF (SEQ ID NO: 321) | 1 | 1 | 0 | 0 |
| CASSDGQNTLYF (SEQ ID NO: 322) | 1 | 0 | 4 | 1 |

TABLE 1-continued

| CDR3 | Single cells detected by iSSAKE | Single cells detected by Trinity | Counts in bulk by iSSAKE | Found in bulk by Trinity |
|---|---|---|---|---|
| CASSQEGPGQLYF (SEQ ID NO: 323) | 1 | 1 | 15 | 1 |
| CASTGQGYNSPLYF (SEQ ID NO: 324) | 1 | 0 | 0 | 0 |

The method 100 can generate one or more TCR sequences from the one or more long reads at 150. In an aspect, generating one or more TCR sequences from the one or more long reads can comprise one or more techniques disclosed in Yang, X. et al. TCRklass: a new K-string-based algorithm for human and mouse TCR repertoire characterization, J. Immunol. 194, 446-454 (2015), incorporated herein by reference in its entirety. Generating one or more TCR sequences from the one or more long reads can comprise translating each of the one or more long reads on all six frames, comparing each translation frame to a 3-string profile of a reference variable (V) and joining (J) amino acid sequence, identifying the translation frame with a highest number of matched k-strings, determining a position of a conserved residue in the long read by determining a conserved residue support score ($S_{cr}$) for each residue in the long read from the translation frame with a highest number of matched k-strings, identifying candidate conserved residues with a highest $S_{cr}$ in V and J gene segments of the long read from the translation frame, and identifying a CDR3 region located between two conserved residues in the V and J gene segments as a TCR sequence. In an aspect, the method 100 can further comprise appending a TCR C region nucleic acid sequence to the TCR sequence.

In another aspect, generating one or more TCR sequences from the one or more long reads can comprise translating the one or more long reads into corresponding amino acid sequences. TCR V region and TCR J region amino acid reference sequences can be fractioned into k-strings of about six amino acids. The k-strings can be aligned with the corresponding amino acid sequences. One or more conserved TCR CDR3 residues can be detected in the k-strings that map to the corresponding amino acid sequences. A detected level of conservation can be scored and corresponding amino acid sequences with a conservation score above a threshold conservation score can be selected. A candidate CDR3 region amino acid sequence can then be detected in the selected corresponding amino acid sequences.

The nucleic acid sequence of the candidate CDR3 region amino acid sequences in the one or more long reads can be identified. The nucleic acid sequence of the one or more long reads upstream of the candidate CDR3 region nucleic acid sequence can be aligned with one or more TCR V gene reference sequences. A degree of alignment can be scored and long reads above a threshold alignment score can be identified as comprising a candidate TCR V gene sequence.

The nucleic acid sequence of the one or more long reads downstream of the candidate CDR3 region nucleic acid sequence can be aligned with one or more TCR J gene reference sequences. A degree of alignment can be scored and long reads above a threshold alignment score can be identified as comprising a candidate TCR J gene sequence, thereby generating a TCR sequence. In an aspect, the method 100 can further comprise appending a TCR C region nucleic acid sequence to the TCR sequence.

The method 100 can further comprise comparing the one or more TCR sequences to a TCR sequence library of known TCR sequences and corresponding treatment responses to one or more treatments, identifying which of the one or more TCR sequences have a match in the TCR sequence library with a high corresponding treatment response, and identifying the one or more treatments to which the subject having the one or more TCR sequences is likely to respond. Once the subject has been identified as having a TCR sequence that is likely to respond to a specific treatment, the subject can be administered the specific treatment.

The method 100 can further comprise performing the method 100 prior to, and after, administration of a treatment of a subject for a disease to assess clonal expansion. For example, a first plurality of cells of a subject can be collected prior to administration of a treatment. The first plurality of T cells can be sequenced and the method 100 can be performed. A number of occurrences of unique TCR sequences present can be determined. The treatment can be administered to the subject and a second plurality of T cells of the subject can be collected. The second plurality of T cells can be sequenced and the method 100 can be performed. A number of occurrences of unique TCR sequences present can be determined. The numbers of occurrences between the first plurality of T cells and the second plurality of T cells can then be determined. In some instances, a specific TCR sequence can be determined to have experienced clonal expansion. In other instances, some, all, or none of the TCR sequences that experienced clonal expansion between the first plurality of T cells and the second plurality of T cells are the same TCR sequence. A result is a T cell clonal expansion signature. The T cell clonal expansion signature can comprise one or more of, a number of T cells that experienced clonal expansion, an identifier of T cells that experienced clonal expansion, an overall quantity of clonal expansion, a quantity of clonal expansion per T cell, combinations thereof, and the like. The subject's response to treatment can be recorded and associated with the cell clonal expansion signature. The process can be repeated for a plurality of subjects, thereby generating a database of T cell clonal expansion signatures and corresponding treatment responses. The disclosed methods and systems can subsequently compare a T cell clonal expansion signature of a new subject to the database to ascertain a likely response to treatment(s) for the subject.

In some aspects of the method 100, the subject can be administered an immunotherapy prior to the collection of T cells for sequencing. The immunotherapy can be a monotherapy or a combination therapy. For example, the immunotherapy can be the combination of a costimulatory agonist and a coinhibitory antagonist. In some aspects, T cell inhibitory receptors or receptors on a tumor cell, including, but not limited to, PD1, PDL1, CTLA4, LAG3 and TIM3, can be targeted during the immunotherapy. Thus, in some aspects, the immunotherapy can comprise an antibody or antigen-binding fragment thereof that specifically binds to one or more of PD1, PDL1, CTLA4, LAG3, and TIM3. As part of an immunotherapy regimen, the subject may be administered an antibody or antigen-binding fragment thereof that specifically binds to one or more of PD1, PDL1, CTLA4, LAG3, and TIM3, or may be administered any combination of two or more such antibodies or antigen-binding fragments thereof.

In some aspects, the immunotherapy comprises administering to the patient an antibody or antigen-binding fragment thereof that binds to PD1. In some preferred embodiments, the antibody or antigen-binding fragment thereof that binds to PD1 comprises at least the heavy chain variable region (HCVR) sequence of SEQ ID NO:21 and the light chain variable region (LCVR) sequence of SEQ ID NO:22. In aspects, any of the antibodies or antigen-binding fragments thereof that bind PD1 can be any of the antibodies or antigen-binding fragments thereof described in U.S. application Ser. No. 14/603,776 (Publication No. US 2015-0203579), which is hereby incorporated by reference herein. For example, in some embodiments, the antibody or antigen-binding fragment thereof that binds to PD1 comprises a HCVR having an amino acid sequence from among the sequences listed in Table 2 and a LCVR. In some embodiments, the antibody or antigen-binding fragment thereof that binds to PD1 comprises a LCVR having an amino acid sequence from among the sequences listed in Table 2 and an HCVR. In some embodiments, the antibody or antigen-binding fragment thereof that binds to PD1 comprises an HCVR and LCVR pair as shown in Table 2. Other antibodies that bind to PD1 can be used (or antigen-binding fragments thereof), and these include but are not limited to pembrolizumab, nivolumab, durvalumab, atezolizumab, pidilizumab, camrelizumab, PDR001, MED10680, JNJ-63723283, and MCLA-134.

TABLE 2

Amino Acid Sequence Identifiers for PD1 antibodies

| HCVR SEQ ID NO: | LCVR SEQ ID NO: |
|---|---|
| 1 | 2 |
| 3 | 4 |
| 5 | 6 |
| 7 | 8 |
| 9 | 10 |
| 11 | 12 |
| 13 | 14 |
| 15 | 16 |
| 17 | 18 |
| 19 | 20 |
| 21 | 22 |
| 23 | 24 |
| 25 | 26 |
| 27 | 26 |
| 28 | 26 |
| 29 | 26 |
| 30 | 26 |
| 31 | 26 |
| 32 | 26 |
| 33 | 26 |
| 34 | 26 |
| 35 | 26 |
| 36 | 26 |
| 37 | 26 |
| 38 | 24 |
| 39 | 24 |
| 40 | 24 |

In some aspects, the immunotherapy comprises administering to the patient an antibody or antigen-binding fragment thereof that binds to the LAG3 protein (aka CD223). In some aspects, the antibody or antigen-binding fragment thereof that binds to LAG3 comprises at least the HCVR sequence of SEQ ID NO:93 and the LCVR sequence of SEQ ID NO:94. In some aspects, the antibodies or antigen-binding fragments thereof that bind LAG3 can be any of the antibodies or antigen-binding fragments thereof described in U.S. application Ser. No. 15/289,032 (Publication No. US 2017-0101472), which is hereby incorporated by reference herein. For example, in some aspects, the antibody or antigen-binding fragment thereof that binds to LAG3 comprises a HCVR having an amino acid sequence from among the sequences listed in Table 3 and a LCVR. In some aspects, the antibody or antigen-binding fragment thereof that binds to LAG3 comprises a LCVR having an amino acid sequence from among the sequences listed in Table 3 and an HCVR. In some embodiments, the antibody or antigen-binding fragment thereof that binds to LAG3 comprises an HCVR and LCVR pair as shown in Table 3. Other antibodies that bind to LAG3 can be used (or antigen-binding fragments thereof), and these include but are not limited to BMS-986016 and GSK2381781.

TABLE 3

Amino Acid Sequence Identifiers for LAG3 antibodies

| HCVR SEQ ID NO: | LCVR SEQ ID NO: |
|---|---|
| 41 | 42 |
| 43 | 44 |
| 45 | 46 |
| 47 | 48 |
| 49 | 50 |
| 51 | 52 |
| 53 | 54 |
| 55 | 56 |
| 57 | 58 |
| 59 | 60 |
| 61 | 62 |
| 63 | 64 |
| 65 | 66 |
| 67 | 68 |
| 69 | 70 |
| 71 | 72 |
| 73 | 74 |
| 75 | 76 |
| 77 | 78 |
| 79 | 80 |
| 81 | 82 |
| 83 | 84 |
| 85 | 86 |
| 87 | 88 |
| 89 | 90 |
| 91 | 92 |
| 93 | 94 |
| 95 | 96 |
| 97 | 98 |
| 99 | 98 |
| 100 | 98 |
| 101 | 98 |
| 102 | 98 |
| 103 | 98 |
| 104 | 105 |
| 106 | 105 |
| 107 | 105 |
| 108 | 109 |
| 110 | 111 |

In some aspects, the immunotherapy comprises administering to the patient an antibody or antigen-binding fragment thereof that binds to PDL1. In some preferred aspects, the antibody or antigen-binding fragment thereof that binds to PDL1 comprises at least the HCVR sequence of SEQ ID NO:122 and the LCVR sequence of SEQ ID NO:123. In some aspects, the antibodies or antigen-binding fragments thereof that bind PDL1 can be any of the antibodies or antigen-binding fragments thereof described in U.S. application Ser. No. 14/603,808 (Publication No. US 2015-0203580), which is hereby incorporated by reference herein. For example, in some aspects, the antibody or antigen-binding fragment thereof that binds to PDL1 comprises a HCVR having an amino acid sequence from among the sequences listed in Table 4 and a LCVR. In some aspects, the antibody or antigen-binding fragment thereof that binds to PDL1 comprises a LCVR having an amino acid sequence from among the sequences listed in Table 4 and an HCVR. In some aspects, the antibody or antigen-binding fragment thereof that binds to PDL1 comprises an HCVR and LCVR pair as shown in Table 4. Other antibodies that bind to PDL1 can be used (or antigen-binding fragments thereof), and these include but are not limited to, one or more of avelumab, atezolizumab, and durvalumab.

TABLE 4

Amino Acid Sequence Identifiers for PDL1 antibodies

| HCVR SEQ ID NO: | LCVR SEQ ID NO: |
|---|---|
| 112 | 113 |
| 114 | 115 |
| 116 | 117 |
| 118 | 119 |
| 120 | 121 |
| 122 | 123 |
| 124 | 125 |
| 126 | 127 |
| 128 | 129 |
| 130 | 131 |
| 132 | 133 |
| 134 | 133 |
| 135 | 136 |
| 137 | 138 |
| 139 | 140 |
| 141 | 142 |
| 143 | 144 |
| 145 | 146 |
| 147 | 146 |
| 148 | 146 |
| 149 | 146 |
| 150 | 146 |
| 151 | 146 |
| 152 | 146 |
| 153 | 146 |
| 154 | 146 |

In some aspects, the immunotherapy comprises administering to the patient an antibody or antigen-binding fragment thereof that binds to CTLA4. In some aspects, the antibodies or antigen-binding fragments thereof that bind CTLA4 can be any of the antibodies or antigen-binding fragments thereof described in U.S. Provisional Application No. 62/537,753, filed on Jul. 27, 2017, which is hereby incorporated by reference herein. For example, in some aspects, the antibody or antigen-binding fragment thereof that binds to CTLA4 comprises a HCVR having an amino acid sequence from among the sequences listed in Table 5 and a LCVR. In some aspects, the antibody or antigen-binding fragment thereof that binds to CTLA4 comprises a LCVR having an amino acid sequence from among the sequences listed in Table 5 and an HCVR. In some aspects, the antibody or antigen-binding fragment thereof that binds to CTLA4 comprises an HCVR and LCVR pair as shown in Table 5. Other antibodies that bind to CTLA4 can be used (or antigen-binding fragments thereof), and these include but are not limited to, one or more of ipilimumab and tremelimumab, as well as any of the antibodies or antigen-binding fragments thereof disclosed in U.S. Pat. Nos. 6,984,720; 7,605,238; or 7,034,121, all of which are hereby incorporated by reference herein.

TABLE 5

Amino Acid Sequence Identifiers for CTLA4 antibodies

| HCVR | LCVR |
|---|---|
| 155 | 156 |
| 157 | 158 |
| 159 | 160 |
| 161 | 162 |
| 163 | 164 |
| 165 | 166 |
| 167 | 168 |
| 169 | 170 |
| 171 | 172 |
| 173 | 174 |
| 175 | 176 |
| 177 | 178 |
| 179 | 180 |
| 181 | 182 |
| 183 | 184 |
| 185 | 186 |
| 187 | 188 |
| 189 | 190 |
| 191 | 192 |
| 193 | 192 |
| 195 | 194 |
| 197 | 196 |
| 199 | 198 |
| 201 | 200 |
| 203 | 202 |
| 205 | 204 |
| 207 | 206 |
| 209 | 208 |
| 211 | 210 |
| 213 | 212 |
| 215 | 214 |
| 217 | 216 |

In some aspects, the immunotherapy comprises administering to the patient an antibody or antigen-binding fragment thereof that binds to GITR. In some preferred embodiments, the antibody or antigen-binding fragment thereof that binds to GITR comprises at least the HCVR sequence of SEQ ID NO:261 and the LCVR sequence of SEQ ID NO:259. In aspects, any of the antibodies or antigen-binding fragments thereof that bind GITR can be any of the antibodies or antigen-binding fragments thereof described in U.S. application Ser. No. 15/619,068, which is hereby incorporated by reference herein. For example, in some aspects, the antibody or antigen-binding fragment thereof that binds to GITR comprises a HCVR having an amino acid sequence from among the sequences listed in Table 6 and a LCVR. In some embodiments, the antibody or antigen-binding fragment thereof that binds to GITR comprises a LCVR having an amino acid sequence from among the sequences listed in Table 6 and an HCVR. In some aspects, the antibody or antigen-binding fragment thereof that binds to GITR comprises an HCVR and LCVR pair as shown in Table 6. Other known antibodies that bind to GITR can be used (or antigen-binding fragments thereof).

TABLE 6

Amino Acid Sequence Identifiers for GITR antibodies

| HCVR | LCVR |
|---|---|
| 218 | 219 |
| 220 | 221 |
| 222 | 223 |
| 224 | 225 |
| 226 | 227 |
| 228 | 229 |
| 230 | 231 |
| 232 | 233 |
| 234 | 235 |
| 236 | 237 |
| 238 | 239 |
| 240 | 241 |
| 242 | 243 |
| 244 | 245 |
| 246 | 247 |
| 248 | 249 |
| 250 | 251 |
| 252 | 253 |
| 254 | 255 |
| 256 | 257 |
| 258 | 259 |
| 260 | 259 |
| 261 | 259 |
| 262 | 259 |
| 263 | 259 |
| 264 | 259 |
| 265 | 259 |
| 266 | 259 |
| 267 | 259 |
| 268 | 259 |

In some aspects, a TCR sequence can be identified as a sequence present in a T cell clone that expands in response to a particular treatment. These identified TCR sequences can be used for T cell therapy. For example, the identified TCR sequence can be used to produce T cells containing this particular TCR sequence. These T cells containing the identified TCR sequence can then be administered to a subject who in turn can then be treated with the particular treatment to which the TCR sequence was determined to respond. In some aspects, the T cell therapy can be administered to the same subject from which the TCR sequence was identified in order to increase the number of T cells responding to the particular treatment. In some aspects, the T cell therapy can be administered to a subject other than the one from which the TCR sequence was identified. Administering the T cell therapy to a subject other than the one from which the TCR sequence was identified gives a subject who otherwise would not necessarily have responded to the particular treatment the ability to respond to the particular treatment.

In some aspects, TCR signaling can be studied in response to particular drugs for those T cells containing the identified TCR sequences. The TCR signaling of those receptors having a specific TCR sequence present in T cells that expand to particular treatments provides insight into tumor immune surveillance.

Another use of the identified TCR sequences can be for determining a target for treating a tumor present in the subject with the identified TCR sequences. The antigen that binds the identified TCR sequence is a target for the tumor present in that subject. Once a target has been identified, treatments can then be determined.

In some aspects, identification of TCR sequences in clonal expansion can be used for prognosis of both viral and bacterial infections and can be used to monitor disease progress of cancer and infectious diseases.

As shown in FIGS. 27-33, the discarding of mapped short reads in step 130 contributes to an improvement in both accuracy and precision as compared to state of the art TCR analysis techniques.

The methods of FIGS. 27-33 use negative control datasets expected to have no TCRs. These samples are all random priming RNA-Seq with reads of length 100 base pairs (bp). Five datasets are from various mouse tumor cell lines (these are shown in Table 7). Two datasets are from spleen samples of mice with Rag1/2 knocked out, which is a gene required for the formation of TCRs. Two datasets are from human cell lines, one of neural progenitor cells (NeuProgCell) and the other of myoblasts (LHCN-M2). The positive control dataset (VI-next-mouse-T cell) is a targeted TCR sequencing of a healthy B6 mouse sample with reads of 300 bp in length. This dataset was manipulated to create simulated testing datasets of various sequencing depths (10 million, 50 million, 100 million, 200 million, or 500 million reads) and read lengths (50 bp or 100 bp).

Another testing dataset is bulk random priming RNA-Seq with read length of 80 bp of sorted T cells from mouse tumor samples. The corresponding positive control datasets consist of single-cell RNA-Seq with read length 75 bp from the C1 Fluidigm platform of the same sorted T cells as the bulk dataset.

The data sets for TCR pipeline benchmarks are shown in Table 7.

TABLE 7

| Classification | File name | Sample type | Sequencing platform | Read length |
|---|---|---|---|---|
| Negative control | M620270 | MC38 colon tumor cell line | Random priming | 100 bp |
| Negative control | M620272 | MC38 colon tumor cell line | Random priming | 100 bp |
| Negative control | M620295 | B16F1 melanoma tumor cell line | Random priming | 100 bp |
| Negative control | M620279 | Colon26 tumor cell line | Random priming | 100 bp |
| Negative control | M620343 | Renca kidney tumor cell line | Random priming | 100 bp |
| Negative control | T-ALL_neg1 | Spleen from Rag½ KO mouse | Random priming | 100 bp |
| Negative control | T-ALL_neg2 | Spleen from Rag½ KO mouse | Random priming | 100 bp |
| Negative control | NeuProgCell | Spleen from Rag½ KO mouse | Random priming | 100 bp |
| Negative control | LHCN-M2 | Human cell line | Random priming | 100 bp |
| Positive control | VI-next-mouse-T cell | Healthy B6 mouse T cells | Targeted PCR (fastq) | 300 bp |
| Positive control | T-ALL | T-All sample | Targeted PCR (fasta) | Merged 2 × 300 bp |
| Positive control | Bulk RNA corresponding C1 data | MC38/41BBL-Puro tumor T cells | Random priming | 75 bp |

TABLE 7-continued

| Classification | File name | Sample type | Sequencing platform | Read length |
|---|---|---|---|---|
| Testing sample | MP100 bp-10M | Healthy B6 mouse T cells | Random priming | 100 bp |
| Testing sample | MP100 bp-50M | Healthy B6 mouse T cells | Random priming | 100 bp |
| Testing sample | MP100 bp-100M | Healthy B6 mouse T cells | Random priming | 100 bp |
| Testing sample | MP100 bp-200M | Healthy B6 mouse T cells | Random priming | 100 bp |
| Testing sample | MP100 bp-500M | Healthy B6 mouse T cells | Random priming | 100 bp |
| Testing sample | MP-50 bp-10M | Healthy B6 mouse T cells | Random priming | 50 bp |
| Testing sample | MP-50 bp-50M | Healthy B6 mouse T cells | Random priming | 50 bp |
| Testing sample | MP-50 bp-100M | Healthy B6 mouse T cells | Random priming | 50 bp |
| Testing sample | MP-50 bp-200M | Healthy B6 mouse T cells | Random priming | 50 bp |
| Testing sample | MP-50 bp-500M | Healthy B6 mouse T cells | Random priming | 50 bp |
| Testing sample | T-ALL | T-ALL | Random priming | 100 bp |
| Testing sample | Bulk RNA | MC38/41BBL-Puro tumor T cells | Random priming | 80 bp |

FIG. 27 shows that the sensitivity of the rpsTCR pipeline is very similar to TCRklass and better than miTCR. Very few, if any, false positives are detected using the rpsTCR pipeline. The rpsTCR pipeline identifies no TCRs in any of the negative control datasets. In comparison, TCRklass identifies very few and MiTCR identifies on average tens of TCRs in each dataset. The rpsTCR pipeline and TCRklass show comparable sensitivity of around 80% in identifying TCR CDR3s in the VI-next-mouse-T cell positive control dataset, whereas MiTCR has lower sensitivity closer to 75%.

FIG. 18 depicts the ability of the rpsTCR pipeline to identify positive data not detected by MiTCR or TCRklass. There is a strong correlation in TCR counts identified in the positive control VI-next dataset amongst all three methods (MiTCR, TCRklass, and the rpsTCR pipeline), with around 10% of total TCRs identified by the rpsTCR pipeline method and TCRklass and not by MiTCR.

FIGS. 28 and 30 shows CDR3 detection comparison between MiTCR, TCRklass, and the rpsTCR pipeline using random miming reads of 50 bp or 100 bp, respectively, of mouse T cells. The sequence of each of the top CDR3s found is listed. FIGS. 29 and 31 shows the top CDR3s found in full VI-next dataset using 50 bp or 100 bp, respectively. The rpsTCR pipeline shows a higher sensitivity.

FIGS. 28 and 29 outline the comparison of CDR3s found in the simulated 50 base pair (bp) read length datasets formed by subsampling the VI-next positive control dataset. Unlike MiTCR and TCRklass, the rpsTCR pipeline implements an assembly of the short 50 bp reads into longer contigs to better identify TCR sequences. The top CDR3s found by MiTCR in the dataset of 500 million reads (MP-50 bp-500M) were not found by any method in the positive control dataset or in MP-50 bp-500M by TCRklass or the rpsTCR pipeline (FIG. 28, left table). The top CDR3s found by TCRklass in MP-50 bp-500M were found by the other methods in both the test dataset and the VI-next dataset (FIG. 28, middle table). The top CDR3s identified by the rpsTCR pipeline were identified in larger numbers by all methods in the VI-next dataset and partially by the other two methods in the MP-50 bp-500M dataset (FIG. 28, right table). The top CDR3s found in the VI-next dataset were found most often by the rpsTCR pipeline in subsampled MP to 10-500 million reads of 50 bp in length (FIG. 29).

FIGS. 30 and 31 outline the comparison of CDR3s found in the simulated 100 bp datasets formed by subsampling 200 million reads from the VI-next positive control dataset to compare the rpsTCR pipeline method without the assembly step to MiTCR and TCRklass. Again, the top CDR3s found by MiTCR in the 500 million reads of length 100 bp (MP-100 bp-500M) were not found by any other method (FIG. 30, left table). The top two CDR3s found by TCRklass appear to be false positives that were not found by any of the other methods (FIG. 30, middle table), but the others correspond well to the top CDR3s found by the rpsTCR pipeline (FIG. 30, right table). All methods have comparable sensitivity at this read length in identifying the top CDR3s from the VI-next dataset (FIG. 31).

FIG. 32 shows that more than half of the CDR3s detected in single cell sequencing also can be detected in bulk RNA sequencing. The final comparison of the three methods involves quantifying how many of the TCRs found in single-cell data can be found in bulk RNA-Sect data from the same sample. The top CDR3s identified in single-cell data are mostly identified by all three methods and are identified in the bulk dataset consistently across all methods (FIG. 32).

The rpsTCR pipeline method is comparable to pre-existing methods in datasets with read length of 100 bp when sequence assembly is unnecessary. However, in short read datasets where the rpsTCR pipeline implements sequence assembly, sensitivity is greatly improved relative to other methods.

Figure 2:
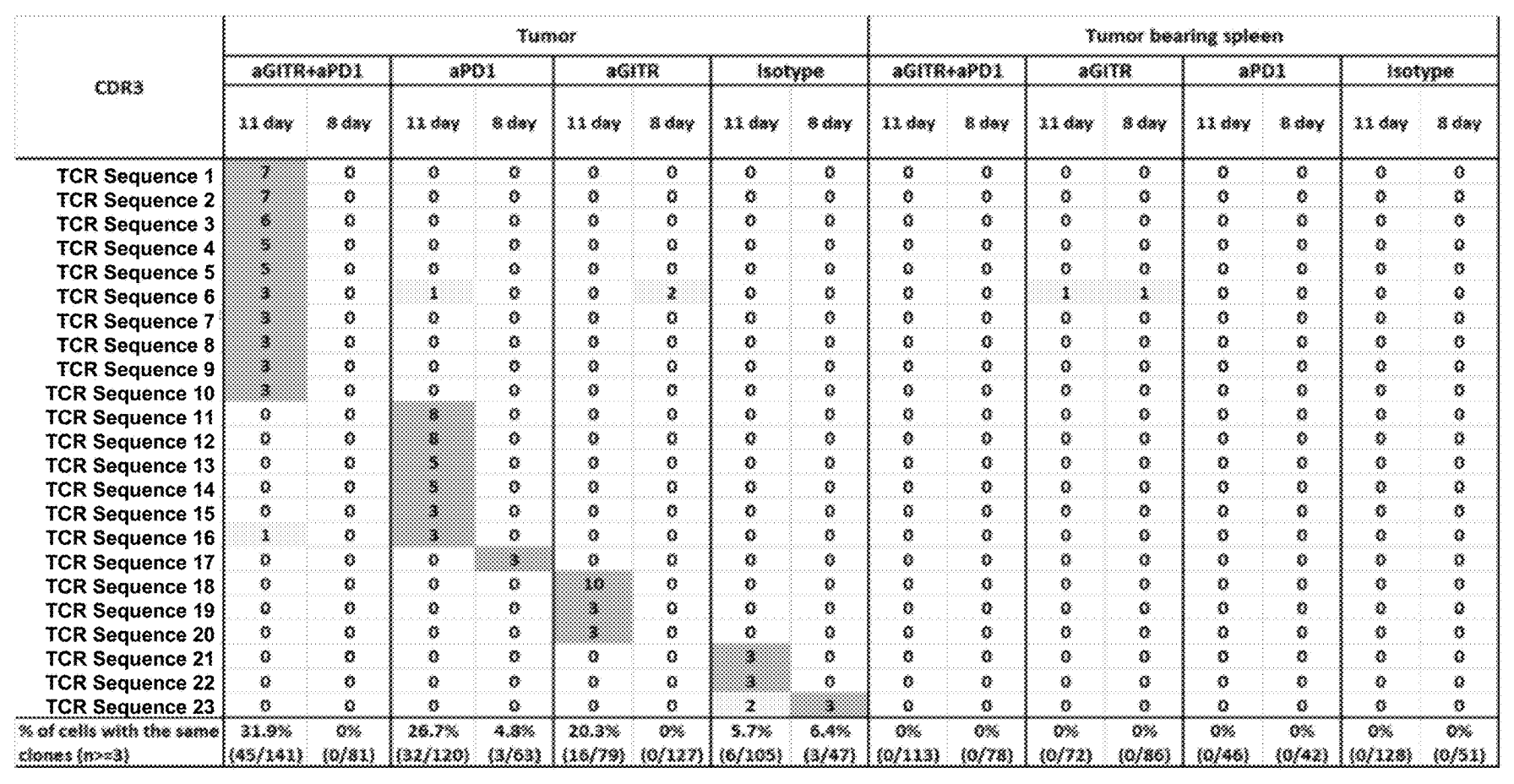

FIG. 2 depicts the CDR3 sequences determined from isolated T cells from a tumor of a tumor-implanted mouse or mouse spleen (from the same tumor-bearing mouse) (Example 1). Identical CDR3 sequences detected from 3 or more single T cells were determined to be clonally expanded T cells. The combination treated group (aGITR+aPD-1) had tumors displaying a diverse fraction of clonally expanded T cells by day 11 post treatment (as indicated by the number of different TCR sequences from T cells having 3 or more clones). In this example, the total number of T cell clones that expanded, not the number of a specific TCR sequence, is used to determine clonal expansion after treatment. In some aspects, clonal expansion is determined by the TCR being identical at the amino acid level but the nucleic acid sequence could comprise variations. T cells isolated from spleen had not clonally expanded. Of note are same TCR CDR3 sequences detected in some PD-1 treated mice, yet those were not considered clonally expanded (<3 detected).

FIG. 2 illustrates an example TCR sequence library of known TCR sequences and corresponding treatment responses to one or more treatments. As shown in FIG. 2, TCR Sequence 1 through TCR Sequence 10 have clonal expansion values of 3 or more in response to treatment by a combination of aGITR and aPD1. A clonal expansion value represents a number of occurrences of a specific TCR sequence among multiple cells, indicating the number of times a cell has been cloned. TCR Sequence 11 through TCR Sequence 17 have clonal expansion values of 3 or more in response to treatment by aPD1 alone. TCR Sequence 18 through TCR Sequence 20 have clonal expansion values of 3 or more in response to treatment by aGITR alone. For a subject whose cell sequence data has been obtained and TCR sequences identified, the identified TCR sequences can be compared to a TCR library as shown in FIG. 2 and matches determined. In an aspect, the number of matches can be indicative of potential response to a particular treatment. In another aspect, a summation of the clonal expansion values associated for matches on a per treatment basis can be used to determine which treatment is associated with a higher cumulative clonal expansion value for a subject. By way of example, patient sequence data having TCR Sequence 1, TCR Sequence 2, TCR Sequence 13, TCR Sequence 14, TCR Sequence 15, and TCR Sequence 16 would have a cumulative clonal expansion value of 14 for aGITR and aPD1 in combination and a cumulative clonal expansion value of 16 for aPD1 alone. Thus, the subject is more likely to respond to aPD1 alone.

Figure 3:
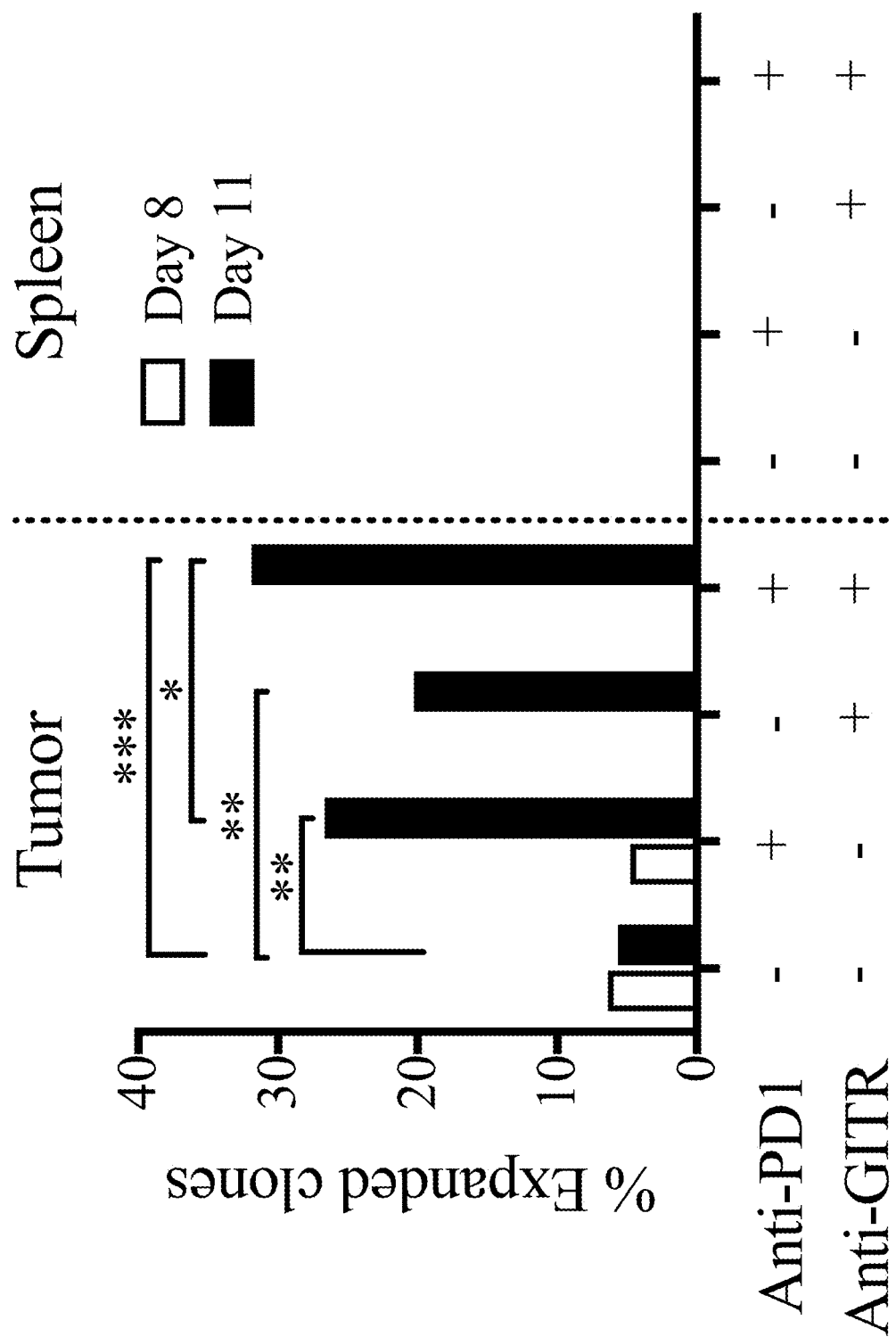
FIG. 3 is a bar chart illustrating significant clonal expansion in intratumoral CD8+ T cells after aGITR/aPD1 combination treatment compared to monotherapy.

FIG. 3 is a graphical illustration of the results contained in FIG. 2. FIG. 3 is a bar chart indicating that the percentage of expanded clones for aGITR and aPD1 in combination is 31.9% 11 days after treatment, the percentage of expanded clones for aPD1 alone is 26.7% 11 days after treatment (4.8% 8 days after treatment), and the percentage of expanded clones for aGITR alone is 20.3% 11 days after treatment. In an aspect, the results of FIG. 2 and the chart of FIG. 3 can be based off of data obtained after administering the one or more treatments to one or more subjects. The method 100 can further comprise administering one or more treatments to the subject. The method 100 can further comprise generating a TCR sequence library of TCR sequences and corresponding clonal expansion associated with the one or more treatments. FIG. 3 shows the significance of the number of clonally expanded T cells identified in combination treatment of tumor-bearing mice compared to single (mono-) therapy administering either anti-PD1 (aPD1) or anti-GITR (aGITR). Both anti-PD1 (aPD1) and anti-GITR (aGITR) treatments are significantly increased with respect to the percentage of expanded clones compared to tumors from mice treated with isotype control.

Figure 4:
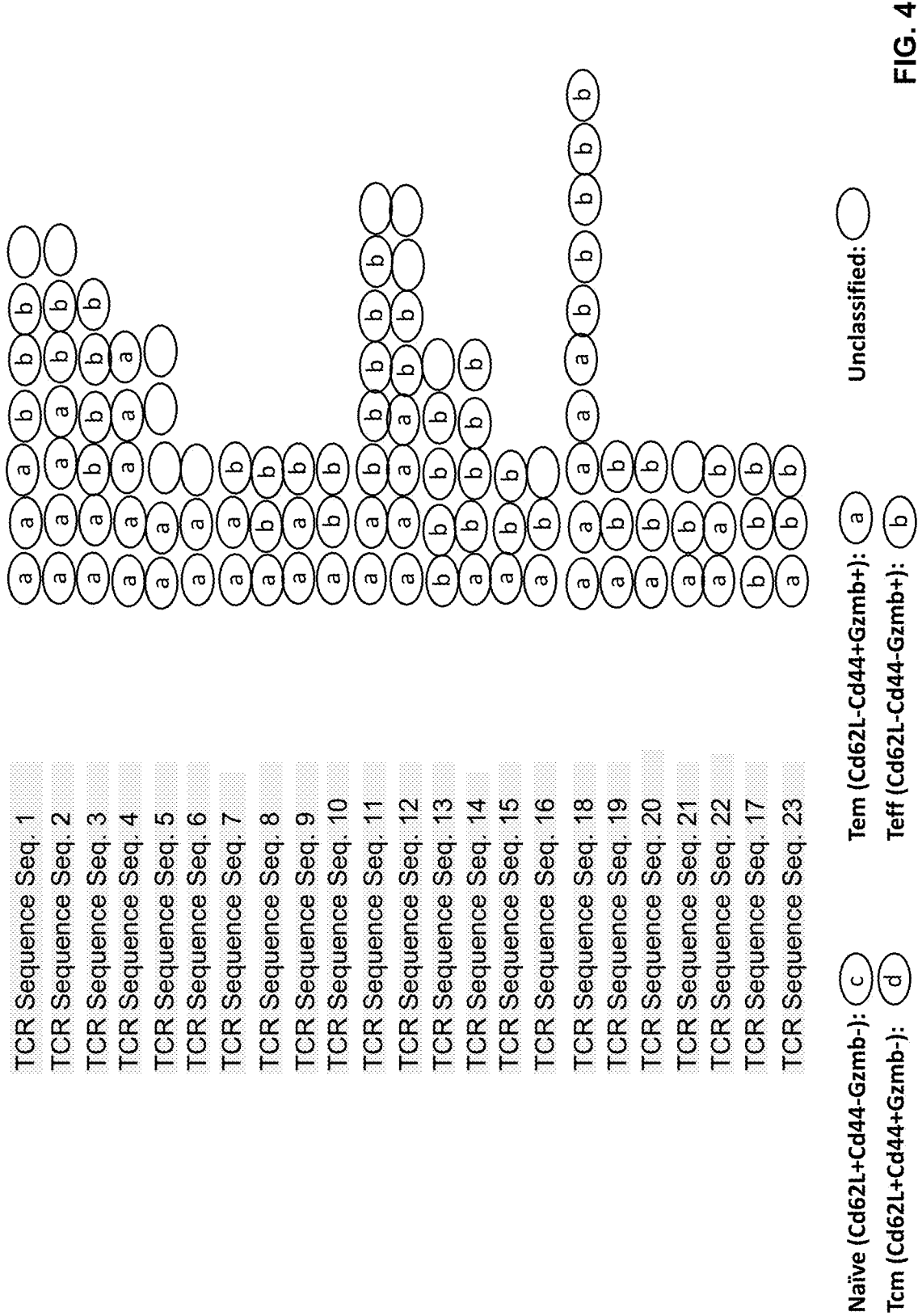
FIG. 4 illustrates T cell lineage after clonal expansion observed using single T cell sequencing.

FIG. 4 illustrates an exemplary output of one embodiment of the method 100 of FIG. 1. FIG. 4 shows T cell lineage after clonal expansion. Within treatment types (e.g., aGITR and aPD1 in combination, aPD1 alone, aGITR alone) clonal expansion occurs across various cell subtypes, such as Naïve, T cell memory (Tcm), T cell effector memory (Tem), T cell effector (Teff), and the like. FIG. 4 indicates sequences associated with specific treatments along with counts (e.g., clonal expansion values), and includes an indication of cell subtypes associated with the clonal expansion values. FIG. 4 depicts the profile of T cells in each set of clones. Each T cell clone identified by the TCR CDR3 sequence expressed, was also characterized (e.g., classified by cell surface markers) as a) a effector memory cell (Tem) (Cd62L−Cd44+ Gzmb+), b) an effector T cell (Teff) (Cd62L−Cd44− Gzmb+), c) a naïve T cell (Cd62L+Cd44−Gzmb−), or d) a central memory cell (Tcm) (Cd62L+Cd44+Gzmb−), or an otherwise unclassified cell (blank oval).

Disclosed are methods of determining one or more TCR sequences comprising obtaining a first sequence data comprising single cell raw reads from a first cell of a subject, using a bioinformatics tool to map the first sequence data to a second sequence data comprising a plurality of non-T cell receptor transcripts to identify one or more unmapped reads in the first sequence data, and determining one or more TCR sequences from the unmapped reads. In some aspects, obtaining first sequence data comprising single cell raw reads from a first cell of a subject comprises performing random primer RNA sequencing on transcripts obtained from the first cell. The random primers can be 4-40 nucleotides in length. In some instances, the random primers can be 4, 5, 6, 7, 8, 9, 10, 11, 12, 13, 14, 15, 16, 17, 18, 19 or 20 nucleotides in length. In some aspects, prior to obtaining a first sequence data, the subject is administered an immunotherapy. The immunotherapy can be a monotherapy or a combination therapy. For example, the immunotherapy can be the combination of a costimulatory agonist and a coinhibitory antagonist.

Disclosed are vectors comprising a CDR3 sequence of a TCRβ chain. In some aspects, the vector can be a viral vector or plasmid. Examples of viral vectors can be but are not limited to lentiviral vectors, adenoviral vectors, and adeno-associated viral vectors. In some aspects, the CDR3 sequence is a nucleic acid sequence that encodes CASSRNTEVFF (SEQ ID NO:269), CASSIGNTEVFF (SEQ ID NO:270), CASSQPGKNTEVFF (SEQ ID NO:271), CASSLGQGNNSPLYF (SEQ ID NO:272), CASSQGQGGAETLYF (SEQ ID NO:273), CASSPPMGGQLYF (SEQ ID NO:274), CASSQEGANTEVFF (SEQ ID NO:275), CASSQVQGTGNTLYF (SEQ ID NO:276), CASSQEGDGYEQYF (SEQ ID NO:277), CTSAEGGGTEVFF (SEQ II) NO:278), CASSPPGGGTEVGG (SEQ ID NO:279), CASSGTDNQDTQYF (SEQ ID NO:280), CASSPGTGGYEQYF (SEQ ID NO:281), CASSLELGFYEQYF (SEQ ID NO:282), CASSLGGAPNERLFF (SEQ ID NO:283), CASSQEGDSYEQYF (SEQ ID NO:284), CASSRNTEVFF (SEQ ID NO:285), CASGDAMGGRDYAEQFF (SEQ ID NO:286), CGAREGQDTQYF (SEQ ID NO:287), CGARTGGEQYF (SEQ ID NO:288), or CTCSAGNQAPLF (SEQ ID NO:289). Thus, in some aspects, disclosed are lentiviral vectors comprising a nucleic acid sequence that encodes the sequence of any one of SEQ ID NOs:269-289.

In an aspect, TCR sequences with similar binding specificities can be clustered as disclosed in Gupta N. T., et al. Hierarchical clustering can identify B cell clones with high confidence in Ig repertoire sequencing data. J. Immunol. 198(6), 2489-2499 (2017). Briefly, CDR3 regions of the TCR sequences can be clustered using single-linkage hierarchical clustering; distance between two CDR3 sequences can be defined as the absolute number of nucleotide differences between the two sequences and a threshold that, in an aspect, can be inferred from the sequence dataset as disclosed in the aforementioned reference.

Also disclosed are recombinant cells comprising a vector comprising a nucleic acid sequence that encodes the sequence of any one of SEQ ID NOs:269-289.

Disclosed are recombinant cells comprising a CDR3 sequence of a TCRβ chain. In some aspects, the CDR3 sequence is derived from a different cell type, cell line, or different species than the recombinant cell comprising the CDR3 sequence. For example, the CDR3 sequence can be from a primary human T cell and the cell comprising the CDR3 sequence can be a T cell line derived from any other T cell than the cell from which the CDR3 sequence was derived. Another example, the CDR3 sequence can be from a human cell and the cell comprising the CDR3 sequence can be a non-human cell. In some aspects, the recombinant cells comprise a CDR3 sequence comprising the sequence of CASSRNTEVFF (SEQ ID NO:269), CASSIGNTEVFF (SEQ ID NO:270), CASSQPGKNTEVFF (SEQ ID NO:271), CASSLGQGNNSPLYF (SEQ ID NO:272), CASSQGQGGAETLYF (SEQ ID NO:273), CASSPPMGGQLYF (SEQ ID NO:274), CASSQEGANTE-VFF (SEQ ID NO:275), CASSQVQGTGNTLYF (SEQ ID NO:276), CASSQEGDGYEQYF (SEQ ID NO:277), CTSAEGGGTEVFF (SEQ ID NO:278), CASSPPGGGTE-VGG (SEQ ID NO:279), CASSGTDNQDTQYF (SEQ ID NO:280), CASSPGTGGYEQYF (SEQ ID NO:281), CASSLELGFYEQYF (SEQ ID NO:282), CASSLGGAP-NERLFF (SEQ ID NO:283), CASSQEGDSYEQYF (SEQ ID NO:284), CASSRNTEVFF (SEQ ID NO:285), CASGDAMGGRDYAEQFF (SEQ ID NO:286), CGAREGQDTQYF (SEQ ID NO:287), CGARTGGEQYF (SEQ ID NO:288), or CTCSAGNQAPLF (SEQ ID NO:289).

In some aspects, the disclosed methods for identifying TCR sequences from random priming RNA sequencing can be used to identify B cell receptors (BCRs) as well. The steps of the pipeline are nearly identical except for the following steps: 1) the negative selection step wherein identifying BCRs involves alignment of short reads to a second reference dataset comprising a plurality of species-specific non-B cell receptor RNA transcripts; 2) the assembly step wherein identifying BCRs involves assembly of the one or more unmapped short reads into one or more long reads for further processing can comprise aligning the one or more unmapped short reads to one or more BCR sequences from a reference database of BCR sequences and assembling the one or more unmapped short reads into long reads (candidate BCR sequences) based on the reference database of BCR sequences; 3) the alignment step wherein identifying BCRs involves alignment of candidate BCR sequences to a reference of BCR V and J genes along with identification of the BCR CDR3 region. In an aspect, generating one or more BCR sequences from the one or more long reads can comprise one or more techniques disclosed in Alamyar, E., et al, IMGT tools for the nucleotide analysis of immunoglobulin (IG) and t cell receptor (TR) V-(D)-J repertoires, polymorphisms, and IG mutations: IMGT/V-QUEST and IMGT/High V-QUEST for NGS. Methods in Mol. Biol. 882, 569-604 (2012).

Figure 8:
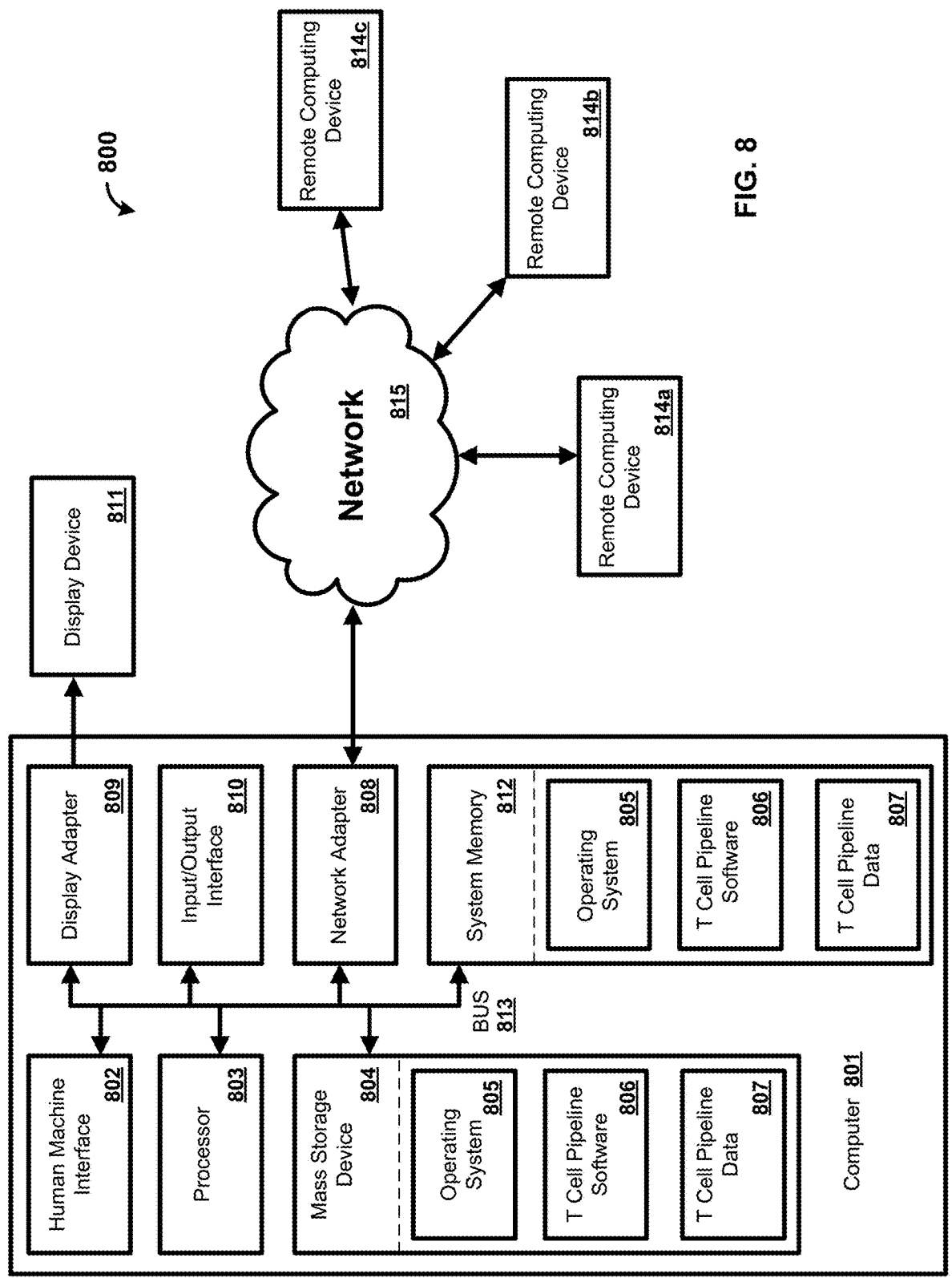
FIG. 8 illustrates an exemplary operating environment.

In an exemplary aspect, the methods and systems can be implemented on a computer 801 as illustrated in FIG. 8 and described below. Similarly, the methods and systems disclosed can utilize one or more computers to perform one or more functions in one or more locations. FIG. 8 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc. that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via a general-purpose computing device in the form of a computer 801. The components of the computer 801 can comprise, but are not limited to, one or more processors 803, a system memory 812, and a system bus 813 that couples various system components including the one or more processors 803 to the system memory 812. The system can utilize parallel processing. Parallel processing can be leveraged to perform the disclosed methods. For example, performance of at least a portion of one or more steps of the disclosed methods can be classified as a job. For example, the disclosed methods can be performed for a plurality of samples in parallel. The workload for each job can then be distributed across several processors. A software application can be used to design and run jobs to process data. A job can, for example, extracts data from one or more data sources, transform the data, and load it into one or more new locations (e.g., stage the data for processing in another job). In a parallel processing topology, the workload for each job can be distributed across several processors on one or more computers, called compute nodes. In an aspect, the user can modify a configuration file or otherwise interface with software configured to define multiple processing nodes. These nodes work concurrently to complete each job quickly and efficiently. A conductor node computer can orchestrate the work. Parallel processing environments can be categorized as symmetric multiprocessing (SMP) or massively parallel processing (MPP) systems. In a symmetric multiprocessing (SMP) environment, multiple processors share other hardware resources. For example, multiple processors can share the same memory and disk space, but use a single operating system. The workload for a parallel job is then distributed across the processors in the system. The actual speed at which the job completes might be limited by the shared resources in the system. To scale the system, the number of processors can be increased, memory can be added, or storage can be increased. In a massively parallel processing (MPP) system, many computers can be physically housed in the same chassis. An MPP system can be physically dispersed. In an MPP environment, performance is improved because no resources must be shared among physical computers. To scale the system, computers, along with associated memory and disk resources can be added. In an MPP system, a file system is commonly shared across the network. In this configuration, program files can be shared instead of installed on individual nodes in the system.

The system bus 813 represents one or more of several possible types of bus structures, including a memory bus or memory controller, a peripheral bus, an accelerated graphics port, or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 813, and all buses specified in this description can also be implemented over a wired or wireless network connection and each of the subsystems, including the one or more processors 803, a mass storage device 804, an operating system 805, T cell pipeline software 806, T cell pipeline data 807, a network adapter 808, the system memory 812, an Input/Output Interface 810, a display adapter 809, a display device 811, and a human machine interface 802, can be contained within one or more remote computing devices 814a,b,c at physically separate locations, connected through buses of this form, in effect implementing a fully distributed system.

The computer 801 typically comprises a variety of computer readable media. Exemplary readable media can be any available media that is accessible by the computer 801 and comprises, for example and not meant to be limiting, both volatile and non-volatile media, removable and non-removable media. The system memory 812 comprises computer readable media in the form of volatile memory, such as random access memory (RAM), and/or non-volatile memory, such as read only memory (ROM). The system memory 812 typically contains data such as the T cell pipeline data 807 and/or program modules such as the operating system 805 and the T cell pipeline software 806 that are immediately accessible to and/or are presently operated on by the one or more processors 803.

In another aspect, the computer 801 can also comprise other removable/non-removable, volatile/non-volatile computer storage media. By way of example, FIG. 8 illustrates the mass storage device 804 which can provide non-volatile storage of computer code, computer readable instructions, data structures, program modules, and other data for the computer 801. For example and not meant to be limiting, the mass storage device 804 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 804, including by way of example, the operating system 805 and the T cell pipeline software 806. Each of the operating system 805 and the T cell pipeline software 806 (or some combination thereof) can comprise elements of the programming and the T cell pipeline software 806. The T cell pipeline data 807 can also be stored on the mass storage device 804. The T cell pipeline data 807 can be stored in any of one or more databases known in the art. Examples of such databases comprise, DB2®, Microsoft® Access, Microsoft® SQL Server, Oracle®, my SQL, PostgreSQL, and the like. The databases can be centralized or distributed across multiple systems.

In another aspect, the user can enter commands and information into the computer 801 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the one or more processors 803 via the human machine interface 802 that is coupled to the system bus 813, but can be connected by other interface and bus structures, such as a parallel port, game port, an IEEE 1394 Port (also known as a Firewire port), a serial port, or a universal serial bus (USB).

In yet another aspect, the display device 811 can also be connected to the system bus 813 via an interface, such as the display adapter 809. It is contemplated that the computer 801 can have more than one display adapter 809 and the computer 801 can have more than one display device 811. For example, the display device 811 can be a monitor, an LCD (Liquid Crystal Display), or a projector. In addition to the display device 811, other output peripheral devices can comprise components such as speakers (not shown) and a printer (not shown) which can be connected to the computer 801 via the Input/Output Interface 810. Any step and/or result of the methods can be output in any form to an output device. Such output can be any form of visual representation, including, but not limited to, textual, graphical, animation, audio, tactile, and the like. The display device 811 and computer 801 can be part of one device, or separate devices.

The computer 801 can operate in a networked environment using logical connections to one or more remote computing devices 814a,b,c. By way of example, a remote computing device can be a personal computer, portable computer, smartphone, a server, a router, a network computer, a peer device or other common network node, and so on. Logical connections between the computer 801 and a remote computing device 814a,b,c can be made via a network 815, such as a local area network (LAN) and/or a general wide area network (WAN). Such network connections can be through the network adapter 808. The network adapter 808 can he implemented in both wired and wireless environments. Such networking environments are conventional and commonplace in dwellings, offices, enterprise-wide computer networks, intranets, and the Internet.

For purposes of illustration, application programs and other executable program components such as the operating system 805 are illustrated herein as discrete blocks, although it is recognized that such programs and components reside at various times in different storage components of the computing device 801, and are executed by the one or more processors 803 of the computer. An implementation of the T cell pipeline software 806 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the scope of the methods and systems. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The methods and systems can employ Artificial intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. Expert inference rules generated through a neural network or production rules from statistical learning).

The following examples are provided to describe the embodiments in greater detail. They are intended to illustrate, not to limit, the claimed embodiments.

Example 1

In Vivo Mouse Studies

For MC38 tumor studies, $3 \times 10^5$ or $5 \times 10^5$ MC38 cells were subcutaneously injected on the right flank of C57BL/6 or humanized GITR/GITRL double knock-in mice, respectively (day 0). On day 6 after tumor implantation, mice were grouped based on tumor size and treated by intraperitoneal injection with 5 mg kg-1 anti-GITR (DTA1) and/or anti-PD-1 (RPM1-14) Ab or isotype control IgGs (rat IgG2b, LTF-2 and rat IgG2a, 2A3) at indicated doses (Abs obtained from Bio X Cell). Antibodies were administered again on day 13. Mice treated with combination of anti-PD-1 (aPD-1) and anti-GITR (aGITR) Ab mice remained tumor-free for over 80 days. These mice were re-challenged with $3 \times 10^5$ of MC38 and $2.5 \times 10^5$ B16F10.9 cells bilaterally. Naïve mice were used as tumor implantation control.

For T cell subset depletion experiments, mice treated with either combination therapy or isotype control IgG were treated with 300 μg depleting mAbs, including anti-CD4, clone GK1.5; anti-CD8 clone 2.43 and rat IgG2b isotype (BioX Cell) and anti-CD25, clone PC61 (eBioscience); rat IgG1 isotype (HPRN, Bio X Cell) Depletion Ab were given at one day prior of tumor challenge (day −1) and twice weekly for total eight doses. The depletion efficiency was confirmed by FACS analysis of peripheral blood samples. Perpendicular tumor diameters were measured blindly 2-3 times per weeks using digital calipers (VWR, Radnor, Pa.). Volume was calculated using the formula L×W×0.5, where L is the longest dimension and W is the perpendicular dimension. Differences in survival were determined for each group by the Kaplan-Meier method and the overall P value was calculated by the log-rank testing using survival analysis by Prism version 6 (GraphPad Software Inc.). An event was defined as death when tumor burden reached the protocol-specified size of 2000 mm³ in maximum tumor volume to minimize morbidity.

Example 2

Single-Cell Sorting RNA-Seq Analysis

On day 8 and 11 post tumor challenge, single cell suspension of tumor was prepared by mouse tumor dissociation kit (Miltenyi Biotec) and spleens were dissociated with gentleMACS Octo Dissociator. Tumors and spleens from the same treatment group were pooled and viable CD8+ T cells were sorted by FACS. FACS sorted T cells were mixed with C1 Cell Suspension Reagent (Fluidigm) before loading onto a 5- to 10-μm C1 Integrated Fluidic Circuit (IFC; Fluidigm). LIVE/DEAD staining solution (Thermo Fisher) was prepared by adding 2.5 μL ethidium homodimer-1 and 0.625 μL calcein AM (Life Technologies) to 1.25 mL C1 Cell Wash Buffer (Fluidigm) and 20 μL was loaded onto the C1 IFC. Each capture site was carefully examined under a Zeiss microscope in bright field, green fluorescent protein (GFP), and Texas Red channels for cell doublets and viability. Cell lysing, reverse transcription, and cDNA amplification were performed on the C1 Single-Cell Auto Prep IFC, as specified by the manufacturer (protocol 100-7168 E1). The SMARTer Ultra Low RNA Kit (Clontech) was used for cDNA synthesis from the single cells. Illumina NGS libraries were constructed using the Nextera XT DNA Sample Prep kit (Illumina), according to the manufacturer's recommendations (protocol 100-7168 E1). A total of 2,222 single cells were sequenced on Illumina NextSeq (Illumina) by multiplexed single-read run with 75 cycles.

TABLE 8

Summary of Captured T cells.

| Treatment | Day post tumor implant | Tissue | # of C1 chips | # of captured cells | # of cells passed QC |
|---|---|---|---|---|---|
| Isotype control | 8 | Tumor | 2 | 98 | 47 |
| | | Spleen | 2 | 102 | 51 |
| | 11 | Tumor | 3 | 194 | 105 |
| | | Spleen | 2 | 157 | 128 |
| | 18 | Tumor | 1 | 66 | |
| | | Spleen | 1 | 69 | |
| aGITR + aPD-1 | 8 | Tumor | 2 | 135 | 81 |
| | | Spleen | 2 | 115 | 78 |
| | 11 | Tumor | 3 | 184 | 141 |
| | | Spleen | 2 | 134 | 113 |
| aGITR alone | 8 | Tumor | 4 | 255 | 127 |
| | | Spleen | 4 | 240 | 86 |
| | 11 | Tumor | 2 | 113 | 79 |
| | | Spleen | 1 | 83 | 72 |
| aPD1 alone | 8 | Tumor | 2 | 115 | 63 |
| | | Spleen | 1 | 57 | 42 |
| | 11 | Tumor | 4 | 177 | 120 |
| | | Spleen | 1 | 63 | 46 |
| Total | | | | 2,357 | 1,379 |

Raw sequence data (BCL files) from each of these cells were converted to FASTQ format via Illumina Casava 1.8.2. Reads were decoded based on their barcodes. Read quality was evaluated using FastQC (www.bioinformatics.babraham.ac.uk/projects/fastqc/). For TCR analysis, the disclosed methods, including random-priming short-read TCR (rpsTCR) analysis, for reconstructing and extracting TCR sequences, especially TCR-CDR3 sequences from random priming short RNA sequencing reads was used. (See FIG. 1). The rpsTCR method provided paired- and single-end short reads and mapped these reads to mouse or human genomes and transcriptomes, but not to TCR gene loci and transcripts, using TopHat43 with default parameters. Thus negative selection allows for mapped reads to be discarded and unmapped reads were recycled for extraction of TCR sequences. Low quality nucleotides in the unmapped reads were trimmed (i.e., reads with length less than 35 bp were filtered out using HTQC toolkit). QC passed short reads were assembled into longer reads using iSSAKE default setting. TCRklass was used to identify CDR3 sequences with Scr (conserved residue support score) set from default 1.7 to 2.

Example 3

Analysis of Tumor-Infiltrating T Cells Isolated from Tumor-Bearing Mice

The disclosed methods (pipeline) were utilized to reconstruct, extract and analyze TCR sequences using single cell sorted RNAseq data, allowing the identification of high-frequency T cell clones potentially associated with tumor reactivity and patient survival. The pipeline was used to profile the transcriptome of 1379 $CD8^+$ T cells isolated from tumor-bearing mice. At the early time point (day 8), very few clones of high-frequency T cells (defined as at least 3 T cells sharing identical TCR sequences) were detected in all treatment groups (FIG. 2). By day 11, we identified 2 high-frequency T cell clones, representing 5.7% of sequenced single CD8+ T cells from isotype control samples; 3 clones/20.3% for anti-GITR samples, 6 clones/26.7% for anti-PD-1 samples and 10 clones/31.9% for combination treated samples. This result indicates that between day 8 and day 11, a strong clonal expansion of intratumoral CD8+ T cells was primarily driven by anti-PD-1 treatment. The significance of the number of clonally expanded T cells identified in combination treatment of tumor-bearing mice compared to single (mono-) therapy administering either anti-PD1 (aPD1) or anti-GITR (aGITR) is depicted in FIG. 3. Anti-GITR and/or anti-PD-1 had no impact on peripheral/spleen T cell clonality (FIG. 2), consistent with patient data showing that anti-PD-1 (pembrolizumab) treatment did not affect peripheral blood T cell clonality. Although single agent therapy expanded intratumoral $CD8^+$ T cell clones and modulated critical gene pathways, it was not sufficient for complete tumor rejection. The data suggests that a profound reprogramming of dysfunctional tumor infiltrating T cells by combination therapy was required for complete tumor rejection.

Example 4

T Cell Activation Assay for Tumor Derived TCRs

Figure 6A:
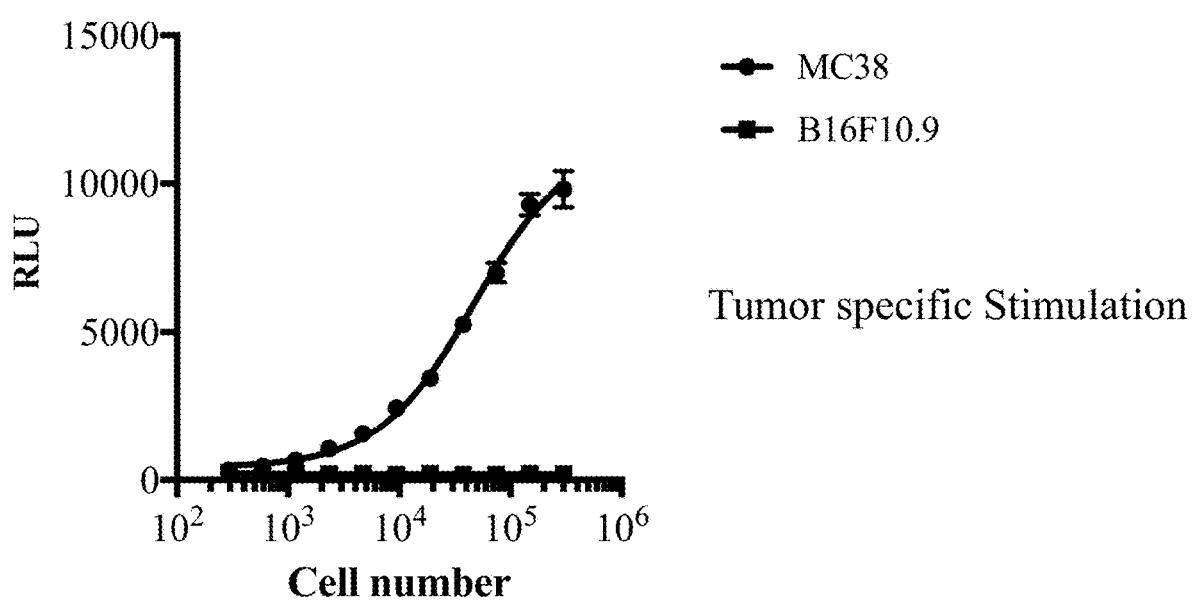
FIGS. 6A-6D illustrate T cell activation assays for tumor derived TCRs.
Figure 6B:
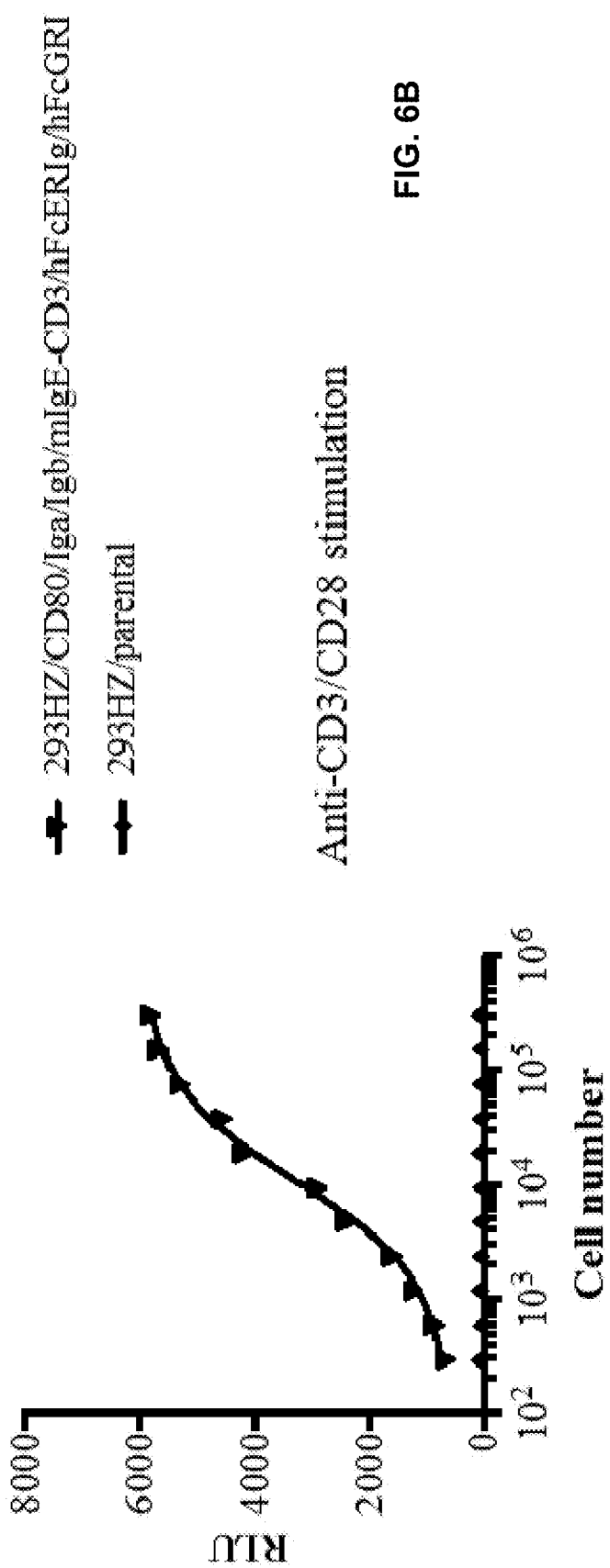
Figure 6C:
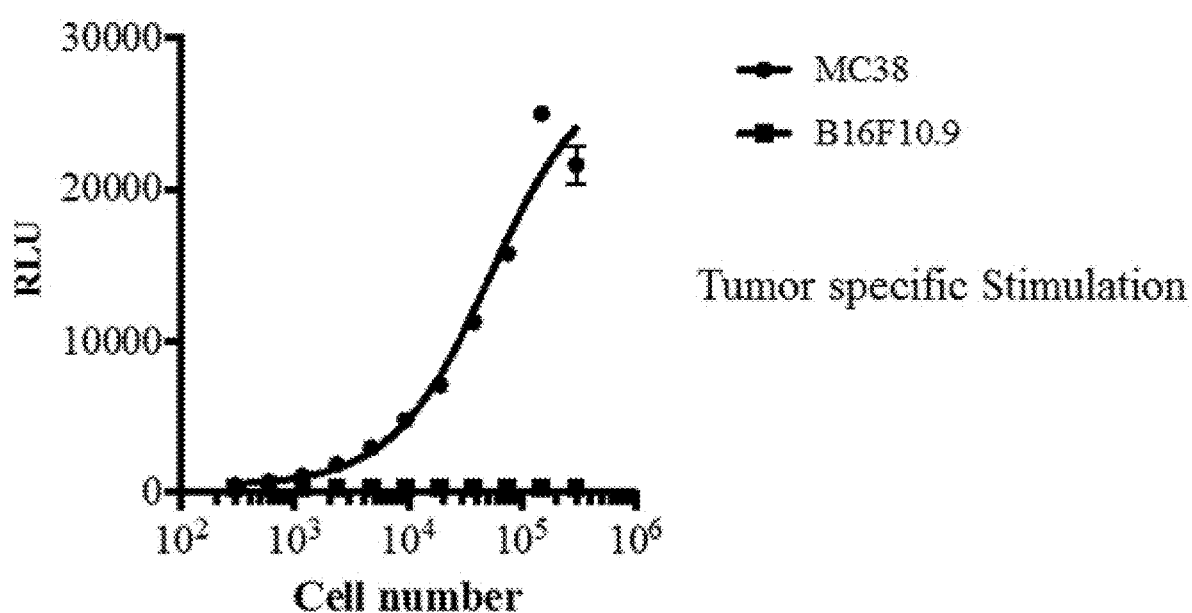
Figure 6D:
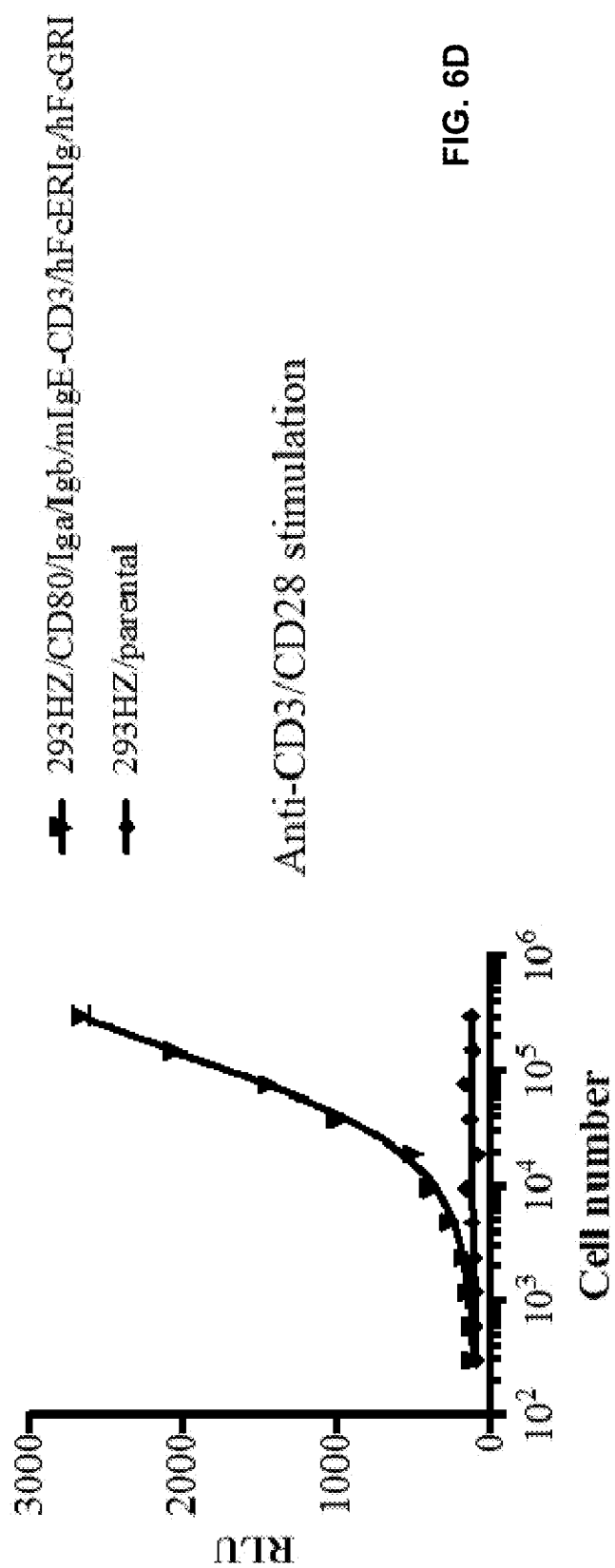

T cell activation assays measured by Luciferase expression in JRT3 cell lines expressing isolated TCRs comprising identified CDR3 sequences (FIGS. 6A-6D). TCR comprising CDR3 sequence (TCR Sequence Seq. 17) isolated from an anti-GITR treated tumor T cell that was highly expanded (i.e., 10 clones identified) was expressed in a JRT3 cell line. The JRT3 becomes activated in the presence of tumor expressing the original antigen, MC38 (FIG. 6A), indicating that the transfected cell line recognizes the antigen. TCR Sequence Seq. 17-expressing cell lines also become activated when anti-CD3/anti-CD28 stimulated (FIG. 6B). Analogous studies using TCR Sequence Seq. 12-expressing cell lines (TCR CDR3 sequence was isolated from a aPD-1 stimulated T cell having a Clone size of 8). The TCR Sequence Seq. 12-expressing cell line was activated in the presence of tumor expressing the original antigen (FIG. 6C) and was activated in the presence of anti-CD3/anti-CD28 (FIG. 6D).

Example 5

Gene Expression Analysis

Gene expression analysis tools were also utilized to profile the transcriptome (mapped portion of sequences) of the 1379 CD8+ T cells isolated from tumor-bearing mice. To identify unique gene signatures in clonal expanded $CD8^+$ T cells from combination treatment samples, comparisons across treatment groups were performed. T cell lineage after clonal expansion was identified by the TCR CDR3 sequence expressed, correlated to the expression pattern of cell surface markers. See FIG. 4. As such, clonal T cells were classified as effector memory cells (Tem) (Cd62L–Cd44+Gzmb+), effector T cells (Teff) (Cd62L–Cd44–Gzmb+) (or unclassified cells, i.e. non-clonally expanded if less than 3 T cells having the expressed TCR, such as naïve T cells (Cd62L+Cd44–Gzmb–) or central memory T cells (Tcm) (Cd62L+Cd44+Gzmb–)).

Figure 5:
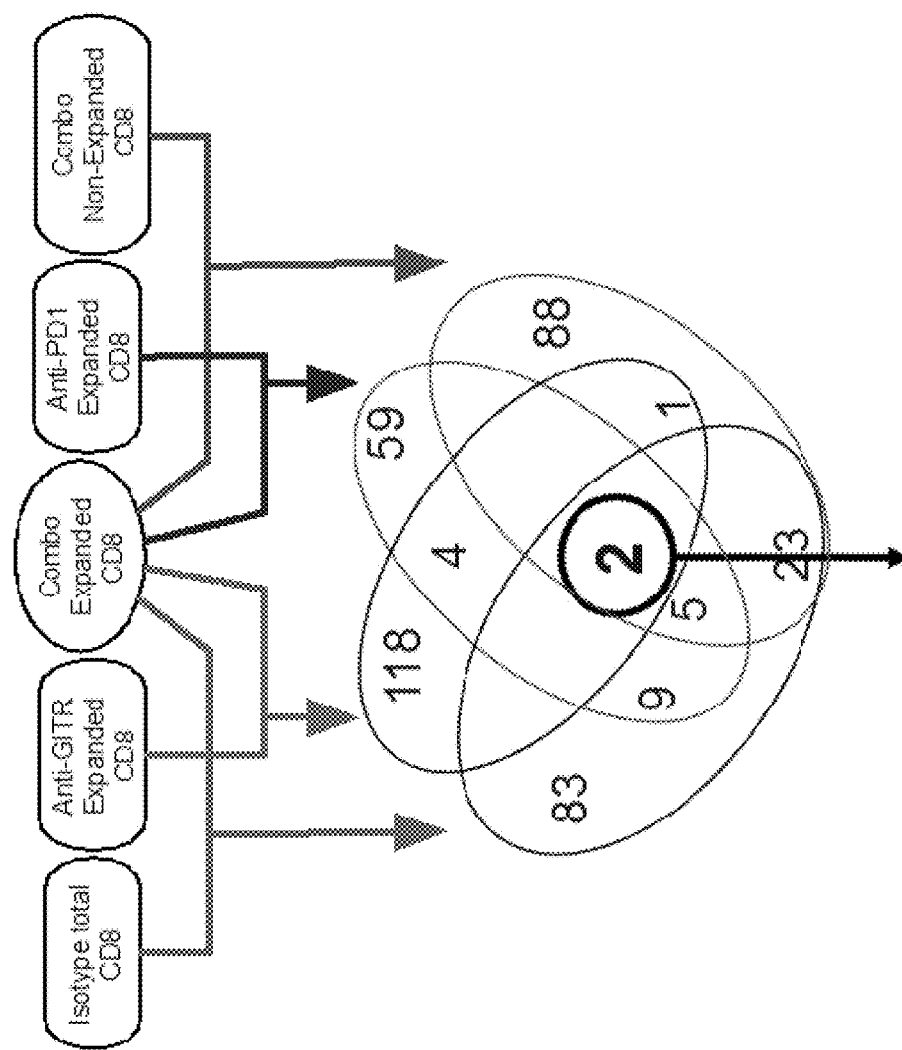
FIG. 5 illustrates intratumoral CD8 T cell clonal analysis based on single cell-sorted RNAseq data.

Gene expression analysis also yielded differentially expressed gene profiles across the clonally expanded and nonclonally expanded cells in each of the treatment groups. CD226 was identified as one of the two genes shared across different comparison pairs (FIG. 5). FIG. 5 is a Venn diagram illustrating genes preferably expressed in expanded intratumoral CD8+ T cells of aGITR+aPD1 treatment group on day 11 of treatment. The Venn diagram summarizes the gene signature analysis of clonal expanded/non-expanded CD8+ T cells among treatment groups. CD226 and PDE4D were identified as two genes shared across different comparison pairs.

FIG. 5 indicates that two genes are preferably expressed when comparing genes expressed under treatment with aGITR and aPD1 in combination to all other treatments. The two genes are CD226 and Pde4d. The table underneath the Venn diagram provides the occurrences of each gene when comparing genes expressed under treatment with aGITR and aPD1 in combination to all other treatments. Thus the disclosed method can be used to identify specific genes that play a role in immune response to tumor cells.

CD226 is a costimulatory molecule that plays an important role in anti-tumor response. Expression analysis in different subsets of intratumoral $CD8^+$ T cells (total, clonal expanded, or non-expanded) across treatment groups revealed that CD226 mRNA levels were significantly increased by combination treatment on clonal expanded T cells. (FIG. 7A), while this difference was diluted in total and non-expanded $CD8^+$ T cells. This observation stresses the importance of performing genome profiling on putative tumor-reactive clones (high-frequency T cell clones) to unmask critical gene changes, and also allows for identification of biomarkers that are informative about efficacious treatments that affect T cell activity.

Figure 7A:
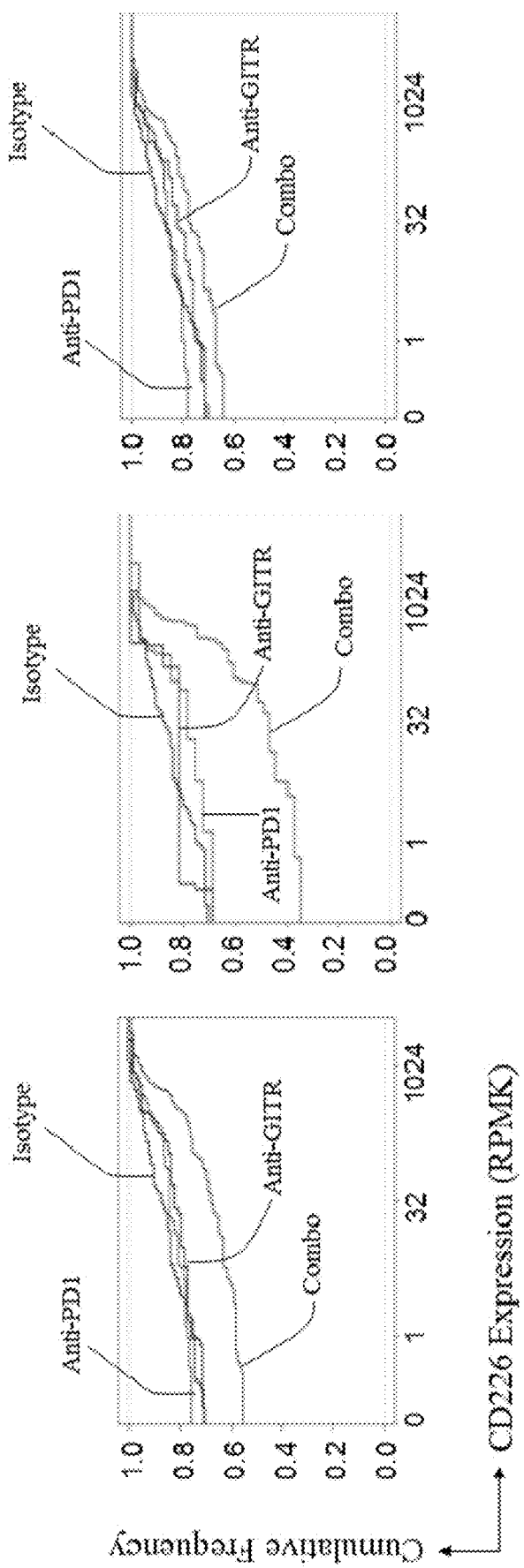
FIGS. 7A-B illustrate gene expression analysis of single T cell transcriptome.
Figure 7B:
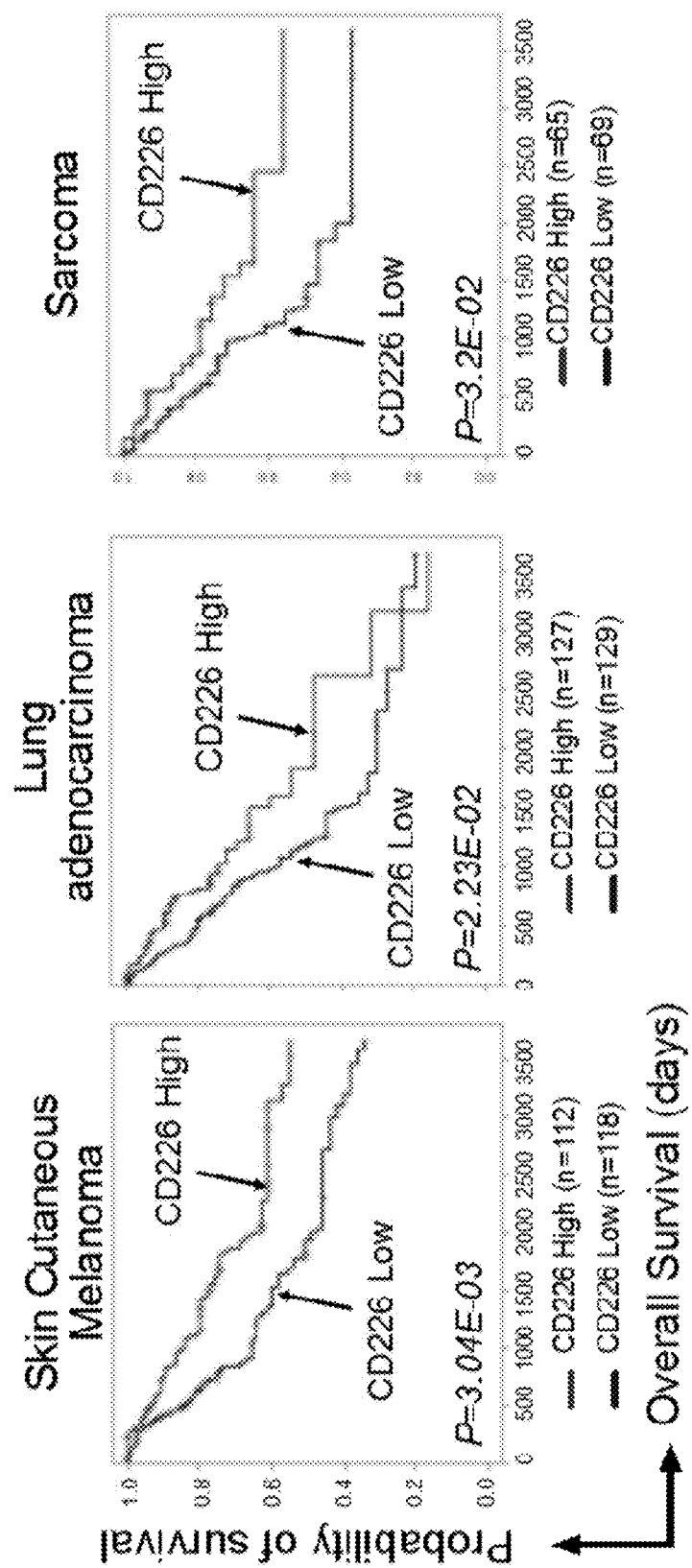

FIG. 7A illustrates cumulative distribution function (CDF) plots showing expression of a key regulated gene, CD226, in total, clonal expanded or non-expanded CD8 T cells. The clonal expanded CD8 cells show the highest expression of CD226. The disclosed method is useful to classify subjects that show better correlation with or expression of particular genes. These data also show the utility of the method to identify prognostic genes that inform whether expression is correlated with T cell expansion during a particular treatment, and therefore indicates likelihood of efficacy. CD226 significantly correlates with improved survival when analyzed from the T cells of patients with melanoma, lung squamous cell carcinoma and sarcoma (FIG. 7B). FIG. 7B illustrates TCGA data analysis of CD226 expression level and overall survival in patients with melanoma, lung squamous cell carcinoma and sarcoma. (*, $P<0.05$, , $P<0.01$; *, $P<0.001$, ****, $P<0.0001$ between selected relevant comparison). As shown, CD226 correlates with improved survival.

Example 6A

CD226/TIGIT Axis Mediates Durable Anti-Tumor Responses Upon PD-1 and GITR Combination Immunotherapy Introduction Single or combination therapy targeting immune checkpoints PD-1 and CTLA-4 shows significant clinical benefit in certain cancer patient populations. However, the majority of patients either are resistant or only respond transiently, raising fundamental questions about the selection of optimal immune-modulatory targets to address patient-specific tumor sensitivity. Combination treatment targeting specific coinhibitory and costimulatory pathways to induce a stronger T cell activation, can lead to more durable anti-tumor responses. Here, PD1 and GITR combination therapy, a pre-clinically validated modality currently in early phase clinical testing, was used to characterize the molecular pathways driving long-term responses. Single cell RNA-seq libraries prepared from over 2,000 tumor infiltrating CD8$^+$ T cells were sequenced and found that the combination of GITR and PD-1 antibodies synergistically enhanced CD8$^+$ T cell effector function by restoring the balance of key homeostatic regulators CD226 and TIGIT, resulting in significant survival benefit. Indeed, anti-PD-1 treatment enhanced CD226 cell surface expression. However, PD-1 monotherapy was insufficient to overcome the inhibitory signaling mediated by TIGIT. Anti-GITR antibody decreased TIGIT expression on T cells. Thus, combination therapy synergistically regulated the strength of CD8$^+$ T cell response, and elicited potent adaptive immunity. Indeed, costimulation via CD226 is essential for anti-tumor immunity as genetic inactivation or pharmacological inhibition of CD226 reversed the tumor regression mediated by combination treatment, while inhibition of other TNF-receptor or B7 superfamily members had no effect. Importantly, RNA-sect analysis on tumor biopsies from 43 advanced cancer patients pre and post-anti-PD-1 therapy revealed that CD226 expression was significantly increased after anti-PD-1 treatment. Further high levels of CD226 were correlated with better prognosis in patients with different types of cancer. Such biomarkers in addition to PD-1/PDL-1 could improve patient selection. Systematic approaches unmasking the molecular pathways driving durable anti-tumor responses by rebalancing homeostatic regulators can be important to optimize combination immunotherapy.

Following the clinical success of PD-1 and CTLA4 antibody treatments, the therapeutic arsenal of agents in immunotherapy is expanding rapidly. A key goal is to improve the limited response rate and/or the durability of the anti-tumor response achieved with monotherapy approaches in cancer patients. Combination treatments targeting specific coinhibitory (PD-1) and costimulatory (GITR, glucocorticoid-induced TNFR-related protein, TNFRSF18) pathways inducing a stronger T cell activation are currently being evaluated in early phase clinical trials for patients with metastatic melanoma and other solid tumors. Indeed, the clinical relevance of T cells in the control of a diverse set of human cancers is now beyond doubt. GITR is constitutively expressed at a high level on T$_{reg}$ cells and can be induced on other lymphocytes upon activation. DTA-1, an agonistic anti-mouse GITR Ab reduces intratumoral T$_{reg}$ cells and mediates FcγR-dependent tumor rejection. Additionally, engaging GITR receptor with an agonistic Ab delivers costimulatory signals directly to effector T cells. While anti-GITR and anti-PD-1 Ab monotherapy has limited efficacy in large or poorly immunogenic tumors, combination therapy promotes long-term survival in ovarian and breast tumor models. However, the molecular mechanism underlying the synergism remains unknown. Here, PD1 and GITR combination therapy was used and over 2000 tumor infiltrating CD8$^+$ T cells in a murine MC38 colon adenocarcinoma model were genetically profiled. The systematic approach unmasked the molecular pathways driving durable anti-tumor responses, providing a basis by which to optimize existing combination immunotherapies, and identify new potential biomarkers to improve patient stratification and tumor sensitivity.

Methods

Cell lines and tissue culture. MC38 mouse colon carcinoma cells and RENCA mouse renal adenocarcinoma cells were obtained from American Type Culture Collection (ATCC) and were cultured at 37° C., 5% CO$_2$ in DMEM media supplied with 10% FBS, 100 U mL$^{-1}$ penicillin and 100 μg ml$^{-1}$ streptomycin, 2 mM $_L$-glutamine, 100 μM NEAA (ThermoFisher Scientific). J.RT3-T3.5 mutant Jurkat cell line lack endogenous TCR expression was obtained from ATCC and maintained in RPMI-1640 media with 10% FBS. Tumor cell lines were tested negative for Mycoplasma and common rodent pathogens by IMPACT test. MC38-OVA-β$_2$m-K$^b$ were generated by transducing MC38 tumor cells with lentiviral vector (LV) encoding a single trimer consisting of SIINFEKL peptide-spacer-β$_2$ microglobulin-spacer MHC class I (K$^b$) heavy chain. Surface expression of single trimer was confirmed with 25D-1.16 Ab (eBioscience, FIG. 21A). MC38-OVA-β$_2$m-K$^b$ were maintained with selection media containing 1.25 μg ml$^{-1}$ puromycin (ThermoFisher Scientific). MC38 tumor cells over-expressing CD155 were generated by transduction with LV encoding mouse full length CD155 and FACS sorted on the top 5% expressing cells. Expression level of CD155 was confirmed by FACS analysis (FIG. 24C).

Mice. Six to eight week old female C57BL/6 mice were obtained from The Jackson Laboratory. CD226$^{-/-}$ and TIGIT$^{-/-}$ mice in C57BL/6 background were generated at Regeneron using the VelociGene® method. Briefly, EGFP (for CD226) or LacZ cDNA (for TIGIT) was inserted in-frame to the start codon, followed by a selection cassette which disrupts transcription of the gene body and results in a CD226 or TIGIT null allele. Heterozygous targeted mice were interbred to produce homozygous knockout mice for study. All animals were maintained under pathogen-free conditions and experiments were performed according to protocols approved by the Institute of Animal Care and Use Committee (IACUC) of Regeneron Pharmaceuticals, Inc.

Figure 16A:
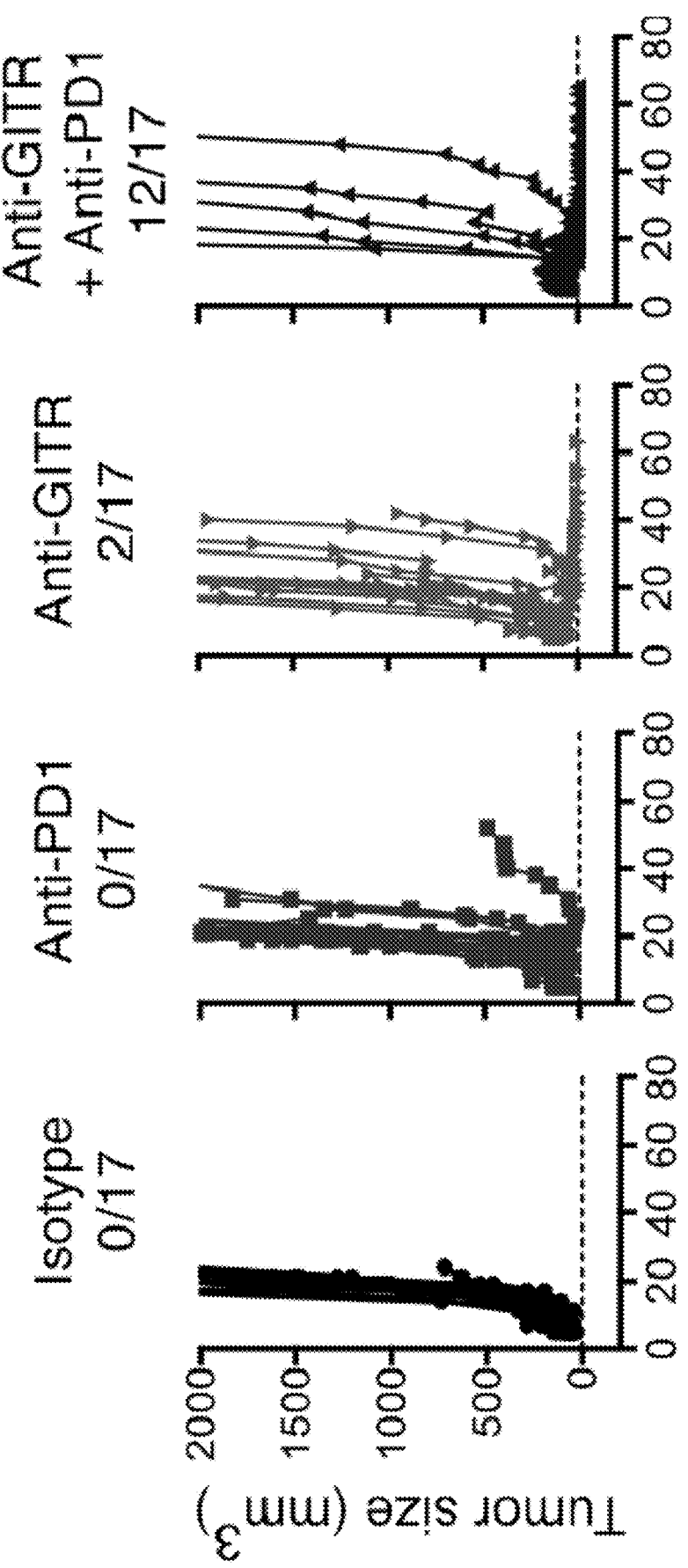
Figure 16B:
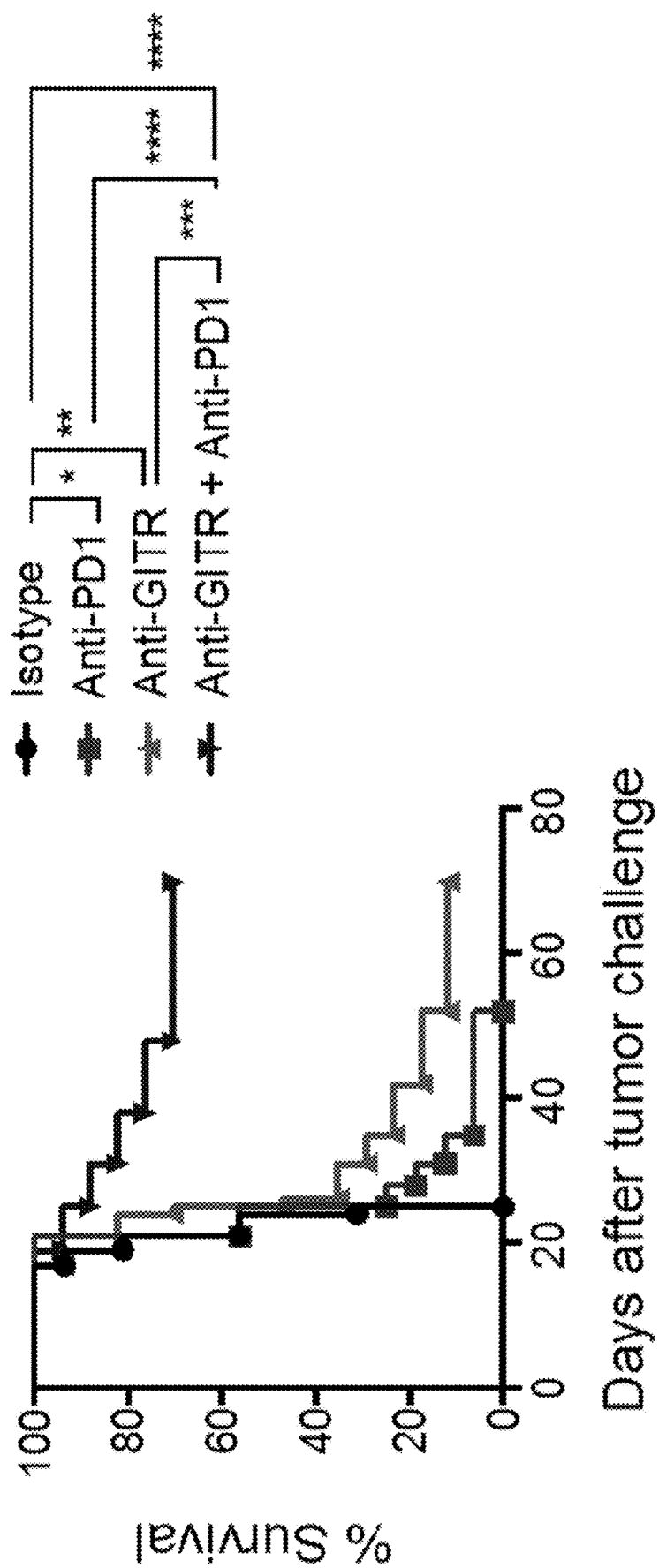
Figure 16C:
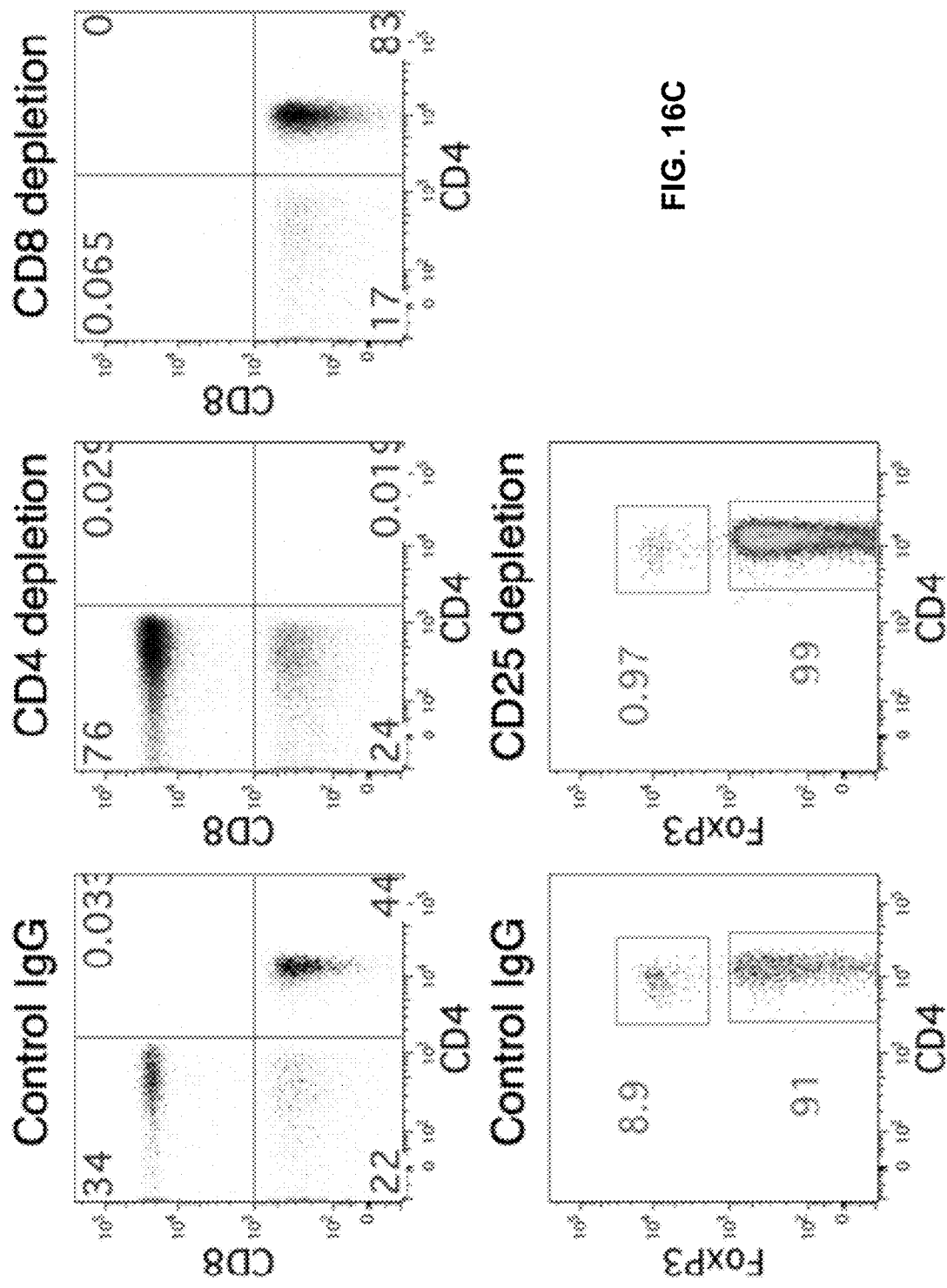

In vivo mouse studies. For MC38 tumor studies. 3×10$^5$ MC38 cells were subcutaneously injected on the right flank of age-matched C57BL/6 mice (day 0). On day 6 after tumor implantation, mice (randomly distributed in different groups) were grouped based on tumor size and treated by intraperitoneal injection with 5 mg kg$^{-1}$ anti-GITR (DTA1) and/or anti-PD-1 (RPM1-14) Ab or isotype control IgGs (rat IgG2b, LTF-2 and rat IgG2a, 2A3) at indicated doses (antibodies were obtained from Bio X Cell). Antibodies were administered again on day 13. For antibody depletion experiments, mice treated with either combination therapy or isotype control IgG were treated with 300 μg depleting or isotype control mAbs, including anti-CD4 (clone GK1.5); anti-CD8 (clone 2.43) and rat IgG2b isotype (clone LTF-2), rat IgG1 isotype (clone HPRN, Bio X Cell) and anti-CD25 (clone PC61, eBioscience). Depletion Ab were given at one day prior of tumor challenge (day −1) and twice weekly for total eight doses. The depletion efficiency was confirmed by FACS analysis of peripheral blood samples (FIG. 16C). Blocking antibodies used in this study include anti-CD226 Ab (clone 10E5, rat IgG2b, eBioscience, 25 mg/kg), CD28 blocking (CTLA4-Fc, Orencia, BMS, 10 mg/kg), anti-OX40L (clone RM134L, rat IgG2b, Bio X Cell, 10 mg/kg) and anti-4-1BBL (clone TKS-1, rat IgG2a, Bio X Cell, 10 mg/kg). Blocking Ab were given twice weekly by i.p. injection starting 1-2 days prior to immunotherapy, for two weeks. Perpendicular tumor diameters were measured blindly 2-3 times per weeks using digital calipers (VWR, Radnor, Pa.). Volume was calculated using the formula L×W×0.5, where L is the longest dimension and W is the perpendicular dimension. Differences in survival were determined for each group by the Kaplan-Meier method and the overall p value was calculated by the log-rank testing using survival analysis by Prism version 6 (GraphPad Software Inc.). An event was defined as death when tumor burden reached the protocol-specified size of 2000 mm$^3$ in maximum tumor volume to minimize morbidity.

Flow cytometry. For flow cytometry analysis of in vivo experiments, blood, spleen, thymus, lymph node and tumor were harvested on indicated days post treatment. Single cell suspensions were prepared and red blood cells were lysed using ACK Lysis buffer (ThermoFisher Scientific). Live/dead cell discrimination was performed using Live/dead fixable blue dead cell staining kit (ThermoFisher Scientific). Cells were first stained with Abs for surface markers for 20-30 min at 4° C. Intracellular staining was done using a fixation/permeabilization kit (eBioscience). To quantify OVA-specific CD8 T-cells, single cell suspension was first stained with H-2Kb/SIINFEKL-Pentamer (ProImmune) for 10 min at room temperature before surface markers staining. For intracellular cytokine staining (ICS), cells were stimulated with or without SIINFEKL peptide for 36 hours and with Protein Transport Inhibitor (BD Bioscience) for the last 4 hours. After stimulation, cells were stained as described above for surface and intracellular proteins. To quantify cell numbers in tissue, a fixed number of CountBright Absolute Counting Beads (ThermoFisher Scientific) were added to each sample prior to acquiring. Samples were acquired on Fortessa X20 or LSR II (BD Bioscience) and analyzed using FlowJo software (TreeStar). See Supplementary Methods for a list of antibodies used.

Single-cell sorting RNA-sea analysis. On day 8 and 11 post tumor challenge, single cell suspensions of tumor were prepared using a mouse tumor dissociation kit (Miltenyi Biotec) and spleens were dissociated with gentle MACS Octo Dissociator. Tumors and spleens from the same treatment group were pooled and viable CD8$^+$ T cells were sorted by FACS. FACS sorted T cells were mixed with C1 Cell Suspension Reagent (Fluidigm) before loading onto a 5- to 10-µm C1 Integrated Fluidic Circuit (IFC; Fluidigm). LIVE/DEAD staining solution was prepared by adding 2.5 µL ethidium homodimer-1 and 0.625 µL calcein AM (Life Technologies) to 1.25 mL C1 Cell Wash Buffer (Fluidigm) and 20 µL was loaded onto the C1 IFC. Each capture site was carefully examined under a Zeiss microscope in bright field, GFP, and Texas Red channels for cell doublets and viability. Cell lysing, reverse transcription, and cDNA amplification were performed on the C1 Single-Cell Auto Prep IFC, as specified by the manufacturer (protocol 100-7168 E1). The SMARTer Ultra Low RNA Kit (Clontech) was used for cDNA synthesis from the single cells. Illumina NGS libraries were constructed using the Nextera XT DNA Sample Prep kit (Illumina), according to the manufacturer's recommendations (protocol 100-7168 E1). A total of 2,222 single cells were sequenced on Illumina NextSeq (Illumina) by multiplexed single-read run with 75 cycles. Raw sequence data (BCL files) were converted to FASTQ format via Illumina Casava 1.8.2. Reads were decoded based on their barcodes. Read quality was evaluated using FastQC (bioinformatics.babraham.ac.uk/projects/fastqc/).

Large Unilamellar Vesicles (LUVs). Phospholipids (79.7% POPC+10% POPS+10% DGS-NTA-Ni+0.3% Rhodatmine-PE) were dried under a stream of Argon, desiccated for at least 1 hour and suspended in 1× Reaction buffer (50 mM HEPES-NaOH, pH 7.5, 150 mM NaCl, 10 mM MgCl2, 1 mM TCEP). LUVs were prepared by extrusion 20 times through a pair of polycarbonate filters with a pore size of 200 nm, as described previously.

LUV Reconstitution and Phosphotyrosine Western Blot. Proteins of interest were pre-mixed at desired ratios in 1× Reaction Buffer containing 0.5 mg/ml BSA, and then mixed with LUVs (1 mM total lipids). The proteins-LUVs mixture incubated at room temperature for 1 hour, during which the His-tagged proteins bound to the liposomes whereas other proteins remained in the extravesicular solution. 2 mM ATP was then in injected and rapidly mixed, to trigger phosphorylation, dephosphorylation and protein interactions at the membrane surface. The reactions were allowed to proceed at room temperature for 30-60 min, and terminated with SDS sample buffer. The samples were heated at 95° C. for 5 min, and subjected to SDS-PAGE. Proteins were transferred to nitrocellulose membranes using iBlot™ Dry Blotting system (ThermoFisher Scientific). The membranes were blocked with 5% BSA in Tris-buffered saline (pH 7.4) with 0.1% Tween-20, incubated with desired phosphotyrosine specific antibodies, and detected with HRP based enhanced chemiluminescence. The following primary antibodies used: anti-pY142-CD3ζ (BD Biosciences #558402), anti-pY20 (Santa Cruz Biotechnology #sc-1624, for detection of tyrosine phosphorylated CD28 in reconstitution assays), anti-pY418-Src (BD Biosciences #560095, for detection of pY394-Lck), anti-pY505-Lck (Cell Signaling #2751), anti-pY315-ZAP70 (Abcam #ab60970), anti-pY493-ZAP70 (Cell Signaling #2704).

Clinical biopsies handling, RNA extraction and RNA-seq. Biopsies were homogenized in at least 600 uLs RLTPlus, with mercaptoethanol added (Sigma Aldrich), on the Omni Shredder (Omni-Inc) for 1 minute at 22,000 RPM. RNA and DNA were extracted using the Qiagen Allprep DNA/RNA Mini Kit (Qiagen) according to the manufactures instructions in the "AllPrep DNA/RNA Mini Handbook" (November 2005) using the protocol on page 26 "Protocol: Simultaneous Purification of Genomic DNA and Total RNA from Animal Tissues." The optional DNAse digestion outlined in Appendix E was used during RNA extraction. An additional 500 uL 70% ethanol wash with a 2-minute spin was run after the Buffer AW2 wash, but before the last drying spin, to remove excess salts from the DNA extraction. RNA was quantified on the Nanodrop (ThermoFisher Scientific), and quality was assessed on the Fragment Analyzer (Advanced Analytical) with the 'Standard Sensitivity RNA Analysis Kit' (Advanced Analytical) according to the manufacture's protocol. DNA was quantified with the Qubit dsDNA BR Assay Kit (ThermoFisher Scientific) on the Infinite M200 Pro (Tecan) according to the custom protocol 'Using the Tecan Microplate Reader for DNA Quantification (BR dsDNA Assay). Completed samples were stored at −80° C. in barcoded screw cap tubes. For RNA-seq, strand-specific RNA-seq libraries were prepared from 100 ng total RNA using KAPA stranded mRNA-Seq Kit (KAPA Biosystems) and the libraries with size between 400 to 600 bp were selected using Pippin system (Sage Science). Pair end 2×100 bp sequencing was done using Illumina 2500. RNA-seq reads was QCed and aligned to the reference genome and gene expression was quantitated using Array Studio (Omicsoft).

Statistical Analysis. Sample sizes were chosen empirically to ensure adequate statistical power and were in the line with field standards for the techniques employed in the study. Statistical significance was determined with ANOVA or un-paired two-tailed Student's t-test assuming unequal variance at P<0.05 level of significance (or indicated in figure legends).

Results

Figure 16E:
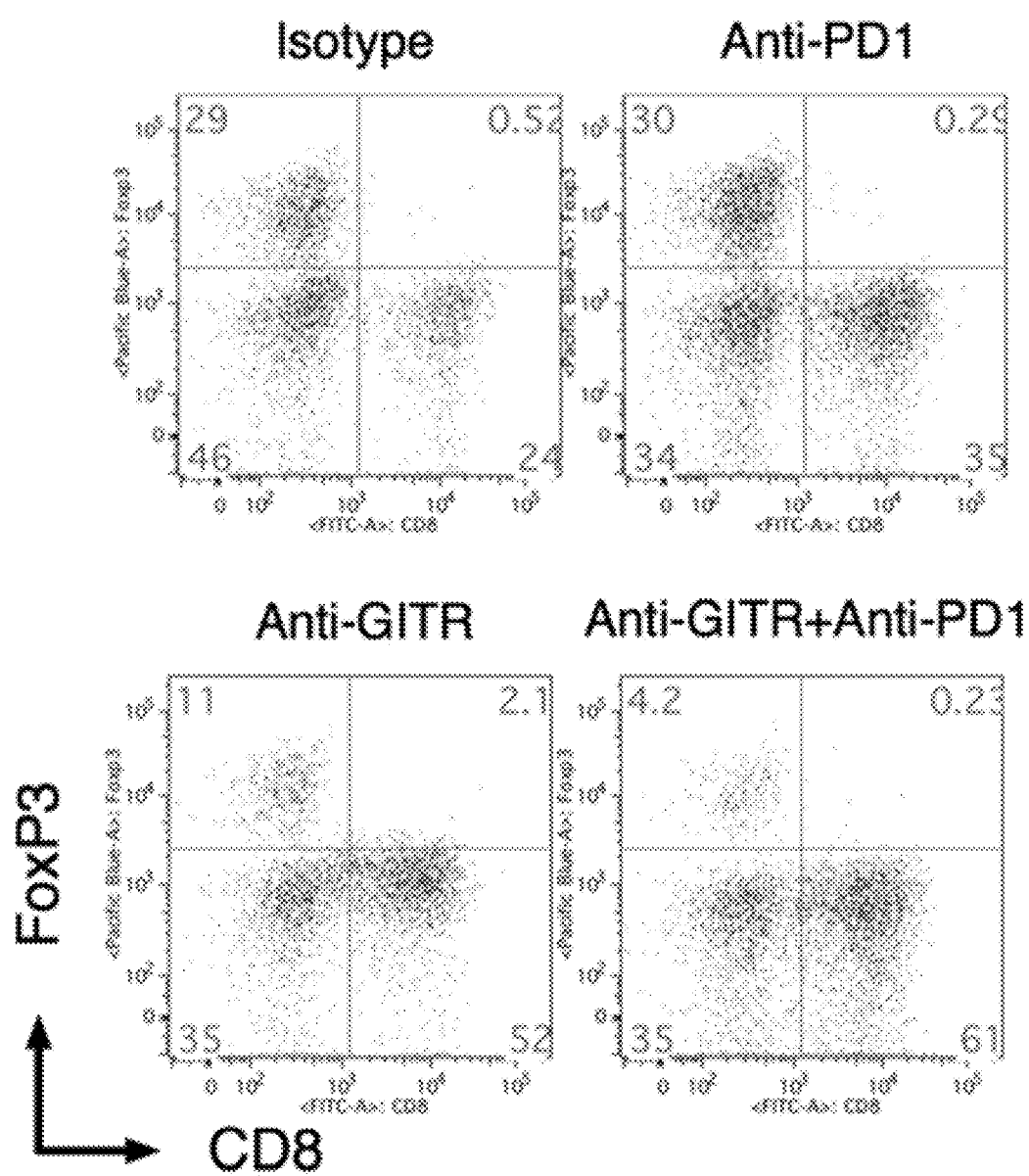
Figure 16F:
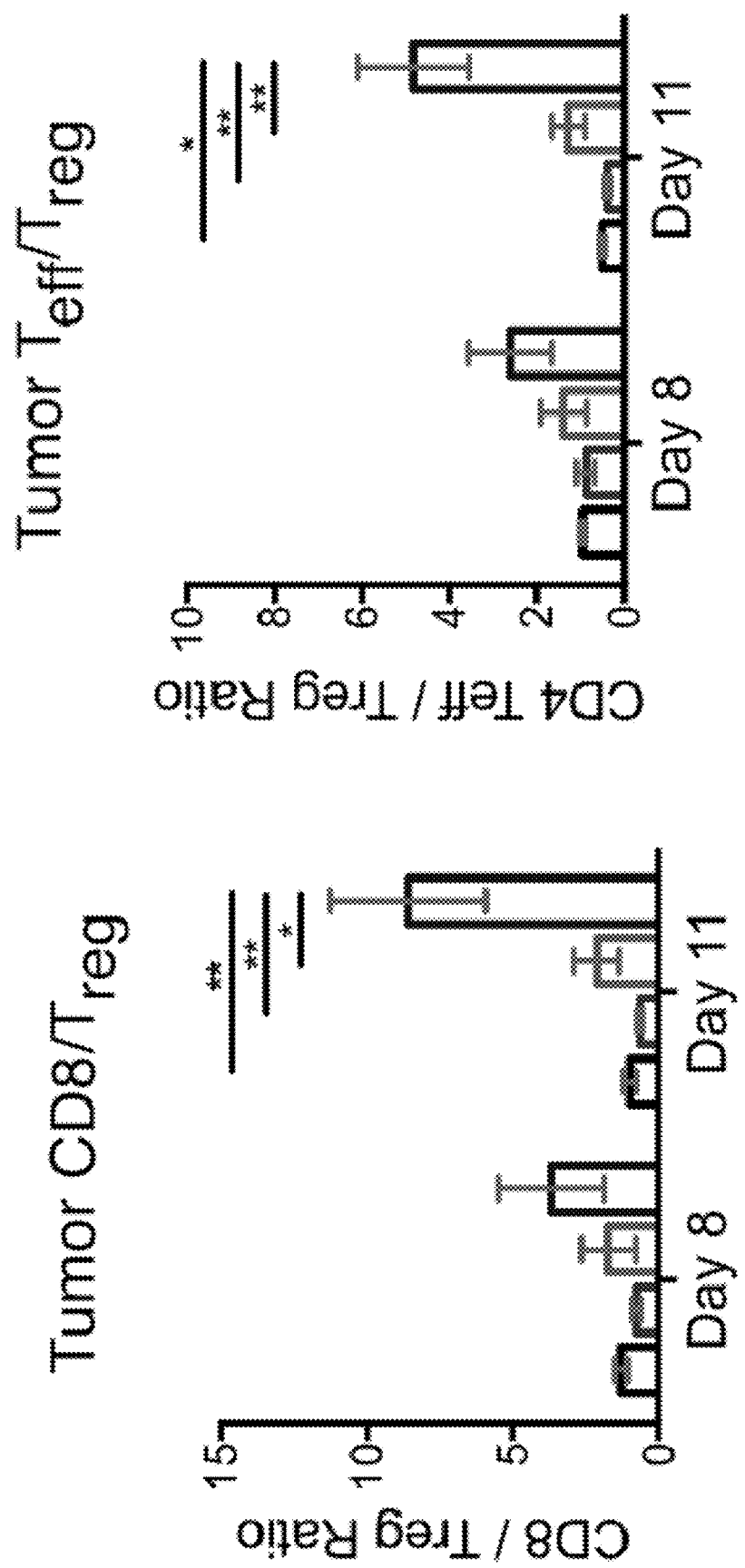
Figure 16J:
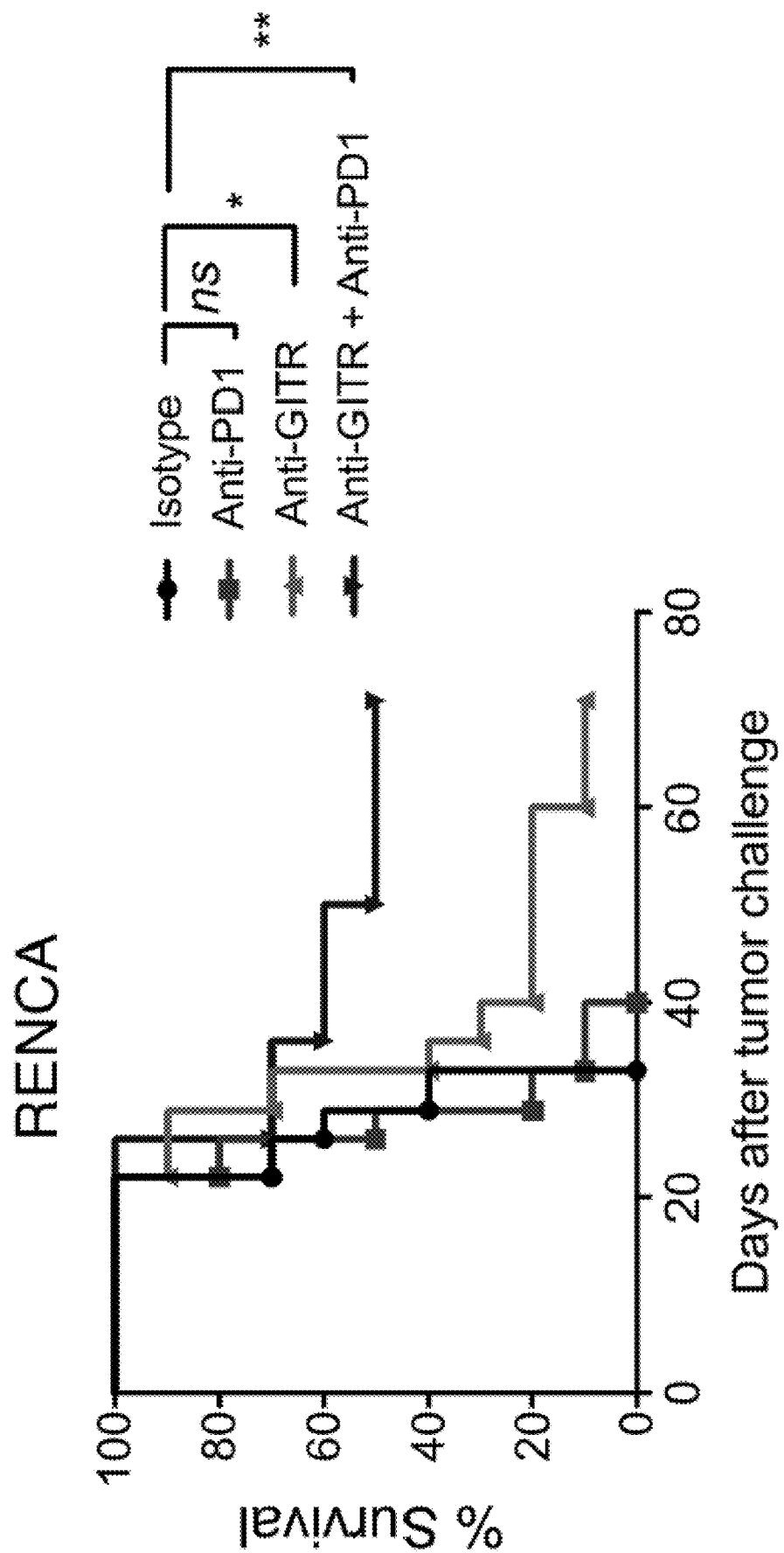

To examine the effect of combination immunotherapy poorly immunogenic tumor models (MC38 and RENCA) were used. Although variable reduction of tumor volume and modestly prolonged survival have been reported, monotherapy with anti-PD-1 or anti-GITR Ab is not effective at inducing complete and durable tumor regression in established tumors. Here, antibodies were administrated 6 and 13 days post-tumor challenge when tumors were palpable. Consistent with published data, anti-GITR or anti-PD-1 treatment alone showed no or little effect. Combination therapy synergistically eradicated tumors in the majority (12 tumor free out of 17) of the mice (FIG. 16A) and promoted long-term survival (70% of mice were tumor-free for >80 days) FIG. 16B), in a CD8$^+$ T cell-dependent manner (FIGS. 16C and 16D), and increased the ratio of intratumoral CD8$^+$/T$_{reg}$ and CD4$^+$ T effector (T$_{eff}$)/T$_{reg}$ cells (FIGS. 16E, 16F) in agreement with previous data. After 50 days, only 0-2 of 17 mice were tumor free and 0-10% were alive in monotherapy treated groups (FIGS. 16A, 16B). Further, the dysfunctional state of the intratumoral CD8$^+$ T cells was significantly reversed only upon combination treatment, as indicated by restored ex viva proliferation potential (expression of Ki67, FIG. 16G) and effector function (expression of granzyme A and granzyme B, FIGS. 16H and 16I). The synergistic anti-tumor effect of combination treatment associated with better survival rate was also confirmed in a second mouse RENCA tumor model (FIG. 16J).

Figure 10A:
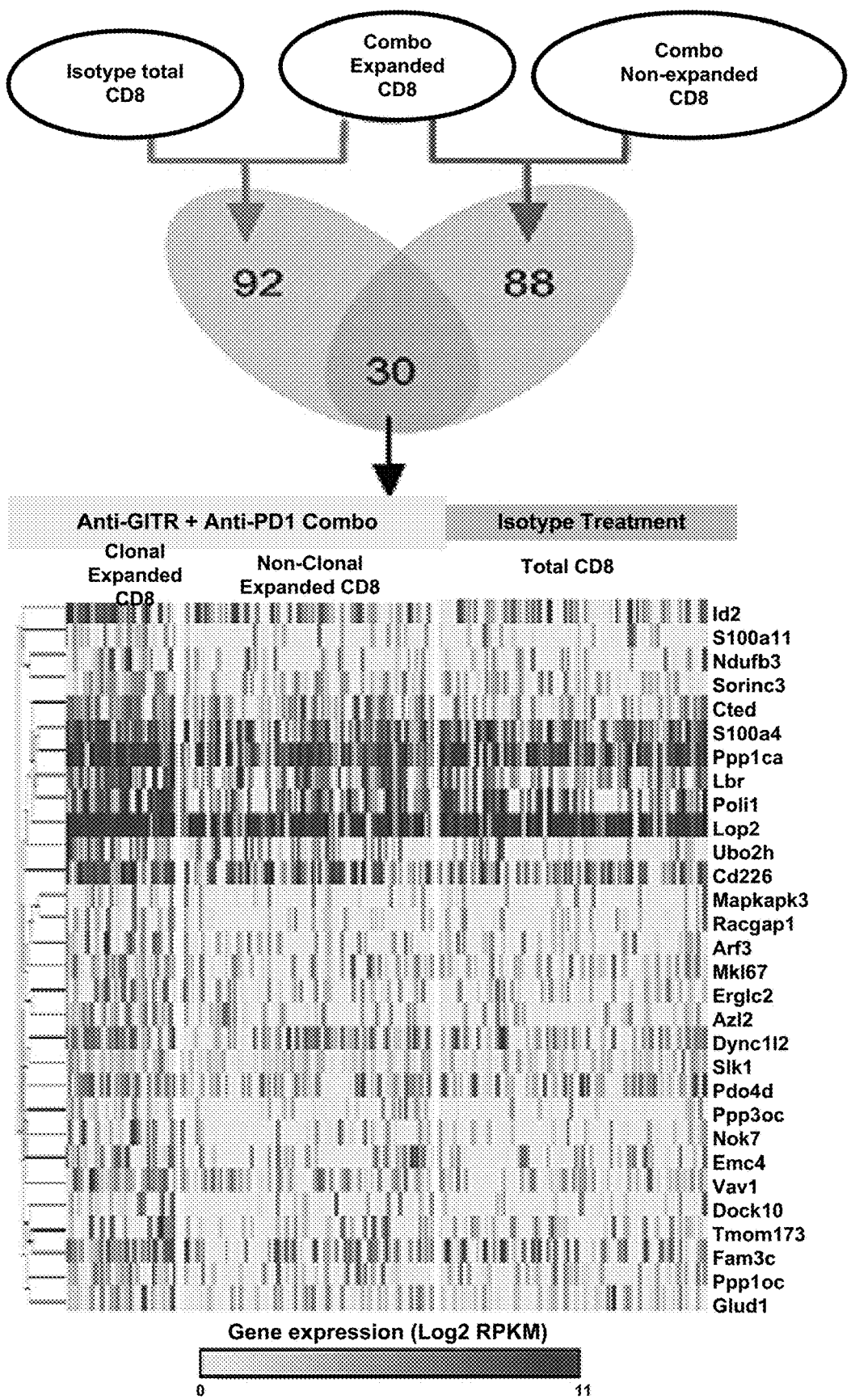
FIGS. 10A-D show the identification of unique gene signature in clonally expanded CD8+ T cells. 10a, Genes upregulated in clonally expanded CD8+ T cells from combination therapy comparing to CD8+ T cells with isotype treatment or non-expanded CD8+ T cells with combination treatment (day 11). Venn diagram shows the number of genes significantly increased (p<0.01, fold change ≥2) comparing indicated CD8+ T cell population. Heat map shows thirty genes overlapping between the comparison. 10b, Identification of genes specifically upregulated in clonally expanded CD8 T cells from combination therapy. Schematic and Venn diagram shows different comparison. 10c, Cumulative distribution function (CDF) plots shows the expression of a uniquely regulated gene by combination treatment, CD226, in total, clonal expanded or non-expanded CD8+ T cells. 10d. Fold changes of CD226 expression level between indicated. CD8+ T cell population (Number indicates fold changes; NS, not significant).
Figure 10B:
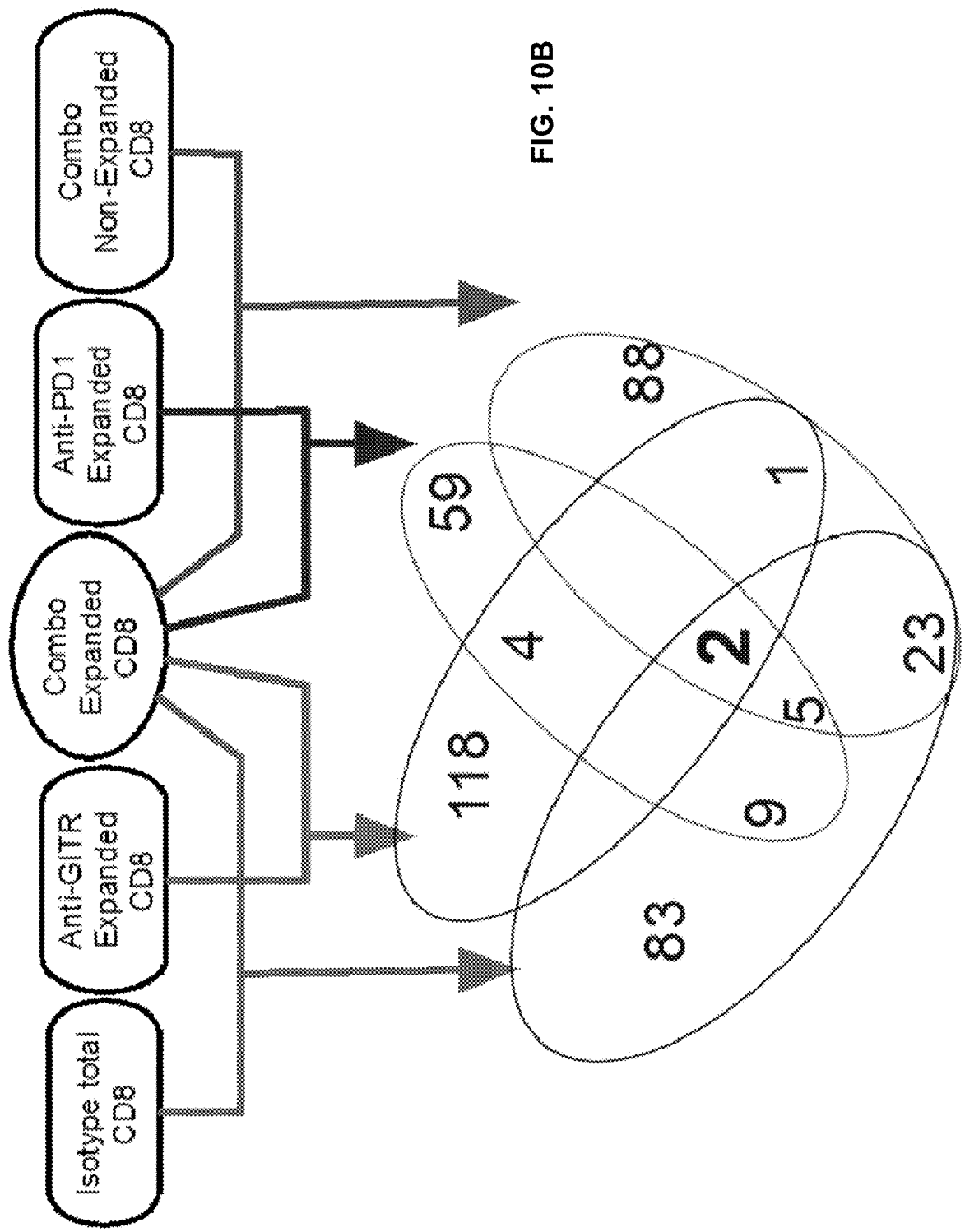
Figure 10C:
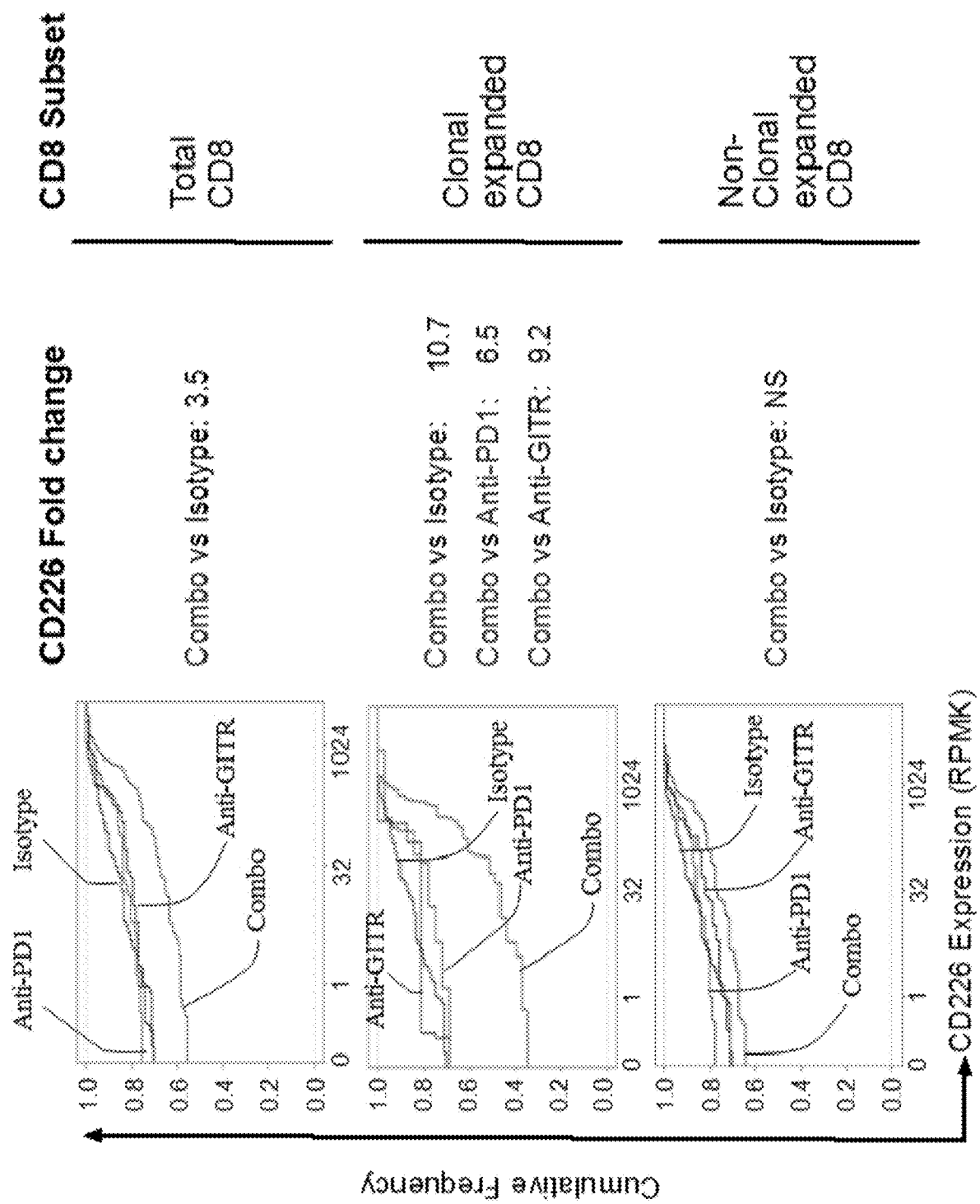
Figure 10D:
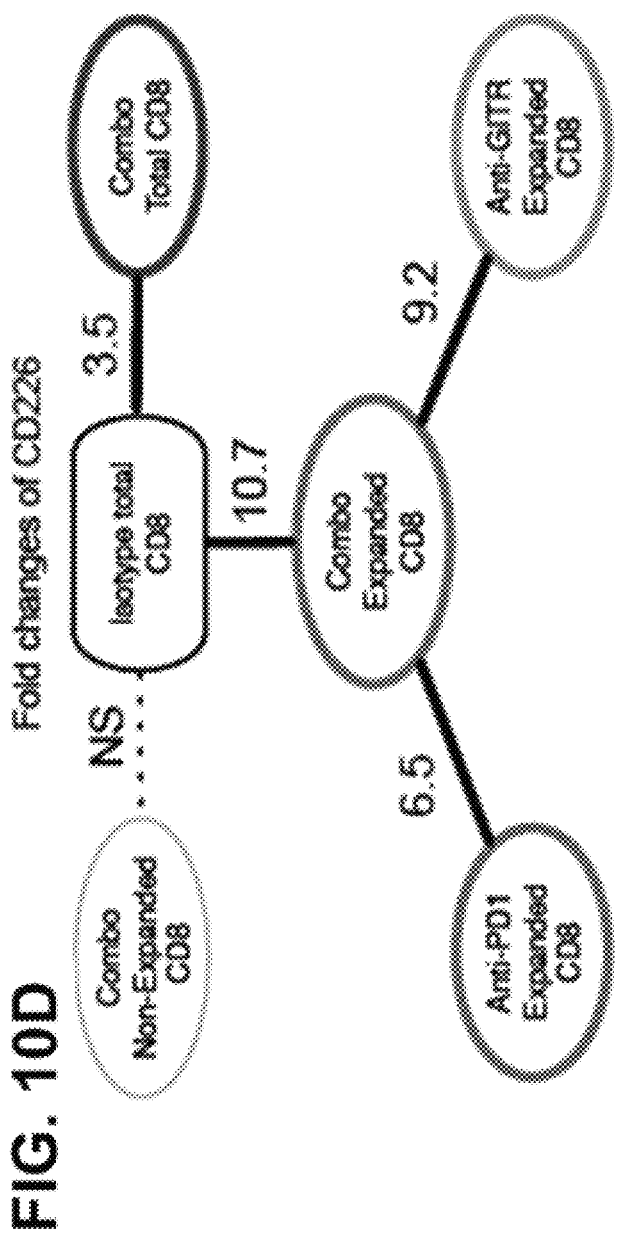

To identify unique gene signatures in clonally expanded CD8$^+$ T cells (tumors harvested at day 11) from combination treatment samples, comprehensive comparisons were performed across different treatment groups. First, an RNA signature change in 30 genes after combination treatment was observed, which it was even more significant within the expanded CD8 T cell population (FIG. 10A and FIG. 20). Next, a four-way comparison was performed across all groups to identify genes specifically regulated upon combination versus monotherapy treatment (FIG. 10B). CD226 was identified as one of the two genes shared across different comparison pairs (FIG. 10B). CD226 is a costimulatory molecule that plays an important role in anti-tumor response. Expression analysis of different subsets of intratumoral CD8$^+$ T cells (total, clonally expanded, or non-expanded) across treatment groups (FIG. 10C) revealed that CD226 mRNA levels were significantly increased by combination treatment on clonally expanded T cells (fold change=10.7), while this difference was diluted in bulk (fold change=3.5) and non-expanded CD8$^+$ T cells (not significant) (FIG. 10D). Further, CD226 mRNA levels were significantly increased by combination treatment on clonally expanded CD8 T cells in comparison to anti-PD-1 (fold change=6.5) and anti-GITR (fold change=9.2) (FIG. 10D). This observation stresses the importance of performing genome profiling on putative tumor-reactive clones (high-frequency T cell clones) to unmask critical gene changes.

Figure 11A:
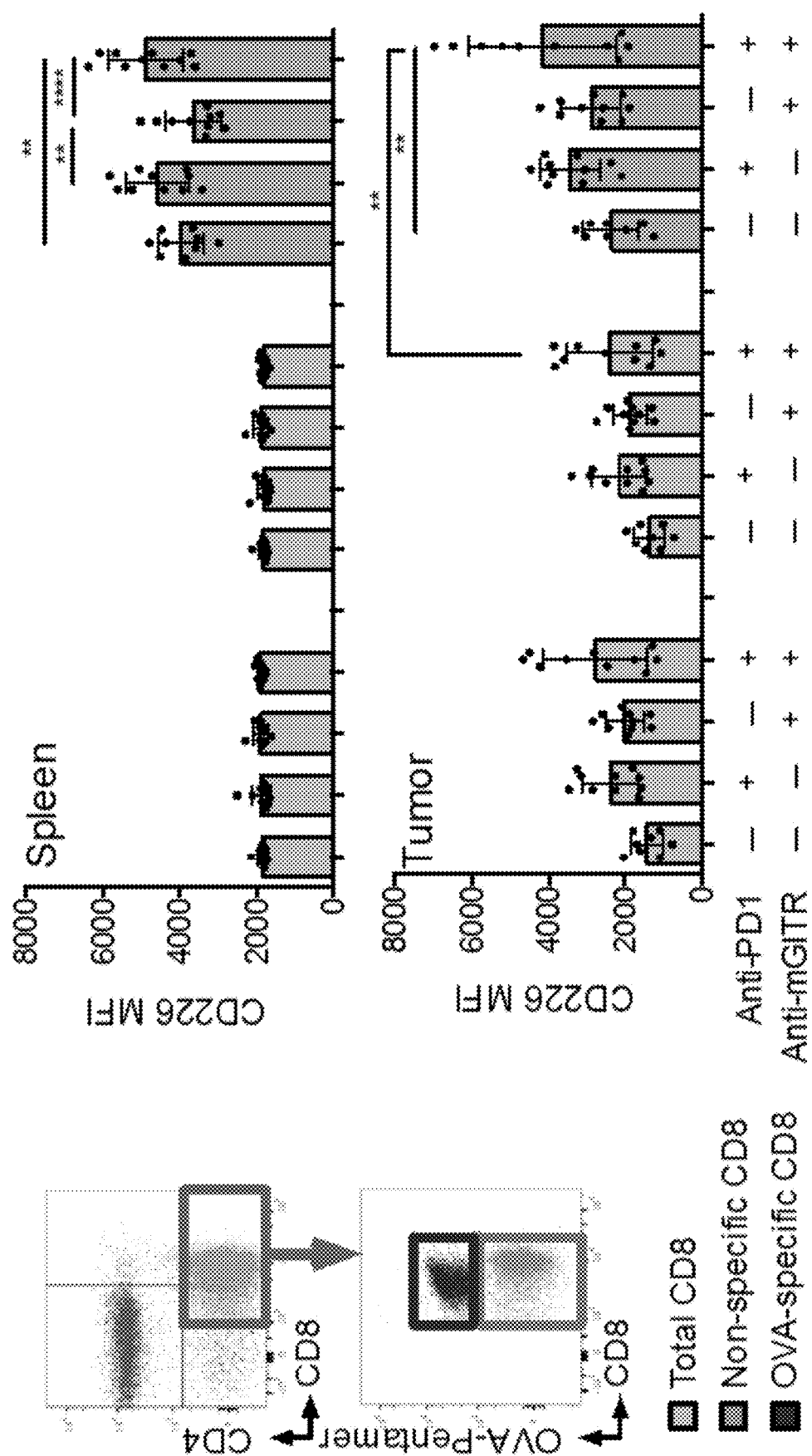
FIGS. 11A-11D show combination treatment synergistically regulates CD226/TIGIT pathway favoring anti-tumor immunity. 11a, FACS analysis of CD226 expression (MFI) on spleen and tumor antigen-specific CD8+ T cell populations, gating strategy indicated in FACS plots. Data show one representative experiment out of two independent experiments (n=9-10 mice per group). In the graphs, total CD8 are four bars on left, Non-specific CD8 are four bars in the middle and Ova-specific CD8 are the four bars on the right. 11b, Schematic shows large unilamellar vesicles (LUVs), reconstituted different components (CD3 and CD226) involved in T cell signaling on the liposomes together with key component of cytosolic tyrosine kinase lck, Zap70, and SLP76, PI3K (p85a), known to be recruited by phosphorylated costimulatory receptor. 11c, CD226, but not CD3ζ, is sensitive to PD-1 bound Shp2. Shp2-containing reactions with increasing PD-1 concentrations terminated at 30 min, and subject to SDS-PAGE and phosphotyrosine Western blots (WB). 11d, FACS analysis of TIGIT expression on spleen and tumor T cell subsets (8 days after tumor implantation). Data show one representative experiment out of two independent experiments (n=9-10 mice per group). (*, p<0.05, , p<0.01, *, p<0.001, One-way ANOVA, Tukey's multiple comparison test).

To evaluate the expression levels of CD226 on intratumoral CD8 T cells after combination treatment MC38 specific TCR clones were tracked in vivo using recently published mutated MC38 tumor epitopes. This approach was not successful. The inability of these T cell clones to recognize previously characterized MC38 tumor neo-epitopes could reflect the different mutation status of tumor cell lines between laboratories, likely due to genome instability of the tumor cells. To functionally validate the findings, an MC38 tumor cell line expressing H-2Kb single-chain trimer of MHC class I with SIINFEKL peptide and $\beta_2$m (OVA-$\beta_2$m-K$^b$) was generated (FIG. 21A), and used SIINFEKL as a surrogate tumor epitope. Consistent with the TCR clonality analysis, anti-PD-1 Ab or combination treatment with anti-GITR induced significant clonal expansion of OVA-specific CD8$^+$ T cells (using K$^b$/OVA pentamer staining) in tumor infiltrating T cells, but only the combination treatment significantly increased the intratumoral density of the Ag-specific CD8$^+$ T cell clones (FIG. 21B). Further, only combination treatment significantly expanded OVA-specific CD8$^+$ T cells in spleen (FIG. 21B) compared to control groups, thus extending previous findings. These clonally expanded OVA-specific T cells were functional and produced higher level of IFNγ upon restimulation with OVA peptide than controls (FIG. 21C). Importantly, using the MC38-OVA-$\beta_2$m-K$^b$ model, it was found that baseline levels of CD226 were highest on spleen OVA-specific CD8$^+$ T cells after anti-PD1 treatment (FIG. 11A) and were further elevated by combination treatment with anti-GITR and anti-PD-1 Ab. The same treatment had no significant effect on the CD226 levels of non-specific CD8$^+$ T cells. Overall anti-PD-1 treatment played a dominant role in driving the increase of CD226 (FIG. 11A) providing key information on the mode of action of anti-PD-1 in anti-tumor immunity.

Figure 11C:
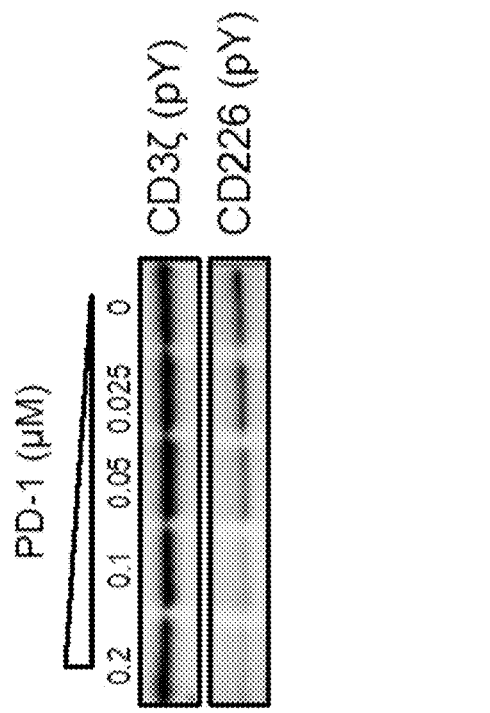
Figure 11B:
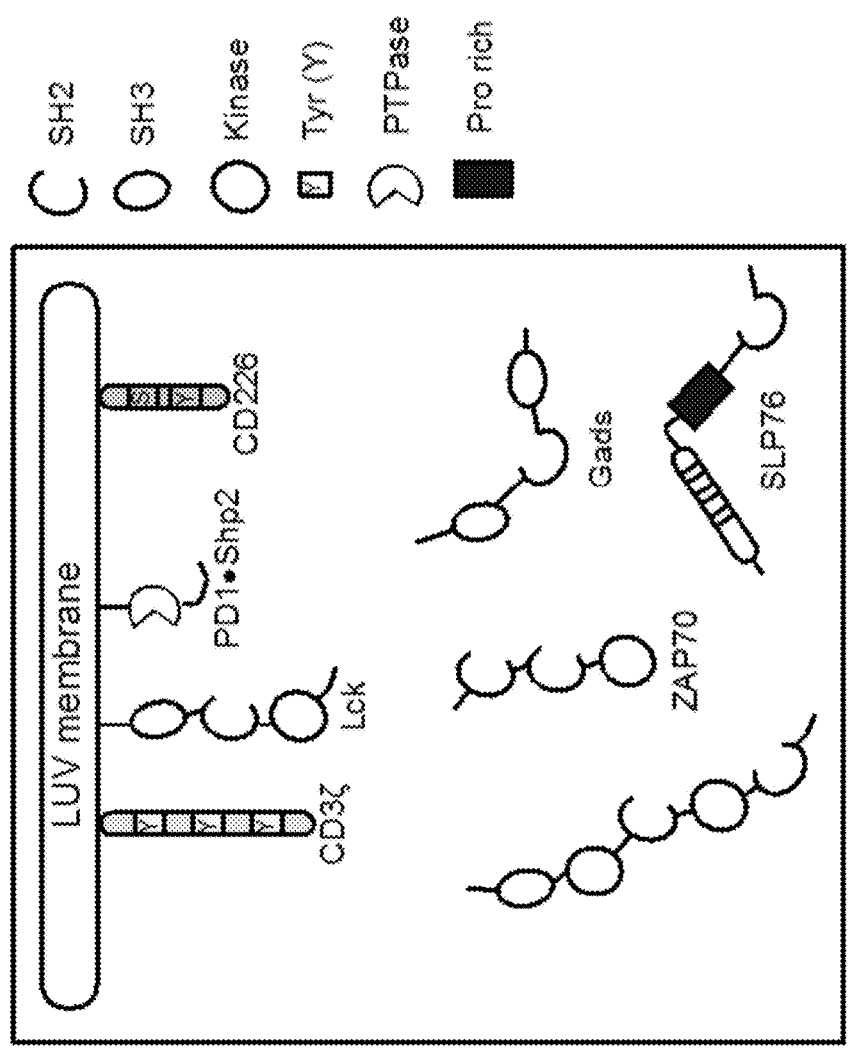

Next, an association between PD1 and CD226 molecules was investigated. Recent data demonstrated a highly specific recruitment of Shp2 by PD1 using Fluorescence Energy Transfer (FRET)-based assay in a cell-free reconstitution system in which cytoplasmic domain of PD1 was bound to the surface of large unilamellar vesicles (LUVs) that mimic the plasma membrane of T cells. To examine if CD226 is a target for desphosphorylation by the PD1-Shp2 complex different components (CD3, CD226, and legend/method) involved in cell signaling were reconstituted on the liposomes (FIG. 11B). The sensitivity of each component in response to PD-1 titration on the LUVs was measured by phosphotyrosine (pY) western blots. Previous published data showing that TCR/CD3ζ was not a sensitive target to desphosphorylation by PD-1-Shp2 was confirmed (FIG. 11C). Importantly, it was found that CD226 was very efficiently dephosphorylated by PD1-Shp2 in a dose dependent manner (FIG. 11C). The data demonstrate an association between PD-1 and CD226.

Figure 11D:
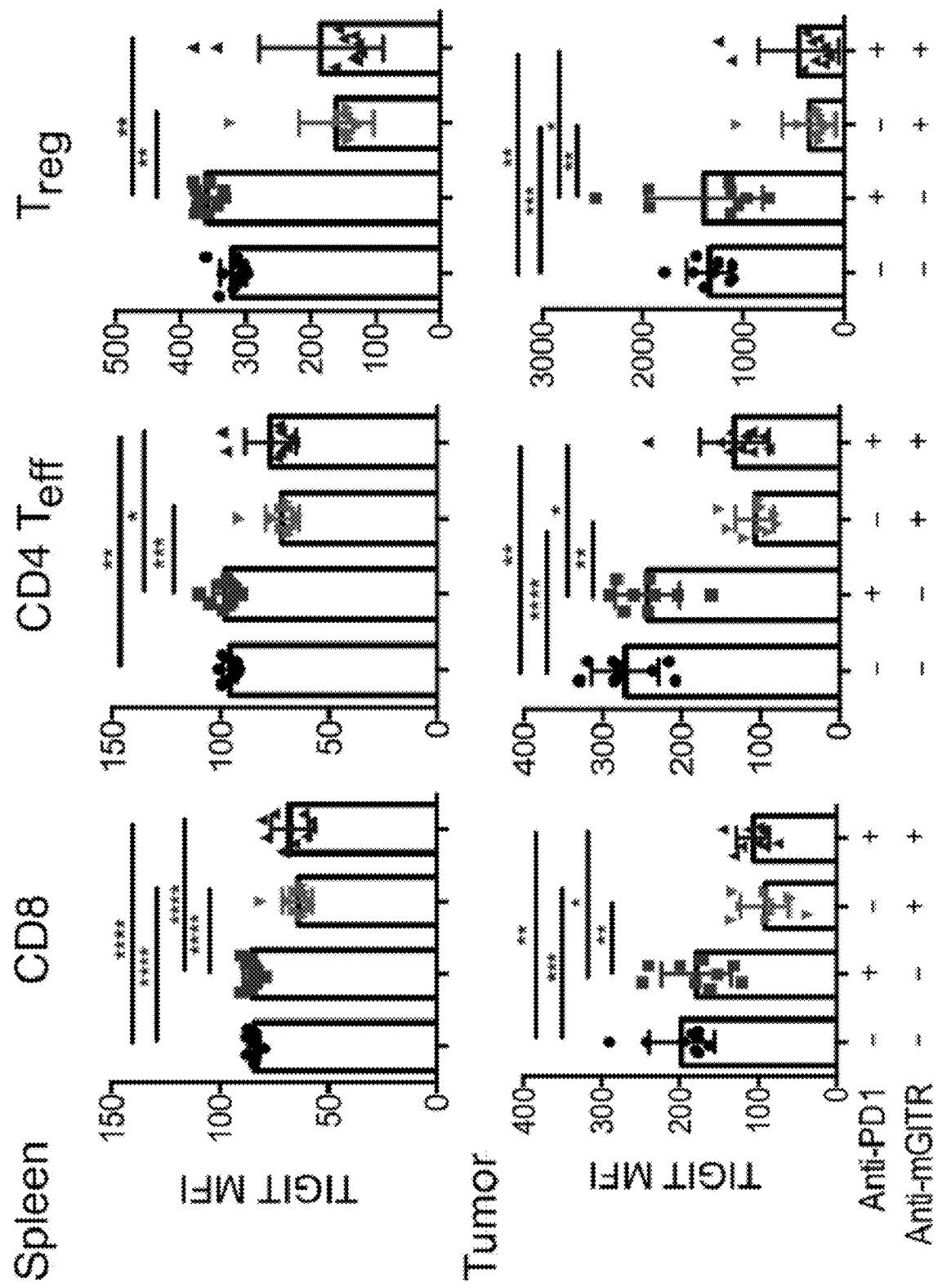
Figure 22A:
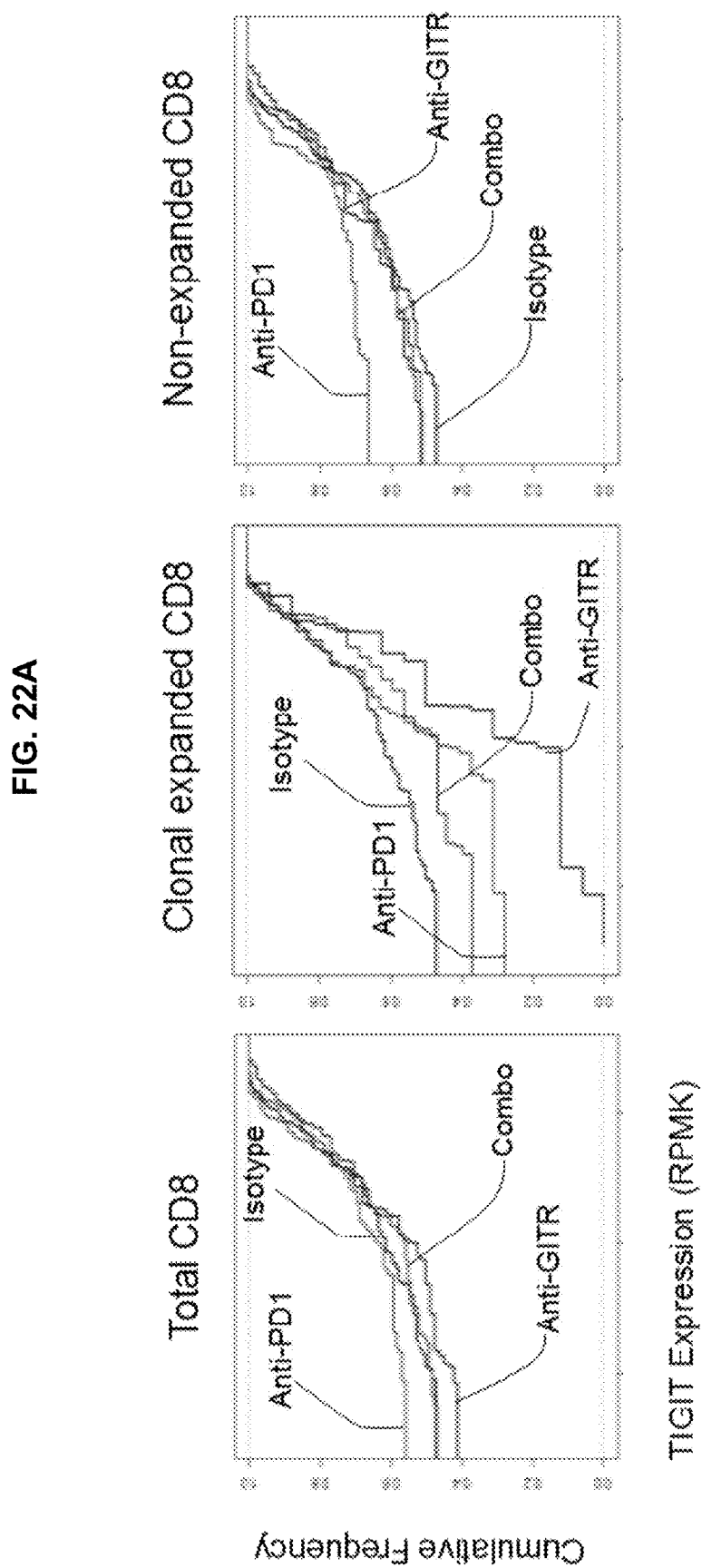
Figure 22B:
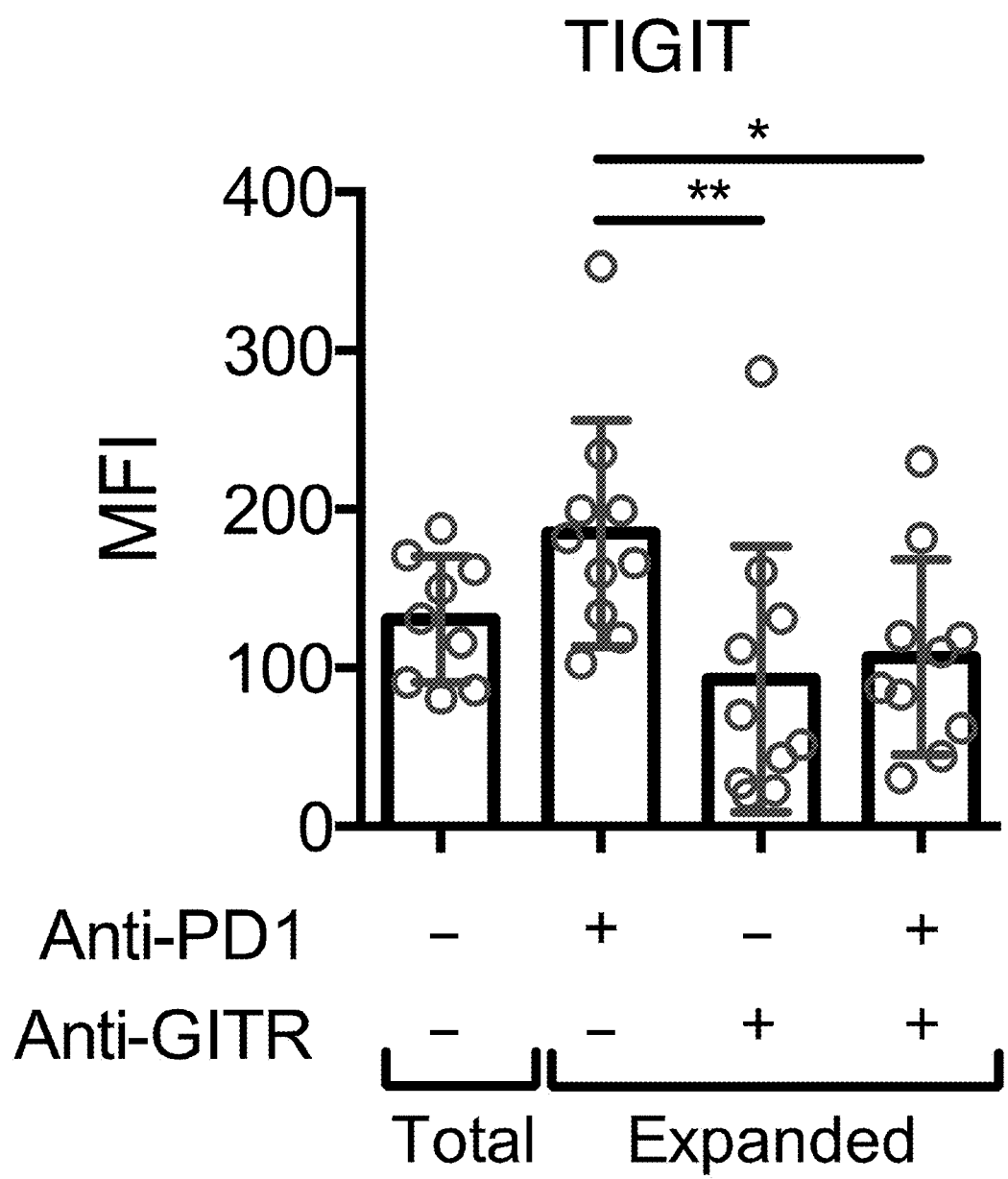
Figure 22C:
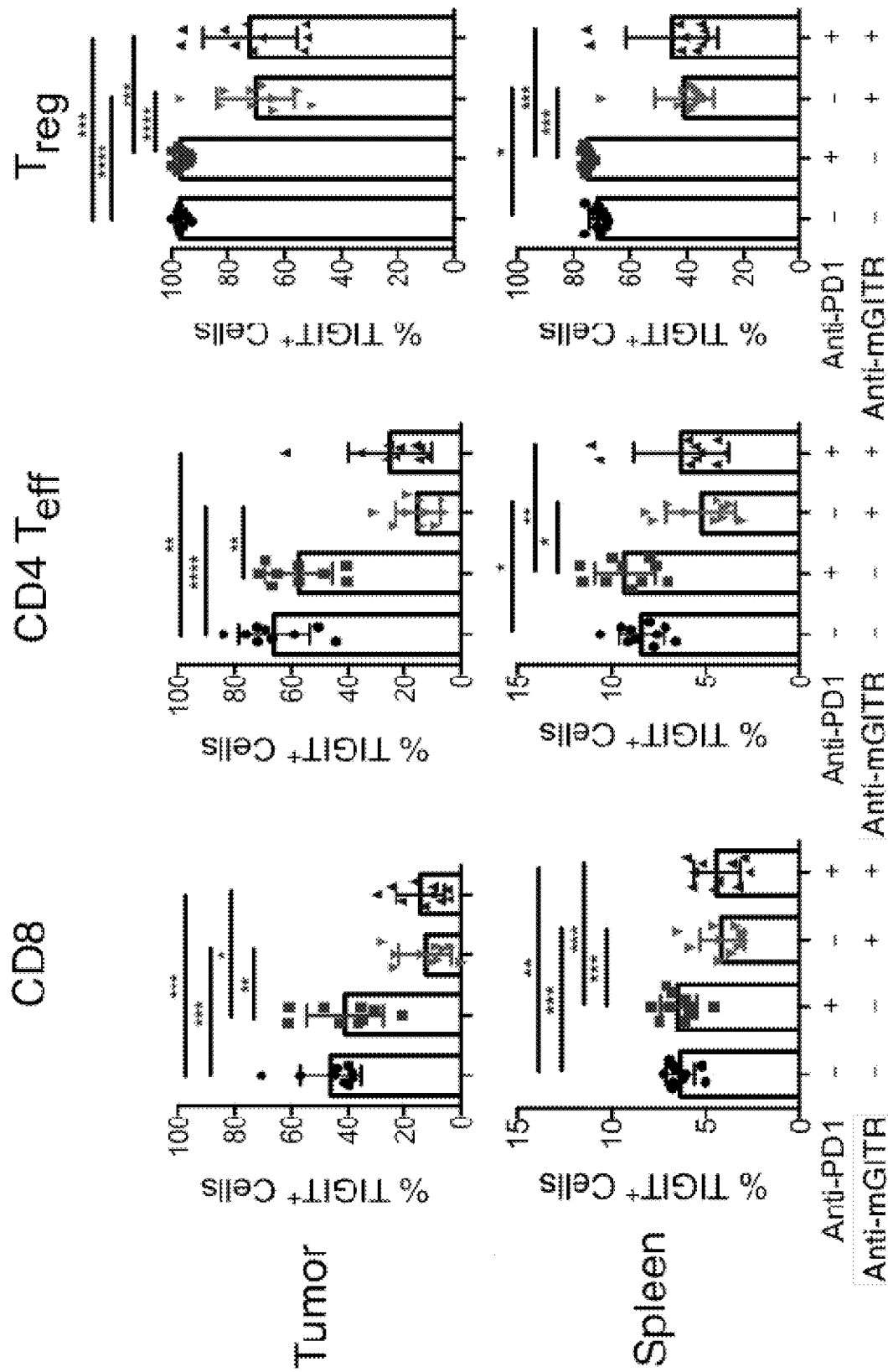
Figure 22D:
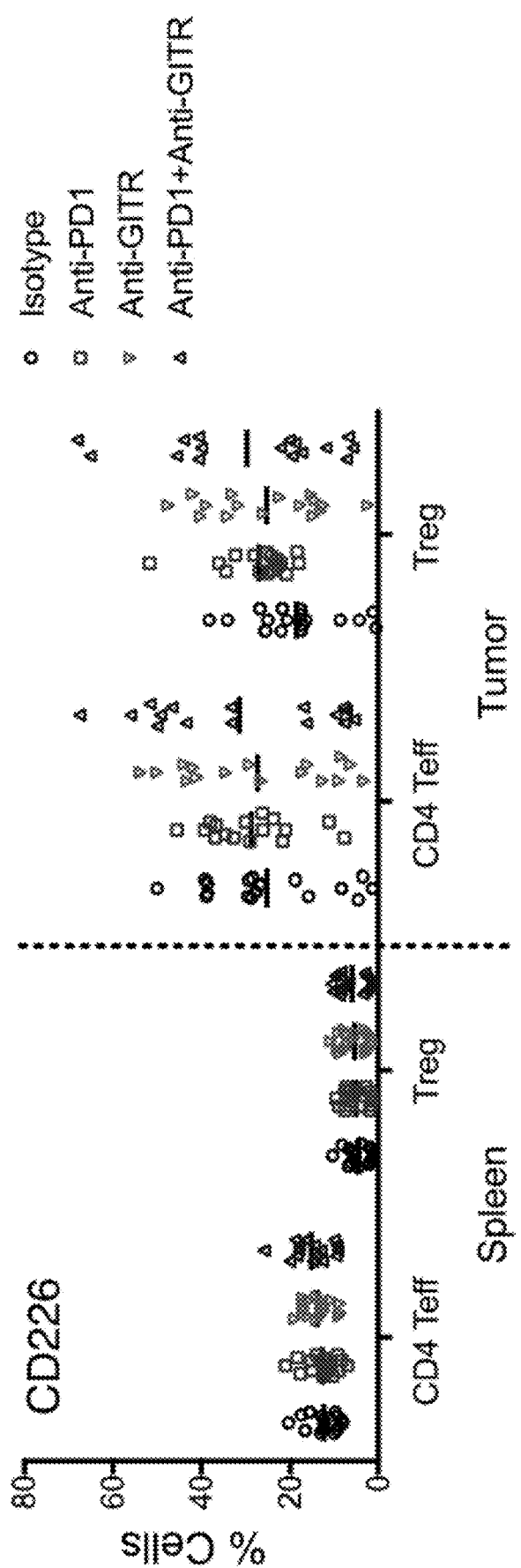

It has been recently shown that the strength of CD8$^+$ T cell response is impacted by the overall balance between CD226 and co-inhibitory receptor TIGIT. Interestingly, using single cell RNA-seq it was found that anti-GITR Ab treatment increased TIGIT transcripts in high-frequency T cell clones (FIG. 22A), while FACS analysis showed a significant decrease in expression of TIGIT on OVA-specific CD8$^+$ T cells (FIG. 22B). This result is consistent with the previous finding that TIGIT expression is tightly regulated at the post-transcriptional level. Both cis- and trans-inhibitory mechanisms have been proposed for the TIGIT/CD226 signaling pathway, therefore the net outcome can result from the balance between the expression level of CD226 on CD8$^+$ T cells and TIGIT on both CD8$^+$ T cells and stand by lymphocytes. Indeed, combination treatment significantly decreased the percentage of TIGIT$^+$ cells and the expression level on a per cell basis on bulk tumor infiltrating CD8$^+$, CD4$^+$ T$_{eff}$ and T$_{reg}$ cells, the effect of which was mainly driven by anti-GITR Ab treatment (FIG. 11D and FIG. 22C). Surprisingly, this effect was also found in spleen T cell subsets (FIG. 11D and FIG. 22C). Combination and/or monotherapy treatment had no effect on bulk CD226$^+$ tumor infiltrating or splenic CD4$^+$ and T$_{reg}$ cells (FIG. 22D). Overall single-cell sorted RNA-seq and FACS phenotyping data showed that anti-PD-1 favored the expression of CD226, while anti-GITR treatment down-regulated surface expression of TIGIT, synergistically restoring the homeostatic T cell function.

Figure 12A:
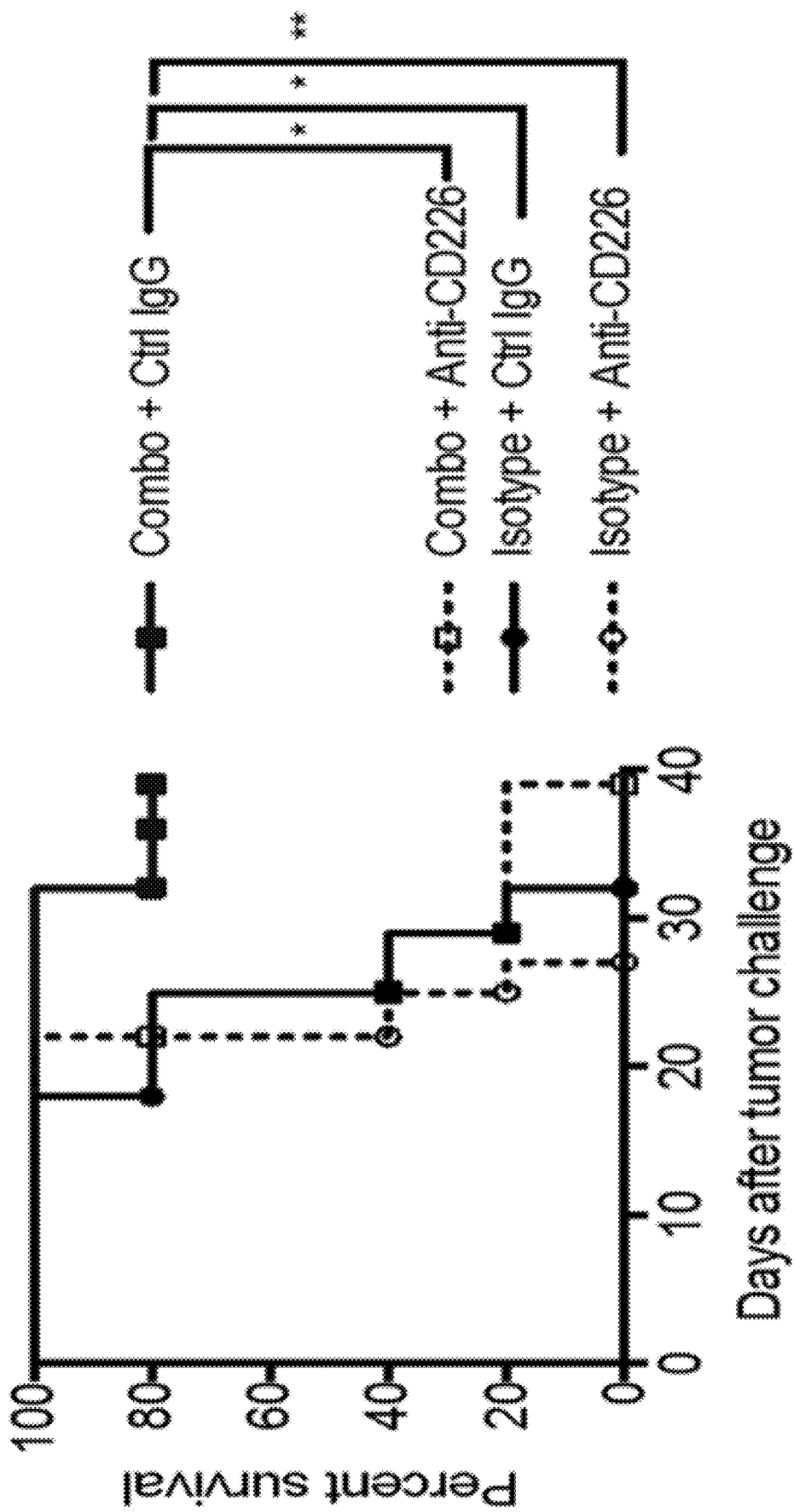
FIGS. 12A-12H shows CD226 signaling pathway plays a crucial role in mediating anti-tumor response induced by combination treatment. 12a, MC38 tumor bearing mice were treated with either CD226 blocking Ab or isotype IgG prior to immunotherapy with anti-GITR+anti-PD-1 or isotype IgGs. Percentage of survival are shown here. Data show one representative experiment out of three independent experiments (n=5 mice per group). 12b, CD226 KO mice or WT littermates were challenged with MC38 tumor cells and treated with either anti-GITR+anti-PD-1 Ab or isotype Abs. on day 6, 13 after tumor implantation. Data show one representative experiment out of two independent experiments (n=7-8 mice per group). (12c-12e) Effectiveness of combination treatment doesn't rely on CD28, OX40 and 4-1BB pathway. 12c, Blocking CD28 signaling with CTLA-4-Ig (10 mg/kg), 12d, Blocking OX40 signaling with OX40L blocking antibody (10 mg/kg). 12e, Blocking 4-1BB signaling with 4-1BBL blocking antibody (10 mg/kg). Data shown are survival curves (n=10 mice per group). 12f, Schematic of anti-PD1 clinical study. 12g, RNA-seq analysis of tumor biopsies shows that CD226 transcripts were significantly increased after anti-PD-1 Ab treatment in advanced cancer patients (n=43, paired t-test). 12h, TCGA data analysis of CD226 transcript expression level and overall survival in patients with indicated cancer types. (*, p<0.05, , p<0.01, *, p<0.001, Log-rank test for survival analysis).
Figure 12B:
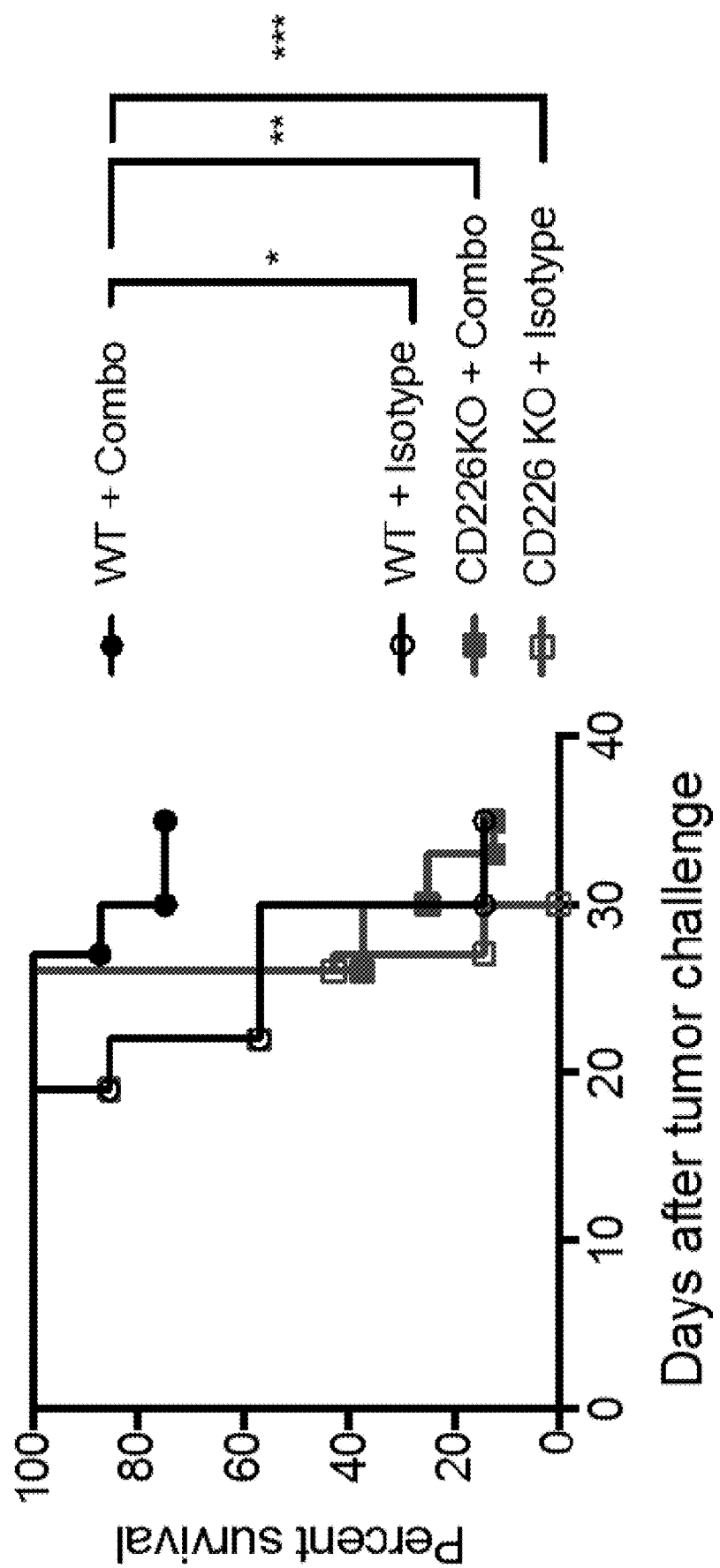
Figure 12C:
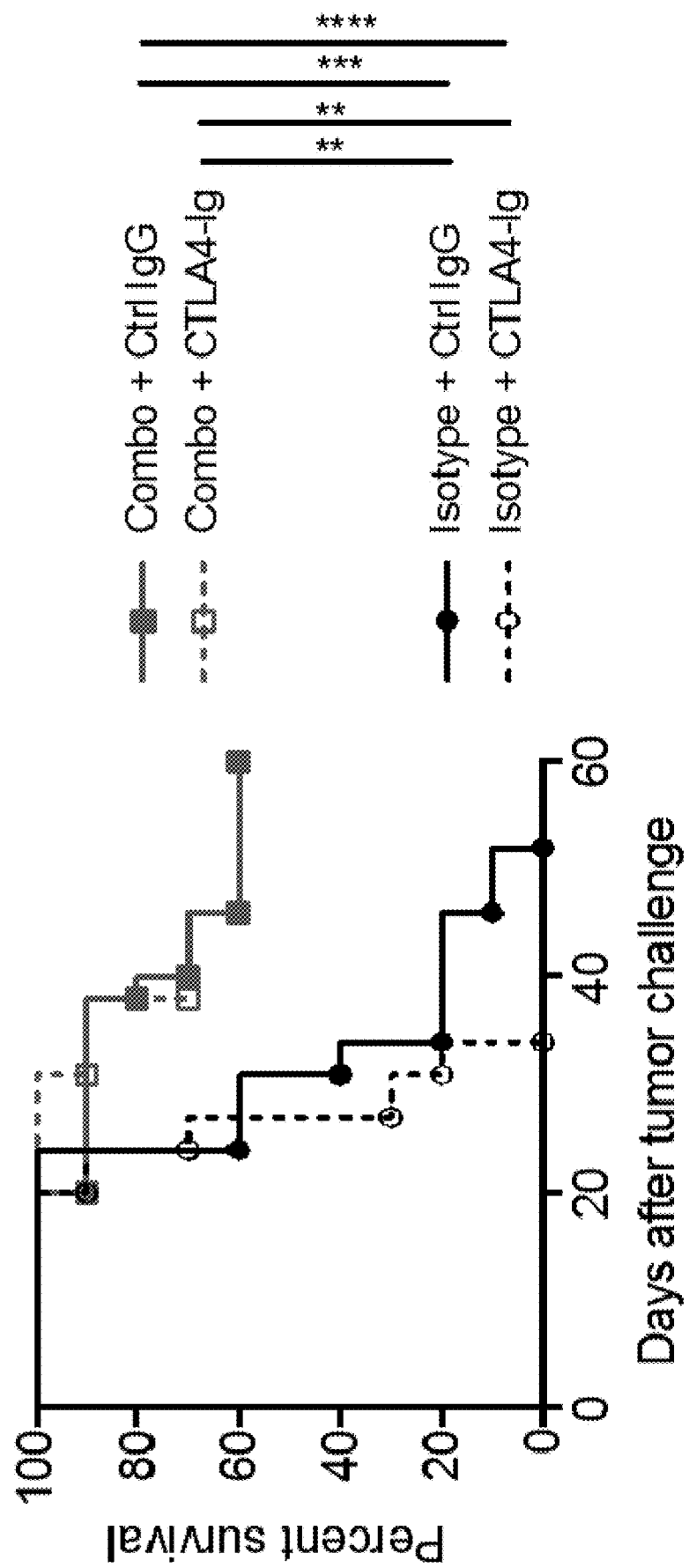
Figure 12D:
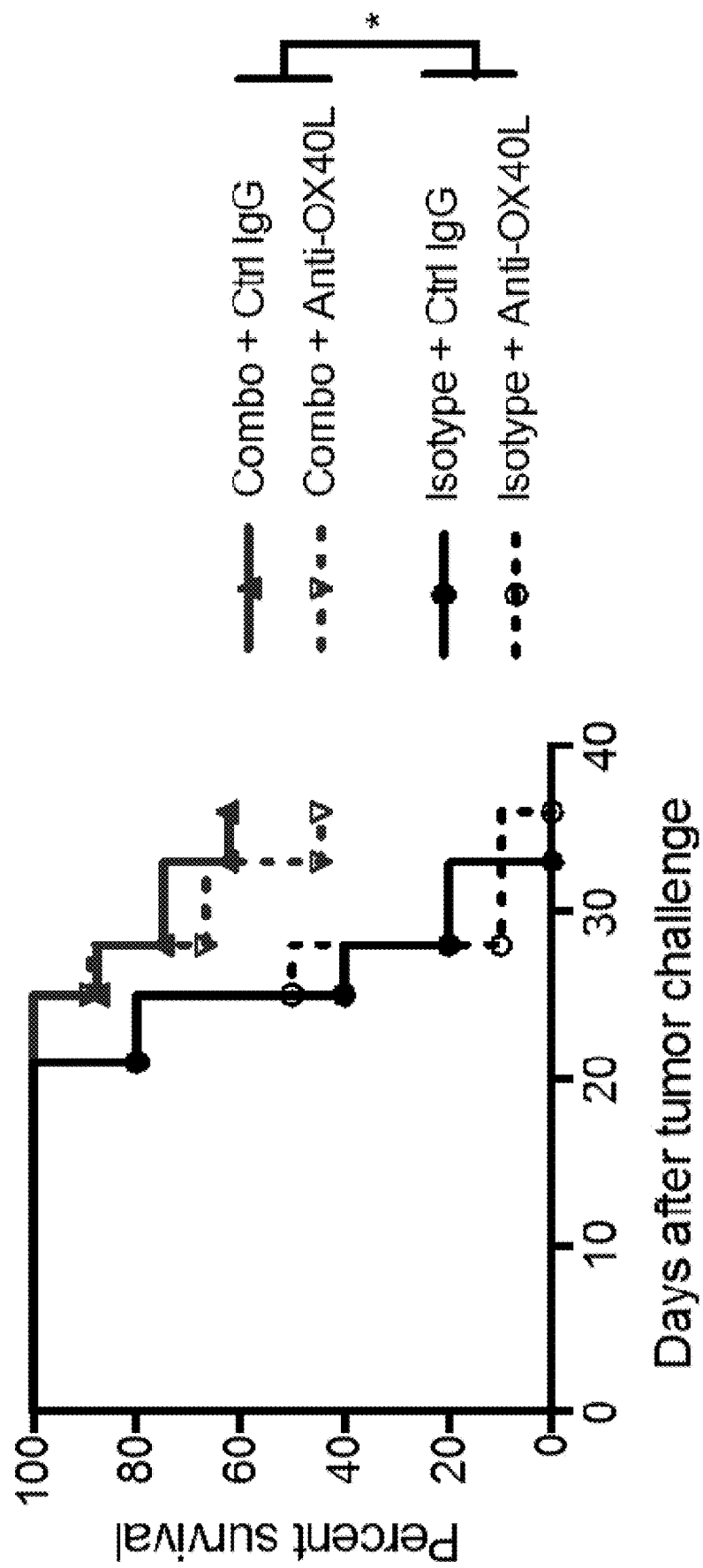
Figure 12E:
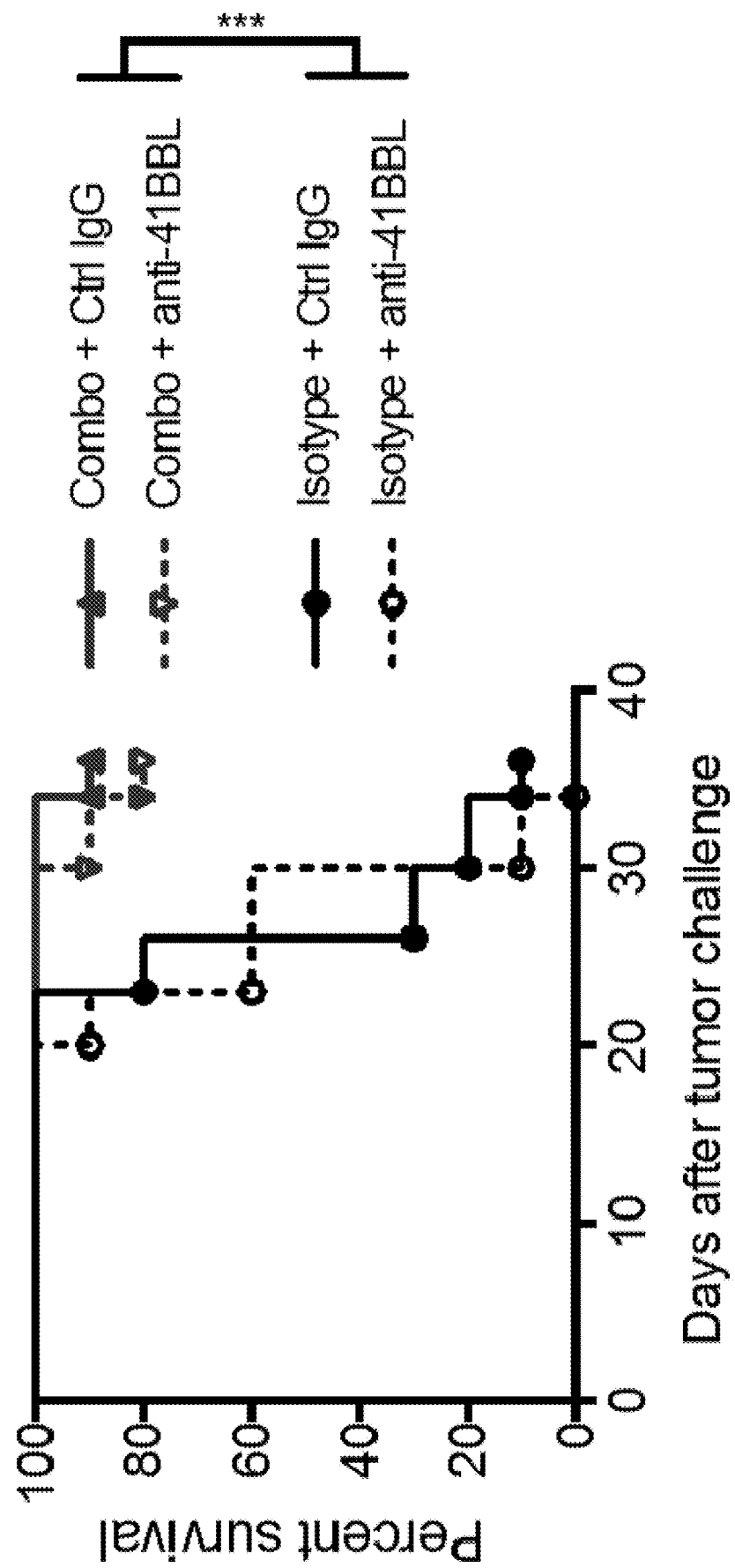
Figure 23A:
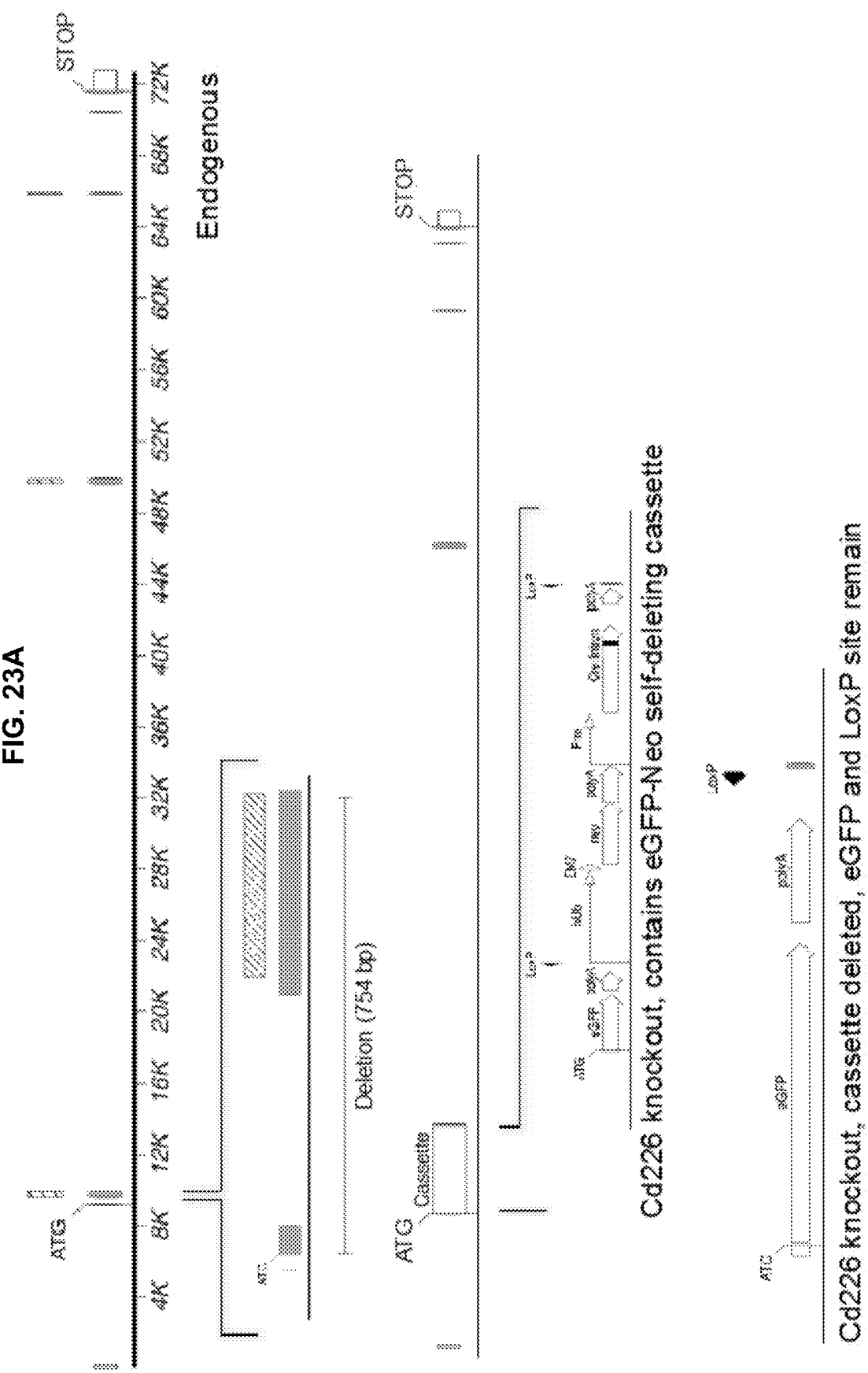
Figure 23B:
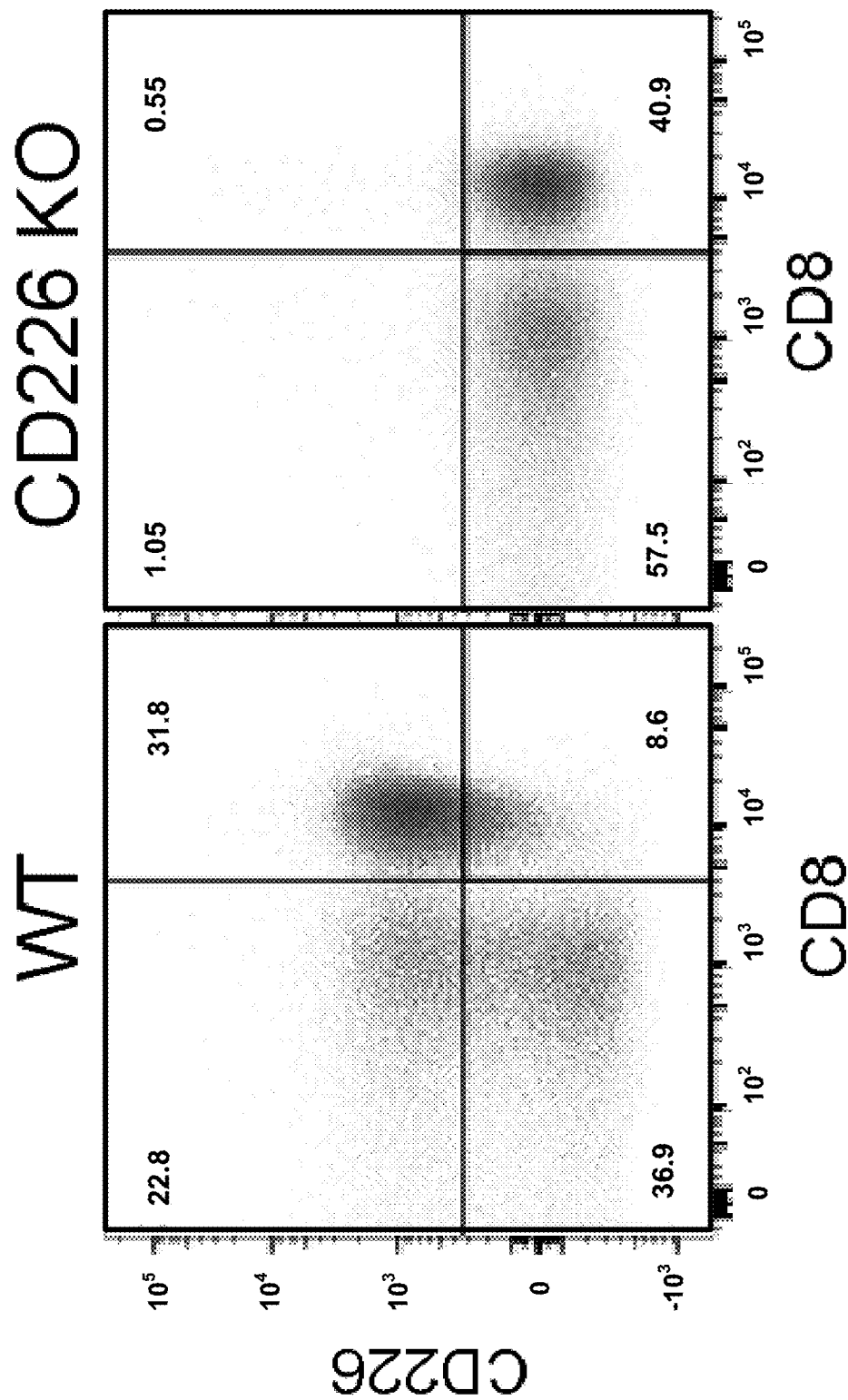
Figure 23C:
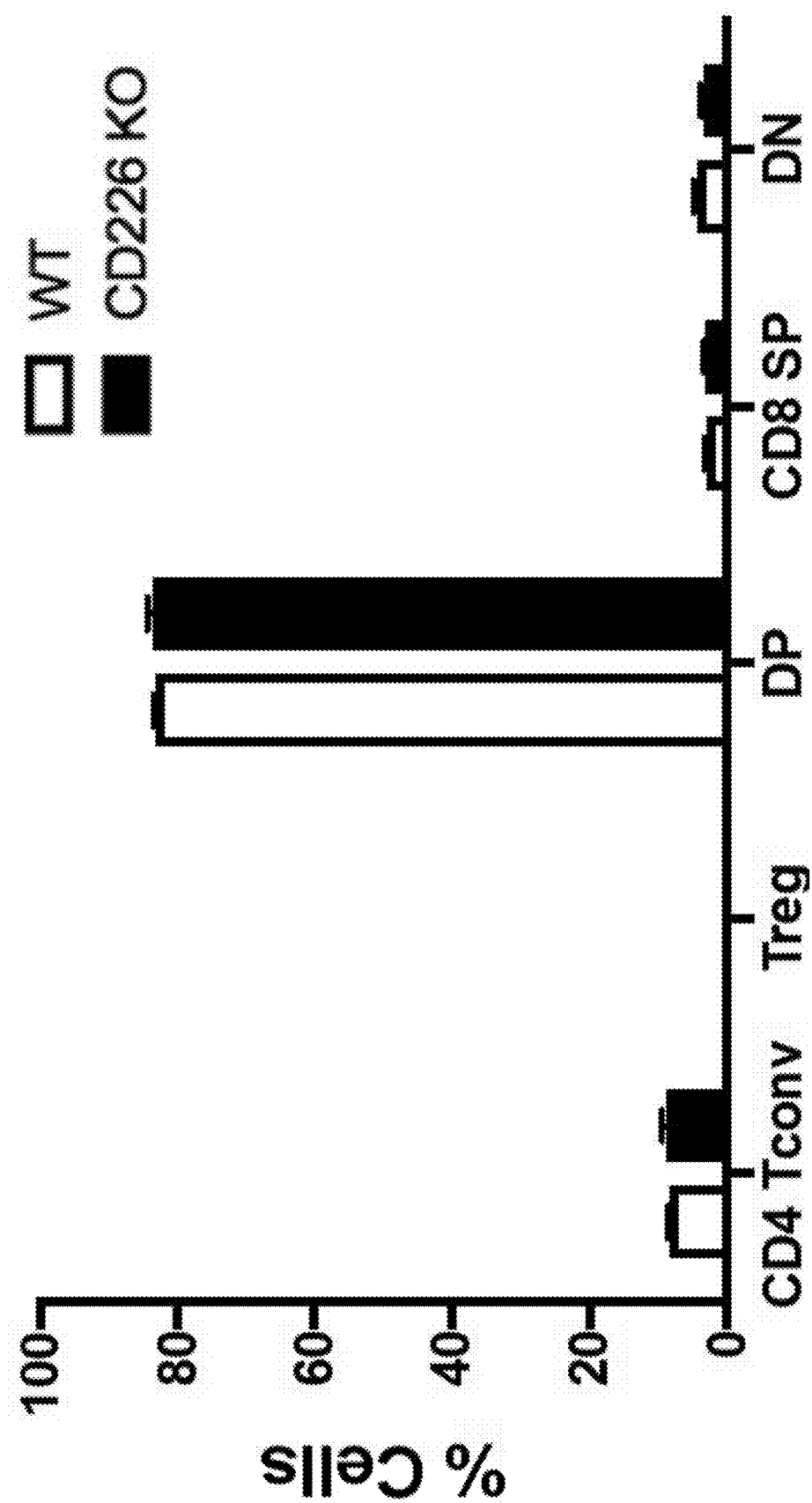
Figure 23D:
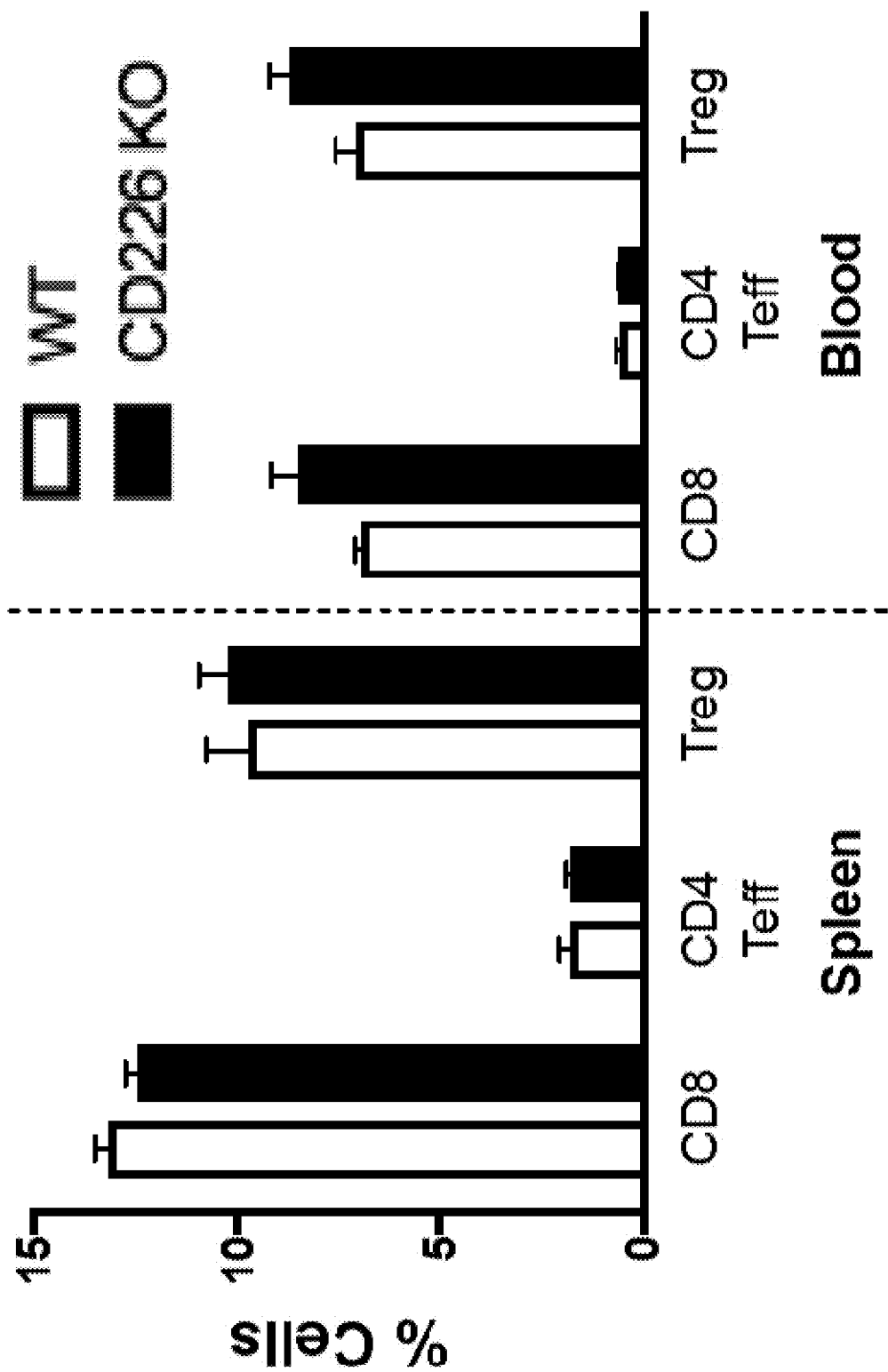
Figure 23E:
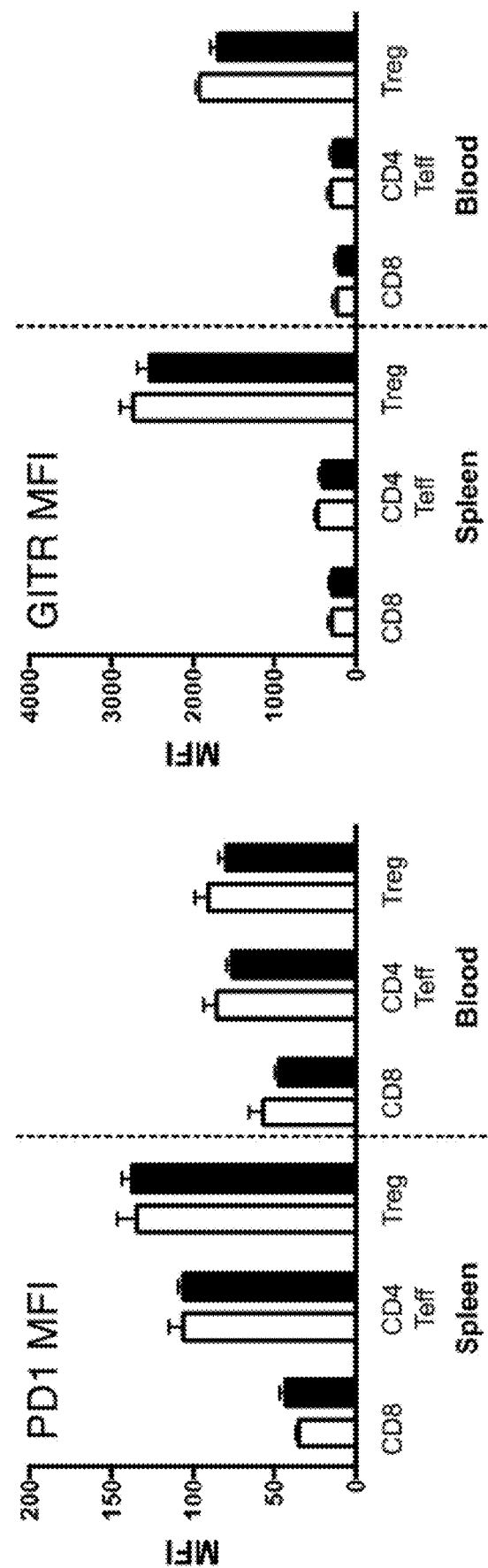
Figure 23F:
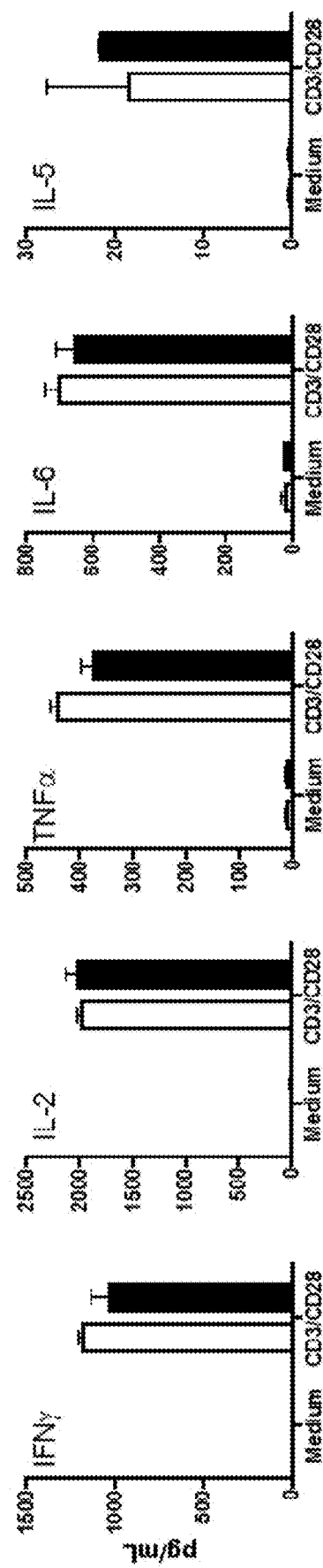

Using a CD226 blocking mAb, it was shown that costimulatory signaling through CD226 is required for the antitumor immunity mediated by combination treatment (FIG. 12A). However, as CD226 Ab could have a potential depleting effect on subset of CD8 T cells, CD226 was genetically inactivated in C57BL/6 background mice to repeat this study (FIGS. 23A, B). CD226$^{-/-}$ mice showed no defect on T cell (CD4$^+$, CD8$^+$, T$_{regs}$) homeostasis (FIGS. 23C-E) and responded similarly to wild-type mice to TCR activation (FIG. 23F). Importantly, it was found that combination treatment no longer conferred anti-tumor effect or survival benefit in CD226$^{-/-}$ mice, indicating that CD226 was essential for observed anti-tumor effects of the combination (FIG. 12B). In addition, the specificity of the CD226 pathway mediating the effect was validated, as inhibition of other members of the TNF receptor superfamily (OX40L or 4-1BBL) or blockade of the B7 costimulatory molecule (CD28) using CTLA4-Ig preserved the anti-tumor effect mediated by the combination therapy (FIG. 12C-E).

Figure 24A:
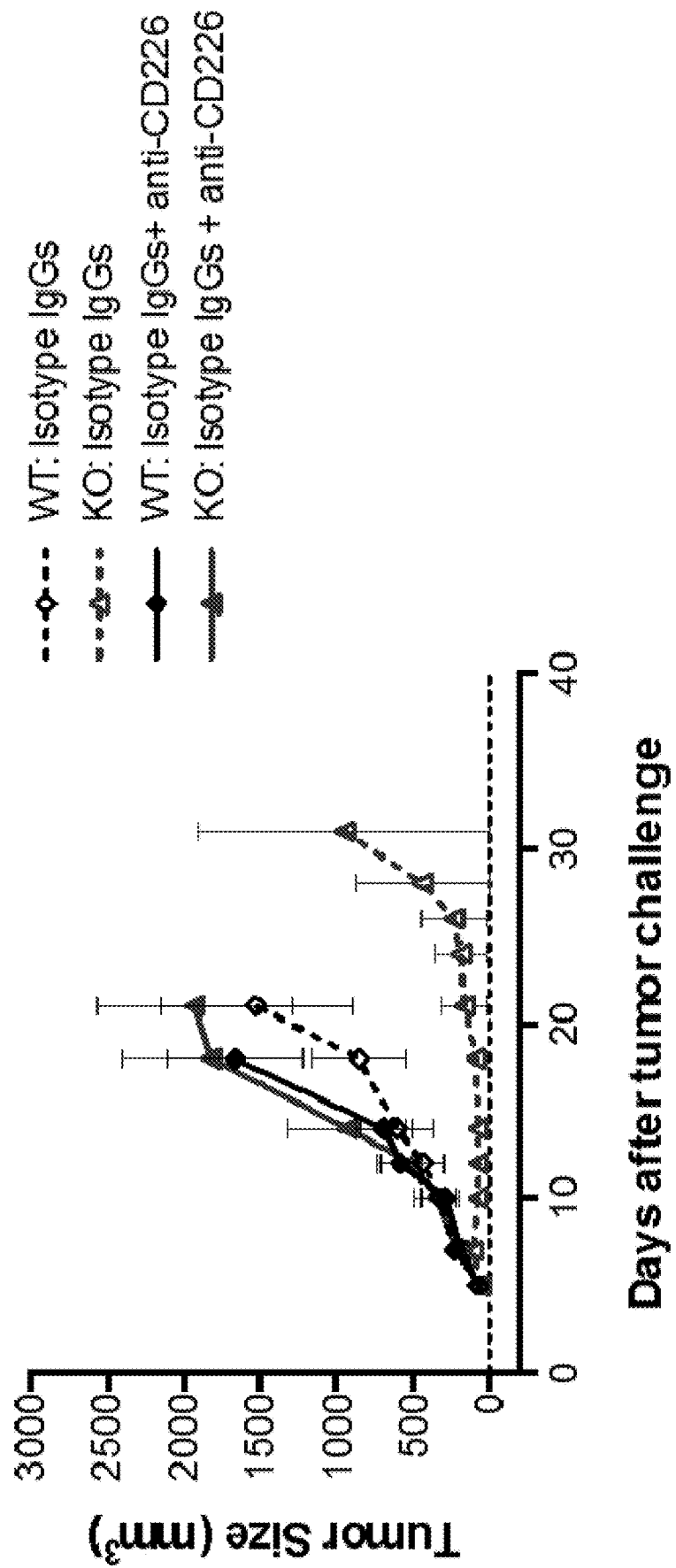
Figure 24B:
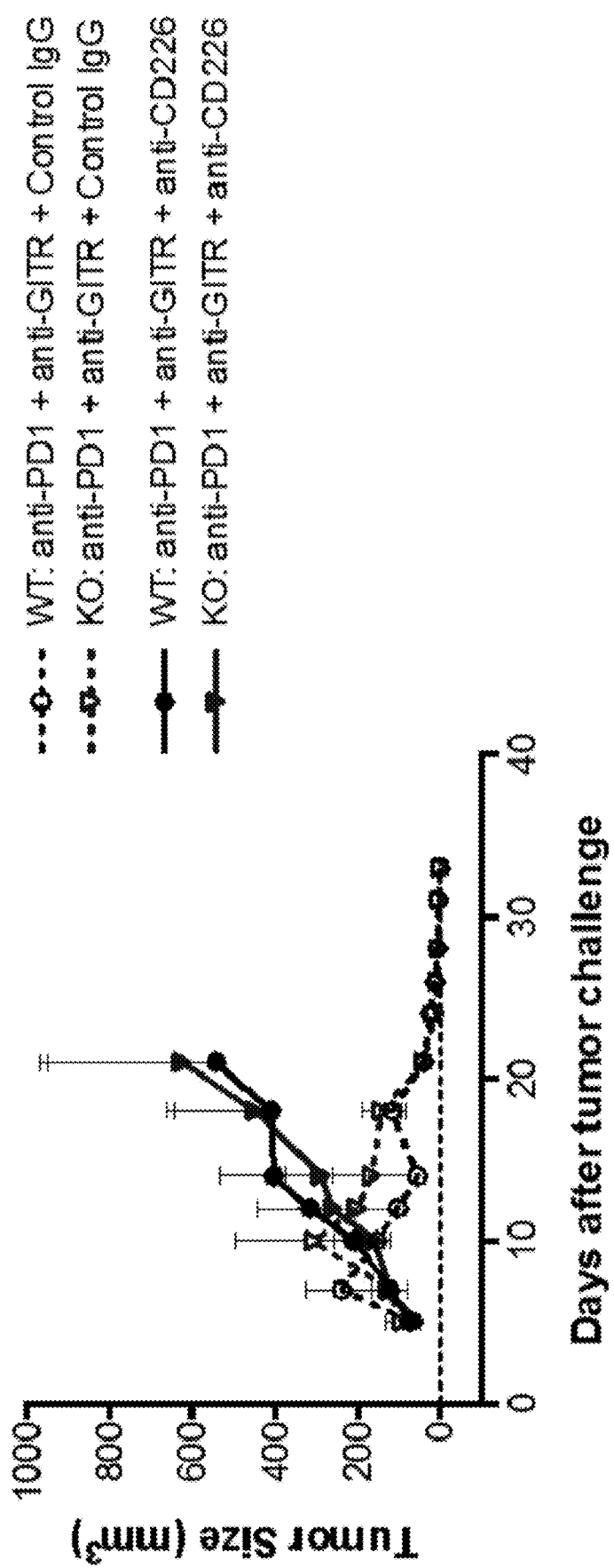
Figure 24D:
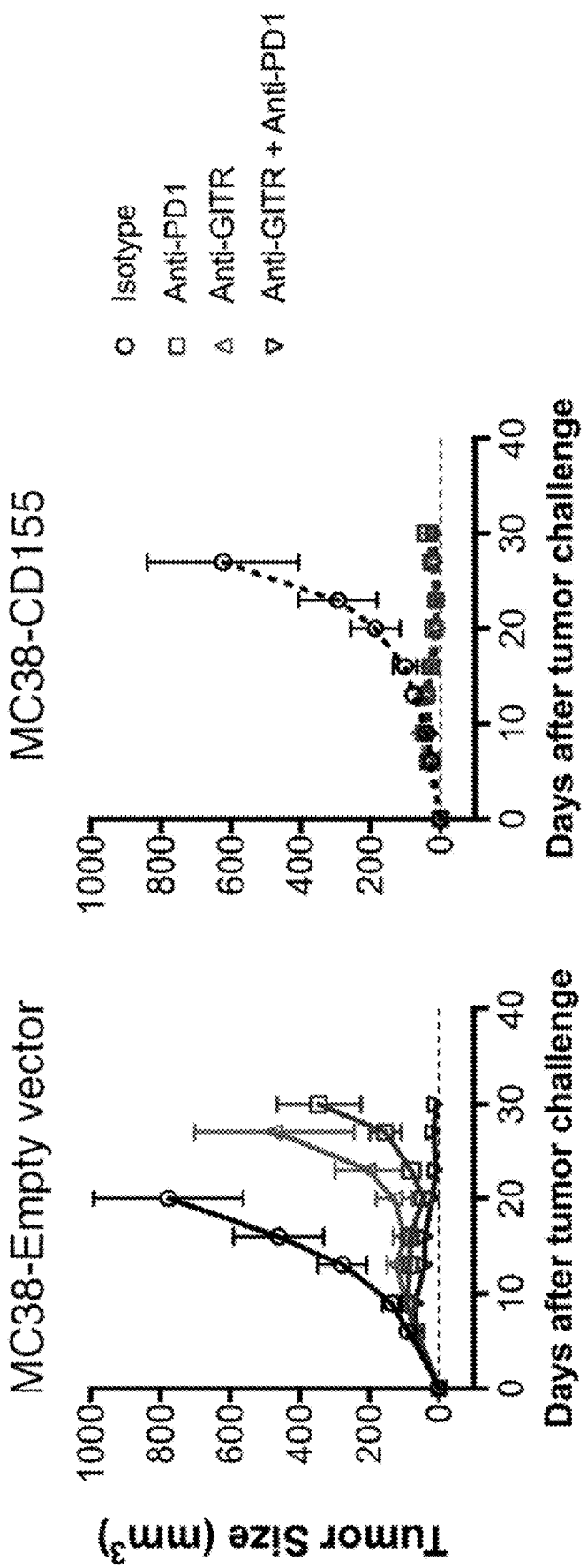
Figure 24F:
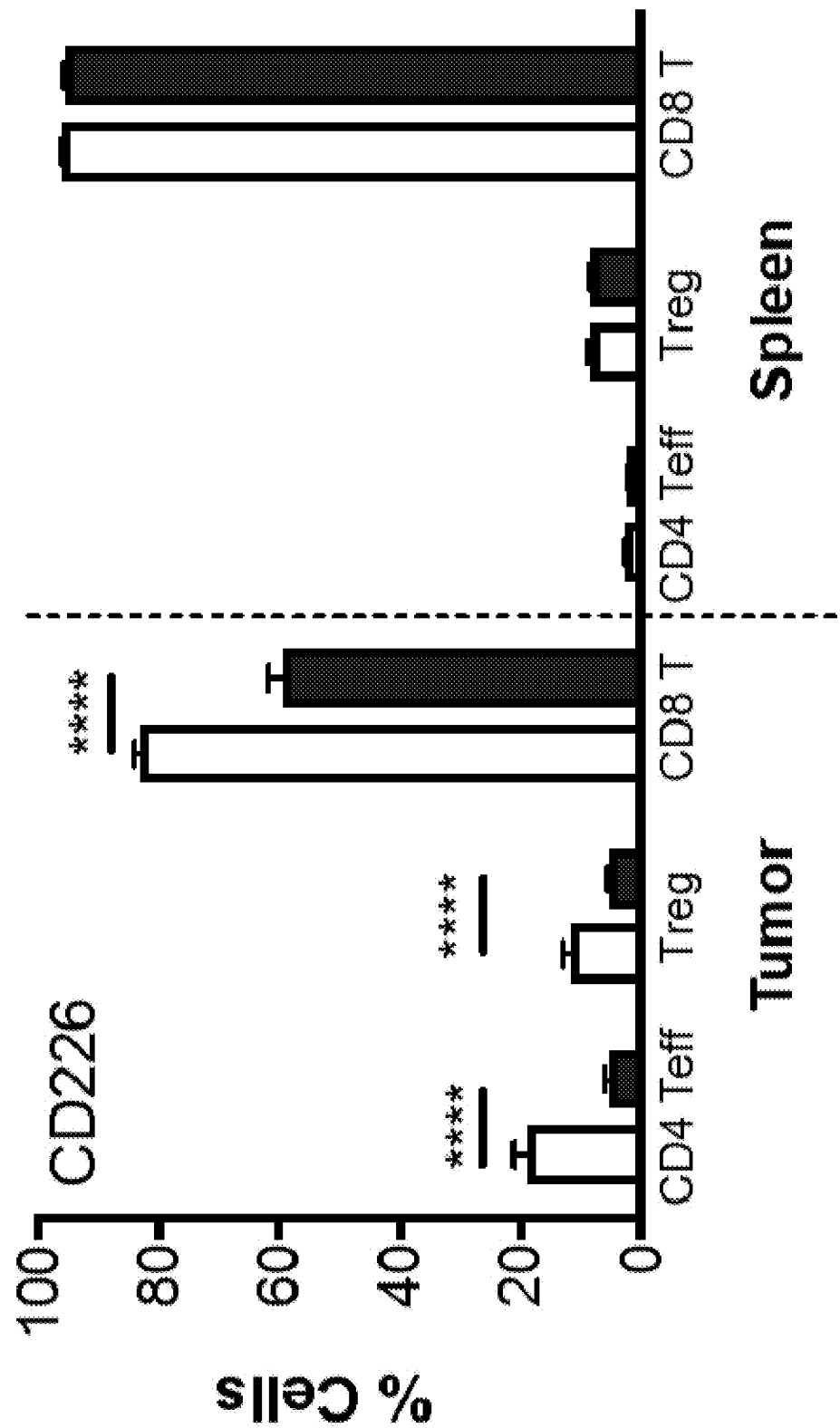
Figure 24G:
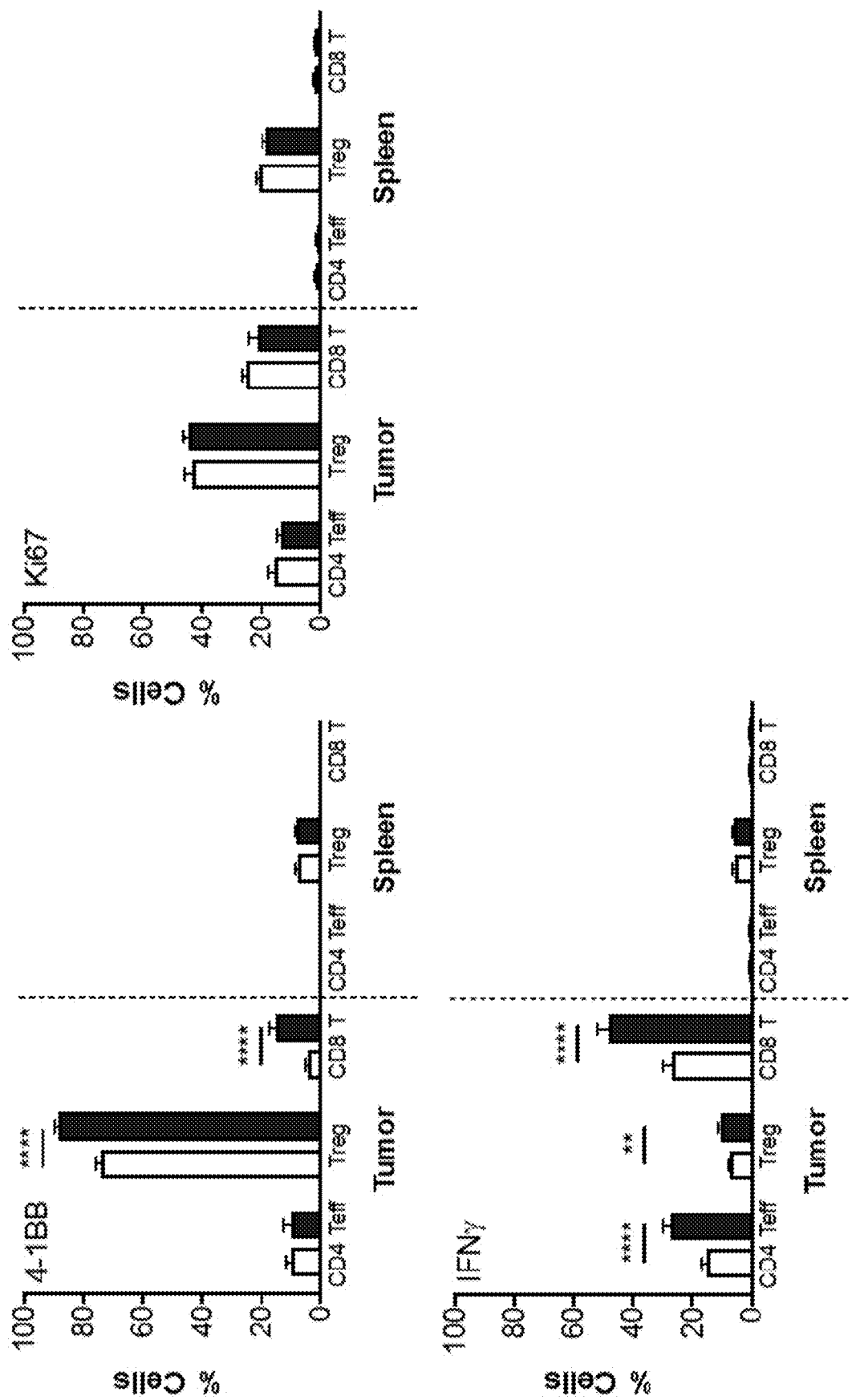

Further, the CD226 signaling pathway was required for enhanced tumor surveillance in TIGIT$^{-/-}$ mice (FIGS. 24A, B). Interestingly, mice bearing MC38 tumor cells overexpressing the major ligand for CD226, CD155/PVR (FIG. 24C) showed significant delay of tumor growth upon anti-PD-1 or anti-GITR or combination therapy in comparison to MC38-empty vector (MC38-EV) tumor cells or mice treated with isotype control (FIG. 24D). Immune profiling analysis of mice transplanted with MC38-CD155 confirmed sustained higher CD155 expression level on MC38-CD155 cells over M38-EV (empty vector) post-implantation (FIG. 24E). CD155 over-expression on MC38 tumor cells was associated with decreased detectable CD226 expression on CD4$^+$, CD8$^+$ T and T$_{regs}$ cells, while it boosted T cell activation as indicated by enhanced IFNγ and 4-1BB expression on intra-tumoral T cells (FIGS. 24F, 24G). As expected, no effect was observed in the periphery.

Figure 12F:
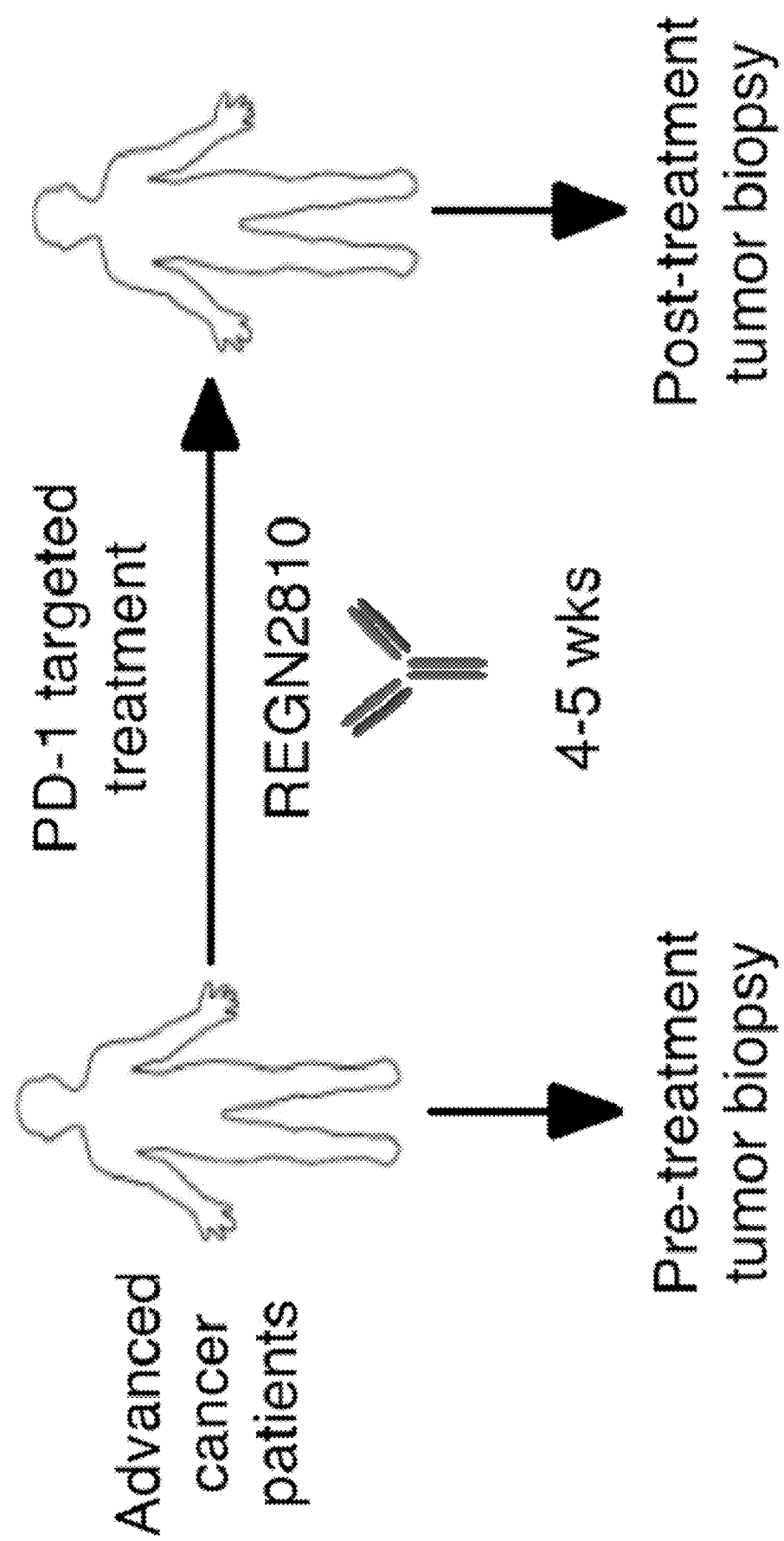
Figure 12G:
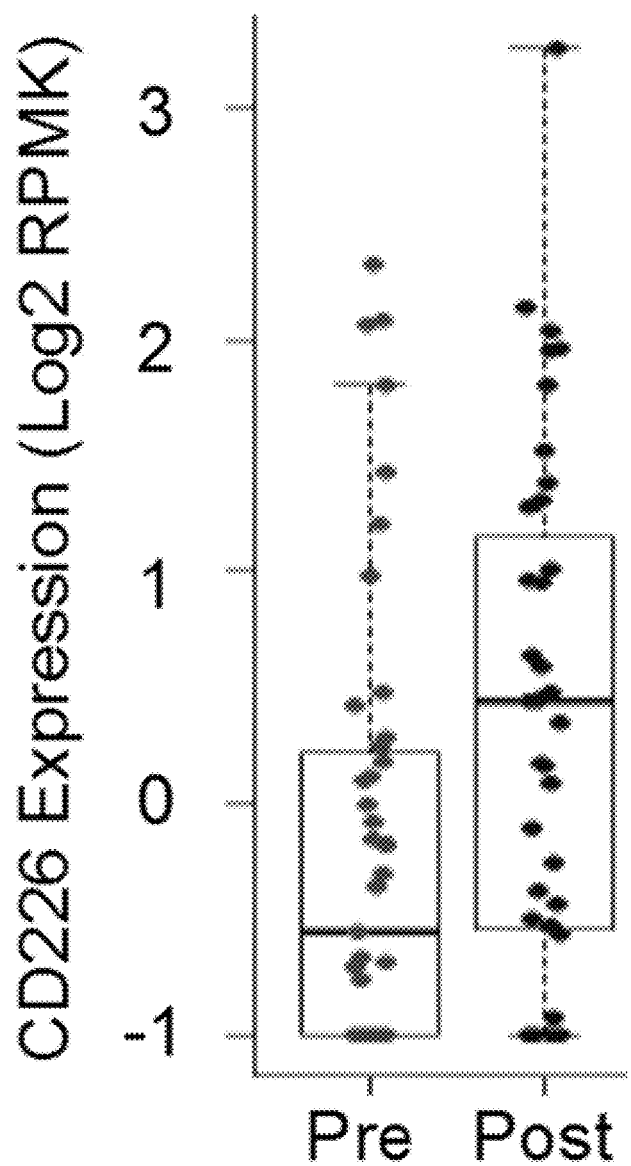
Figure 12H:
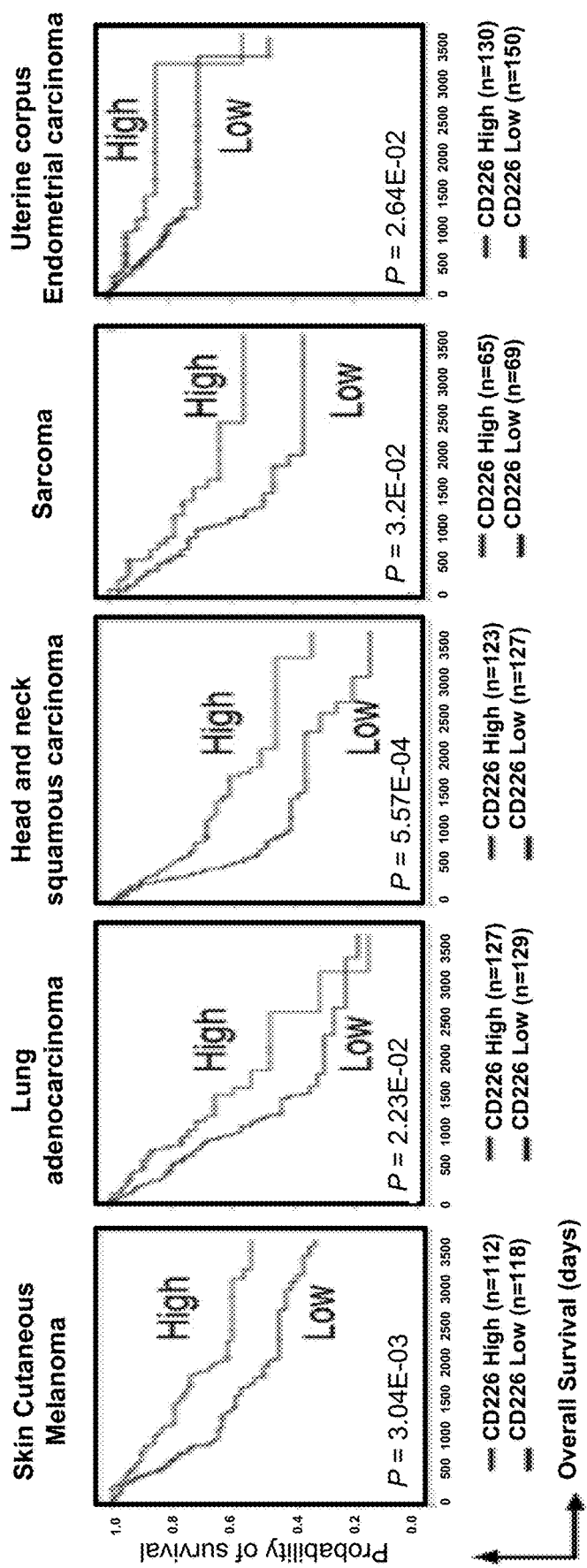

Next, the relationship between PD-1 inhibition and CD226 expression was investigated in a clinical setting. RNA-seq analysis was performed on tumor biopsies collected from 43 advanced cancer patients pre- and post-PD-1 targeted treatment (FIG. 12F). Importantly, CD226 expression was significantly increased after two doses of anti-hPD-1 treatment in cancer patients (FIG. 12G). Further, clinical data from The Cancer Genome Atlas (TCGA) was interrogated to examine if CD226 expression level correlates with the overall T cell activation strength and can be predictive of a better prognosis in cancer patients. Indeed, patients with high baseline CD226 expression have significantly higher survival probabilities in five (skin cutaneous melanoma, lung adenocarcinoma, head and neck squamous carcinoma, uterine corpus endometrial carcinoma and sarcoma) out of twenty different types of cancer evaluated here (FIG. 12H and FIG. 25). Overall, these results support an immunotherapy strategy that boosts CD226 signaling while blocking TIGIT simultaneously for maximum T cell activation.

Here, the use of technology platforms to unveil molecular mechanisms driving the potent synergism of a costimulatory agonist and a coinhibitory antagonist, elucidated the parameters required for durable anti-tumor responses and shed light on key functional T cell regulatory pathways that could shape the next generation of tumor specific combination therapies.

Example 6B

TCR Repertoire Analysis Bioinformatics Pipeline rpsTCR and its Validation

TCR sequence extraction and assembly. Given the V and J allele information, and the CDR3 amino acid sequence, the amino acid sequences of the V and J alleles was extracted from the IMGT database (imgt.org). Next, the CDR3 sequence were aligned with the C-terminal of the V sequence and the N-terminal of the J sequence, to create a contiguous VDJ amino acid sequence. For each V allele, the leader sequence(L) was then identified from IMGT if it is available and appended it to the C-terminal of the VDJ sequence. If the leader sequence was not available, then the most frequent leader sequence was used. The LVDJ amino acid sequence was then back-translated to a codon-optimized nucleotide sequence using the EMBOSS Backtranseq tool (ebi.ac.uk./Tools/st/emboss_backtranseq). Finally, the nucleotide sequences of the constant (C) regions of the TCRA/TCRB (derived from IMGT) were appended to the N-terminal of the LVDJ nucleotide sequence, and thus obtained the full LVDJC sequences for cloning.

A bioinformatics pipeline was developed and validated to extract, reconstruct and analyze TCR sequences using random priming RNAseq data generated from sorted single cells allowing the identification of T cell clones potentially associated with tumor reactivity and patient survival. Unlike conventional TCR-seq methods using targeted TCR amplicon sequencing with long reads (2×300 bp), a very small portion of random priming RNA-seq reads are TCR sequences and the read length is short (usually =<100 bp), which usually only covers part of the V(D)J regions of the TCRs. To address these issues, a negative TCR sequence selection step was integrated and a short read assembly step in the pipeline. In brief, the pipeline takes paired or single-end short reads and maps these reads to human or mouse genomes and transcriptomes, but not TCR gene loci and transcripts (FIG. 17 and Methods). The results indicated that the method is a highly sensitive and accurate CDR3 assembler for random priming RNA-seq data (FIG. 18, FIG. 13 and Example 6A Methods, above). Finally, the pipeline was applied to a library of 1,379 CD8+ single cell RNA-seq data. The detection rates of TCRB-CDR3 (86%), TCRA-CDR3 (78.2%) and paired TCRB and TCRA (73.1%) were comparable to the reported detection rates using targeted TCR sequencing from single T cells (FIG. 14).

Figure 9A:
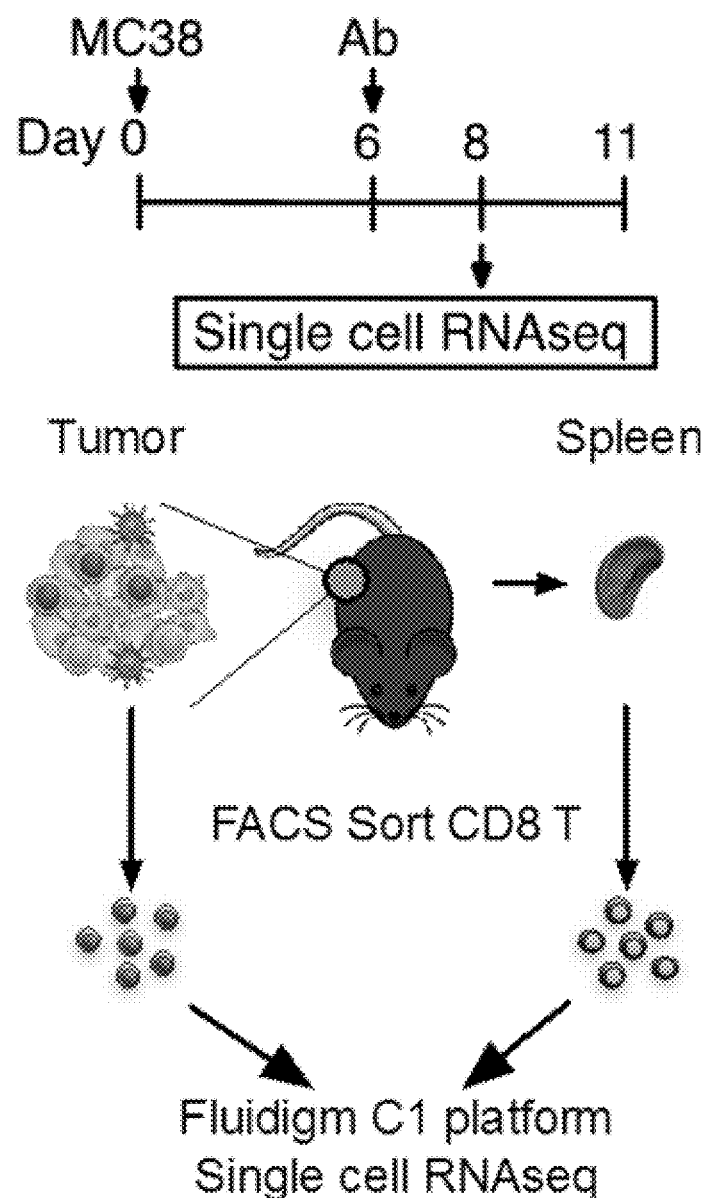
FIGS. 9A-9E show combination therapy expands intratumoral high frequency CD8+ T cell clones. 9a, Schematic of tumor immunotherapy and single cell sorting study design. 9b, intratumoral CD8+ T cell clonal analysis based on single cell-sorted RNAseq data on day 8 and 11 post tumor challenge. Each circle represents a single CD8+ T cell. T cell sharing the same TCR sequence is color-coded, number indicates frequency of individual clone followed by the sequence of CDR3 region of TCRβ chain. Day 8: Isotype—SEQ ID NO:290; Anti-GITR—SEQ ID NO:269; Anti-PD1—SEQ ID NO:270; Day 11: Isotype—SEQ NO:291, SEQ ID NO:292 (top to bottom, respectively); Anti-GITR—SEQ ID NO:271-273 (top to bottom, respectively); Anti-PD1—SEQ ID NO:274-279 (top to bottom, respectively); Anti-GITR+Anti-PD1—SEQ ID NO:280-289 (top to bottom, respectively) 9c, Quantitative analysis of T cell clonality. Data depicts cumulative frequency of expanded CD8+ T cell clones from each group (*, p<0.05, , p<0.01, *, p<0.001, Fisher's test). 9d, 9e, Identification, expression and functional validation of TCRs from intratumoral CD8+ T cell clones. High frequency TCR clones were cloned into J.RT3-T3.5 Jurkat T cell line with an AP-1 luciferase reporter gene (9d) and their reactivity was tested in vitro against MC38 (tumor specific) versus irrelevant tumor cells (B16F10.9 or TRAMP-C2). 9e, Representative AP-1 luciferase reporter bioassay result with MC38-specific CD8+ T cell clone isolated from combination treatment is shown, anti-CD3 and anti-CD28 stimulation was used as positive control.
Figure 9B:
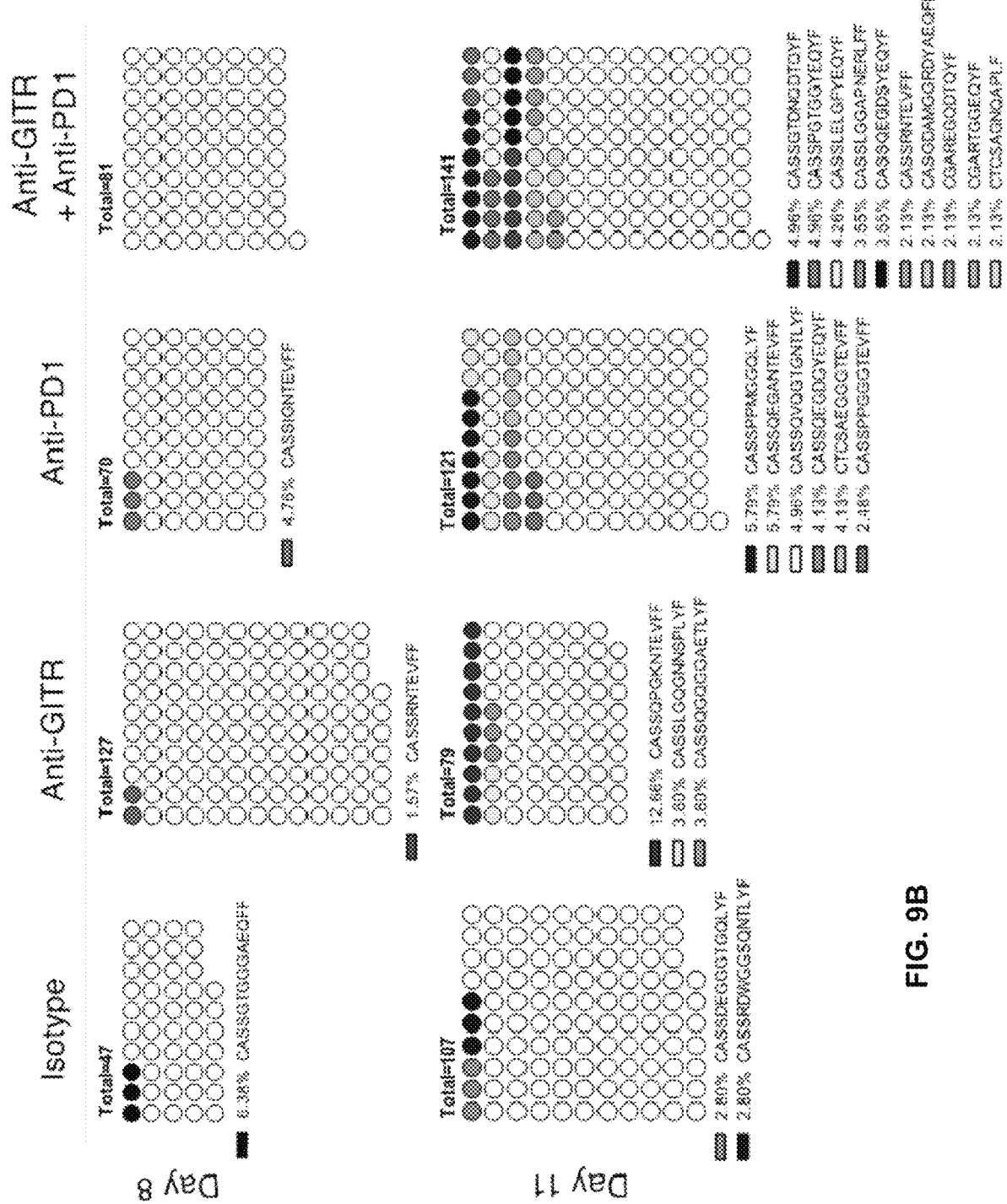
Figure 9C:
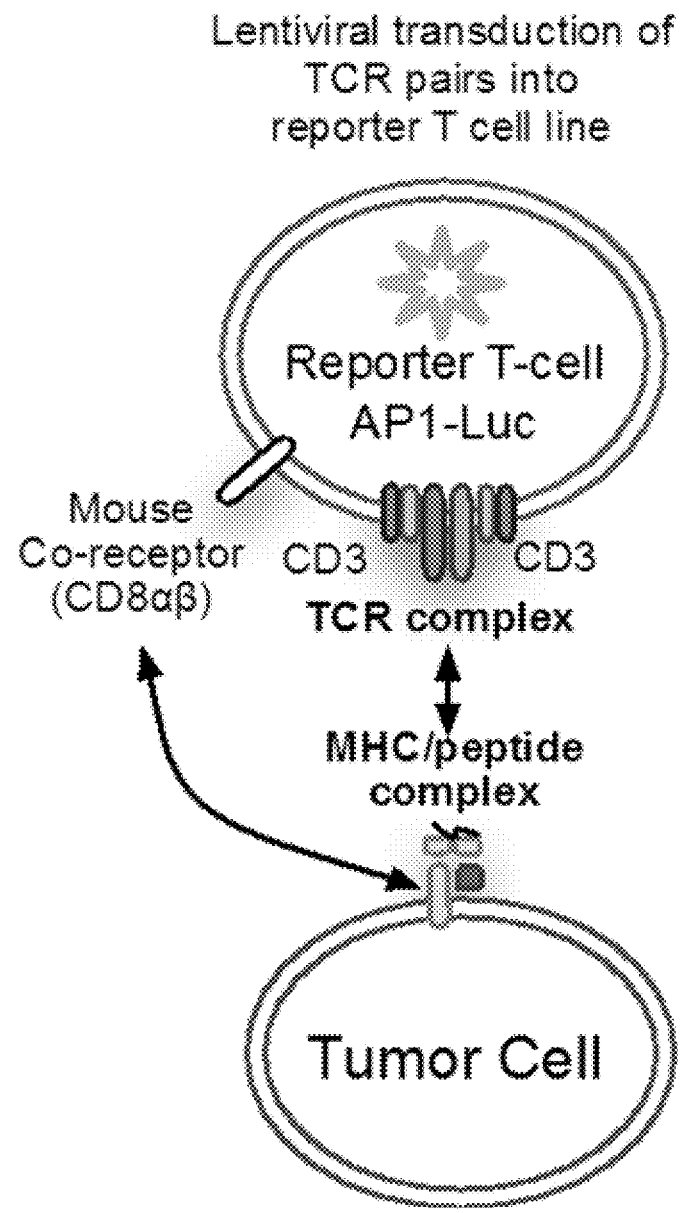

Antibodies were administered 6 days post-tumor challenge when tumors were palpable (FIG. 9A). The above bioinformatics tool was used to profile the transcriptome of 1379 CD8$^+$ T cells single cell sorted from tumor-bearing mice at day 8 and day 11 post-tumor challenge. At the early time point (day 8), very few clones of high-frequency T cells (defined as at least 3 T cells sharing identical TCR sequences) were detected in all treatment groups (FIG. 9B). By day 11, two high-frequency T cell clones were identified, representing 5.7% of sequenced single CD8+ T cells from isotype control samples; 3 clones/20.3% for anti-GITR samples, 6 clones/26.7% for anti-PD-1 samples and 10 clones/31.9% for combination treated samples. Indeed, between day 8 and day 11, a significant clonal expansion of intratumoral CD8+ T cells was induced by anti-PD-1 monotherapy. This result is in agreement with published data detecting an increase in TCR clonality after anti-PD-1 therapy (pembrolizumab). The results extend these findings by showing that anti-PD-1 Ab seems to be the main driver of clonal expansion, and that dual targeting of PD-1 and GITR further enhances intra-tumoral CD8 T cell TCR clonality (FIGS. 9B and 9C). Anti-GITR and/or anti-PD-1 had no impact on peripheral/spleen T cell clonality (FIG. 9C), consistent with patient data using pembrolizumab treatment.

Figure 9D:
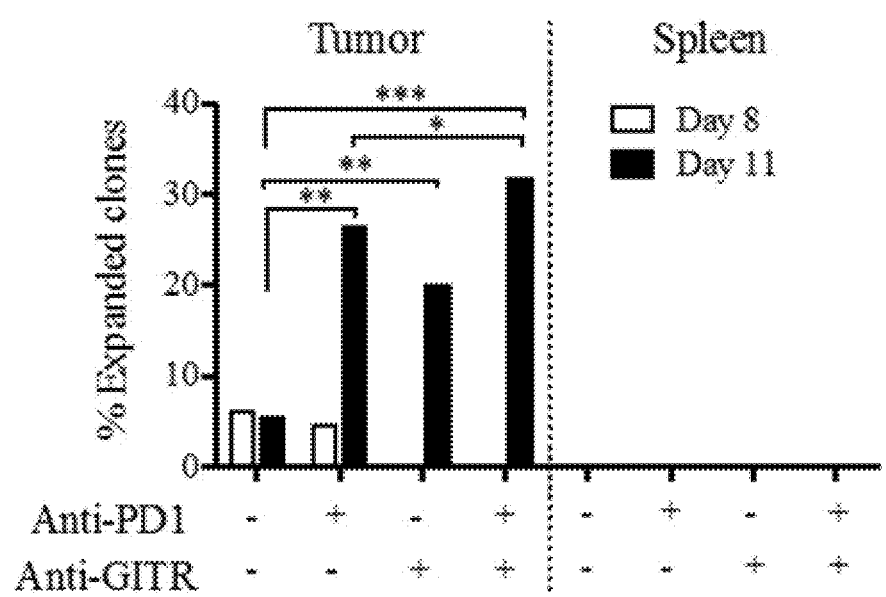
Figure 9E:
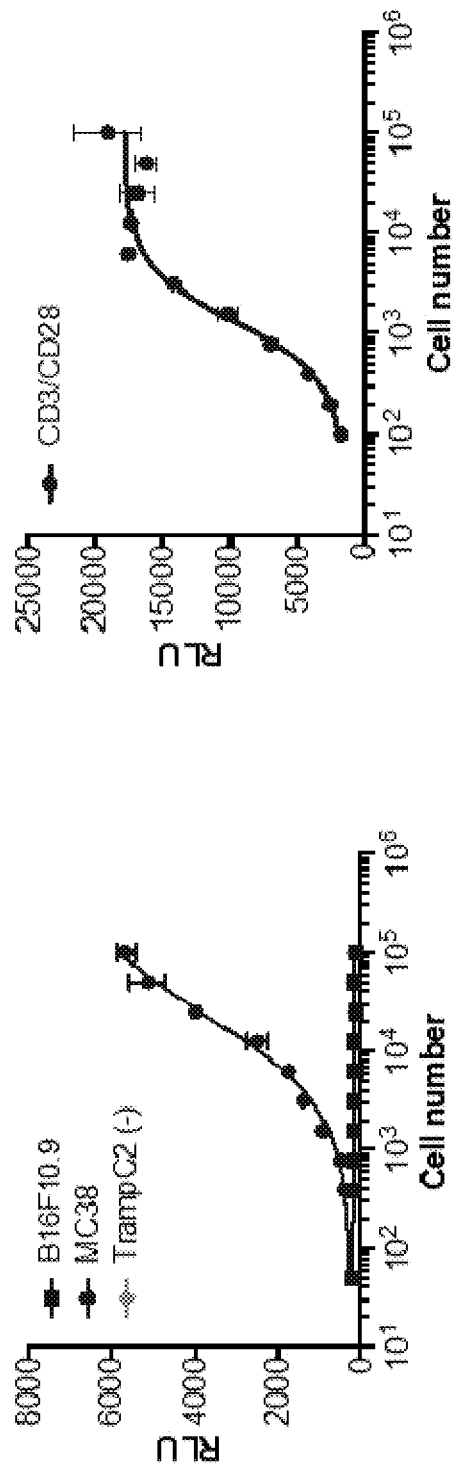

To validate the tumor antigen specificity of the TCRs enriched within the MC38 tumors upon combination treatment, bioinformatics analysis was performed to extract and assemble the full length paired TCR alpha/beta sequences (Example 6A Methods). Full length TCR pairs derived from expanded CD8+ T cells were cloned into lentiviral constructs and transduced into a Jurkat T cell line lacking endogenous TCR expression. AP-1 driven luciferase reporter was used as a read-out of TCR specificity of these engineered T cell lines (FIG. 9D). This assay was validated using a well-characterized LCMV TCR (P14) (FIG. 19). The TCRs from high frequency clones (5 cells sharing the same TCR) can recognize epitopes that are presented specifically by wild type MC38 tumor cells but not by irrelevant syngeneic C57BL/6 tumor cell lines (B16F10.9 or TRAMP-C2) (FIG. 9E showing a representative TCR clone), thus validating their specificity.

Further, it was determined that anti-GITR and anti-PD-1 regulate distinct molecular pathways in these clonally expanded CD8+ T cells, (FIG. 15). Combination treatment synergistically integrated the pathways modulated by single agent treatment and promoted strong adaptive immune responses, and responses in pathways associated with cell cycle and metabolic activity. Although single agent therapy expanded intratumoral CD8+ T cell clones and modulated critical gene pathways, this was not sufficient for complete and long lasting tumor rejection. The findings indicate that a profound reprogramming of dysfunctional tumor infiltrating T cells by combination therapy was required for complete tumor rejection. This result is supported by a recent study showing that CD8+ T cells become dysfunctional at early stages of tumor development and gradually evolve into a less flexible state.

Next-generation sequencing technology has made whole-genome and transcriptome sequencing routine and provided opportunities for detection of whole genome gene expression and extraction of TCR sequences simultaneously. However, unlike conventional TCR-seq methods using targeted TCR amplicon sequencing with long reads (2×300 bp), very small portion of random priming RNA-seq reads are TCR sequences and also the read length is short (usually =<100 bp), which usually only cover part of V(D)J regions of TCRs. The rpsTCR pipeline was developed for assembling and extracting TCR-CDR3 sequences from random priming short RNA sequencing reads to address this problem (FIG. 17). The rpsTCR took paired- and single-end short reads and mapped these reads to mouse or human genomes and transcriptomes, but not TCR gene loci and transcripts using Tophat with default parameters. Mapped reads were discarded and unmapped reads were recycled for extraction of TCR sequences. Low quality nucleotides in the unmapped reads were trimmed. Then reads with length less than 35 bp were filtered out using HTQC toolkit. QC passed short reads were assembled into longer reads using iSSAKE default setting. TCRklass was used to identify CDR3 sequences with Scr (conserved residue support score) set from default 1.7 to 2. A targeted TCR-seq data from a healthy human PBMC samples was used as a positive control to evaluate whether the extra steps introduced to the pipeline result in higher false positive or false negative rates comparing to TCRklass alone. Majority of unique CDR3 sequences from TCRB (64,031) or TCRA (51,448) were detected by both rpsTCR and TCRklass. The squared correlations between rpsTCR and TCRklass were 0.9999 and 0.9365 for TCRB-CDR3 and TCRA-CDR3, respectively (FIG. 17). Six TCR-negative cancer or non-cancer cell lines were used as negative controls. rpsTCR didn't detected any CDR3 sequences, while TCRklass extracted a few CDR3 sequences from some of these TCR-negative cancer cell lines (FIG. 13). To further validate the performance of the pipeline, a healthy mouse PBMC sample was sequenced using both targeted TCR-seq and random priming RNA-seq approaches (200M, 2×100 bp). Although the number of CDR3 sequences assembled from RNA-seq data was much smaller than that from the targeted TCR-seq approach, about 45% of the CDR3 sequences identified from RNA-seq data using rpsTCR were also observed among CDR3 sequences from targeted TCR-seq. Because of the technique limitation of targeted TCR-seq, it is not surprising that a fraction of the CDR3 sequences extracted from RNA-seq data were not present in the TCR-seq results. For example, the efficiency of 5' race adapter used for targeted TCR-seq is generally low and the multiply PCR tends to amplify high frequency TCRs, thus only a small portion of TCRs can be targeted. As expected, much higher percentage (~70%) of the CDR3 sequences identified from RNA-seq data using rpsTCR were also observed among high frequency CDR3 sequences (>=0.1%) from targeted TCR-seq, while only about 40% extracted using TCRklass alone. Moreover, the 100 bp read length was cut into 50 bp segments and randomly selected 200M reads. Among the top 10 CDR3 sequences ranked by targeted TCR-seq approach, 8 CDR3 sequences were detected by the rpsTCR, while only 3 were detected by TCRklass. The rpsTCR pipeline was then applied to extracting CDR3 sequences from the single cell RNA-seq data generated from intratumoral CD8 T cells of MC38 treated with different antibodies. The CDR3_beta and CDR3_alpha sequence detection rates were comparable to published data (FIG. 14) using targeted TCR-seq approach to detect TCR sequences from single cell sequencing of T cells.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow;

plain meaning derived from grammatical organization or punctuation; the number or type of embodiments described in the specification.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for identifying a T cell receptor (TCR), comprising:
   a) sequencing, using a high-throughput sequencing device, short reads of less than about 100 base pairs of RNA obtained from a T cell and storing, in system memory of a computing device, a sequence data structure comprising the short reads and a reference data structure comprising a reference sequence;
   b) aligning, by the computing device, the short reads with the reference sequence, wherein the reference sequence does not contain a TCR gene sequence, thereby generating, in the sequence data structure in the system memory, mapped short reads and unmapped short reads;
   c) discarding, by the computing device, mapped short reads from the sequence data structure in the system memory;
   d) assembling, by the computing device, the unmapped short reads remaining in the sequence data structure in the system memory into one or more long reads by aligning the unmapped short reads in the sequence data structure to one or more reference TCR sequences from a reference database of TCR sequences;
   e) translating, by the computing device, the one or more long reads into corresponding amino acid sequences in the sequence data structure in the system memory;
   f) fractioning, by the computing device, TCR V region and TCR J region amino acid reference sequences, from the reference database of TCR sequences, into k-strings of about six amino acids,
      aligning, by the computing device, the k-strings with the corresponding amino acid sequences in the sequence data structure in the system memory from step (e),
      detecting, by the computing device, one or more conserved TCR CDR3 residues in the k-strings that map to the corresponding amino acid sequences in the sequence data structure in the system memory,
      scoring, by the computing device, based on the one or more conserved TCR CDR3 residues that map to the corresponding amino acid sequences in the sequence data structure in the system memory, a level of conservation for each of the corresponding amino acid sequences in the sequence data structure in the system memory,
      selecting, by the computing device, one or more of the corresponding amino acid sequences in the sequence data structure in the system memory, wherein the level of conservation for the one or more corresponding amino acid sequences in the sequence data structure in the system memory is above a threshold conservation score, and
      detecting, by the computing device, a candidate CDR3 region amino acid sequence in the selected corresponding amino acid sequences in the sequence data structure in the system memory;
   g) identifying, by the computing device, a nucleic acid sequence of the candidate CDR3 region amino acid sequence in the one or more long reads, in the sequence data structure in the system memory, as a candidate CDR3 region nucleic acid sequence;
   h) aligning, by the computing device, a nucleic acid sequence of the one or more long reads, in the sequence data structure in the system memory, that is upstream of the candidate CDR3 region nucleic acid sequence with one or more TCR V gene reference sequences from the reference database of TCR sequences,
      scoring, by the computing device, a degree of the alignment of the nucleic acid sequence of the one or more long reads, in the sequence data structure in the system memory, that is upstream of the candidate CDR3 region nucleic acid sequence with the one or more TCR V gene reference sequences from the reference database of TCR sequences, and
      identifying, by the computing device, at least one portion of the one or more long reads, in the sequence data structure in the system memory, as comprising a candidate TCR V gene sequence, wherein the scored degree of alignment for the at least one portion of the one or more long reads, in the sequence data structure in the system memory, that is upstream of the candidate CDR3 region nucleic acid sequence is above a threshold alignment score; and
   i) aligning, by the computing device, a nucleic acid sequence of the one or more long reads, in the sequence data structure in the system memory, that is downstream of the candidate CDR3 region nucleic acid sequence with one or more TCR J gene reference sequences from the reference database of TCR sequences, scoring a degree of the alignment of the nucleic acid sequence of the one or more long reads, in the sequence data structure in the system memory, that is downstream of the candidate CDR3 region nucleic acid sequence with the one or more TCR J gene reference sequences from the reference database of TCR sequences, and identifying at least one portion of the one or more long reads, in the sequence data structure in the system memory, as comprising a candidate TCR J gene sequence, wherein the scored degree of alignment for the at least one portion of the one or more long reads, in the sequence data structure in the system memory, that is downstream of the candidate CDR3 region nucleic acid sequence is above the threshold alignment score, wherein the candidate TCR V gene sequence combined with the candidate TCR J gene sequence comprise a TCR sequence.

2. The method of claim 1, wherein the short reads are obtained from random-priming of RNA.

3. The method of claim 1, wherein the T cell is obtained from a human or mouse.

4. The method of claim 1, wherein the reference sequence comprises a human genome, a mouse genome, a human transcriptome, or a mouse transcriptome.

5. The method of claim 1, wherein discarding mapped short reads from the read set further comprises discarding unmapped short reads from the read set that are less than about 35 base pairs.

6. The method of claim 1, wherein assembling the unmapped short reads remaining in the read set into one or more long reads comprises:

aligning the one or more unmapped short reads to one or more TCR sequences from a reference database of TCR sequences; and assembling, based on the alignment, the one or more unmapped short reads into long reads.

7. The method of claim 1 further comprising appending a TCR C region nucleic acid sequence to the TCR sequence.

8. The method of claim 1 further comprising, prior to sequencing the short reads of less than about 100 base pairs of RNA obtained from the T cell, administering an immunotherapy to a subject from which the T cell is obtained.

9. The method of claim 8, wherein the immunotherapy comprises a monotherapy or a combination therapy.

10. The method of claim 9, wherein the combination therapy comprises a costimulatory agonist and a coinhibitory antagonist.

11. The method of claim 1, further comprising:

repeating steps a-i for a first plurality of T cells of a subject, wherein the T cells are collected prior to administration of a treatment;

determining a number of occurrences of unique TCR sequences present in the first plurality of T cells;

administering the treatment to the subject;

repeating steps a-i for a second plurality of T cells of the subject, wherein the T cells are collected after the administration of the treatment;

determining a number of occurrences of unique TCR sequences present in the second plurality of T cells; and determining, based on the number of occurrences of unique TCR sequences present in the first plurality of T cells being less than the number of occurrences of unique TCR sequences present in the second plurality of T cells, one or more unique TCR sequences that experienced clonal expansion.

12. The method of claim 11, further comprising determining a T cell clonal expansion signature based on the one or more unique TCR sequences that experienced clonal expansion.

13. The method of claim 12, further comprising:

querying a database of T cell clonal expansion signatures and corresponding treatment responses using the T cell clonal expansion signature;

determining, based on the query, the subject's likelihood of responding to the treatment.

14. The method of claim 12, further comprising:

determining the subject's response to the treatment;

storing the T cell clonal expansion signature in a database; and associating the subject's response to the treatment with the T cell clonal expansion signature in the database.

15. The method of claim 1, further comprising:

determining that the TCR sequence is present in a T cell clone that expands in response to a treatment;

producing one or more T cells containing the TCR sequence;

administering the one or more T cells to a subject; and administering the treatment to the subject.

16. The method of claim 1, wherein sequencing short reads of less than about 100 base pairs of RNA obtained from a T cell comprises bulk sequencing of short reads of less than about 100 base pairs of RNA obtained from a plurality of T cells.

17. The method of claim 16, further comprising performing steps b-i for each of the plurality of T cells.

18. The method of claim 17, wherein performing steps b-i for each of the plurality of T cells comprising performing steps b-i comprises:

classifying, by the computing device, at least a portion of one or more of steps b-i as a job; and distributing, by the computing device, a workload for each job across a plurality of processors in parallel.

19. An apparatus comprising:

one or more processors; and a memory comprising processor executable instructions that, when executed by the one or more processors, cause the apparatus to:

a) receive, from a high-throughput sequencing device, a sequence data structure comprising short reads of less than about 100 base pairs of RNA obtained from a T cell and store, in the memory, the sequence data structure and a reference data structure comprising a reference sequence;

b) align the short reads with the reference sequence, wherein the reference sequence does not contain a TCR gene sequence, thereby generating in the sequence data structure in the memory, mapped short reads and unmapped short reads;

c) discard mapped short reads from the sequence data structure in the memory;

d) assemble the unmapped short reads remaining in the sequence data structure in the memory into one or more long reads by aligning the unmapped short reads in the sequence data structure to one or more reference TCR sequences from a reference database of TCR sequences;

e) translate the one or more long reads into corresponding amino acid sequences in the sequence data structure in the memory;

f) fraction TCR V region and TCR J region amino acid reference sequences, from the reference database of TCR sequences, into k-strings of about six amino acids, aligning the k-strings with the corresponding amino acid sequences in the sequence data structure in the memory from step (e), detect one or more conserved TCR CDR3 residues in the k-strings that map to the corresponding amino acid sequences in the sequence data structure in the memory, score, based on the one or more conserved TCR CDR3 residues that map to the corresponding amino acid sequences in the sequence data structure in the memory, a level of conservation for each of the corresponding amino acid sequences in the sequence data structure in the memory, select one or more of the corresponding amino acid sequences in the sequence data structure in the memory, wherein the level of a conservation for the one or more corresponding amino acid sequences in the sequence data structure in the memory is above a threshold conservation score, and detect a candidate CDR3 region amino acid sequence in the selected corresponding amino acid sequences in the sequence data structure in the memory;

g) identify a nucleic acid sequence of the candidate CDR3 region amino acid sequence in the one or more long reads, in the sequence data structure in the memory, as a candidate CDR3 region nucleic acid sequence;

h) align a nucleic acid sequence of the one or more long reads, in the sequence data structure in the memory, that is upstream of the candidate CDR3 region nucleic acid sequence with one or more TCR V gene reference sequences from the reference database of TCR sequences, score a degree of the alignment of the nucleic acid sequence of the one or more long reads, in the sequence data structure in the memory, that is upstream of the candidate CDR3 region nucleic acid sequence with the one or more TCR V gene reference sequences from the reference database of TCR sequences, and identify at least one portion of the one or more long reads, in the sequence data structure in the memory, as comprising a candidate TCR V gene sequence, wherein the scored degree of alignment for the at least one portion of the one or more long reads, in the sequence data structure in the memory, that is upstream of the candidate CDR3 region nucleic acid sequence is above a threshold alignment score; and i) align a nucleic acid sequence of the one or more long reads, in the sequence data structure in the memory, that is downstream of the candidate CDR3 region nucleic acid sequence with one or more TCR J gene reference sequences, score a degree of the alignment of the nucleic acid sequence of the one or more long reads, in the sequence data structure in the memory, that is downstream of the candidate CDR3 region nucleic acid sequence with the one or more TCR J gene reference sequences from the reference database of TCR sequences, and identify at least one portion of the one or more long reads, in the sequence data structure in the memory, as comprising a candidate TCR J gene sequence, wherein the scored degree of alignment for the at least one portion of the one or more long reads, in the sequence data structure in the memory, that is downstream of the candidate CDR3 region nucleic acid sequence is above the threshold alignment score, wherein the candidate TCR V gene sequence combined with the candidate TCR J gene sequence comprise a TCR sequence.

20. A method for identifying a T cell receptor (TCR), comprising:

sequencing, using a high-throughput sequencing device, short reads of less than about 100 base pairs of RNA obtained from a T cell and storing, in a system memory of a computing device, a sequence data structure comprising the short reads and a reference data structure comprising a reference sequence, wherein the reference sequence does not contain a TCR gene sequence;

aligning, by the computing device, the short reads with the reference sequence, thereby generating, in the sequence data structure in the system memory, mapped short reads and unmapped short reads;

discarding, by the computing device, the mapped short reads from the sequence data structure in the system memory;

assembling, by the computing device, the unmapped short reads remaining in the sequence data structure in the system memory into one or more long reads by aligning the unmapped short reads in the sequence data structure to one or more reference TCR sequences from a reference database of TCR sequences;

translating, by the computing device, the one or more long reads into corresponding amino acid sequences in the sequence data structure in the system memory;

detecting, by the computing device, a candidate CDR3 region amino acid sequence in the corresponding amino acid sequences, in the sequence data structure in the system memory, associated with a level of conservation above a threshold conservation score;

identifying, by the computing device, a nucleic acid sequence of the candidate CDR3 region amino acid sequence in the one or more long reads, in the sequence data structure in the system memory, as a candidate CDR3 region nucleic acid sequence;

aligning, by the computing device, a nucleic acid sequence of the one or more long reads, in the sequence data structure in the system memory, that is upstream of the candidate CDR3 region nucleic acid sequence with one or more TCR V gene reference sequences from the reference database of TCR sequences to identify at least one portion of the one or more long reads, in the sequence data structure in the system memory, as comprising a candidate TCR V gene sequence; and aligning, by the computing device, a nucleic acid sequence of the one or more long reads, in the sequence data structure in the system memory, that is downstream of the candidate CDR3 region nucleic acid sequence with one or more TCR J gene reference sequences from the reference database of TCR sequences to identify at least one portion of the one or more long reads, in the sequence data structure in the system memory, as comprising a candidate TCR J gene sequence, wherein the candidate TCR V gene sequence combined with the candidate TCR J gene sequence comprise a TCR sequence.

* * * * *

SEQUENCE LISTING

```
<160> NUMBER OF SEQ ID NOS: 324

<210> SEQ ID NO 1
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Gly Ile Ser Asp Thr Gly Gly Asn Thr Tyr Tyr Thr Asp Ser Val
    50                  55                  60

Lys Gly Arg Phe Thr Val Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Asp Gln Gly Gly Ser Tyr Pro Tyr Tyr Phe His Tyr Trp Gly
            100                 105                 110

Gln Gly Ser Leu Val Thr Val Ser Ser
        115                 120

<210> SEQ ID NO 2
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ile Trp Tyr Gln Gln Lys Pro Gly Thr Ala Pro Lys Phe Leu Ile
        35                  40                  45

Tyr Ala Ala Ser Ser Leu Gln Ser Gly Val Pro Ser Arg Phe Ser Gly
    50                  55                  60

Cys Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

```
<210> SEQ ID NO 3
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asn Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Phe Thr Tyr Tyr Thr Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Tyr Tyr Asp Thr Ser Asp Tyr Trp Thr Phe Phe Asp Tyr Trp
            100                 105                 110

Gly Gln Gly Thr Leu Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 4

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Gly Asp Phe Ala Val Tyr Tyr Cys Gln Gln Tyr Asn Asn Trp Pro Leu
                85                  90                  95

Thr Phe Gly Gly Gly Thr Lys Val Glu Ile Asn
            100                 105

<210> SEQ ID NO 5
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Asn Asn
            20                  25                  30
```

```
Tyr Met Ser Trp Val Arg Gln Ala Pro Gly Lys Gly Leu Glu Trp Val
        35                  40                  45

Ser Val Ile Tyr Ser Gly Gly Phe Thr Tyr Tyr Thr Asp Ser Val Lys
50                      55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Tyr Tyr Asp Thr Ser Asp Tyr Trp Thr Phe Phe Asp Tyr Trp
            100                 105                 110

Gly Gln Gly Thr Leu Val Thr Val Ser Ser
            115                 120

<210> SEQ ID NO 6
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 6

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Gly Asp Phe Ala Val Tyr Tyr Cys Gln Gln Tyr Asn Asn Trp Pro Leu
                85                  90                  95

Thr Phe Gly Gly Gly Thr Lys Val Glu Ile Asn
            100                 105

<210> SEQ ID NO 7
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 7

Gln Val Gln Leu Val Glu Ser Gly Gly Gly Val Val Gln Ser Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Ile Tyr Tyr Ser Asp Ser Val
50                  55                  60

Lys Gly Arg Phe Thr Ile Ser Arg Ala Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Pro Gly His Trp Asn Tyr Phe Phe Glu Tyr Trp Gly Gln Gly
```

Thr Leu Val Thr Val Ser Ser
            115

<210> SEQ ID NO 8
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Leu Thr Phe Gly Gln Gly Thr Gln Leu Glu Ile Lys
            100                 105

<210> SEQ ID NO 9
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Gly Ala Ser Gly Phe Thr Phe Arg Asn Tyr
            20                  25                  30

Asp Met His Trp Val Arg Gln Ile Thr Gly Lys Gly Leu Glu Trp Val
        35                  40                  45

Ser Ala Ile Gly Ser Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Val Gly Asp Thr Ala Val Tyr Tyr Cys Thr
                85                  90                  95

Arg Asp Ile His Cys Ser Ser Thr Arg Cys Tyr Gly Met Asp Val Trp
            100                 105                 110

Gly Gln Gly Thr Thr Val Thr Val Ser Ser
        115                 120

<210> SEQ ID NO 10
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 11
<211> LENGTH: 130
<212> TYPE: PRT
<213> ORGANISM: Artificial Sequence
<220> FEATURE:
<223> OTHER INFORMATION: synthetic construct; antigen binding domain

<400> SEQUENCE: 11

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Lys Phe Ser Asn Glu
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Gln Asp Phe Trp Ser Gly Tyr Tyr Thr Gly Ala
            100                 105                 110

Asp Tyr Tyr Gly Met Asp Val Trp Gly Gln Gly Thr Met Val Thr Val
        115                 120                 125

Ser Ser
130
```

<210> SEQ ID NO 12
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                     85                  90                  95

Ile Thr Phe Gly Gln Gly Thr Arg Leu Glu Ile Lys
                    100                 105

<210> SEQ ID NO 13
<211> LENGTH: 116
<212> TYPE: PRT
<213> ORGANISM: Artificial Sequence
<220> FEATURE:
<223> OTHER INFORMATION: synthetic construct; antigen binding domain

<400> SEQUENCE: 13

Gln Met Gln Leu Gln Gln Trp Gly Ala Gly Leu Leu Lys Pro Ser Glu
  1               5                  10                  15

Thr Leu Ser Leu Thr Cys Val Val Tyr Gly Gly Ser Leu Asn Gly Tyr
                 20                  25                  30

Tyr Trp Ser Trp Ile Arg Gln Ser Pro Gly Lys Gly Leu Glu Trp Ile
             35                  40                  45

Gly Glu Ile Asp His Ser Gly Ser Thr Asn Tyr Asn Pro Ser Leu Lys
 50                  55                  60

Asn Arg Val Thr Met Ser Val Asp Thr Ser Lys Ile Gln Phe Ser Leu
 65                  70                  75                  80

Lys Leu Thr Ser Val Thr Val Ala Asp Thr Ala Val Tyr Tyr Cys Ala
                 85                  90                  95

Arg Glu Gly Leu Leu Pro Phe Asp Tyr Trp Gly Gln Gly Thr Leu Val
                100                 105                 110

Thr Val Ser Ser
            115

<210> SEQ ID NO 14
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 14

Glu Ile Val Leu Thr Gln Ser Pro Gly Thr Leu Ser Leu Ser Pro Gly
  1               5                  10                  15

Glu Arg Val Thr Leu Ser Cys Arg Ala Ser Gln Ser Val Tyr Ser Asn
                 20                  25                  30

Tyr Leu Ala Trp Tyr Gln Gln Asn Pro Gly Gln Ala Pro Arg Leu Leu
             35                  40                  45

Ile Tyr Ala Ala Ser Asn Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys His Gln Tyr Ala Thr Ser Pro
                 85                  90                  95

Trp Thr Phe Gly Gln Gly Thr Lys Val Glu Ile Lys
                100                 105

<210> SEQ ID NO 15
<211> LENGTH: 123
```

```
<212> TYPE: PRT
<213> ORGANISM: Artificial Sequence
<220> FEATURE:
<223> OTHER INFORMATION: synthetic construct; antigen binding domain

<400> SEQUENCE: 15

Gln Leu Gln Leu Gln Glu Ser Gly Pro Asp Leu Val Lys Pro Ser Asp
1               5                   10                  15

Thr Leu Ser Leu Thr Cys Thr Val Ser Asp Ser Ile Ser Ser Thr
            20                  25                  30

Thr Tyr Tyr Trp Ala Trp Ile Arg Gln Pro Pro Gly Lys Gly Leu Glu
        35                  40                  45

Trp Ile Gly Ser Met Ser Tyr Asn Gly Asn Asn Tyr Tyr Asn Pro Ser
    50                  55                  60

Leu Lys Ser Arg Val Ala Ile Ser Ala Gly Thr Ser Gln Lys Gln Phe
65                  70                  75                  80

Ser Leu Lys Leu Thr Ser Val Thr Ala Ala Asp Thr Ala Val Tyr His
                85                  90                  95

Cys Ala Arg His Leu Gly Tyr Asn Gly Asn Trp Tyr Pro Phe Asp Phe
            100                 105                 110

Trp Gly Gln Gly Ile Leu Val Thr Val Ser Ser
        115                 120

<210> SEQ ID NO 16
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 16

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 17
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 17

Glu Val Gln Val Val Glu Ser Gly Gly Gly Leu Val Glu Pro Gly Arg
1               5                   10                  15

Ser Leu Arg Leu Ser Cys Lys Ala Ser Gly Phe Thr Phe Asp Asp Tyr
            20                  25                  30

Ala Met His Trp Val Arg Gln Thr Pro Gly Lys Ala Leu Glu Trp Val
```

```
                    35                  40                  45
Ser Gly Ile Asn Trp Ser Gly Asn Asn Ile Gly Tyr Ala Asp Ser Val
            50                  55                  60
Lys Gly Arg Phe Thr Ile Ser Lys Asp Asp Ala Lys Asn Ser Leu Tyr
65                  70                  75                  80
Leu Gln Met Asn Ser Leu Arg Pro Glu Asp Thr Ala Leu Tyr Tyr Cys
                85                  90                  95
Thr Lys Asp Ile Ser Ile Thr Gly Thr Leu Asp Ala Phe Asp Val Trp
            100                 105                 110
Gly Gln Gly Thr Met Val Thr Val Ser Ser
            115                 120
```

```
<210> SEQ ID NO 18
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 18

Asp Ile Gln Met Thr Gln Ser Pro Ile Ser Val Ser Ala Ser Val Gly
1               5                   10                  15
Asp Arg Val Thr Ile Thr Cys Arg Ala Ser Gln Gly Ile Ser Asn Trp
            20                  25                  30
Leu Ala Trp Tyr Gln Gln Lys Pro Gly Ile Ala Pro Lys Leu Leu Ile
        35                  40                  45
Tyr Ser Ala Ser Ser Leu Gln Ser Gly Val Pro Ser Arg Phe Arg Gly
    50                  55                  60
Ser Gly Ser Gly Thr Asp Phe Thr Leu Thr Ile Gly Ser Leu Gln Pro
65                  70                  75                  80
Glu Asp Phe Ala Thr Tyr Tyr Cys Gln Gln Ala His Ser Phe Pro Leu
                85                  90                  95
Thr Phe Gly Gly Gly Thr Lys Val Glu Ile Lys
            100                 105
```

```
<210> SEQ ID NO 19
<211> LENGTH: 116
<212> TYPE: PRT
<213> ORGANISM: Artificial Sequence
<220> FEATURE:
<223> OTHER INFORMATION: synthetic construct; antigen binding domain

<400> SEQUENCE: 19

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Ile Ile Trp Ser Asp Gly Asp Ser Glu Tyr Asn Leu Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Val Glu Asp Ser Ala Val Tyr Tyr Cys
                85                  90                  95
Ala Arg Asp Arg Asp Leu Glu Asp Ile Trp Gly Gln Gly Thr Met Val
            100                 105                 110
```

Thr Val Ser Ser
        115

<210> SEQ ID NO 20
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105

<210> SEQ ID NO 21
<211> LENGTH: 117
<212> TYPE: PRT
<213> ORGANISM: Artificial Sequence
<220> FEATURE:
<223> OTHER INFORMATION: synthetic construct; antigen binding domain

<400> SEQUENCE: 21

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Thr Phe Ser Asn Phe
            20                  25                  30

Gly Met Thr Trp Val Arg Gln Ala Pro Gly Lys Gly Leu Glu Trp Val
        35                  40                  45

Ser Gly Ile Ser Gly Gly Gly Arg Asp Thr Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Lys Gly Glu Asp Thr Ala Val Tyr Tyr Cys
                85                  90                  95

Val Lys Trp Gly Asn Ile Tyr Phe Asp Tyr Trp Gly Gln Gly Thr Leu
            100                 105                 110

Val Thr Val Ser Ser
        115

<210> SEQ ID NO 22
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 22

Asp Ile Gln Met Thr Gln Ser Pro Ser Ser Leu Ser Ala Ser Val Gly

```
             1               5                  10                 15
Asp Ser Ile Thr Ile Thr Cys Arg Ala Ser Leu Ser Ile Asn Thr Phe
                    20                  25                 30
Leu Asn Trp Tyr Gln Gln Lys Pro Gly Lys Ala Pro Asn Leu Leu Ile
            35                  40                 45
Tyr Ala Ala Ser Ser Leu His Gly Gly Val Pro Ser Arg Phe Ser Gly
        50                  55                 60
Ser Gly Ser Gly Thr Asp Phe Thr Leu Thr Ile Arg Thr Leu Gln Pro
65                  70                  75                 80
Glu Asp Phe Ala Thr Tyr Tyr Cys Gln Gln Ser Ser Asn Thr Pro Phe
                        85                  90                 95
Thr Phe Gly Pro Gly Thr Val Val Asp Phe Arg
                100                 105
```

<210> SEQ ID NO 23
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 23

```
Glu Val Gln Leu Val Glu Ser Gly Gly Val Val Arg Pro Gly Gly
1               5                  10                 15
Ser Leu Arg Leu Ser Cys Ala Ala Ser Gly Phe Thr Phe Asp Asp Tyr
                    20                  25                 30
Gly Met Ser Trp Val Arg Gln Val Pro Gly Lys Gly Leu Glu Trp Val
            35                  40                 45
Ser Gly Ile Ser Trp Asn Asp Gly Lys Thr Val Tyr Ala Glu Ser Val
        50                  55                 60
Lys Gly Arg Phe Ile Ile Ser Arg Asp Asn Ala Lys Asn Ser Leu Tyr
65                  70                  75                 80
Leu Glu Met Asn Ser Leu Arg Ala Glu Asp Thr Ala Leu Tyr Tyr Cys
                        85                  90                 95
Ala Arg Asp Trp Gln Tyr Leu Ile Glu Arg Tyr Phe Asp Tyr Trp Gly
                100                 105                110
Gln Gly Thr Leu Val Thr Val Ser Ser
            115                 120
```

<210> SEQ ID NO 24
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 24

```
Glu Ile Val Leu Thr Gln Ser Pro Gly Thr Leu Ser Leu Ser Pro Gly
1               5                  10                 15
Glu Arg Ala Thr Leu Ser Cys Arg Ala Ser Gln Ser Val Ser Ser Ser
                    20                  25                 30
Tyr Leu Ala Trp Tyr Gln Gln Lys Pro Gly Gln Ala Pro Arg Leu Leu
            35                  40                 45
Ile Tyr Gly Ala Ser Ser Arg Ala Thr Gly Ile Pro Asp Arg Phe Ser
        50                  55                 60
Gly Ser Gly Ser Gly Thr Asp Phe Thr Leu Thr Ile Ser Arg Leu Glu
65                  70                  75                 80
```

```
Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 25
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 25

```
Glu Val Gln Leu Val Glu Ser Gly Gly Gly Val Val Arg Pro Gly Gly
1               5                   10                  15

Ser Leu Arg Leu Ser Cys Thr Ala Ser Gly Phe Thr Phe Asp Asp Tyr
            20                  25                  30

Gly Met Ser Trp Val Arg Gln Ala Pro Gly Lys Gly Leu Glu Trp Ile
        35                  40                  45

Ser Gly Ile Gly Trp Thr Gly Gly Arg Ser Ser Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Gly Ala Glu Asp Thr Ala Leu Tyr Tyr Cys
                85                  90                  95

Ala Arg Asp Arg Gln Trp Leu Val Gly Trp Tyr Phe Asp Tyr Trp Gly
            100                 105                 110

Gln Gly Thr Leu Val Thr Val Ser Ser
        115                 120
```

<210> SEQ ID NO 26
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 27
<211> LENGTH: 121
<212> TYPE: PRT
<213> ORGANISM: Artificial Sequence
<220> FEATURE:
<223> OTHER INFORMATION: synthetic construct; antigen binding domain -continued

<400> SEQUENCE: 27

Glu Val Gln Leu Val Glu Ser Gly Gly Arg Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Leu Pro Gly Lys Gly Leu Glu Trp Val
        35                  40                  45

Ala Gly Ile Ser Trp Asn Asp Gly Lys Thr Val Tyr Ala Glu Ser Val
    50                  55                  60

Lys Gly Arg Phe Ile Ile Ser Arg Asp Asn Ala Lys Asn Ser Leu His
65                  70                  75                  80

Leu Glu Met Asn Ser Leu Arg Ala Glu Asp Thr Ala Leu Tyr Tyr Cys
                85                  90                  95

Ala Arg Asp Trp Gln Tyr Leu Ile Asp Arg Tyr Phe Asp Phe Trp Gly
            100                 105                 110

Gln Gly Thr Leu Val Thr Val Ser Ser
        115                 120

<210> SEQ ID NO 28
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Gly Trp Ser Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Pro Glu Asp Ser Ala Leu Tyr Tyr Cys
                85                  90                  95

Ala Lys Ala Tyr Thr Phe Met Ile Thr Leu Tyr Phe Asp Tyr Trp Gly
            100                 105                 110

Gln Gly Thr Leu Val Thr Val Ser Ser
        115                 120

<210> SEQ ID NO 29
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 29

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Asp Met His Trp Val Arg Gln Ala Pro Gly Lys Gly Leu Glu Trp Val
        35                  40                  45

```
Ser Gly Ser Gly Trp Asn Arg Gly Ser Leu Gly Tyr Ala Asp Ser Val
    50                  55                  60

Lys Gly Arg Phe Thr Ile Ser Arg Asp Asn Ala Lys Lys Ser Leu Tyr
 65                  70                  75                  80

Leu Gln Met Asn Ser Val Arg Val Glu Asp Thr Ala Leu Tyr Tyr Cys
                 85                  90                  95

Ala Lys Gly Phe Val Val Ser Ala Ala Tyr Phe Asp Tyr Trp Gly
            100                 105                 110

Gln Gly Thr Leu Val Thr Val Ser Ser
            115                 120
```

<210> SEQ ID NO 30
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 30

```
Gln Val Gln Leu Val Gln Ser Gly Ala Glu Val Lys Arg Pro Gly Ser
  1               5                  10                  15

Ser Val Lys Val Ser Cys Lys Val Ser Gly Val Thr Phe Arg Asn Phe
                 20                  25                  30

Ala Ile Ile Trp Val Arg Gln Ala Pro Gly Gln Gly Leu Glu Trp Met
             35                  40                  45

Gly Gly Ile Ile Pro Phe Phe Ser Ala Ala Asn Tyr Ala Gln Ser Phe
    50                  55                  60

Gln Gly Arg Val Thr Ile Thr Pro Asp Glu Ser Thr Ser Thr Ala Phe
 65                  70                  75                  80

Met Glu Leu Ala Ser Leu Arg Ser Glu Asp Thr Ala Val Tyr Tyr Cys
                 85                  90                  95

Ala Arg Glu Gly Glu Arg Gly His Thr Tyr Gly Phe Asp Tyr Trp Gly
            100                 105                 110

Gln Gly Thr Leu Val Thr Val Ser Ser
            115                 120
```

<210> SEQ ID NO 31
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 31

```
Glu Val Gln Leu Val Glu Ser Gly Gly Gly Leu Val Gln Ser Gly Arg
  1               5                  10                  15

Ser Leu Arg Leu Ser Cys Ala Ala Ser Gly Phe Thr Phe Asp Asp Tyr
                 20                  25                  30

Ala Met His Trp Val Arg Gln Pro Pro Gly Lys Gly Leu Glu Trp Val
             35                  40                  45

Ser Gly Ile Asn Trp Asn Arg Gly Arg Thr Gly Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Asp Leu Arg Val Glu Asp Thr Ala Leu Tyr Tyr Cys
                 85                  90                  95

Ala Lys Ala Glu Gln Trp Leu Asp Glu Gly Tyr Phe Asp Tyr Trp Gly
            100                 105                 110
```

Gln Gly Thr Leu Val Thr Val Ser Ser
        115                 120

<210> SEQ ID NO 32
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 32

Glu Val Gln Leu Val Glu Ser Gly Gly Gly Leu Val Gln Arg Gly Gly
1               5                   10                  15

Ser Leu Arg Leu Ser Cys Ala Ala Ser Gly Phe Ser Phe Ser Ser Tyr
            20                  25                  30

Ala Met Asn Trp Val Arg Gln Ala Pro Gly Lys Gly Leu Glu Trp Val
        35                  40                  45

Ser Thr Ile Ser Asp Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Glu Asp Thr Ala Val Tyr Tyr Cys
                85                  90                  95

Ala Lys Asp Gln Gly Gly Ser Tyr Pro Tyr Tyr Phe His Tyr Trp Gly
            100                 105                 110

Gln Gly Thr Leu Val Thr Val Ser Ser
        115                 120

<210> SEQ ID NO 33
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 33

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Glu Asp Tyr
            20                  25                  30

Ala Met His Trp Val Arg Gln Ala Pro Gly Lys Gly Leu Glu Trp Val
        35                  40                  45

Ser Gly Ile Gly Trp Ser Asn Val Lys Ile Gly Tyr Ala Asp Ser Val
    50                  55                  60

Lys Gly Arg Phe Thr Ile Ser Arg Asp Asn Val Arg Asn Ser Leu Tyr
65                  70                  75                  80

Leu Gln Met Asn Ser Leu Arg Thr Glu Asp Thr Ala Phe Tyr Tyr Cys
                85                  90                  95

Val Lys Ala Tyr Thr Ser Met Leu Thr Leu Tyr Phe Asp Tyr Trp Gly
            100                 105                 110

Gln Gly Thr Leu Val Thr Val Ser Ser
        115                 120

<210> SEQ ID NO 34
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 34

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Phe
            20                  25                  30

Tyr Met Tyr Trp Val Arg Gln Ala Pro Gly Gln Gly Leu Glu Trp Met
        35                  40                  45

Gly Ile Ile Asn Pro Ser Asp Gly Ser Thr Ser Asn Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Val Ala Gly Asp Ile Phe Asp Ile Trp Gly Gln Gly Thr
            100                 105                 110

Met Val Thr Val Ser Ser
        115

<210> SEQ ID NO 35
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 35

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

His Trp Asn Trp Ile Arg Gln Ser Pro Gly Lys Gly Leu Glu Trp Ile
        35                  40                  45

Gly Tyr Ile Tyr Tyr Ile Gly Ser Thr Asp Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Pro Val Gly Ala Thr Gly Ala Ser Asp Val Trp Gly Gln Gly
            100                 105                 110

Thr Met Val Thr Val Ser Ser
        115

<210> SEQ ID NO 36
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 36

Glu Val Gln Leu Val Glu Ser Gly Gly Ser Val Val Arg Pro Gly Gly
1               5                   10                  15

Ser Leu Arg Leu Ser Cys Val Val Ser Gly Phe Thr Phe Glu Asp Tyr
            20                  25                  30

Gly Leu Ser Trp Val Arg Gln Ile Pro Gly Lys Gly Leu Glu Trp Val
        35                  40                  45

```
Ser Gly Ile Ser Trp Thr Gly Gly Asn Thr Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                 85                  90                  95

Thr Arg Asp Arg Gln Trp Leu Met Gln Trp Tyr Phe Asp Tyr Trp Gly
             100                 105                 110

Gln Gly Thr Leu Val Thr Val Ser Ser
             115                 120

<210> SEQ ID NO 37
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 37

Gln Val Gln Leu Val Glu Ser Gly Gly Gly Val Val Gln Pro Gly Arg
 1               5                  10                  15

Ser Leu Arg Leu Ser Cys Ser Ala Ser Gly Phe Thr Phe Ser Ala Tyr
                 20                  25                  30

Ala Met His Trp Val Arg Gln Ala Pro Gly Lys Gly Leu Glu Trp Val
             35                  40                  45

Ala Ala Ile Ser Tyr Gly Gly Ser Asp Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Thr Asp Asp Thr Ala Val Tyr Tyr Cys
                 85                  90                  95

Ala Lys Ser Ala His Trp Asn Phe Phe Phe Asp Tyr Trp Gly Gln Gly
             100                 105                 110

Thr Leu Val Thr Val Ser Ser
         115

<210> SEQ ID NO 38
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 38

Glu Val Gln Leu Val Glu Ser Gly Gly Gly Leu Val Gln Pro Gly Arg
 1               5                  10                  15

Ser Leu Arg Leu Ser Cys Val Ala Ser Gly Phe Ala Leu His Asp Tyr
                 20                  25                  30

Ala Met His Trp Val Arg Gln Val Pro Gly Lys Gly Leu Glu Trp Val
             35                  40                  45

Ser Ser Ile Ser Trp Asn Ser Gly Val Ile Gly Tyr Ala Asp Ser Leu
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Gly Ser Gly Ser Tyr Tyr Val Ser Trp Phe Asp Pro Trp Gly
```

```
                    100                 105                 110

Gln Gly Thr Leu Val Thr Val Ser Ser
            115                 120

<210> SEQ ID NO 39
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 39

Gln Leu Gln Leu Gln Glu Ser Gly Pro Gly Leu Val Gln Pro Ser Glu
1               5                   10                  15

Thr Leu Ser Leu Thr Cys Thr Val Ser Gly Asp Ser Ile Ser Ser Thr
            20                  25                  30

Ala Tyr His Trp Asp Trp Ile Arg Gln Pro Pro Gly Lys Gly Leu Glu
        35                  40                  45

Trp Ile Gly Thr Ile Thr Tyr Asn Gly Asn Thr Tyr Phe Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Leu Ser Met Thr Ala Ala Glu Thr Ala Val Phe Tyr
                85                  90                  95

Cys Ala Arg His Leu Gly Tyr Asn Ser Asp Phe Phe Pro Phe Asp Phe
            100                 105                 110

Trp Gly Gln Gly Thr Leu Val Thr Val Ser Ser
        115                 120

<210> SEQ ID NO 40
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 40

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Thr Tyr
            20                  25                  30

Ala Met Ala Trp Val Arg Gln Thr Pro Gly Lys Gly Leu Glu Gly Val
        35                  40                  45

Ser Ala Ile Gly Gly Ser Gly Asp Ser Thr Tyr Tyr Val Asp Ser Val
    50                  55                  60

Lys Gly Arg Phe Thr Ile Ser Arg Asp Asn Ser Lys Ser Thr Leu Phe
65                  70                  75                  80

Leu Gln Met Asn Ser Leu Arg Ala Glu Asp Thr Ala Val Tyr Tyr Cys
                85                  90                  95

Val Lys Val Arg Asn Tyr Asp Gly Ser Phe Asp Ile Trp Gly Gln Gly
            100                 105                 110

Thr Met Val Thr Val Ser Ser
        115

<210> SEQ ID NO 41
<211> LENGTH: 124
<212> TYPE: PRT
<213> ORGANISM: Artificial Sequence
<220> FEATURE:
```

<223> OTHER INFORMATION: synthetic construct; antigen binding domain

<400> SEQUENCE: 41

```
Glu Val Gln Leu Leu Glu Ser Gly Gly Gly Leu Val Gln Pro Gly Gly
1               5                   10                  15

Ser Leu Arg Leu Ser Cys Val Ala Ser Gly Phe Thr Phe Ser Thr Tyr
            20                  25                  30

Ala Met Ser Trp Val Arg Gln Ala Pro Gly Met Gly Leu Glu Trp Val
        35                  40                  45

Ser Ser Ile Ser Gly Ser Gly Arg Asn Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Glu Ser Val Thr Gly Thr Ser Ser Tyr Tyr Tyr Gly Val Asp
            100                 105                 110

Val Trp Gly Gln Gly Thr Thr Val Thr Val Ser Ser
        115                 120
```

<210> SEQ ID NO 42
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr His Gln Lys Pro Gly Lys Ala Pro Lys Leu Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ser Tyr Arg Thr Pro Leu
                85                  90                  95

Thr Phe Gly Gly Gly Thr Lys Val Glu Ile Lys
            100                 105
```

<210> SEQ ID NO 43
<211> LENGTH: 128
<212> TYPE: PRT
<213> ORGANISM: Artificial Sequence
<220> FEATURE:
<223> OTHER INFORMATION: synthetic construct; antigen binding domain

<400> SEQUENCE: 43

```
Gln Val Gln Leu Glu Glu Ser Gly Gly Gly Val Val Gln Pro Gly Arg
1               5                   10                  15

Ser Leu Arg Leu Ser Cys Ala Ala Ser Gly Phe Thr Phe Ser Trp Tyr
            20                  25                  30

Gly Met His Trp Val Arg Gln Ala Pro Gly Lys Gly Leu Glu Trp Val
        35                  40                  45

Ala Leu Ile Trp Tyr Asp Gly Thr Asn Lys Lys Tyr Gly Asp Ser Val
```

```
              50                  55                  60
Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Arg Asp Cys Gly His Ser Gly Asn Asp Arg Gly Thr Tyr Tyr Tyr
                100                 105                 110

Tyr Tyr Gly Met Asp Val Trp Gly Gln Gly Thr Thr Val Thr Val Ser
            115                 120                 125

<210> SEQ ID NO 44
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 44

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
                100                 105

<210> SEQ ID NO 45
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 45

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                20                  25                  30

Tyr Trp Asn Trp Ile Arg Gln Pro Pro Gly Lys Gly Leu Glu Trp Val
            35                  40                  45

Gly Glu Ile Ser His Arg Gly Thr Thr Asn Tyr Asn Pro Ser Leu Lys
        50                  55                  60

Ser Arg Val Thr Ile Ser Leu Asp Thr Ser Lys Asn Gln Phe Ser Leu
 65                  70                  75                  80

Lys Leu Thr Ser Val Thr Ala Ala Asp Thr Ala Val Tyr Tyr Cys Ser
                 85                  90                  95

Arg Asp Glu Glu Leu Glu Phe Arg Phe Phe Asp Tyr Trp Gly Gln Gly
                100                 105                 110

Thr Leu Val Thr Val Ser Ser
            115
```

```
<210> SEQ ID NO 46
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Val
        35                  40                  45

Tyr Gly Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 47
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 47

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ile Ser Asn
            20                  25                  30

Ser Tyr Tyr Trp Gly Trp Ile Arg Gln Pro Pro Gly Lys Gly Leu Glu
        35                  40                  45

Trp Ile Gly Asn Phe Phe Tyr Thr Gly Ala Thr Tyr Tyr Asn Pro Ser
50                  55                  60

Leu Lys Ser Arg Val Thr Ile Ser Ala Asp Thr Ser Lys Asn Gln Phe
65                  70                  75                  80

Ser Leu Lys Leu Ser Ser Val Thr Ala Ala Asp Thr Ala Leu Tyr Tyr
                85                  90                  95

Cys Ala Ser Tyr Asn Arg Asn Tyr Arg Phe Asp Pro Trp Gly Gln Gly
            100                 105                 110

Thr Leu Val Thr Val Ser Ser
        115

<210> SEQ ID NO 48
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
```

```
                20                  25                  30
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 49
<211> LENGTH: 127
<212> TYPE: PRT
<213> ORGANISM: Artificial Sequence
<220> FEATURE:
<223> OTHER INFORMATION: synthetic construct; antigen binding domain

<400> SEQUENCE: 49

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Thr Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asn Ala Asp Tyr Asn Pro Ser Leu Lys
    50                  55                  60

Ser Arg Val Ser Ile Ser Val Asp Thr Ser Lys Asn Gln Phe Ser Leu
65                  70                  75                  80

Arg Leu Ser Ser Val Thr Ala Ala Asp Thr Ala Ile Tyr Tyr Cys Ala
                85                  90                  95

Arg Ala Gly Tyr Cys Ser Ser Pro Thr Cys Tyr Ser Tyr Tyr Tyr Phe
            100                 105                 110

Gly Met Asp Val Trp Gly Gln Gly Thr Thr Val Thr Val Ser Ser
        115                 120                 125
```

<210> SEQ ID NO 50
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 50

```
Glu Ile Val Leu Thr Gln Ser Pro Gly Thr Leu Ser Leu Ser Leu Gly
1               5                   10                  15

Glu Arg Ala Thr Leu Ser Cys Arg Ala Ser Gln Ser Val Ile Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Ser Arg Ala Thr Gly Phe Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Phe Ala Val Tyr Tyr Cys Gln Gln Tyr Gly Asn Ser Pro
                85                  90                  95
```

```
Trp Thr Phe Gly Gln Gly Thr Lys Val Glu Ile Lys
            100                 105
```

<210> SEQ ID NO 51
<211> LENGTH: 129
<212> TYPE: PRT
<213> ORGANISM: Artificial Sequence
<220> FEATURE:
<223> OTHER INFORMATION: synthetic construct; antigen binding domain

<400> SEQUENCE: 51

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Gly Met Gly Val Ser Trp Val Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Arg Thr Arg Leu Thr Ile Ser Lys Asp Thr Ser Lys Ser Gln Val
65                  70                  75                  80

Val Leu Thr Val Thr Asn Leu Asp Pro Val Asp Thr Ala Thr Tyr Phe
                85                  90                  95

Cys Ala Arg Ile Pro Glu Phe Thr Ser Ser Ser Trp Ala Leu Tyr Tyr
            100                 105                 110

Phe Tyr Gly Met Asp Val Trp Gly Gln Gly Thr Thr Val Thr Val Ser
        115                 120                 125

Ser
```

<210> SEQ ID NO 52
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 52

```
Glu Ile Val Leu Thr Gln Ser Pro Gly Thr Leu Ser Leu Ser Pro Gly
1               5                   10                  15

Glu Ser Ala Thr Leu Ser Cys Arg Ala Ser Gln Ser Ile Thr Ser Thr
            20                  25                  30

Tyr Phe Ala Trp Tyr Gln Gln Lys Pro Gly Gln Ala Pro Arg Leu Leu
        35                  40                  45

Ile Tyr Ala Thr Ser Ser Arg Ala Thr Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Asp Asp Phe Ala Val Tyr Tyr Cys Gln Gln Tyr Gly Arg Ser Pro
                85                  90                  95

Trp Thr Phe Gly Gln Gly Thr Lys Val Glu Val Lys
            100                 105
```

<210> SEQ ID NO 53
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 53

Gln Val Gln Leu Val Gln Ser Gly Ala Glu Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Asp Asn Thr Asn Tyr Ala Gln Lys Leu
50                  55                  60

Gln Gly Arg Val Thr Met Thr Ala Asp Thr Ser Thr Asn Thr Ala Tyr
65                  70                  75                  80

Met Glu Leu Arg Ser Leu Arg Ser Asp Asp Thr Ala Ile Tyr Tyr Cys
                85                  90                  95

Val Arg Trp Asn Trp Gly Ser Val Tyr Trp Tyr Phe Asp Leu Trp Gly
            100                 105                 110

Arg Gly Thr Leu Val Thr Val Ser Ser
        115                 120

<210> SEQ ID NO 54
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 54

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ile Ile Ser Ser Ser
            20                  25                  30

Tyr Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Val Ser Gly Thr Asp Phe Thr Leu Thr Ile Ser Arg Leu Glu
65                  70                  75                  80

Pro Glu Asp Phe Ala Met Tyr Phe Cys Gln Gln Tyr Gly Asn Ser Pro
                85                  90                  95

Trp Thr Phe Gly Gln Gly Thr Lys Val Glu Ile Lys
            100                 105

<210> SEQ ID NO 55
<211> LENGTH: 117
<212> TYPE: PRT
<213> ORGANISM: Artificial Sequence
<220> FEATURE:
<223> OTHER INFORMATION: synthetic construct; antigen binding domain

<400> SEQUENCE: 55

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr His
            20                  25                  30

Arg Val Gly Val Gly Trp Ile Arg Gln Pro Pro Gly Lys Ala Leu Glu
        35                  40                  45

Trp Leu Ala Leu Ile Tyr Gly Asn Asp Val Lys Asn Tyr Ser Pro Ser
50                  55                  60

Leu Glu Thr Arg Leu Thr Ile Ala Lys Asp Thr Ser Lys Asn Gln Val

```
                65                  70                  75                  80
Val Leu Thr Met Thr Asn Met Asp Pro Val Asp Thr Ala Thr Tyr Phe
                    85                  90                  95

Cys Ser Tyr Ile Thr Gly Glu Gly Met Tyr Trp Gly Gln Gly Thr Leu
                100                 105                 110

Val Thr Val Ser Ser
            115

<210> SEQ ID NO 56
<211> LENGTH: 111
<212> TYPE: PRT
<213> ORGANISM: Artificial Sequence
<220> FEATURE:
<223> OTHER INFORMATION: synthetic construct; antigen binding domain

<400> SEQUENCE: 56

Asp Val Val Met Thr Gln Ser Pro Leu Ser Leu Ser Val Thr Leu Gly
1               5                   10                  15

Gln Pro Ala Ser Ile Ser Cys Arg Ser Ser Gln Asn Leu Met Tyr Ser
            20                  25                  30

Asp Gly Asn Thr Tyr Leu Asn Trp Phe His Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Tyr Thr Phe Gly Gln Gly Thr Lys Leu Glu Ile Lys
                100                 105                 110

<210> SEQ ID NO 57
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 57

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Arg Gly Asn Thr Asn Tyr Asn Pro Ser Leu Lys
    50                  55                  60

Ser Arg Val Thr Ile Ser Leu Asp Thr Ser Lys Lys Gln Phe Ser Leu
65                  70                  75                  80

Asn Leu Ser Ser Val Thr Ala Ala Asp Thr Ala Met Tyr Tyr Cys Thr
                85                  90                  95

Arg Asp Glu Glu Gln Glu Leu Arg Phe Leu Asp Tyr Trp Gly Gln Gly
                100                 105                 110

Thr Leu Val Thr Val Ser Ser
            115

<210> SEQ ID NO 58
<211> LENGTH: 107
```

```
<212> TYPE: PRT
<213> ORGANISM: Artificial Sequence
<220> FEATURE:
<223> OTHER INFORMATION: synthetic construct; antigen binding domain

<400> SEQUENCE: 58
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Thr Tyr
            20                  25                  30

Leu Ala Trp Tyr Gln Gln Arg Ala Gly Gln Ala Pro Arg Leu Leu Ile
        35                  40                  45

Tyr Gly Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Leu
                85                  90                  95

Thr Phe Gly Gly Gly Thr Glu Val Glu Ile Lys
            100                 105

```
<210> SEQ ID NO 59
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 59
```

Gln Val Gln Leu Gln Gln Trp Gly Ala Gly Leu Leu Lys Pro Ser Glu
1               5                   10                  15

Thr Leu Ser Leu Thr Cys Val Val His Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Arg Gly Asn Thr Asn Tyr Asn Pro Ser Leu Lys
50                  55                  60

Ser Arg Val Thr Val Ser Glu Asp Thr Ser Lys Asn Gln Phe Ser Leu
65                  70                  75                  80

Lys Leu Ser Ser Leu Thr Ala Ala Asp Thr Ala Val Tyr Tyr Cys Val
                85                  90                  95

Arg Gly Glu Asp Tyr Asp Phe Trp Ser Asp Tyr Tyr Asn Asp Tyr Trp
            100                 105                 110

Gly Gln Gly Thr Leu Val Thr Val Ser Ser
        115                 120

```
<210> SEQ ID NO 60
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 60
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Ser Ser Tyr
            20                  25                  30

Leu Ala Trp His Gln Gln Lys Pro Gly Gln Ala Pro Arg Leu Leu Ile

```
            35                  40                  45
Tyr Asp Ala Ser Lys Arg Ala Thr Gly Ile Pro Ala Arg Phe Ser Gly
         50                  55                  60
Ser Gly Ser Gly Thr Asp Phe Thr Leu Thr Ile Thr Ser Leu Glu Pro
 65                  70                  75                  80
Glu Asp Phe Ala Val Tyr Tyr Cys Gln Gln Arg Ser Asn Trp Pro Leu
                 85                  90                  95
Thr Phe Gly Gly Gly Thr Lys Val Glu Ile Lys
            100                 105
```

<210> SEQ ID NO 61
<211> LENGTH: 124
<212> TYPE: PRT
<213> ORGANISM: Artificial Sequence
<220> FEATURE:
<223> OTHER INFORMATION: synthetic construct; antigen binding domain

<400> SEQUENCE: 61

```
Gln Val Gln Leu Gln Gln Trp Gly Ala Gly Leu Leu Pro Pro Ser Glu
 1               5                  10                  15
Thr Leu Ser Leu Ile Cys Ala Val Tyr Gly Gly Ser Phe Ser Gly Tyr
             20                  25                  30
Tyr Trp Ser Trp Ile Arg Gln Pro Pro Gly Lys Gly Leu Glu Trp Ile
         35                  40                  45
Gly Glu Ile Asn His Arg Gly Ser Thr Asn Tyr Asn Pro Ser Leu Lys
     50                  55                  60
Ser Arg Ala Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ser
                 85                  90                  95
Arg Gly Glu Asp Tyr Tyr Asp Ser Ser Gly Tyr Ser Tyr Tyr Phe Asp
            100                 105                 110
Tyr Trp Gly Gln Gly Thr Leu Val Thr Val Ser Ser
            115                 120
```

<210> SEQ ID NO 62
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 62

```
Glu Ile Val Leu Thr Gln Ser Pro Ala Thr Leu Ser Leu Ser Pro Gly
 1               5                  10                  15
Glu Arg Ala Thr Leu Ser Cys Arg Ala Ser Gln Ser Val Ser Ser Tyr
             20                  25                  30
Leu Ala Trp Tyr Gln Gln Lys Pro Gly Gln Ala Pro Arg Leu Leu Ile
         35                  40                  45
Tyr Asp Ala Ser Asn Arg Ala Thr Gly Ile Pro Ala Arg Phe Ser Gly
         50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Leu
                 85                  90                  95
Thr Phe Gly Gly Gly Thr Lys Val Glu Ile Lys
            100                 105
```

```
<210> SEQ ID NO 63
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 63

Gln Val Gln Leu Gln Gln Trp Gly Ala Gly Leu Leu Arg Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Ser Pro Gly Thr Gly Leu Glu Trp Ile
        35                  40                  45

Gly Glu Ile Asn His Arg Gly Asn Ile Asn Phe Asn Pro Ser Leu Lys
    50                  55                  60

Ser Arg Val Thr Ile Ser Glu Asp Thr Ser Lys Asn Gln Phe Ser Leu
65                  70                  75                  80

Arg Leu Asn Ser Val Thr Ala Ala Asp Thr Ala Val Tyr Tyr Cys Ala
                85                  90                  95

Arg Gly Glu Asp Tyr Asp Ile Trp Ser Gly Tyr Tyr Arg Glu Tyr Trp
            100                 105                 110

Gly Gln Gly Thr Leu Val Thr Val Ser Ser
        115                 120

<210> SEQ ID NO 64
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 64

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Ala Phe Gly Gly Gly Thr Lys Val Glu Ile Lys
            100                 105

<210> SEQ ID NO 65
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 65

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Glu Phe
```

```
                   20                  25                  30

Tyr Trp Asn Trp Ile Arg Gln Pro Pro Glu Lys Gly Leu Glu Trp Ile
            35                  40                  45

Gly Glu Ile Asn His Arg Gly Asn Thr Asn Tyr Asn Pro Ser Leu Lys
    50                  55                  60

Ser Arg Val Thr Ile Ser Val Asp Met Ser Lys Asn Gln Phe Ser Leu
65                  70                  75                  80

Gln Leu Asn Ser Val Thr Val Ala Asp Thr Ala Leu Tyr Tyr Cys Ala
                85                  90                  95

Phe Gly Tyr Asp Phe Arg Ser Ser Tyr Glu Asp Val Trp Gly Gln Gly
            100                 105                 110

Thr Thr Val Thr Val Ser Ser
        115

<210> SEQ ID NO 66
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 66

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Thr Tyr
            20                  25                  30

Leu Ala Trp His Gln Gln Lys Pro Gly Gln Pro Arg Leu Leu Ile
            35                  40                  45

Tyr Gly Ser Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 67
<211> LENGTH: 124
<212> TYPE: PRT
<213> ORGANISM: Artificial Sequence
<220> FEATURE:
<223> OTHER INFORMATION: synthetic construct; antigen binding domain

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
            35                  40                  45

Ser Val Ile Ser Gly Gly Gly Arg Thr Tyr Tyr Thr Asp Ser Val
    50                  55                  60

Lys Gly Arg Phe Thr Ile Ser Arg Asp Asn Ser Lys Ser Met Leu Tyr
65                  70                  75                  80

Leu Gln Met Asn Ser Leu Arg Ala Glu Asp Thr Ala Ile Tyr Tyr Cys
                85                  90                  95
```

```
Ala Lys Glu Arg Val Thr Gly Ile Asp His Tyr Tyr Gly Val Asp
            100                 105                 110

Val Trp Gly Gln Gly Thr Thr Val Thr Val Ser Ser
        115                 120
```

<210> SEQ ID NO 68
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 68

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
50                  55                  60

Ser Ala Ser Gly Thr Asp Phe Thr Leu Ala Ile Ser Ser Leu Gln Pro
65                  70                  75                  80

Glu Asp Phe Ala Thr Tyr Tyr Cys Gln Gln Ser Tyr Thr Thr Pro Leu
                85                  90                  95

Thr Phe Gly Gly Gly Thr Lys Val Glu Ile Lys
            100                 105
```

<210> SEQ ID NO 69
<211> LENGTH: 130
<212> TYPE: PRT
<213> ORGANISM: Artificial Sequence
<220> FEATURE:
<223> OTHER INFORMATION: synthetic construct; antigen binding domain

<400> SEQUENCE: 69

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Asn Thr Lys Asp Tyr Ala Gly Ser Val
50                  55                  60

Lys Gly Arg Val Thr Ile Ser Arg Asp Asn Ala Lys Asn Leu Leu Tyr
65                  70                  75                  80

Leu Gln Met Asn Ser Leu Arg Ala Glu Asp Thr Ala Val Tyr His Cys
                85                  90                  95

Ala Arg Asp Gly Gly His Tyr Asp Ile Leu Thr Gly Ser Met Ser Tyr
            100                 105                 110

Tyr Tyr Tyr Ala Leu Asp Val Trp Gly Gln Gly Thr Thr Val Thr Val
        115                 120                 125

Ser Ser
    130
```

<210> SEQ ID NO 70
<211> LENGTH: 108
<212> TYPE: PRT
<213> ORGANISM: Artificial Sequence

```
<220> FEATURE:
<223> OTHER INFORMATION: synthetic construct; antigen binding domain

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 71
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Lys Thr Tyr
            20                  25                  30

Ala Met Ser Trp Val Arg Gln Ala Pro Gly Arg Gly Leu Glu Trp Val
        35                  40                  45

Ser Gly Ile Ser Gly Ser Gly Ser Thr Ser Tyr Tyr Ala Asp Ser Val
50                  55                  60

Lys Gly Arg Phe Thr Ile Ser Arg Asp Asn Tyr Lys Lys Thr Leu Ser
65                  70                  75                  80

Leu Gln Met Asn Ser Leu Arg Ala Glu Asp Thr Ala Val Tyr Tyr Cys
                85                  90                  95

Ala Leu Asp Ile Met Ala Thr Val Gly Gly Leu Phe Asn Asn Trp Gly
            100                 105                 110

Gln Gly Thr Leu Val Thr Val Ser Ser
        115                 120

<210> SEQ ID NO 72
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 72

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
             100                 105
```

<210> SEQ ID NO 73
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 73

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Arg His
                 20                  25                  30

Thr Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala His Lys Phe
 50                  55                  60

Gln Gly Arg Val Thr Ile Thr Thr Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Pro Tyr Thr Arg Gln Gly Tyr Phe Asp Leu Trp Gly Arg
             100                 105                 110

Gly Thr Leu Val Thr Val Ser Ser
         115                 120
```

<210> SEQ ID NO 74
<211> LENGTH: 113
<212> TYPE: PRT
<213> ORGANISM: Artificial Sequence
<220> FEATURE:
<223> OTHER INFORMATION: synthetic construct; antigen binding domain

<400> SEQUENCE: 74

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                 20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Asp Tyr Ser Thr Pro Trp Thr Phe Gly Gln Gly Thr Lys Val Glu Ile
             100                 105                 110

Lys
```

<210> SEQ ID NO 75
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 75

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Asp Trp Met
        35                  40                  45

Gly Ile Ile Asn Pro Gly Gly Gly Asn Thr Asn Tyr Ala Gln Lys Phe
    50                  55                  60

Leu Gly Arg Val Thr Met Thr Arg Asp Thr Ser Thr Thr Thr Val Tyr
65                  70                  75                  80

Met Glu Leu Ser Ser Leu Arg Ser Glu Asp Thr Ala Ile Tyr Tyr Cys
                85                  90                  95

Ala Arg Glu Asn Trp Asn Ser Tyr Phe Asp Asn Trp Gly Gln Gly Thr
            100                 105                 110

Leu Val Thr Val Ser Ser
        115
```

<210> SEQ ID NO 76
<211> LENGTH: 113
<212> TYPE: PRT
<213> ORGANISM: Artificial Sequence
<220> FEATURE:
<223> OTHER INFORMATION: synthetic construct; antigen binding domain

<400> SEQUENCE: 76

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Leu Tyr Tyr Cys Gln Gln
                85                  90                  95

Tyr Tyr Gly Ala Pro Trp Thr Phe Gly Gln Gly Thr Lys Val Glu Ile
            100                 105                 110

Lys
```

<210> SEQ ID NO 77
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 77

```
Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
        20                  25                  30

Thr Ile Asn Trp Val Arg Gln Ala Pro Gly Gln Gly Leu Glu Trp Met
            35                  40                  45

Gly Gly Ile Ile Pro Ile Phe Gly Ile Ala Asn Tyr Ala Gln Lys Phe
 50                  55                  60

Gln Gly Arg Val Thr Ile Thr Thr Asp Glu Ser Thr Asn Thr Ala Tyr
 65                  70                  75                  80

Met Glu Leu Ser Ser Leu Arg Ser Glu Asp Thr Ala Ile Tyr Tyr Cys
                85                  90                  95

Ala Arg Ala Arg Tyr Gly Ser Gly Ser Tyr Asp Tyr Trp Gly Gln Gly
            100                 105                 110

Thr Leu Val Thr Val Ser Ser
        115

<210> SEQ ID NO 78
<211> LENGTH: 113
<212> TYPE: PRT
<213> ORGANISM: Artificial Sequence
<220> FEATURE:
<223> OTHER INFORMATION: synthetic construct; antigen binding domain

<400> SEQUENCE: 78

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Thr
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Tyr Asn Thr Pro Trp Thr Phe Gly Gln Gly Thr Lys Val Glu Ile
            100                 105                 110

Lys

<210> SEQ ID NO 79
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 79

Gln Ile Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Asn
            20                  25                  30

Gly Val Gly Val Gly Trp Ile Arg Gln Pro Pro Gly Lys Ala Leu Glu
        35                  40                  45

Trp Leu Gly Ile Ile Tyr Trp Asn Asp Asp Lys Arg Tyr Ser Pro Ser
 50                  55                  60

Leu Arg Ser Arg Leu Thr Ile Thr Lys Asp Thr Ser Lys Asn Gln Val
 65                  70                  75                  80
```

-continued

Val Leu Thr Met Thr Asn Met Asp Pro Val Asp Thr Ala Thr Tyr Tyr
                85                  90                  95

Cys Ala His Arg Gly Leu Phe Gly Gly Trp Phe Asp Pro Trp Gly Gln
            100                 105                 110

Gly Thr Leu Val Thr Val Ser Ser
        115                 120

<210> SEQ ID NO 80
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Asn Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Asn Thr Pro Leu
                85                  90                  95

Thr Phe Gly Gly Gly Thr Lys Val Glu Ile Lys
            100                 105

<210> SEQ ID NO 81
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ile Ser Gly Phe Thr Phe Arg Ser Tyr
            20                  25                  30

Ala Met Thr Trp Val Arg Gln Ala Pro Gly Lys Ala Leu Glu Trp Val
        35                  40                  45

Ser Val Ile Ser Gly Ser Gly Gly Asn Thr Tyr Tyr Ala Asp Ser Val
    50                  55                  60

Lys Gly Arg Phe Thr Val Ser Arg Asp Asn Ser Arg Asn Thr Leu Tyr
65                  70                  75                  80

Leu Gln Met Asn Ser Leu Arg Ala Glu Asp Thr Ala Val Tyr Phe Cys
                85                  90                  95

Ser Lys Val Ala Ala Ala Asn Asn Tyr Tyr Tyr Ala Leu Asp Val Trp
            100                 105                 110

Gly Gln Gly Thr Thr Val Thr Val Ser Ser
        115                 120

<210> SEQ ID NO 82
<211> LENGTH: 112
<212> TYPE: PRT

<213> ORGANISM: Artificial Sequence
<220> FEATURE:
<223> OTHER INFORMATION: synthetic construct; antigen binding domain

<400> SEQUENCE: 82

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Lys Tyr Leu Asp Trp Tyr Leu Gln Lys Pro Gly Gln Ser
        35                  40                  45

Pro Gln Leu Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

<210> SEQ ID NO 83
<211> LENGTH: 127
<212> TYPE: PRT
<213> ORGANISM: Artificial Sequence
<220> FEATURE:
<223> OTHER INFORMATION: synthetic construct; antigen binding domain

<400> SEQUENCE: 83

```
Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Ser Ser Leu Arg Ala Asp Asp Thr Ala Val Tyr Tyr Cys
                85                  90                  95

Ala Arg Asp Gly Glu Val Glu Tyr Ser Ser Ser Asn Tyr Asn Tyr Tyr
            100                 105                 110

Gly Leu Asp Val Trp Gly Gln Gly Thr Thr Val Thr Val Ser Ser
        115                 120                 125
```

<210> SEQ ID NO 84
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 84

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

Tyr Asp Ala Ser Asn Leu Glu Thr Gly Val Pro Ser Arg Phe Ser Gly
            50                  55                  60

Ser Gly Ser Gly Thr Asp Phe Thr Phe Thr Ile Ser Ser Leu Gln Pro
 65                  70                  75                  80

Glu Asp Ile Val Thr Tyr Tyr Cys Gln Gln Tyr Asp Asp Leu Pro Ile
                    85                  90                  95

Thr Phe Gly Gln Gly Thr Arg Leu Glu Ile Lys
                100                 105

<210> SEQ ID NO 85
<211> LENGTH: 125
<212> TYPE: PRT
<213> ORGANISM: Artificial Sequence
<220> FEATURE:
<223> OTHER INFORMATION: synthetic construct; antigen binding domain

<400> SEQUENCE: 85

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Ser Phe His Asn Phe
                20                  25                  30

Ala Met Asn Trp Val Arg Gln Ala Pro Gly Lys Gly Leu Glu Trp Val
            35                  40                  45

Ser Val Ile Thr Gly Ser Gly Thr Ser Thr His Tyr Ala Asp Ser Val
         50                  55                  60

Lys Gly Arg Phe Thr Ile Ser Arg Asp Asn Ser Lys Lys Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Arg Gly Tyr Asp Tyr Ser Gly Ser Tyr Tyr Asn Trp Phe
                100                 105                 110

Asp Pro Trp Gly Gln Gly Thr Leu Val Thr Val Ser Ser
            115                 120                 125

<210> SEQ ID NO 86
<211> LENGTH: 109
<212> TYPE: PRT
<213> ORGANISM: Artificial Sequence
<220> FEATURE:
<223> OTHER INFORMATION: synthetic construct; antigen binding domain

<400> SEQUENCE: 86

Asp Ile Gln Met Thr Gln Ser Pro Ser Ser Leu Ser Ala Ser Val Gly
 1               5                   10                  15

Asp Arg Ile Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Phe Ala Ala Ser Asn Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Ser
                85                  90                  95

Leu Phe Thr Phe Gly Pro Gly Thr Lys Val Asp Ile Lys
                100                 105

```
<210> SEQ ID NO 87
<211> LENGTH: 128
<212> TYPE: PRT
<213> ORGANISM: Artificial Sequence
<220> FEATURE:
<223> OTHER INFORMATION: synthetic construct; antigen binding domain

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser His Ile Ser Ser Ser Gly Ser Thr Ile Tyr Tyr Ala Asp Ser Val
    50                  55                  60

Lys Gly Arg Phe Thr Met Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Asn Ile Trp Ser Gly Tyr Tyr Ala Ala Tyr Tyr Phe
            100                 105                 110

Tyr Gly Met Asp Val Trp Gly Gln Gly Thr Thr Val Thr Val Ser Ser
        115                 120                 125

<210> SEQ ID NO 88
<211> LENGTH: 112
<212> TYPE: PRT
<213> ORGANISM: Artificial Sequence
<220> FEATURE:
<223> OTHER INFORMATION: synthetic construct; antigen binding domain

<400> SEQUENCE: 88

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Lys Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Ile Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Val Gln Phe Pro Arg Thr Phe Gly Gln Gly Thr Lys Val Glu Ile Lys
            100                 105                 110

<210> SEQ ID NO 89
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 89

Gln Val Gln Leu Gln Gln Trp Gly Ala Gly Leu Leu Asn Pro Ser Glu
1               5                   10                  15

Thr Leu Ser Leu Thr Cys Ala Val Tyr Gly Gly Ala Phe Ser Asp Tyr
            20                  25                  30
```

Tyr Trp Asn Trp Ile Arg Gln Pro Pro Gly Lys Gly Leu Glu Trp Ile
            35                  40                  45

Gly Glu Ile Asn His Arg Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Met Ser Ser Val Thr Ala Ala Asp Ala Ala Val Tyr Tyr Cys Ala
                85                  90                  95

Arg Gly Glu Asp Tyr Asp Ile Trp Asn Gly Tyr Tyr Gln Glu Lys Trp
            100                 105                 110

Gly Gln Gly Thr Leu Val Thr Val Ser Ser
            115                 120

<210> SEQ ID NO 90
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 90

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Tyr
            20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Val Val Tyr Tyr Cys His Gln Arg Ser Asn Trp Pro Leu
                85                  90                  95

Thr Phe Gly Gly Gly Thr Lys Val Glu Ile Lys
            100                 105

<210> SEQ ID NO 91
<211> LENGTH: 117
<212> TYPE: PRT
<213> ORGANISM: Artificial Sequence
<220> FEATURE:
<223> OTHER INFORMATION: synthetic construct; antigen binding domain

<400> SEQUENCE: 91

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser Tyr
            20                  25                  30

Tyr Trp Ser Trp Leu Arg Gln Pro Pro Gly Lys Gly Leu Glu Trp Ile
            35                  40                  45

Gly Tyr Ile Phe Tyr Ser Gly Ser Thr Asp Tyr Asn Pro Ser Leu Lys
    50                  55                  60

Ser Arg Val Thr Ile Ser Val Asp Thr Ser Lys Lys Gln Phe Ser Leu
65                  70                  75                  80

Lys Leu Thr Ser Val Thr Ala Ala Asp Thr Ala Val Tyr Tyr Cys Ala
                85                  90                  95

Arg Thr Ile Ser Thr Trp Trp Phe Ala Pro Trp Gly Gln Gly Thr Leu

```
<210> SEQ ID NO 92
<211> LENGTH: 106
<212> TYPE: PRT
<213> ORGANISM: Artificial Sequence
<220> FEATURE:
<223> OTHER INFORMATION: synthetic construct; antigen binding domain

<400> SEQUENCE: 92

Glu Ile Val Met Thr Gln Ser Pro Ala Thr Leu Ser Val Ser Pro Gly
1               5                   10                  15
Gly Arg Ala Thr Leu Ser Cys Arg Ala Ser Gln Ser Val Ser Asn Asn
            20                  25                  30
Val Ala Trp Tyr Gln Gln Lys Pro Gly Gln Ala Pro Arg Leu Leu Ile
        35                  40                  45
Tyr Gly Ala Ser Thr Arg Ala Thr Gly Ile Pro Gly Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Ser Cys Gln Gln Tyr Asn Asn Trp Leu Thr
                85                  90                  95
Phe Gly Gly Gly Thr Lys Val Glu Ile Lys
            100                 105

<210> SEQ ID NO 93
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 93

Gln Val Gln Leu Val Glu Ser Gly Gly Gly Val Val Gln Pro Gly Arg
1               5                   10                  15
Ser Leu Arg Leu Ser Cys Val Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Ile Ile Trp Tyr Asp Gly Ser Asn Lys Tyr Tyr Ala Asp Ser Val
    50                  55                  60
Lys Gly Arg Phe Thr Ile Ser Arg Asp Asn Ser Lys Asn Thr Gln Tyr
65                  70                  75                  80
Leu Gln Met Asn Ser Leu Arg Ala Glu Asp Thr Ala Val Tyr Tyr Cys
                85                  90                  95
Ala Ser Val Ala Thr Ser Gly Asp Phe Asp Tyr Tyr Gly Met Asp Val
            100                 105                 110
Trp Gly Gln Gly Thr Thr Val Thr Val Ser Ser
            115                 120

<210> SEQ ID NO 94
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 94
```

```
Glu Ile Val Leu Thr Gln Ser Pro Ala Thr Leu Ser Leu Ser Pro Gly
1               5                   10                  15

Glu Arg Thr Thr Leu Ser Cys Arg Ala Ser Gln Arg Ile Ser Thr Tyr
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
50                  55                  60

Ser Gly Ser Gly Thr Gly Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

<210> SEQ ID NO 95
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 95

```
Glu Val Gln Leu Val Gln Ser Gly Ala Glu Val Arg Lys Pro Gly Glu
1               5                   10                  15

Ser Leu Lys Ile Ser Cys Lys Gly Ser Gly Tyr Ser Phe Thr Asn Tyr
                20                  25                  30

Trp Ile Val Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Asp Thr Ile Phe Pro Ser Tyr Pro Leu Trp Gly Gln Gly
                100                 105                 110

Thr Leu Val Thr Val Ser Ser
        115
```

<210> SEQ ID NO 96
<211> LENGTH: 112
<212> TYPE: PRT
<213> ORGANISM: Artificial Sequence
<220> FEATURE:
<223> OTHER INFORMATION: synthetic construct; antigen binding domain

<400> SEQUENCE: 96

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asn Ser
                20                  25                  30

Asn Gly Tyr Asn Phe Leu Asp Trp Tyr Leu Gln Lys Pro Gly Gln Ser
            35                  40                  45

Pro Gln Leu Leu Ile Tyr Leu Val Ser Asn Arg Ala Ser Gly Val Pro
50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Ile Gly Val Tyr Tyr Cys Met Gln Ala
                    85                  90                  95

Leu Gln Thr Pro Ile Thr Phe Gly Gln Gly Thr Arg Leu Glu Ile Lys
                    100                 105                 110
```

<210> SEQ ID NO 97
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 97

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Asn
            20                  25                  30

Gly Val Gly Val Gly Trp Ile Arg Gln Pro Pro Gly Lys Ala Leu Glu
        35                  40                  45

Trp Leu Thr Leu Ile Tyr Trp Asn Glu Asn Lys His Tyr Ser Pro Ser
50                  55                  60

Leu Lys Asn Arg Ile Thr Ile Thr Lys Asp Thr Ser Lys Asn Gln Val
65                  70                  75                  80

Val Leu Thr Met Thr Asn Leu Asp Pro Val Asp Thr Ala Thr Tyr Tyr
                85                  90                  95

Cys Val His Arg Gly Trp Leu Gly Ala Ile Phe Ala Tyr Trp Gly Gln
                100                 105                 110

Gly Thr Leu Val Thr Val Ser Ser
        115                 120
```

<210> SEQ ID NO 98
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 99
<211> LENGTH: 126
<212> TYPE: PRT
<213> ORGANISM: Artificial Sequence
<220> FEATURE:

<223> OTHER INFORMATION: synthetic construct; antigen binding domain

<400> SEQUENCE: 99

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ala Met Thr Trp Val Arg Gln Ala Pro Gly Lys Gly Leu Glu Trp Val
        35                  40                  45

Ser Asp Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ile Leu Arg Ala Glu Asp Thr Ala Val Tyr His Cys
                85                  90                  95

Ala Lys Gly Thr Gly Gln Gln Val Asp Leu Tyr Asn Tyr Tyr Tyr Ala
            100                 105                 110

Leu Asp Val Trp Gly Gln Gly Thr Thr Val Thr Val Ser Ser
        115                 120                 125
```

<210> SEQ ID NO 100
<211> LENGTH: 129
<212> TYPE: PRT
<213> ORGANISM: Artificial Sequence
<220> FEATURE:
<223> OTHER INFORMATION: synthetic construct; antigen binding domain

<400> SEQUENCE: 100

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Arg Asp Lys Gly Ile Ser Gly Ile Lys Gly Gly Ser Tyr Tyr Tyr
            100                 105                 110

Tyr Tyr Ala Met Asp Val Trp Gly Gln Gly Thr Thr Val Thr Val Ser
        115                 120                 125

Ser
```

<210> SEQ ID NO 101
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 101

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30
```

```
Trp Met Thr Trp Val Arg Gln Ala Pro Gly Lys Gly Leu Glu Trp Val
        35                  40                  45

Gly Arg Ile Lys Asn Lys Ile Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Val Tyr Leu Gln Met Asn Ser Leu Lys Thr Glu Asp Thr Ala Val Tyr
                85                  90                  95

Tyr Cys Ser Thr Val Asp Tyr Asn Trp Tyr Phe Asp Phe Trp Gly Arg
            100                 105                 110

Gly Thr Leu Val Thr Val Ser Ser
        115                 120

<210> SEQ ID NO 102
<211> LENGTH: 129
<212> TYPE: PRT
<213> ORGANISM: Artificial Sequence
<220> FEATURE:
<223> OTHER INFORMATION: synthetic construct; antigen binding domain

<400> SEQUENCE: 102

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Phe Phe
            20                  25                  30

Gly Met His Trp Val Arg Gln Ala Pro Gly Lys Gly Leu Glu Trp Val
        35                  40                  45

Ala Leu Ile Trp Tyr Asp Gly Thr Asn Glu Asn Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Val Ala Thr Phe Thr Arg Gly Asn Tyr Tyr Tyr
            100                 105                 110

Asn Tyr Gly Met Asp Val Trp Gly Gln Gly Thr Thr Val Thr Val Ser
        115                 120                 125

Ser

<210> SEQ ID NO 103
<211> LENGTH: 129
<212> TYPE: PRT
<213> ORGANISM: Artificial Sequence
<220> FEATURE:
<223> OTHER INFORMATION: synthetic construct; antigen binding domain

<400> SEQUENCE: 103

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Phe Tyr
            20                  25                  30

Gly Met His Trp Val Arg Gln Ala Pro Gly Lys Gly Leu Glu Gly Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80
```

Leu Gln Met Thr Ser Leu Arg Ala Glu Asp Thr Ala Val Tyr Tyr Cys
            85                  90                  95

Ala Arg Asp Ser Gly Lys Thr Gly Thr Gly Ile Thr Gly Tyr Ser Tyr
        100                 105                 110

Tyr Tyr Gly Met Asp Val Trp Gly Gln Gly Thr Thr Val Thr Val Ser
        115                 120                 125

Ser

<210> SEQ ID NO 104
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 104

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ile Thr Asn
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Arg Thr Tyr Tyr Asn Pro Ser
    50                  55                  60

Leu Glu Ser Arg Val Thr Ile Ser Val Asp Thr Ser Lys Asn Gln Phe
65                  70                  75                  80

Ser Leu Lys Leu Thr Ser Val Thr Ala Ala Asp Thr Ala Ile Tyr Tyr
                85                  90                  95

Cys Ala Arg Glu Gly Asp Pro Ser Leu Asp Pro Trp Gly Gln Gly Thr
            100                 105                 110

Leu Val Thr Val Ser Ser
        115

<210> SEQ ID NO 105
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 105

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
        100                 105

<210> SEQ ID NO 106

```
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 106

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser His Ile Ser Gly Ser Gly Gly Asn Ser Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ser Leu Asp Ile Met Ala Thr Val Gly Gly Leu Phe Ala Tyr Trp Gly
            100                 105                 110

Gln Gly Thr Leu Val Thr Val Ser Ser
        115                 120

<210> SEQ ID NO 107
<211> LENGTH: 131
<212> TYPE: PRT
<213> ORGANISM: Artificial Sequence
<220> FEATURE:
<223> OTHER INFORMATION: synthetic construct; antigen binding domain

<400> SEQUENCE: 107

Gln Val Gln Leu Val Glu Ser Gly Gly Gly Val Val Gln Pro Gly Arg
1               5                   10                  15

Ser Leu Arg Leu Ser Cys Val Ala Ser Gly Phe Ile Phe Ser Phe Tyr
            20                  25                  30

Gly Met His Trp Val Arg Gln Ala Pro Asp Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Asp Gln Gly Ile Ser Tyr Tyr Asp Ile Leu Thr Gly Asn Tyr
            100                 105                 110

Asn Tyr Tyr Tyr Gly Val Asp Val Trp Gly Gln Gly Thr Thr Val Thr
        115                 120                 125

Val Ser Ser
    130

<210> SEQ ID NO 108
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 108
```

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Val
        35                  40                  45

Gly Glu Ile Ser His Arg Gly Ser Thr Asn Tyr Asn Pro Ser Leu Lys
50                  55                  60

Ser Arg Val Thr Ile Ser Leu Asp Thr Ser Lys Asn Gln Phe Ser Leu
65                  70                  75                  80

Lys Leu Thr Ser Val Thr Ala Ala Asp Thr Ala Val Tyr Tyr Cys Ser
                85                  90                  95

Arg Asp Glu Glu Leu Glu Phe Arg Phe Phe Asp Tyr Trp Gly Gln Gly
            100                 105                 110

Thr Leu Val Thr Val Ser Ser
            115
```

```
<210> SEQ ID NO 109
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 109

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Val
        35                  40                  45

Tyr Gly Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln Gln Arg Ser Asn Trp Pro Leu
                85                  90                  95

Thr Phe Gly Gly Gly Thr Lys Val Glu Ile Lys
            100                 105
```

```
<210> SEQ ID NO 110
<211> LENGTH: 124
<212> TYPE: PRT
<213> ORGANISM: Artificial Sequence
<220> FEATURE:
<223> OTHER INFORMATION: synthetic construct; antigen binding domain

<400> SEQUENCE: 110

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Leu Tyr
            20                  25                  30

Ala Met Thr Trp Val Arg Gln Val Pro Gly Lys Gly Leu Glu Trp Val
        35                  40                  45

Ser Thr Ile Ser Gly Ser Gly Gly Thr Tyr Tyr Thr Asp Ser Val
50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Asp Asp Thr Ala Val Phe Tyr Cys
                85                  90                  95

Thr Lys Glu Ser Thr Thr Gly Thr Tyr Ser Tyr Phe Tyr Gly Met Asp
            100                 105                 110

Val Trp Gly Gln Gly Thr Thr Val Thr Val Ser Ser
        115                 120

<210> SEQ ID NO 111
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Leu Ser Gly Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 112
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Trp Met Ser Trp Val Arg Gln Ala Pro Gly Lys Gly Leu Glu Trp Val
        35                  40                  45

Ala Asn Ile Asn Gln Asp Gly Thr Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Gly Asp Thr Ala Val Tyr Tyr Cys
                85                  90                  95

Ala Asn Thr Tyr Tyr Asp Phe Trp Ser Gly His Phe Asp Tyr Trp Gly
            100                 105                 110

Gln Gly Thr Leu Val Thr Val Ser Ser
        115                 120

<210> SEQ ID NO 113
<211> LENGTH: 107
<212> TYPE: PRT
```

<213> ORGANISM: Artificial Sequence
<220> FEATURE:
<223> OTHER INFORMATION: synthetic construct; antigen binding domain

<400> SEQUENCE: 113

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Tyr Ser Tyr
                85                  90                  95

Thr Phe Gly Gln Gly Thr Lys Leu Glu Ile Lys
            100                 105

<210> SEQ ID NO 114
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 114

Gln Glu His Leu Val Glu Ser Gly Gly Val Val Gln Pro Gly Arg
1               5                   10                  15

Ser Leu Arg Leu Ser Cys Glu Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Ala Leu Trp Ser Asp Gly Ser Asn Lys Tyr Tyr Ala Asp Ser Val
50                  55                  60

Lys Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Gly Ala Pro Gly Ile Pro Ile Phe Gly Tyr Trp Gly
            100                 105                 110

Gln Gly Thr Leu Val Thr Val Ser Ser
        115                 120

<210> SEQ ID NO 115
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

```
Tyr Thr Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Leu
                 85                  90                  95

Thr Phe Gly Gly Gly Thr Lys Val Ala Ile Lys
            100                 105
```

<210> SEQ ID NO 116
<211> LENGTH: 130
<212> TYPE: PRT
<213> ORGANISM: Artificial Sequence
<220> FEATURE:
<223> OTHER INFORMATION: synthetic construct; antigen binding domain

<400> SEQUENCE: 116

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asn Ala
             20                  25                  30

Trp Met Ser Trp Val Arg Gln Ala Pro Gly Lys Gly Leu Glu Trp Val
         35                  40                  45

Gly Arg Ile Lys Arg Lys Thr Asp Gly Thr Thr Asp Tyr Ala Ala
     50                  55                  60

Pro Val Lys Gly Arg Phe Thr Ile Ser Arg Asp Asp Ser Lys Asn Thr
 65                  70                  75                  80

Leu His Leu Gln Met Asn Ser Leu Lys Thr Glu Asp Thr Ala Val Tyr
                 85                  90                  95

Tyr Cys Thr Thr Asp Asp Ile Val Val Pro Ala Val Met Arg Glu
            100                 105                 110

Tyr Tyr Phe Gly Met Asp Val Trp Gly Gln Gly Thr Thr Val Thr Val
        115                 120                 125

Ser Ser
    130
```

<210> SEQ ID NO 117
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 117

```
Asp Ile Gln Met Thr Gln Ser Pro Ser Ser Leu Ser Ala Ser Val Gly
 1               5                  10                  15

Asp Arg Val Thr Ile Thr Cys Arg Thr Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Asn Tyr Pro Tyr
                 85                  90                  95

Thr Phe Gly Gln Gly Thr Lys Leu Glu Ile Lys
            100                 105
```

-continued

<210> SEQ ID NO 118
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 118

```
Gln Val Gln Leu Val Gln Ser Gly Ala Glu Val Lys Lys Pro Gly Ala
1               5                   10                  15

Ser Val Gln Val Ser Cys Lys Ala Ser Gly Tyr Ser Phe Thr Gly Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Thr Lys Lys Tyr Ala His Lys Phe
    50                  55                  60

Gln Gly Arg Val Thr Met Thr Arg Asp Thr Ser Ile Asp Thr Ala Tyr
65                  70                  75                  80

Met Ile Leu Ser Ser Leu Ile Ser Asp Asp Thr Ala Val Tyr Tyr Cys
                85                  90                  95

Ala Arg Asp Glu Asp Trp Asn Phe Gly Ser Trp Phe Asp Ser Trp Gly
            100                 105                 110

Gln Gly Thr Leu Val Thr Val Ser Ser
        115                 120
```

<210> SEQ ID NO 119
<211> LENGTH: 112
<212> TYPE: PRT
<213> ORGANISM: Artificial Sequence
<220> FEATURE:
<223> OTHER INFORMATION: synthetic construct; antigen binding domain

<400> SEQUENCE: 119

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Thr Leu Val His Gly
            20                  25                  30

Asp Gly Asn Thr Tyr Leu Ser Trp Ile Gln Gln Arg Pro Gly Gln Pro
        35                  40                  45

Pro Arg Leu Leu Ile Tyr Lys Val Ser Asn Gln Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Leu Tyr Phe Cys Met Gln Ala
                85                  90                  95

Thr His Phe Pro Ile Thr Phe Gly Gln Gly Thr Arg Leu Glu Ile Lys
            100                 105                 110
```

<210> SEQ ID NO 120
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 120

```
Gln Val His Leu Val Gln Ser Gly Ala Glu Val Lys Lys Pro Gly Ala
1               5                   10                  15
```

-continued

```
Ser Val Lys Val Ser Cys Lys Ala Ser Gly Tyr Thr Phe Thr Gly Tyr
            20                  25                  30

Tyr Ile His Trp Val Arg Gln Ala Pro Gly His Gly Leu Glu Trp Met
        35                  40                  45

Gly Trp Leu Asn Pro Asn Thr Gly Thr Thr Lys Tyr Ile Gln Asn Phe
 50                  55                  60

Gln Gly Arg Val Thr Met Thr Arg Asp Thr Ser Ser Ser Thr Ala Tyr
65                  70                  75                  80

Met Glu Leu Thr Arg Leu Arg Ser Asp Asp Thr Ala Val Tyr Tyr Cys
                85                  90                  95

Ala Arg Asp Glu Asp Trp Asn Tyr Gly Ser Trp Phe Asp Thr Trp Gly
            100                 105                 110

Gln Gly Thr Leu Val Thr Val Ser Ser
        115                 120
```

<210> SEQ ID NO 121
<211> LENGTH: 112
<212> TYPE: PRT
<213> ORGANISM: Artificial Sequence
<220> FEATURE:
<223> OTHER INFORMATION: synthetic construct; antigen binding domain

<400> SEQUENCE: 121

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Pro Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
     50                 55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Phe Pro Ile Thr Phe Gly Gln Gly Thr Arg Leu Glu Ile Arg
            100                 105                 110
```

<210> SEQ ID NO 122
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 122

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Thr Trp Val Arg Gln Ala Pro Gly Arg Gly Leu Glu Trp Val
        35                  40                  45

Ser Gly Ile His Trp His Gly Lys Arg Thr Gly Tyr Ala Asp Ser Val
     50                 55                  60

Lys Gly Arg Phe Thr Ile Ser Arg Asp Asn Ala Lys Lys Ser Leu Tyr
65                  70                  75                  80

Leu Gln Met Asn Ser Leu Lys Gly Glu Asp Thr Ala Leu Tyr His Cys
```

```
                    85                  90                  95
Val Arg Gly Gly Met Ser Thr Gly Asp Trp Phe Asp Pro Trp Gly Gln
            100                 105                 110

Gly Thr Leu Val Ile Val Ser Ser
        115                 120

<210> SEQ ID NO 123
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 123

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 124
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 124

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Thr Trp Val Arg Gln Val Pro Gly Lys Gly Leu Glu Trp Val
        35                  40                  45

Ser Gly Ile His Trp Ser Gly Arg Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Gly Gly Met Ser Thr Gly Asp Trp Phe Asp Pro Trp Gly Gln
            100                 105                 110

Gly Thr Leu Val Thr Val Ser Ser
        115                 120

<210> SEQ ID NO 125
<211> LENGTH: 108
<212> TYPE: PRT
<213> ORGANISM: Artificial Sequence
<220> FEATURE:
```

```
<223> OTHER INFORMATION: synthetic construct; antigen binding domain

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 126
<211> LENGTH: 115
<212> TYPE: PRT
<213> ORGANISM: Artificial Sequence
<220> FEATURE:
<223> OTHER INFORMATION: synthetic construct; antigen binding domain

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Gly Ser Asn
            20                  25                  30

Tyr Met Asn Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Leu Thr Ser Lys Asn Thr Leu Tyr Leu
65                  70                  75                  80

Gln Met Ser Ser Leu Arg Pro Glu Asp Thr Ala Val Tyr Tyr Cys Ala
                85                  90                  95

Arg Gly Ile Arg Gly Leu Asp Val Trp Gly Gln Gly Thr Thr Val Thr
            100                 105                 110

Val Ser Ser
        115

<210> SEQ ID NO 127
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Ile Tyr
            20                  25                  30

Leu Asn Trp Tyr Gln Gln Lys Pro Gly Arg Ala Pro Arg Leu Leu Ile
        35                  40                  45

Tyr Ala Ala Ser Ser Leu Gln Ser Gly Val Pro Ser Arg Phe Ser Gly
```

```
                    50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys His Gln Ser Tyr Ser Thr Pro Pro
                     85                  90                  95

Ile Thr Phe Gly Gln Gly Thr Arg Leu Glu Ile Lys
                100                 105

<210> SEQ ID NO 128
<211> LENGTH: 115
<212> TYPE: PRT
<213> ORGANISM: Artificial Sequence
<220> FEATURE:
<223> OTHER INFORMATION: synthetic construct; antigen binding domain

<400> SEQUENCE: 128

Glu Glu Arg Leu Val Glu Ser Gly Gly Asp Leu Val Gln Pro Gly Gly
 1               5                  10                  15

Ser Leu Arg Leu Ser Cys Ala Ala Ser Gly Ile Thr Val Gly Thr Asn
                20                  25                  30

Tyr Met Asn Trp Val Arg Gln Ala Pro Gly Lys Gly Leu Glu Trp Val
             35                  40                  45

Ser Val Ile Ser Ser Gly Gly Asn Thr His Tyr Ala Asp Ser Val Lys
         50                  55                  60

Gly Arg Phe Ile Met Ser Arg Gln Thr Ser Lys Asn Thr Leu Tyr Leu
 65                  70                  75                  80

Gln Met Asn Ser Leu Glu Thr Glu Asp Thr Ala Val Tyr Tyr Cys Ala
                 85                  90                  95

Arg Gly Ile Arg Gly Leu Asp Val Trp Gly Gln Gly Thr Met Val Thr
            100                 105                 110

Val Ser Ser
        115

<210> SEQ ID NO 129
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 129

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Met Ser Ser Tyr
                20                  25                  30

Leu Asn Trp Tyr Gln Gln Lys Pro Gly Arg Ala Pro Lys Leu Leu Ile
             35                  40                  45

Phe Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105

<210> SEQ ID NO 130
<211> LENGTH: 118
```

<212> TYPE: PRT
<213> ORGANISM: Artificial Sequence
<220> FEATURE:
<223> OTHER INFORMATION: synthetic construct; antigen binding domain

<400> SEQUENCE: 130

Gln Val Gln Leu Val Gln Ser Gly Ala Glu Val Lys Met Pro Gly Ser
1               5                   10                  15

Ser Val Arg Val Ser Cys Lys Ala Ser Gly Gly Ile Phe Ser Ser Ser
            20                  25                  30

Thr Ile Ser Trp Val Arg Gln Ala Pro Gly Gln Gly Leu Glu Trp Met
        35                  40                  45

Gly Glu Ile Ile Pro Val Phe Gly Thr Val Asn Tyr Ala Gln Lys Phe
    50                  55                  60

Gln Asp Arg Val Ile Phe Thr Ala Asp Glu Ser Thr Thr Thr Ala Tyr
65                  70                  75                  80

Met Glu Leu Ser Ser Leu Lys Ser Gly Asp Thr Ala Val Tyr Phe Cys
                85                  90                  95

Ala Arg Asn Trp Gly Leu Gly Ser Phe Tyr Ile Trp Gly Gln Gly Thr
            100                 105                 110

Met Val Thr Val Ser Ser
        115

<210> SEQ ID NO 131
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 131

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Asn Phe Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Gly Val Phe Tyr Cys Gln Gln Tyr Glu Ser Ala Pro
                85                  90                  95

Trp Thr Phe Gly Gln Gly Thr Lys Val Glu Ile Lys
            100                 105

<210> SEQ ID NO 132
<211> LENGTH: 115
<212> TYPE: PRT
<213> ORGANISM: Artificial Sequence
<220> FEATURE:
<223> OTHER INFORMATION: synthetic construct; antigen binding domain

<400> SEQUENCE: 132

Glu Val Gln Leu Val Glu Ser Gly Gly Asp Leu Val His Pro Gly Arg
1               5                   10                  15

Ser Leu Arg Leu Ser Cys Ala Ala Ser Gly Phe Pro Phe Asp Glu Tyr
            20                  25                  30

Ala Met His Trp Val Arg Gln Val Pro Gly Lys Gly Leu Glu Trp Val

```
                35                  40                  45
Ser Gly Ile Ser Trp Ser Asn Asn Ile Gly Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Pro Glu Asp Thr Ala Phe Tyr Tyr Cys
                 85                  90                  95

Ala Lys Ser Gly Ile Phe Asp Ser Trp Gly Gln Gly Thr Leu Val Thr
            100                 105                 110

Val Ser Ser
        115

<210> SEQ ID NO 133
<211> LENGTH: 105
<212> TYPE: PRT
<213> ORGANISM: Artificial Sequence
<220> FEATURE:
<223> OTHER INFORMATION: synthetic construct; antigen binding domain

<400> SEQUENCE: 133

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Leu Leu Ile Tyr Ala Ala
         35                  40                  45

Ser Ser Leu Gln Ser Gly Val Pro Ser Arg Phe Ser Gly Gly Gly Ser
 50                  55                  60

Gly Thr Asp Phe Thr Leu Thr Ile Ser Ser Leu Arg Pro Glu Asp Phe
 65                  70                  75                  80

Ala Thr Tyr Tyr Cys Gln Gln Ser Tyr Cys Thr Pro Pro Ile Thr Phe
                 85                  90                  95

Gly Gln Gly Thr Arg Leu Glu Ile Lys
            100                 105

<210> SEQ ID NO 134
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 134

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Thr Leu Ile Ser Tyr Glu Gly Arg Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Thr Leu Tyr Gly Met Asp Val Trp Gly Gln Gly Thr
            100                 105                 110
```

Thr Val Thr Val Ser Ser
          115

<210> SEQ ID NO 135
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 135

Gln Val Thr Leu Arg Glu Ser Gly Pro Ala Leu Val Lys Thr Thr Gln
1               5                   10                  15

Thr Leu Thr Leu Thr Cys Thr Phe Ser Gly Phe Ser Leu Ser Thr Asn
            20                  25                  30

Arg Met Cys Val Thr Trp Ile Arg Gln Pro Pro Gly Lys Ala Leu Glu
        35                  40                  45

Trp Leu Ala Arg Ile Asp Trp Asp Gly Val Lys Tyr Tyr Asn Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Phe Tyr
                85                  90                  95

Cys Ala Arg Ser Thr Ser Leu Thr Phe Tyr Tyr Phe Asp Tyr Trp Gly
            100                 105                 110

Gln Gly Thr Leu Val Thr Val Ser Ser
        115                 120

<210> SEQ ID NO 136
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 137
<211> LENGTH: 115
<212> TYPE: PRT
<213> ORGANISM: Artificial Sequence
<220> FEATURE:
<223> OTHER INFORMATION: synthetic construct; antigen binding domain

<400> SEQUENCE: 137

Glu Val Gln Leu Val Glu Ser Gly Gly Gly Leu Val Gln Pro Gly Gly

```
                1               5                   10                  15
Ser Leu Arg Leu Ser Cys Ala Ala Ser Glu Phe Thr Val Gly Thr Asn
            20                  25                  30

His Met Asn Trp Val Arg Gln Ala Pro Gly Lys Gly Leu Glu Trp Val
            35                  40                  45

Ser Val Ile Tyr Ser Gly Gly Asn Thr Phe Tyr Ala Asp Ser Val Lys
            50                  55                  60

Gly Arg Phe Thr Ile Ser Arg His Thr Ser Lys Asn Thr Leu Tyr Leu
65                  70                  75                  80

Gln Met Asn Ser Leu Thr Ala Glu Asp Thr Ala Val Tyr Tyr Cys Ala
            85                  90                  95

Arg Gly Leu Gly Gly Met Asp Val Trp Gly Gln Gly Thr Thr Val Thr
            100                 105                 110

Val Ser Ser
            115
```

<210> SEQ ID NO 138
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 138

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Ser Asn Tyr
            20                  25                  30

Leu Ala Trp Tyr Gln Gln Lys Pro Gly Lys Val Pro Arg Leu Leu Ile
            35                  40                  45

Tyr Ala Ala Ser Thr Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Arg
            85                  90                  95

Thr Phe Gly Gln Gly Thr Lys Val Glu Ile Lys
            100                 105
```

<210> SEQ ID NO 139
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 139

```
Glu Val Gln Leu Val Glu Ser Gly Gly Gly Leu Val Gln Arg Gly Glu
1               5                   10                  15

Ser Leu Arg Leu Tyr Cys Ala Ala Ser Gly Phe Thr Phe Ser Lys Tyr
            20                  25                  30

Trp Met Asn Trp Val Arg Gln Ala Pro Gly Lys Gly Leu Glu Trp Val
            35                  40                  45

Ala Asn Ile Lys Gly Asp Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
65                  70                  75                  80
```

-continued

```
Leu Gln Met Asn Ser Leu Arg Ala Glu Asp Thr Ala Val Tyr Tyr Cys
                85                  90                  95

Ala Arg Asp Tyr Trp Gly Ser Gly Tyr Tyr Phe Asp Phe Trp Gly Gln
            100                 105                 110

Gly Thr Leu Val Thr Val Ser Ser
        115                 120

<210> SEQ ID NO 140
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Phe Gln Asn Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Leu
                85                  90                  95

Thr Phe Gly Gly Gly Thr Lys Val Glu Ile Lys
            100                 105

<210> SEQ ID NO 141
<211> LENGTH: 130
<212> TYPE: PRT
<213> ORGANISM: Artificial Sequence
<220> FEATURE:
<223> OTHER INFORMATION: synthetic construct; antigen binding domain

<400> SEQUENCE: 141

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Asp Ile Val Val Pro Ala Pro Met Gly Tyr Tyr Tyr
            100                 105                 110

Tyr Tyr Phe Gly Met Asp Val Trp Gly Gln Gly Thr Thr Val Thr Val
        115                 120                 125

Ser Ser
    130

<210> SEQ ID NO 142
```

```
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 143
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 143

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Phe
            20                  25                  30

Ala Met His Trp Val Arg Gln Ala Pro Gly Lys Gly Leu Glu Trp Val
        35                  40                  45

Ser Gly Ile Ser Trp Thr Gly Gly Asn Met Asp Tyr Ala Asn Ser Val
50                  55                  60

Lys Gly Arg Phe Thr Ile Ser Arg Glu Asp Ala Lys Asn Ser Leu Tyr
65                  70                  75                  80

Leu Gln Met Asn Ser Leu Arg Ala Ala Asp Thr Ala Leu Tyr Tyr Cys
                85                  90                  95

Val Lys Asp Ile Arg Gly Ile Val Ala Thr Gly Gly Ala Phe Asp Ile
            100                 105                 110

Trp Gly Arg Gly Thr Met Val Thr Val Ser Ser
        115                 120

<210> SEQ ID NO 144
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 144

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Thr Ile Ser Thr Tyr
            20                  25                  30
```

```
Leu Asn Trp Phe Gln Gln Lys Pro Gly Lys Ala Pro Lys Leu Leu Ile
            35                  40                  45

Tyr Val Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Phe
                 85                  90                  95

Thr Phe Gly Pro Gly Thr Lys Val Asp Ile Lys
            100                 105
```

<210> SEQ ID NO 145
<211> LENGTH: 115
<212> TYPE: PRT
<213> ORGANISM: Artificial Sequence
<220> FEATURE:
<223> OTHER INFORMATION: synthetic construct; antigen binding domain

<400> SEQUENCE: 145

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Gly Thr Asn
            20                  25                  30

Tyr Met Asn Trp Val Arg Gln Ala Pro Gly Lys Gly Leu Glu Trp Ile
            35                  40                  45

Ser Val Ile Tyr Ser Gly Gly Ser Thr Phe Tyr Ala Asp Ser Val Lys
 50                  55                  60

Gly Arg Phe Thr Ile Ser Arg Gln Thr Ser Gln Asn Thr Leu Tyr Leu
 65                  70                  75                  80

Gln Met Asn Ser Leu Arg Pro Glu Asp Thr Ala Val Tyr Tyr Cys Ala
                 85                  90                  95

Arg Gly Ile Arg Gly Phe Asp Ile Trp Gly Gln Gly Thr Met Val Thr
            100                 105                 110

Val Ser Ser
        115
```

<210> SEQ ID NO 146
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 146

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Pro
                 85                  90                  95

Ile Thr Phe Gly Gln Gly Thr Arg Leu Glu Ile Lys
            100                 105
```

<210> SEQ ID NO 147
<211> LENGTH: 115
<212> TYPE: PRT
<213> ORGANISM: Artificial Sequence
<220> FEATURE:
<223> OTHER INFORMATION: synthetic construct; antigen binding domain

<400> SEQUENCE: 147

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Thr Asn
            20                  25                  30

Tyr Met Asn Trp Val Arg Gln Ala Pro Gly Lys Gly Leu Glu Trp Val
        35                  40                  45

Ala Val Ile Tyr Ser Ser Gly Ser Thr Tyr Tyr Ile Asp Ser Val Lys
    50                  55                  60

Gly Arg Phe Thr Ile Ser Arg Leu Thr Ser Lys Asn Thr Val Tyr Leu
65                  70                  75                  80

Gln Met Ser Ser Leu Asn Ser Glu Asp Thr Ala Val Tyr Tyr Cys Ala
                85                  90                  95

Arg Gly Ile Arg Gly Phe Asp Ile Trp Gly Gln Gly Thr Met Val Thr
            100                 105                 110

Val Ser Ser
        115
```

<210> SEQ ID NO 148
<211> LENGTH: 124
<212> TYPE: PRT
<213> ORGANISM: Artificial Sequence
<220> FEATURE:
<223> OTHER INFORMATION: synthetic construct; antigen binding domain

<400> SEQUENCE: 148

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Ile Asp Asp Ser
            20                  25                  30

Ala Met His Trp Val Arg Gln Thr Pro Gly Lys Gly Leu Glu Trp Val
        35                  40                  45

Ser Gly Ile Ser Trp Lys Ser Gly Ser Ile Gly Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Leu Tyr Tyr Cys
                85                  90                  95

Val Lys Asp Ile Arg Gly Asn Trp Asn Tyr Gly Gly Asn Trp Phe Asp
            100                 105                 110

Pro Trp Gly Gln Gly Thr Leu Val Thr Val Ser Ser
        115                 120
```

<210> SEQ ID NO 149
<211> LENGTH: 115
<212> TYPE: PRT
<213> ORGANISM: Artificial Sequence
<220> FEATURE:
<223> OTHER INFORMATION: synthetic construct; antigen binding domain

<400> SEQUENCE: 149

```
Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Val Gly Val Asn
            20                  25                  30

His Met Asn Trp Val Arg Gln Ala Pro Gly Lys Gly Leu Glu Trp Val
        35                  40                  45

Ser Val Ile Phe Ser Ser Gly Arg Thr Phe Tyr Gly Asp Tyr Val Lys
    50                  55                  60

Gly Arg Leu Thr Ile Phe Arg Gln Thr Ser Gln Asn Thr Val Tyr Leu
65                  70                  75                  80

Gln Met Asn Ser Leu Arg Ser Glu Asp Thr Ala Ile Tyr Tyr Cys Ala
            85                  90                  95

Arg Gly Ile Gly Gly Leu Asp Ile Trp Gly Arg Gly Thr Met Val Thr
        100                 105                 110

Val Ser Ser
        115
```

<210> SEQ ID NO 150
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 150

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Leu His Trp Val Arg Gln Ala Pro Gly Lys Gly Leu Glu Trp Val
        35                  40                  45

Ser Gly Ile Ser Trp Thr Gly Gly Thr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Thr Glu Asp Thr Ala Ile Tyr Tyr Cys
            85                  90                  95

Thr Arg Asp Ile Arg Gly Asn Trp Lys Tyr Gly Gly Trp Phe Asp Pro
        100                 105                 110

Trp Gly Gln Gly Thr Leu Val Thr Val Ser Ser
        115                 120
```

<210> SEQ ID NO 151
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 151

```
Gln Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Thr Ala Tyr
            20                  25                  30

Tyr Met His Trp Val Arg Gln Ala Pro Gly Gln Gly Leu Asp Trp Met
        35                  40                  45

Gly Trp Ile Ser Pro Asn Ser Gly Phe Thr Asn Tyr Ala Gln Lys Phe
    50                  55                  60
```

```
Gln Gly Arg Val Thr Met Thr Arg Asp Thr Ser Ile Asn Thr Phe Tyr
65                  70                  75                  80

Met Glu Leu Ser Gly Leu Arg Ser Asp Asp Thr Ala Val Tyr Tyr Cys
                85                  90                  95

Ala Arg Glu Gly Ser Thr His His Asn Ser Phe Asp Pro Trp Gly Gln
            100                 105                 110

Gly Thr Leu Val Thr Val Ser Ser
        115                 120
```

<210> SEQ ID NO 152
<211> LENGTH: 114
<212> TYPE: PRT
<213> ORGANISM: Artificial Sequence
<220> FEATURE:
<223> OTHER INFORMATION: synthetic construct; antigen binding domain

<400> SEQUENCE: 152

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Val Gly Thr Asn
                20                  25                  30

Phe Met Asn Trp Val Arg Gln Ala Pro Gly Lys Gly Leu Glu Trp Val
            35                  40                  45

Ser Ala Ile Tyr Ser Gly Gly Thr Ala Asn Tyr Ala Asp Ser Val Lys
        50                  55                  60

Gly Arg Phe Thr Ile Ser Arg Asp Thr Ser Arg Asn Thr Leu Tyr Leu
65                  70                  75                  80

Gln Met Asn Ser Leu Arg Thr Glu Asp Thr Ala Val Tyr Tyr Cys Ala
                85                  90                  95

Arg Gly Gly Gly Met Asp Val Trp Gly Gln Gly Thr Thr Val Thr Val
            100                 105                 110

Ser Ser
```

<210> SEQ ID NO 153
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 153

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Thr Tyr
                20                  25                  30

Val Leu Ser Trp Val Arg Gln Ala Pro Gly Gln Gly Leu Glu Trp Met
            35                  40                  45

Gly Glu Ile Ile Pro Ile Leu Gly Ala Ala Asn Tyr Ala Gln Asn Phe
        50                  55                  60

Gln Gly Arg Val Thr Phe Thr Thr Asp Glu Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Asp Arg Thr Ser Gly Gly Phe Asp Pro Trp Gly Gln Gly Thr
            100                 105                 110

Leu Val Thr Val Ser Ser
            115
```

<210> SEQ ID NO 154
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 154

Gln Val Gln Leu Val Gln Ser Gly Ala Glu Val Glu Lys Pro Gly Ala
1               5                   10                  15

Ser Val Lys Val Ser Cys Lys Ala Ser Gly Tyr Ile Phe Thr His Tyr
            20                  25                  30

Gly Ile Ser Trp Val Arg Gln Ala Pro Gly Gln Gly Leu Glu Trp Val
        35                  40                  45

Gly Trp Ile Ser Pro Tyr Asn Gly Tyr Thr Asp Tyr Ala Gln Lys Leu
    50                  55                  60

Gln Gly Arg Val Thr Leu Thr Thr Asp Thr Ser Thr Thr Thr Ala Tyr
65                  70                  75                  80

Met Glu Leu Arg Asn Leu Arg Ser Asp Thr Ala Met Tyr Tyr Cys
                85                  90                  95

Ser Arg Gly Arg Gly Pro Tyr Trp Ser Phe Asp Leu Trp Gly Arg Gly
            100                 105                 110

Thr Leu Val Thr Val Ser Ser
        115

<210> SEQ ID NO 155
<211> LENGTH: 117
<212> TYPE: PRT
<213> ORGANISM: Artificial Sequence
<220> FEATURE:
<223> OTHER INFORMATION: synthetic construct; antigen binding domain

<400> SEQUENCE: 155

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Val Tyr Asn Gly Asn Ile Asn Tyr Ala Gln Lys Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Met Ala Val Tyr Tyr Cys
                85                  90                  95

Ala Arg Val Thr Gln Phe Gly Met Asp Val Trp Gly Gln Gly Thr Thr
            100                 105                 110

Val Thr Val Ser Ser
        115

<210> SEQ ID NO 156
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 156

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Asn
            20                  25                  30

Leu Asn Trp Tyr Gln Gln Asn Pro Gly Lys Ala Pro Lys Leu Leu Ile
        35                  40                  45

Tyr Thr Thr Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Arg Thr Pro Phe
                85                  90                  95

Thr Phe Gly Pro Gly Thr Lys Val Asp Ile Lys
            100                 105
```

<210> SEQ ID NO 157
<211> LENGTH: 128
<212> TYPE: PRT
<213> ORGANISM: Artificial Sequence
<220> FEATURE:
<223> OTHER INFORMATION: synthetic construct; antigen binding domain

<400> SEQUENCE: 157

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Gly Lys Ala Asn Ser Phe Ala Thr Ala Tyr Ser Ala
    50                  55                  60

Ser Val Lys Gly Arg Phe Thr Ile Ser Arg Asp Asp Ser Lys Asn Thr
65                  70                  75                  80

Ala Ser Leu Gln Met Asn Ser Leu Arg Thr Glu Asp Thr Ala Val Tyr
                85                  90                  95

Phe Cys Thr Arg Glu Asp Gln Gln Leu Val Arg Pro Tyr Tyr Tyr His
            100                 105                 110

Tyr Gly Met Asp Val Trp Gly Gln Gly Thr Thr Val Thr Val Ser Ser
        115                 120                 125
```

<210> SEQ ID NO 158
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 158

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Thr Asn Tyr
            20                  25                  30

Leu Asn Trp Tyr Gln Gln Lys Pro Gly Lys Ala Pro Lys Leu Leu Ile
        35                  40                  45

Tyr Ala Thr Ala Ser Leu Gln Ser Gly Val Pro Ser Arg Phe Ser Gly
    50                  55                  60

Ser Gly Ser Glu Thr Asp Phe Thr Leu Thr Ile Ser Ser Leu Gln Pro
65                  70                  75                  80
```

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 159
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 159

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Ser Pro Gly Arg Ala Leu Glu
        35                  40                  45

Trp Leu Ala Leu Ile Tyr Trp Asn Asp His Glu Arg Tyr Ser Pro Ser
    50                  55                  60

Leu Lys Ser Arg Leu Thr Ile Thr Lys Asp Thr Ser Lys Asn Leu Val
65                  70                  75                  80

Val Leu Ala Met Ala Asn Met Asp Pro Val Asp Thr Ala Thr Tyr Phe
                85                  90                  95

Cys Ala His Arg Asn Ile Glu Tyr Arg Arg Ser Tyr Phe Phe Asp Tyr
            100                 105                 110

Trp Gly Gln Gly Thr Leu Val Thr Val Ser Ser
        115                 120

<210> SEQ ID NO 160
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 160

Asp Ile Gln Met Thr Gln Ser Pro Ser Ser Val Ser Ala Ser Val Arg
1               5                   10                  15

Asp Arg Val Thr Val Thr Cys Arg Ala Ser Gln Asp Ile Asn Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Thr Phe Pro Phe
                85                  90                  95

Thr Phe Gly Pro Gly Thr Lys Val Asp Ile Lys
            100                 105

<210> SEQ ID NO 161
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 161

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Ser Tyr
            20                  25                  30

Tyr Trp Thr Trp Ile Arg Gln Pro Pro Gly Lys Gly Leu Glu Trp Ile
        35                  40                  45

Gly Tyr Val Tyr Tyr Ser Gly Ser Thr Thr Tyr Asn Pro Ser Leu Lys
50                  55                  60

Ser Arg Val Thr Ile Ser Val Asp Thr Ser Lys Asn Gln Phe Phe Leu
65                  70                  75                  80

Asn Leu Asn Ser Val Thr Ala Ala Glu Thr Ala Val Tyr Tyr Cys Ala
                85                  90                  95

Arg Gly Thr Leu Gly Tyr Tyr Gly Met Asp Val Trp Gly Gln Gly Thr
            100                 105                 110

Thr Val Thr Val Ser Ser
            115

<210> SEQ ID NO 162
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 162

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Phe Ser Asn Asn
            20                  25                  30

Tyr Leu Ala Trp Tyr Gln Gln Lys Pro Gly Gln Ala Pro Arg Leu Leu
        35                  40                  45

Ile Tyr Gly Thr Ser Ile Arg Ala Thr Gly Ile Pro Asp Arg Phe Ser
50                  55                  60

Gly Ser Gly Ser Gly Thr Asp Phe Thr Leu Ala Ile Ser Arg Leu Glu
65                  70                  75                  80

Pro Glu Asp Phe Ala Val Tyr Tyr Cys Gln Gln Tyr Gly Arg Ser Pro
                85                  90                  95

Leu Thr Phe Gly Gly Gly Thr Lys Val Glu Ile Lys
            100                 105

<210> SEQ ID NO 163
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 163

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Asn Trp Val Arg Gln Ala Pro Gly Lys Gly Leu Glu Trp Val
        35                  40                  45

Ala Val Thr Trp Tyr Asp Gly Ser Asn Lys His Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Tyr Ser Leu Arg Ala Glu Asp Thr Ala Met Tyr Tyr Cys
            85                  90                  95

Val Arg Gly Gly His Leu Gly Ala Phe Asp Ile Trp Gly Gln Gly Thr
        100                 105                 110

Met Val Thr Val Ser Ser
        115

<210> SEQ ID NO 164
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 164

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Phe
            85                  90                  95

Thr Phe Gly Pro Gly Thr Lys Val Asp Ile Lys
        100                 105

<210> SEQ ID NO 165
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 165

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Asn Gly Val Ser Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Asp Leu Ile Arg Leu Arg Ser Asp Asp Thr Ala Val Tyr Tyr Cys
            85                  90                  95

Ala Arg Glu Arg Ala Ser Trp Asp Tyr Asn Gly Val Asp Val Trp Gly
        100                 105                 110

Gln Gly Thr Thr Val Thr Val Ser Ser
        115                 120

```
<210> SEQ ID NO 166
<211> LENGTH: 112
<212> TYPE: PRT
<213> ORGANISM: Artificial Sequence
<220> FEATURE:
<223> OTHER INFORMATION: synthetic construct; antigen binding domain

<400> SEQUENCE: 166

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Ser Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Pro Pro Asn Thr Phe Gly Gln Gly Thr Lys Leu Glu Ile Lys
            100                 105                 110

<210> SEQ ID NO 167
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 167

Gln Leu Gln Leu Gln Glu Ser Gly Pro Gly Leu Val Lys Pro Ser Glu
1               5                   10                  15

Thr Leu Ser Leu Thr Cys Ile Val Ser Gly Gly Ser Thr Ser Ser Asn
            20                  25                  30

Thr Tyr Tyr Trp Gly Trp Ile Arg Gln Pro Pro Gly Lys Gly Leu Glu
        35                  40                  45

Trp Ile Gly Thr Ile His Tyr Ser Gly Asn Pro Tyr Tyr Asp Pro Ser
    50                  55                  60

Leu Lys Ser Arg Val Thr Ile Ser Val Asp Thr Ser Lys Asn His Phe
65                  70                  75                  80

Ser Leu Lys Leu Asn Ser Val Thr Ala Ala Asp Thr Ala Val Tyr Tyr
                85                  90                  95

Cys Thr Arg Gln Tyr Ile Asn Phe Phe Asp Phe Trp Gly Gln Gly Thr
            100                 105                 110

Leu Val Thr Val Ser Ser
        115

<210> SEQ ID NO 168
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 168

Glu Ile Val Leu Thr Gln Ser Pro Ala Thr Leu Ser Leu Ser Pro Gly
1               5                   10                  15

Glu Arg Val Thr Leu Ser Cys Arg Ala Ser Gln Ser Ile Ser Arg Tyr
            20                  25                  30
```

```
Leu Ala Trp Tyr Gln Gln Lys Pro Gly Gln Ala Pro Arg Val Leu Ile
        35                  40                  45

Tyr Asp Ala Ser Asn Arg Ala Thr Asp Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
                100                 105

<210> SEQ ID NO 169
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 169

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Thr Phe Ser Tyr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Asp Leu Gly Gly Asp Asp Tyr Tyr Gly Met Asp Val Trp Gly
                100                 105                 110

Gln Gly Thr Thr Val Thr Val Ser Ser
        115                 120

<210> SEQ ID NO 170
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 170

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Thr
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys
```

<210> SEQ ID NO 171
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 171

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Val
        35                  40                  45

Ser Tyr Ile Ser Ser Gly Gly Asn Ile Phe Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
                85                  90                  95

Ala Arg Gly Leu Glu Pro Tyr His Tyr Tyr Tyr Gly Met Asp Val Trp
            100                 105                 110

Gly Gln Gly Thr Thr Val Thr Val Ser Ser
        115                 120

<210> SEQ ID NO 172
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln His Tyr Asp Asn Leu Pro Phe
                85                  90                  95

Thr Phe Gly Pro Gly Thr Lys Val Asp Ile Lys
            100                 105

<210> SEQ ID NO 173
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 173

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Leu Ser Asn Tyr
            20                  25                  30

Val Met Thr Trp Val Arg Gln Ala Pro Gly Lys Gly Leu Glu Trp Val
        35                  40                  45

Ser Ala Ile Ser Gly Arg Gly Gly Asn Ser Tyr Tyr Ala Asp Ser Val
    50                  55                  60

Lys Gly Arg Phe Ser Ile Ser Arg Asp His Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Ala Lys Ala Glu Arg Gly Tyr Ser Tyr Gly Phe Asn Trp Phe Asp Pro
            100                 105                 110

Trp Gly Gln Gly Thr Leu Val Thr Val Ser Ser
        115                 120
```

<210> SEQ ID NO 174
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 174

```
Asp Ile Gln Met Thr Gln Ser Pro Ser Ser Val Ser Ala Ser Ala Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Gly Asn Asn Phe Pro Leu
                85                  90                  95

Thr Phe Gly Gly Gly Thr Lys Val Glu Ile Lys
            100                 105
```

<210> SEQ ID NO 175
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 175

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Thr Val Ile Trp Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Leu Tyr Tyr Cys
```

```
                 85                  90                  95
Ala Arg Gly Gly Gly Arg Leu Ser Tyr Tyr His Asp Tyr Trp Gly Gln
            100                 105                 110

Gly Thr Leu Val Thr Val Ser Ser
        115                 120

<210> SEQ ID NO 176
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Phe
            20                  25                  30

Leu Asn Trp Tyr Gln Gln Lys Pro Gly Lys Ala Pro Asn Leu Leu Ile
        35                  40                  45

Tyr Gly Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Ala Tyr Tyr Cys Gln Gln Thr Tyr Ser Thr Pro Phe
                85                  90                  95

Thr Phe Gly Pro Gly Thr Lys Val Asp Ile Lys
            100                 105

<210> SEQ ID NO 177
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 177

Gln Val Gln Leu Val Gln Ser Gly Ala Glu Val Lys Met Ser Gly Ala
1               5                   10                  15

Ser Val Arg Val Ser Cys Lys Ala Ser Gly Tyr Thr Phe Thr Ser Tyr
            20                  25                  30

Gly Ile Ser Trp Met Arg Gln Ala Pro Gly Gln Gly Leu Glu Trp Met
        35                  40                  45

Gly Trp Ile Thr Ala Tyr Asn Gly Asn Ser Asn Tyr Ala Gln Lys Leu
    50                  55                  60

Gln Gly Arg Val Thr Met Thr Thr Asp Thr Ser Thr Gly Thr Ala Tyr
65                  70                  75                  80

Met Glu Leu Arg Ser Leu Thr Ser Asp Asp Thr Ala Val Tyr Tyr Cys
                85                  90                  95

Ala Arg Arg Gly Asp Tyr Leu Gly Val Phe Pro Tyr Trp Gly Gln Gly
            100                 105                 110

Thr Leu Val Thr Val Ser Ser
        115

<210> SEQ ID NO 178
<211> LENGTH: 107
<212> TYPE: PRT
<213> ORGANISM: Artificial Sequence
<220> FEATURE:
```

<223> OTHER INFORMATION: synthetic construct; antigen binding domain

<400> SEQUENCE: 178

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Thr Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Leu
                85                  90                  95

Thr Phe Gly Gly Gly Thr Lys Val Glu Ile Lys
            100                 105
```

<210> SEQ ID NO 179
<211> LENGTH: 116
<212> TYPE: PRT
<213> ORGANISM: Artificial Sequence
<220> FEATURE:
<223> OTHER INFORMATION: synthetic construct; antigen binding domain

<400> SEQUENCE: 179

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Ser Trp Val Arg Gln Ala Pro Gly Lys Gly Leu Glu Trp Val
        35                  40                  45

Ser Ser Ile Arg Thr Ser Gly Thr Thr Lys Tyr Tyr Ala Asp Ser Met
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Gly Gly Gly Thr Phe Leu His Tyr Trp Gly Gln Gly Thr Leu Val
            100                 105                 110

Thr Val Ser Ser
        115
```

<210> SEQ ID NO 180
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 180

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ala Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Thr Gly Val Pro Ser Arg Phe Ser Gly
```

```
                    50                  55                  60
Ser Gly Tyr Gly Thr Asp Phe Thr Leu Thr Ile Ser Ser Leu Gln Pro
 65                  70                  75                  80

Glu Asp Phe Ala Thr Tyr Tyr Cys Gln Gln Ala Lys Ser Phe Pro Met
                 85                  90                  95

Tyr Thr Phe Gly Gln Gly Thr Lys Leu Glu Ile Lys
            100                 105
```

<210> SEQ ID NO 181
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 181

```
Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Thr Ser Gly
                 20                  25                  30

Gly Tyr Tyr Trp Ser Trp Ile Arg Gln His Pro Gly Lys Gly Leu Glu
             35                  40                  45

Trp Ile Gly Tyr Ile Phe Tyr Ser Gly Ile Thr Asn Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Thr Ser Val Thr Ala Ala Asp Thr Ala Val Tyr Tyr
                 85                  90                  95

Cys Ala Thr Tyr Asn Ser Leu Arg Leu Tyr Tyr Gly Met Asp Val Trp
            100                 105                 110

Gly Gln Gly Thr Thr Val Thr Val Ser Ser
            115                 120
```

<210> SEQ ID NO 182
<211> LENGTH: 112
<212> TYPE: PRT
<213> ORGANISM: Artificial Sequence
<220> FEATURE:
<223> OTHER INFORMATION: synthetic construct; antigen binding domain

<400> SEQUENCE: 182

```
Asp Val Val Met Thr Gln Ser Pro Leu Ser Leu Pro Val Ile Leu Gly
  1               5                  10                  15

Gln Pro Ala Ser Ile Ser Cys Arg Ser Ser Gln Ser Leu Val Tyr Gly
                 20                  25                  30

Asp Gly Asn Thr Tyr Leu Asn Trp Phe Gln Gln Arg Pro Gly Gln Ser
             35                  40                  45

Pro Arg Arg Leu Ile Tyr Lys Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ser
                 85                  90                  95

Thr His Trp Pro Leu Thr Phe Gly Gly Gly Thr Lys Val Glu Ile Lys
            100                 105                 110
```

<210> SEQ ID NO 183
<211> LENGTH: 120

```
<212> TYPE: PRT
<213> ORGANISM: Artificial Sequence
<220> FEATURE:
<223> OTHER INFORMATION: synthetic construct; antigen binding domain

<400> SEQUENCE: 183

Glu Val Gln Leu Val Glu Ser Gly Gly Gly Leu Val Gln Pro Gly Gly
1               5                   10                  15

Ser Leu Arg Leu Ala Cys Ala Ala Ser Gly Phe Thr Phe Ser Asp Tyr
            20                  25                  30

Tyr Met Asp Trp Val Arg Gln Val Pro Gly Lys Gly Leu Glu Trp Val
        35                  40                  45

Gly Arg Ser Arg Asp Lys Ala Asn Ser Phe Thr Thr Glu Tyr Val Ala
    50                  55                  60

Ser Val Lys Gly Arg Phe Thr Ile Ser Arg Glu Asp Ser Lys Asn Ser
65                  70                  75                  80

Val Tyr Leu Gln Met Asn Ser Leu Lys Thr Glu Asp Thr Ala Val Tyr
                85                  90                  95

Tyr Cys Ala Arg Thr Asn Tyr Asp Phe Ser Leu Asp Val Trp Gly Gln
            100                 105                 110

Gly Thr Thr Val Thr Val Ser Ser
        115                 120

<210> SEQ ID NO 184
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 184

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Asn Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Tyr Pro Ile
                85                  90                  95

Thr Phe Gly Gln Gly Thr Arg Leu Glu Ile Lys
            100                 105

<210> SEQ ID NO 185
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 185

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

His Trp Ser Trp Ile Arg Gln Pro Leu Gly Lys Gly Leu Glu Trp Ile
```

-continued

```
                35                  40                  45
Gly Tyr Ile Tyr Tyr Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Ser Ser Ile Trp Pro Phe Asp Tyr Trp Gly Gln Gly Thr
            100                 105                 110

Leu Val Thr Val Ser Ser
        115

<210> SEQ ID NO 186
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 186

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Ser Gly Lys Ala Pro Lys Leu Leu Ile
        35                  40                  45

Ser Lys Ala Ser Thr Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ile Tyr Ser Trp
                85                  90                  95

Thr Phe Gly Gln Gly Thr Lys Val Glu Ile Lys
            100                 105

<210> SEQ ID NO 187
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 187

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Val Ala Leu Glu
        35                  40                  45

Trp Leu Ala Leu Ile Tyr Trp Asn Asp Lys Arg Phe Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg Arg Leu Gly Leu Tyr Tyr Phe Asp Tyr Trp Gly Gln
            100                 105                 110
```

```
Gly Thr Leu Val Thr Val Ser Ser
        115             120
```

<210> SEQ ID NO 188
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 188

```
Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Val His Ile Tyr Pro Phe
                85                  90                  95

Thr Phe Gly Pro Gly Thr Lys Val Asp Ile Lys
            100                 105
```

<210> SEQ ID NO 189
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 189

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Ser Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Leu Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ser Arg Asp Gly Pro Phe Lys Ile Ser Phe Phe Gly Met Asp Val Trp
            100                 105                 110

Gly Gln Gly Thr Thr Val Thr Val Ser Ser
        115             120
```

<210> SEQ ID NO 190
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 190

```
Asp Ile Gln Met Thr Gln Ser Pro Ser Ser Leu Ser Ala Ser Val Gly
```

```
                1               5                  10                  15
Asp Arg Val Thr Ile Thr Cys Arg Ala Ser Gln Ser Ile Ser Ser Tyr
                    20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Ser Tyr Ser Thr Pro Pro
                    85                  90                  95

Ile Thr Phe Gly Gln Gly Thr Arg Leu Glu Ile Lys
                100                 105
```

<210> SEQ ID NO 191
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 191

```
Gln Val Gln Leu Val Glu Ser Gly Gly Gly Val Gln Pro Gly Arg
 1               5                  10                  15

Ser Leu Arg Leu Ser Cys Ala Ala Ser Gly Phe Thr Phe Ser Ser Tyr
                    20                  25                  30

Gly Met His Trp Val Arg Gln Ala Pro Gly Lys Gly Leu Glu Trp Val
            35                  40                  45

Ala Val Ile Trp Tyr Asp Gly Arg Asn Lys His Tyr Val Asp Ser Val
        50                  55                  60

Lys Gly Arg Phe Thr Ile Ser Arg Asp Asn Ser Lys Asn Thr Val Tyr
 65                 70                  75                  80

Leu Gln Met Asn Ser Leu Arg Ala Glu Asp Ser Ala Val Tyr Tyr Cys
                    85                  90                  95

Val Arg Gly Gly Gln Leu Gly Ala Phe Asp Tyr Trp Gly Gln Gly Thr
                100                 105                 110

Leu Val Thr Val Ser Ser
        115
```

<210> SEQ ID NO 192
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 192

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                    20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                 70                  75                  80
```

```
Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 193
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 193

```
Gln Val Gln Leu Val Glu Ser Gly Gly Gly Val Gln Pro Gly Arg
1               5                   10                  15

Ser Leu Arg Leu Ser Cys Ala Ala Ser Gly Phe Thr Ser Ser Tyr
                20                  25                  30

Gly Ile His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Pro Trp Gly Ala Phe Asp Ile Trp Gly Gln Gly Thr
            100                 105                 110

Met Val Thr Val Ser Ser
        115
```

<210> SEQ ID NO 194
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 194

```
Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Thr Val Asn Thr Phe
                20                  25                  30

Leu Asn Trp Tyr Gln Gln Lys Pro Gly Lys Ala Pro Lys Leu Leu Ile
            35                  40                  45

Phe Gly Ala Ser Ser Leu Gln Ser Gly Val Pro Ser Arg Phe Ser Gly
        50                  55                  60

Ser Gly Ser Gly Thr Asp Phe Thr Leu Thr Ile Ser Leu Gln Pro
65                  70                  75                  80

Glu Asp Phe Ala Ile Tyr Tyr Cys Gln Gln Ser Tyr Ser Val Pro Pro
                85                  90                  95

Ile Thr Phe Gly Gln Gly Thr Arg Leu Glu Ile Glu
            100                 105
```

<210> SEQ ID NO 195
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 195

Gln Val Gln Leu His Glu Ser Gly Pro Gly Leu Val Lys Pro Ser Gln
1               5                   10                  15

Thr Leu Ser Leu Thr Cys Ser Val Ser Gly Gly Ser Ile Ser Asn Gly
            20                  25                  30

Gly Tyr Tyr Trp Ser Trp Ile Arg Gln His Pro Gly Gln Gly Leu Glu
        35                  40                  45

Trp Ile Gly Tyr Ile Tyr Tyr Ile Gly Asn Thr Tyr Tyr Asn Pro Ser
50                  55                  60

Leu Glu Ser Arg Val Thr Met Ser Ile Asp Thr Ser Lys Asn Gln Phe
65                  70                  75                  80

Ser Leu Lys Leu Ser Ser Val Thr Ala Ala Asp Thr Ala Ile Tyr Tyr
                85                  90                  95

Cys Ala Arg Gln Glu Phe Val Pro Gly Ala Glu Tyr Phe Leu His Trp
            100                 105                 110

Gly Gln Gly Ile Leu Val Thr Val Ser Ser
        115                 120

<210> SEQ ID NO 196
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp His Gln Gln Lys Ser Gly Lys Ala Pro Lys Ser Leu Ile
        35                  40                  45

Tyr Ala Ala Ser Ser Leu Gln Ser Gly Ala Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Ser Ala Thr Tyr Tyr Cys Leu Gln Gln Asn Ser Tyr Pro Pro
                85                  90                  95

Thr Phe Gly Gln Gly Thr Lys Val Glu Ile Lys
            100                 105

<210> SEQ ID NO 197
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 197

Glu Val Gln Leu Val Glu Ser Gly Gly Gly Leu Val Gln Pro Gly Arg
1               5                   10                  15

Ser Leu Arg Leu Ser Cys Ala Gly Thr Gly Phe Ile Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Asn Ser Leu Gly Tyr Ala Asp Ser Val
50                  55                  60

```
Lys Gly Arg Phe Thr Ile Ser Arg Asp Asn Ala Lys Lys Ser Leu Tyr
 65                  70                  75                  80

Leu Gln Met Ser Ser Leu Arg Ala Glu Asp Thr Ala Leu Tyr Tyr Cys
                 85                  90                  95

Val Lys Asp Val Thr Arg Leu Glu Leu Arg Gly Phe Leu Asp Tyr Trp
            100                 105                 110

Gly Gln Gly Thr Gln Val Thr Val Ser Ser
            115                 120
```

<210> SEQ ID NO 198
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 198

```
Glu Ile Val Leu Thr Gln Ser Pro Asp Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Phe Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Arg Ser Pro
                 85                  90                  95

Trp Thr Phe Gly Gln Gly Thr Lys Val Ala Ile Lys
            100                 105
```

<210> SEQ ID NO 199
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 199

```
Asp Arg Gln Met Val Glu Ser Gly Gly Gly Val Val Gln Pro Gly Arg
  1               5                  10                  15

Ser Leu Arg Leu Ser Cys Ile Ala Ser Gly Phe Ile Ile Ser Arg Tyr
                 20                  25                  30

Gly Met His Trp Val Arg Gln Ala Pro Gly Lys Gly Leu Glu Trp Val
             35                  40                  45

Ala Val Ile Trp Tyr Asp Gly Arg Asn Lys Asn Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Glu Met Asn Ser Leu Arg Ala Glu Asp Thr Ala Val Tyr Tyr Cys
                 85                  90                  95

Gly Arg Val His Gln Phe Gly Ala Phe Asp Ile Trp Gly Gln Gly Thr
            100                 105                 110

Met Val Thr Val Ser Ser
        115
```

<210> SEQ ID NO 200

```
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 200

Asp Ile Gln Met Thr Gln Ser Pro Ser Ser Leu Ser Ala Ser Val Gly
1               5                   10                  15

Asp Arg Ile Thr Ile Thr Cys Arg Gly Ser Gln Asn Ile Gly Ser Phe
            20                  25                  30

Leu Ser Trp Tyr Gln Gln Arg Pro Gly Lys Ala Pro Lys Leu Leu Ile
        35                  40                  45

Phe Gly Ala Tyr Asn Leu Gln Gly Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 201
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 201

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Gly
            20                  25                  30

Gly His Tyr Trp Thr Trp Ile Arg Gln His Pro Gly Lys Gly Leu Glu
        35                  40                  45

Trp Ile Gly Tyr Ile Tyr Tyr Ile Gly Thr Thr Tyr Tyr Asn Pro Ser
50                  55                  60

Leu Glu Ser Arg Leu Ser Leu Val Asp Thr Ser Lys Asn Gln Phe
65                  70                  75                  80

Ser Leu Lys Leu Ser Ser Val Thr Ala Ala Asp Thr Ala Ile Tyr Tyr
                85                  90                  95

Cys Ala Arg Ser Ser Leu Ser Val Ser Glu Ala Phe Asp Val Trp Gly
            100                 105                 110

Gln Gly Thr Met Val Thr Val Ser Ser
        115                 120

<210> SEQ ID NO 202
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 202

Asp Ile Gln Met Thr Gln Ser Pro Ser Ser Leu Ser Ala Ser Val Gly
1               5                   10                  15

Asp Arg Phe Thr Ile Thr Cys Arg Ala Ser Gln Ser Ile Gly Ser Phe
            20                  25                  30
```

```
Leu Ser Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asn Thr Pro Pro
                 85                  90                  95

Ile Thr Phe Gly Gln Gly Thr Arg Leu Glu Ile Lys
            100                 105
```

```
<210> SEQ ID NO 203
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 203

Gln Val Gln Leu Gln Glu Ser Gly Pro Gly Leu Val Arg Pro Ser Gln
 1               5                  10                  15

Thr Leu Ser Leu Thr Cys Thr Val Ser Gly Gly Ser Ile Ser Asn Gly
            20                  25                  30

Gly Tyr Tyr Trp Thr Trp Ile Arg Gln Asn Pro Gly Lys Gly Leu Glu
        35                  40                  45

Trp Ile Gly Tyr Ile Tyr Tyr Ile Gly Thr Thr Tyr Tyr Asn Pro Ser
 50                  55                  60

Leu Glu Ser Arg Leu Ser Leu Ser Val Asp Thr Ser Lys Asn Gln Phe
 65                  70                  75                  80

Ser Leu Lys Leu Thr Ser Val Thr Ala Ala Asp Thr Ala Val Tyr Tyr
                 85                  90                  95

Cys Ala Arg Ser Ser Leu Ala Val Ser Glu Ala Phe Asp Ile Trp Gly
            100                 105                 110

Gln Gly Thr Met Val Thr Val Ser Ser
        115                 120
```

```
<210> SEQ ID NO 204
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 204

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Gln Thr Ile Ser Thr Tyr
            20                  25                  30

Leu Asn Trp Tyr Gln Gln Lys Pro Gly Asn Ala Pro Lys Leu Leu Ile
        35                  40                  45

Tyr Ala Ala Ser Ser Leu Gln Ser Gly Val Pro Ser Arg Phe Ser Gly
 50                  55                  60

Arg Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Thr Thr Pro Pro
                 85                  90                  95

Ile Thr Phe Gly Gln Gly Thr Arg Leu Glu Ile Lys
            100                 105
```

```
<210> SEQ ID NO 205
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 205

Gln Val Gln Leu Val Gln Ser Gly Thr Glu Val Lys Arg Pro Gly Ala
1               5                   10                  15

Ser Val Lys Val Ser Cys Lys Ala Ser Gly Phe Thr Phe Thr Gly Tyr
            20                  25                  30

Tyr Ile Tyr Trp Val Arg Gln Ala Pro Gly Glu Gly Leu Glu Trp Met
        35                  40                  45

Gly Trp Ile Asn Pro His Ser Gly Gly Thr Lys Tyr Ala Gln Lys Phe
    50                  55                  60

Gln Gly Arg Val Thr Leu Thr Arg Asp Thr Ser Ile Asn Thr Ala Tyr
65                  70                  75                  80

Leu Asp Leu Ile Ser Leu Arg Ser Asp Asp Thr Ala Val Tyr Tyr Cys
                85                  90                  95

Ala Arg Ile Gly Gly Gly Tyr Ser Ser Tyr Phe Asp Tyr Trp Gly
            100                 105                 110

Gln Gly Thr Leu Val Thr Val Ser Ser
        115                 120

<210> SEQ ID NO 206
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 206

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Thr Thr Ala Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Ala Asn Ser Phe Pro Phe
                85                  90                  95

Thr Phe Gly Ser Gly Thr Lys Val Asp Ile Lys
            100                 105

<210> SEQ ID NO 207
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 207

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Asp Ile Ser Gly Ser Gly Leu Ser Thr Tyr Tyr Ala Asp Ser Val
50                  55                  60

Lys Gly Arg Phe Ala Ile Ser Arg Asp Asn Ser Lys Asn Met Leu Tyr
65                  70                  75                  80

Leu Gln Met Asn Arg Leu Arg Ala Glu Asp Thr Ala Val Tyr Tyr Cys
                85                  90                  95

Ala Lys Glu Pro Ser His Trp Asn Gly Glu Ala Phe Asp Ile Trp Gly
            100                 105                 110

Gln Gly Thr Met Val Thr Val Ser Ser
            115                 120

<210> SEQ ID NO 208
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 208

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Thr Val Ser Asn Ser
            20                  25                  30

His Leu Ala Trp Tyr Gln Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
50                  55                  60

Gly Ser Gly Ser Gly Thr Asp Phe Ser Leu Thr Ile Arg Leu Glu
65                  70                  75                  80

Pro Asp Asp Phe Ala Val Tyr Phe Cys Gln Gln His Glu Ser Ser Pro
                85                  90                  95

Pro Thr Phe Gly Gln Gly Ala Lys Leu Glu Ile Lys
            100                 105

<210> SEQ ID NO 209
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 209

Gln Leu Gln Leu Gln Glu Ser Gly Pro Gly Leu Val Lys Pro Ser Glu
1               5                   10                  15

Thr Leu Ser Phe Thr Cys Thr Val Ser Gly Gly Ser Ile Ser Ser Asn
            20                  25                  30

Tyr Tyr Tyr Trp Gly Trp Val Arg Gln Ser Pro Gly Lys Gly Leu Glu
        35                  40                  45

Trp Ile Gly Ser Ile Tyr His Thr Gly Asn Ala Tyr Asp Asn Pro Ser
50                  55                  60

Leu Lys Ser Arg Val Thr Ile Ser Val Asp Thr Ser Lys Asn Gln Phe
65                  70                  75                  80

Ser Leu Asn Leu Asn Ser Val Thr Ala Ala Asp Thr Ala Ile Tyr Tyr
                85                  90                  95
```

-continued

Cys Ala Arg His His Ser Ser Ser Trp Trp Tyr Phe Asp Val Trp
            100                 105                 110

Gly Arg Gly Thr Leu Val Ile Val Ser Ser
        115                 120

<210> SEQ ID NO 210
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 210

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Trp Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Pro Gly Ile Pro Gly Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Asn
            100                 105

<210> SEQ ID NO 211
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 211

Gln Val Gln Leu Val Glu Ser Gly Gly Val Val Gln Pro Gly Arg
1               5                   10                  15

Ser Leu Arg Leu Ser Cys Ala Ala Ser Gly Ile Thr Phe Ser Ser Tyr
            20                  25                  30

Gly Met His Trp Val Arg Gln Ala Pro Gly Lys Gly Leu Glu Trp Val
        35                  40                  45

Ala Leu Thr Ser Tyr Asp Gly Ser Lys Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Asp Lys Gly Gly Asp Asp Tyr Tyr Gly Met Asp Val Trp Gly
            100                 105                 110

Gln Gly Thr Thr Val Thr Val Ser Ser
        115                 120

<210> SEQ ID NO 212
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Gly Gly
50                  55                  60

Ser Gly Ser Gly Thr Asp Phe Thr Leu Thr Val Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Asn
            100                 105

<210> SEQ ID NO 213
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 213

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asn Asn
            20                  25                  30

Gly Ile Ser Trp Val Arg Gln Val Pro Gly Gln Gly Leu Glu Trp Met
        35                  40                  45

Gly Trp Ile Ser Pro Tyr Asn Gly Asn Thr Lys Tyr Ala Gln Lys Phe
50                  55                  60

Gln Gly Arg Val Thr Met Thr Thr Asp Thr Ser Thr Thr Thr Val Tyr
65                  70                  75                  80

Met Asp Val Arg Ser Leu Arg Ser Asp Asp Thr Ala Val Tyr Phe Cys
                85                  90                  95

Ala Arg Asp Gly Pro Ile Thr Ile Ser Tyr Phe Gly Met Asp Val Trp
            100                 105                 110

Gly Gln Gly Thr Thr Val Thr Val Ser Ser
        115                 120

<210> SEQ ID NO 214
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 214

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ser Val Ala Gly Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

-continued

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Trp Thr Phe Gly Gln Gly Thr Lys Val Glu Ile Thr
            100                 105

<210> SEQ ID NO 215
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 215

Gln Val Gln Leu Val Glu Ser Gly Gly Val Gln Pro Gly Arg
1               5                   10                  15

Ser Leu Arg Leu Ser Cys Ala Ala Ser Gly Phe Thr Val Asn Arg Tyr
                20                  25                  30

Gly Ile His Trp Val Arg Gln Ala Pro Gly Lys Gly Leu Glu Trp Val
            35                  40                  45

Ala Val Thr Trp Tyr Asp Gly Arg Asn Lys Tyr Phe Ala Asp Ser Val
        50                  55                  60

Lys Gly Arg Phe Ser Phe Ser Arg Asp Ser Thr Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Phe Gly Tyr Phe Asp Tyr Trp Gly Gln Gly Thr
            100                 105                 110

Leu Val Thr Val Ser Ser
        115

<210> SEQ ID NO 216
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 216

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
        50                  55                  60

Ser Gly Ser Gly Thr Asp Phe Ile Leu Thr Ile Asn Arg Leu Glu Pro
65                  70                  75                  80

Glu Asp Phe Ala Val Tyr Tyr Cys Gln His Tyr Gly Asn Ser Pro Trp
                85                  90                  95

Thr Phe Gly Gln Gly Thr Lys Val Glu Ile Lys
            100                 105

<210> SEQ ID NO 217
<211> LENGTH: 118
<212> TYPE: PRT

<213> ORGANISM: Artificial Sequence
<220> FEATURE:
<223> OTHER INFORMATION: synthetic construct; antigen binding domain

<400> SEQUENCE: 217

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Val Ile Trp Tyr Gly Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr His Cys
                85                  90                  95

Ala Arg Ser Gly Asn Phe Gly Ala Phe Asp Ile Trp Gly Gln Gly Thr
            100                 105                 110

Met Val Thr Val Ser Ser
        115
```

<210> SEQ ID NO 218
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 218

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Asp Trp Val Arg Gln Ala Pro Gly Lys Gly Leu Glu Trp Val
        35                  40                  45

Ala Val Ile Trp Tyr Pro Gly Ser Asn Lys Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Glu Leu Gly Leu Asp Tyr Tyr Ser Gly Met Asp Val
            100                 105                 110

Trp Gly Gln Gly Thr Thr Val Thr Val Ser Ser
        115                 120
```

<210> SEQ ID NO 219
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 219

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30
```

```
Leu Asn Trp Tyr Gln Gln Lys Pro Gly Lys Ala Pro Lys Arg Leu Ile
        35                  40                  45

Asn Gly Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Leu Asn Ser Tyr Pro Arg
                 85                  90                  95

Thr Phe Gly Gln Gly Thr Lys Val Glu Ile Lys
            100                 105
```

<210> SEQ ID NO 220
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 220

```
Gln Val Gln Leu Val Glu Ser Gly Gly Gly Val Val Gln Pro Gly Arg
1                5                  10                  15

Ser Leu Arg Leu Ser Cys Ala Ala Ser Gly Phe Thr Phe Ser Asn Tyr
                20                  25                  30

Gly Met His Trp Val Arg Gln Ala Pro Gly Lys Gly Leu Glu Trp Val
        35                  40                  45

Ala Val Ile Trp Tyr Pro Gly Ser Asn Lys Phe Tyr Thr Asp Ser Val
 50                  55                  60

Glu Gly Arg Phe Thr Ile Ser Arg Asp Asn Ser Lys Asn Thr Val Tyr
65                  70                  75                  80

Leu Gln Met Asp Ser Leu Arg Ala Glu Asp Thr Ala Val Tyr Tyr Cys
                 85                  90                  95

Ala Arg Gly Gly Ala Leu Gly Val Asp Tyr Tyr Tyr Gly Met Asp Val
            100                 105                 110

Trp Gly Gln Gly Thr Thr Val Thr Val Ser Ser
        115                 120
```

<210> SEQ ID NO 221
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 221

```
Ala Ile Gln Met Thr Gln Ser Pro Ser Ser Leu Ser Ala Ser Val Gly
1                5                  10                  15

Asp Arg Val Thr Leu Thr Cys Arg Ala Ser Gln Gly Ile Arg Asn Asp
                20                  25                  30

Leu Gly Trp Tyr Gln Gln Lys Pro Gly Lys Ala Pro Asn Phe Leu Ile
        35                  40                  45

Tyr Ser Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asn Tyr Asn Tyr Pro Trp
                 85                  90                  95

Thr Phe Gly Gln Gly Thr Lys Val Glu Ile Lys
```

-continued

```
                100                 105

<210> SEQ ID NO 222
<211> LENGTH: 124
<212> TYPE: PRT
<213> ORGANISM: Artificial Sequence
<220> FEATURE:
<223> OTHER INFORMATION: synthetic construct; antigen binding domain

<400> SEQUENCE: 222

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Trp Tyr Glu Gly Ser Asn Lys Tyr Tyr Ala Asp Ser Val
    50                  55                  60

Thr Gly Arg Phe Thr Ile Ser Arg Asp Asn Ser Lys Asn Thr Leu Phe
65                  70                  75                  80

Leu Gln Met Asn Ser Leu Lys Ala Glu Asp Thr Ala Glu Tyr Tyr Cys
                85                  90                  95

Ala Lys Asp Gly Gly Gln Leu Ala Tyr Gln Tyr Tyr Gly Met Asp
            100                 105                 110

Val Trp Gly Gln Gly Thr Thr Val Thr Val Ser Ser
        115                 120

<210> SEQ ID NO 223
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 223

Ala Ile Gln Met Thr Gln Ser Pro Ser Ser Leu Ser Ala Ser Val Gly
1               5                   10                  15

Asp Arg Val Thr Leu Thr Cys Arg Ala Ser Gln Gly Ile Arg Asn Asp
            20                  25                  30

Leu Gly Trp Tyr Gln Gln Lys Pro Gly Lys Ala Pro Lys Ser Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105

<210> SEQ ID NO 224
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 224

Gln Val Gln Leu Val Glu Ser Gly Gly Gly Val Val Gln Pro Gly Arg
1               5                   10                  15
```

Ser Leu Arg Leu Ser Cys Ala Ala Ser Gly Phe Asn Phe Arg Ser Tyr
            20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Ser Ser Arg Asp Thr Leu Phe
65                  70                  75                  80

Leu Gln Met Asn Ser Leu Arg Ala Gly Asp Thr Ala Val Tyr Tyr Cys
                85                  90                  95

Ala Arg Gly Gly Met Leu Gly Arg Asp Tyr Tyr Tyr Gly Met Asp Val
            100                 105                 110

Trp Gly Gln Gly Thr Thr Val Thr Val Ser Ser
            115                 120

<210> SEQ ID NO 225
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 225

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Asn
                85                  90                  95

Thr Phe Gly Gln Gly Thr Lys Leu Glu Ile Lys
            100                 105

<210> SEQ ID NO 226
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 226

Gln Val Gln Leu Val Glu Ser Gly Gly Gly Ala Val Gln Pro Gly Thr
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
            35                  40                  45

Ser Val Ile Trp Tyr Glu Gly Ser Asn Lys Tyr Tyr Ala Asp Ser Val
 50                  55                  60

Lys Gly Arg Phe Thr Ile Ser Arg Asp Asn Ser Arg Asn Thr Leu Ser
65                  70                  75                  80

Leu Gln Met Asp Ser Leu Arg Val Glu Asp Thr Ala Val Tyr Tyr Cys

<210> SEQ ID NO 227
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 227

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Lys Asn Asp
            20                  25                  30
Leu Gly Trp Phe Gln Gln Lys Ala Gly Lys Ala Pro Lys Arg Leu Phe
        35                  40                  45
Tyr Ala Thr Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln Val His Ser Tyr Pro Arg
                85                  90                  95
Thr Phe Gly Gln Gly Thr Lys Val Glu Ile Lys
            100                 105
```

<210> SEQ ID NO 228
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 228

```
Gln Val Gln Leu Val Glu Ser Gly Gly Val Val Gln Pro Gly Arg
1               5                   10                  15
Ser Leu Arg Leu Ser Cys Glu Ala Ser Gly Phe Thr Phe Ser Asn Tyr
            20                  25                  30
Gly Phe His Trp Val Arg Gln Ala Pro Gly Lys Gly Leu Asp Trp Val
        35                  40                  45
Ala Val Ile Trp Tyr Ala Gly Ser Asn Lys Phe Tyr Val Asp Ser Val
    50                  55                  60
Gln Gly Arg Phe Thr Ile Ser Arg Asp Asn Ser Lys Gln Ile Leu Phe
65                  70                  75                  80
Leu Gln Met Asn Ser Leu Arg Ala Glu Asp Ser Ala Val Tyr Tyr Cys
                85                  90                  95
Val Arg Gly Gly Ile Leu Gly Ile Asp Tyr Tyr Ser Gly Met Asp Val
            100                 105                 110
Trp Gly Gln Gly Thr Thr Val Thr Val Ser Ser
        115                 120
```

<210> SEQ ID NO 229
<211> LENGTH: 107
<212> TYPE: PRT
<213> ORGANISM: Artificial Sequence
<220> FEATURE:

<223> OTHER INFORMATION: synthetic construct; antigen binding domain

<400> SEQUENCE: 229

```
Ala Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
             20                  25                  30

Leu Gly Trp Tyr Gln Gln Arg Pro Gly Lys Ala Pro Lys Phe Leu Ile
         35                  40                  45

Tyr Ser Thr Ser Ser Leu Gln Ser Gly Val Pro Ser Arg Phe Ser Gly
 50                  55                  60

Ser Gly Ser Gly Thr Asp Phe Ile Leu Thr Ile Ser Ser Leu Gln Pro
 65                  70                  75                  80

Glu Asp Phe Ala Thr Tyr Tyr Cys Leu Gln Ser His Asn Tyr Pro Trp
             85                  90                  95

Thr Phe Gly His Gly Thr Lys Val Glu Ile Lys
            100                 105
```

<210> SEQ ID NO 230
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 230

```
Gln Val Gln Leu Val Glu Ser Gly Gly Val Val Gln Pro Gly Arg
 1               5                  10                  15

Ser Leu Arg Leu Ser Cys Ala Val Ser Gly Phe Thr Leu Ser Ser Tyr
             20                  25                  30

Gly Met Asp Trp Val Arg Gln Ala Pro Gly Lys Gly Leu Glu Trp Val
         35                  40                  45

Ala Val Ile Trp Tyr Asp Gly Ser Asn Lys Tyr Tyr Ser Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Ala Asp Thr Ala Val Tyr Tyr Cys
             85                  90                  95

Ala Arg Asp Gly Glu Leu Gly Leu Asp Tyr Tyr Ser Gly Met Asp Val
            100                 105                 110

Trp Gly Gln Gly Thr Thr Val Thr Val Ser Ser
        115                 120
```

<210> SEQ ID NO 231
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 231

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
             20                  25                  30

Leu Gly Trp Tyr Gln Gln Lys Pro Gly Lys Ala Pro Lys Arg Leu Ile
         35                  40                  45

Tyr Gly Ala Ser Ser Leu Gln Ser Gly Val Pro Ser Arg Phe Ser Gly
```

```
                50                  55                  60
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Leu Asn Ser Tyr Pro Arg
                 85                  90                  95

Thr Phe Gly Gln Gly Thr Lys Val Glu Ile Lys
            100                 105

<210> SEQ ID NO 232
<211> LENGTH: 118
<212> TYPE: PRT
<213> ORGANISM: Artificial Sequence
<220> FEATURE:
<223> OTHER INFORMATION: synthetic construct; antigen binding domain

<400> SEQUENCE: 232

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Phe
                20                  25                  30

Gly Met His Trp Val Arg Gln Ala Pro Gly Lys Gly Leu Glu Trp Val
            35                  40                  45

Ala Val Ile Ser Tyr Asp Gly Arg Asn Arg Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Ser Ala Glu Asp Thr Ala Met Phe Tyr Cys
                 85                  90                  95

Ala Lys Asp Gly Phe Gly Asn Ser Phe Asp Tyr Trp Gly Gln Gly Thr
            100                 105                 110

Leu Val Thr Val Ser Ser
        115

<210> SEQ ID NO 233
<211> LENGTH: 112
<212> TYPE: PRT
<213> ORGANISM: Artificial Sequence
<220> FEATURE:
<223> OTHER INFORMATION: synthetic construct; antigen binding domain

<400> SEQUENCE: 233

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Leu Tyr Ser
                20                  25                  30

Asp Gly Asn Thr Tyr Leu Thr Trp Phe Gln Gln Arg Pro Gly Gln Ser
            35                  40                  45

Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Thr Ile
 65                  70                  75                  80

Ser Arg Val Glu Ala Glu Asp Val Gly Ile Tyr Tyr Cys Met Gln Gly
                 85                  90                  95

Thr His Trp Pro Trp Thr Phe Gly Gln Gly Thr Lys Val Glu Ile Lys
            100                 105                 110

<210> SEQ ID NO 234
<211> LENGTH: 123
```

```
<212> TYPE: PRT
<213> ORGANISM: Artificial Sequence
<220> FEATURE:
<223> OTHER INFORMATION: synthetic construct; antigen binding domain

<400> SEQUENCE: 234

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Ser Glu Ser Asn Lys Tyr Tyr Thr Asp Ser Met
50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Leu Gly Lys Tyr Tyr Tyr Gly Met Asp Val
            100                 105                 110

Trp Gly Gln Gly Thr Thr Val Thr Val Ser Ser
        115                 120

<210> SEQ ID NO 235
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 235

Asp Ile Gln Met Thr Gln Ser Pro Ser Ser Leu Ser Ala Ser Val Gly
1               5                   10                  15

Asp Arg Val Ile Ile Thr Cys Arg Ala Ser Gln Asp Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Phe Tyr Cys Leu Gln Leu Asn Ser Tyr Pro Tyr
                85                  90                  95

Thr Phe Gly Gln Gly Thr Lys Leu Glu Ile Lys
            100                 105

<210> SEQ ID NO 236
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 236

Gln Val Gln Leu Val Glu Ser Gly Gly Gly Val Ala Gln Pro Gly Arg
1               5                   10                  15

Ser Leu Ser Leu Ser Cys Ala Ala Ser Gly Phe Thr Phe Ser Asp Tyr
            20                  25                  30

Gly Met His Trp Val Arg Gln Ala Pro Gly Lys Gly Leu Glu Trp Val
```

```
                35                  40                  45
Ala Val Ile Trp Tyr Ala Gly Ser Asn Lys Tyr Tyr Ala Asp Ser Val
        50                  55                  60
Lys Asp Arg Phe Thr Ile Ser Arg Asp Asn Ser Lys Asn Thr Leu Tyr
65                  70                  75                  80
Leu Gln Met Arg Ser Leu Arg Val Glu Asp Thr Ala Val Tyr Tyr Cys
                85                  90                  95
Ala Arg Gly Gly Glu Leu Arg Leu Asp Tyr Tyr Ser Gly Leu Asp Val
        100                 105                 110
Trp Gly Gln Gly Thr Thr Val Thr Val Ser Ser
            115                 120
```

<210> SEQ ID NO 237
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 237

```
Asp Ile Gln Met Thr Gln Ser Pro Ser Ser Leu Ser Ala Ser Val Gly
1               5                   10                  15
Asp Arg Val Thr Val Thr Cys Arg Ala Ser Gln Gly Ile Arg Ser Asp
            20                  25                  30
Leu Gly Trp Tyr Gln Gln Lys Pro Gly Lys Ala Pro Lys Arg Leu Ile
        35                  40                  45
Tyr Ala Ala Ser Ser Phe Gln Ser Gly Val Pro Ser Arg Phe Ser Gly
    50                  55                  60
Ser Gly Ser Gly Thr Glu Phe Thr Leu Thr Ile Ser Ser Leu His Pro
65                  70                  75                  80
Glu Asp Phe Ala Thr Tyr Tyr Cys Leu Gln Ser Asn Asn Tyr Pro Trp
                85                  90                  95
Thr Phe Gly Gln Gly Thr Lys Val Glu Ile Lys
            100                 105
```

<210> SEQ ID NO 238
<211> LENGTH: 124
<212> TYPE: PRT
<213> ORGANISM: Artificial Sequence
<220> FEATURE:
<223> OTHER INFORMATION: synthetic construct; antigen binding domain

<400> SEQUENCE: 238

```
Gln Val Gln Leu Val Glu Ser Gly Gly Gly Val Val Gln Pro Gly Gly
1               5                   10                  15
Ser Leu Arg Leu Ser Cys Ala Val Ser Gly Phe Thr Phe Ser Asp Tyr
            20                  25                  30
Gly Met His Trp Val Arg Gln Val Pro Gly Ala Gly Leu Glu Trp Val
        35                  40                  45
Ala Val Ile Tyr Tyr Glu Gly Ser Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Val Glu Asp Thr Ser Met Tyr Phe Cys
                85                  90                  95
Ala Arg Gly Pro Leu Leu Gly Gly Asn Phe Tyr Ser Tyr Leu Met Asp
            100                 105                 110
```

Val Trp Gly Gln Gly Thr Thr Val Thr Val Ser Ser
            115                 120

<210> SEQ ID NO 239
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 239

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Gly
            20                  25                  30

Leu Gly Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Phe
                85                  90                  95

Ser Phe Gly Pro Gly Thr Lys Val Asp Ile Lys
            100                 105

<210> SEQ ID NO 240
<211> LENGTH: 124
<212> TYPE: PRT
<213> ORGANISM: Artificial Sequence
<220> FEATURE:
<223> OTHER INFORMATION: synthetic construct; antigen binding domain

<400> SEQUENCE: 240

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Val Arg Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Gly Gly Glu Leu Val Arg Gly Asp Tyr Tyr Tyr Gly Met Asp
            100                 105                 110

Val Trp Gly Gln Gly Thr Thr Val Thr Val Ser Ser
            115                 120

<210> SEQ ID NO 241
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 241

Asp Ile Gln Met Thr Gln Ser Pro Ser Ser Leu Ser Ala Ser Val Gly

```
             1               5                  10                 15
Asp Arg Val Thr Ile Thr Cys Arg Ala Ser Gln Gly Ile Arg Asn Asp
                    20                  25                  30

Leu Gly Trp Tyr Gln Gln Lys Pro Gly Lys Ala Pro Lys Arg Leu Ile
            35                  40                  45

Tyr Gly Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                    85                  90                  95

Thr Phe Gly Gln Gly Thr Lys Leu Glu Ile Lys
                100                 105

<210> SEQ ID NO 242
<211> LENGTH: 117
<212> TYPE: PRT
<213> ORGANISM: Artificial Sequence
<220> FEATURE:
<223> OTHER INFORMATION: synthetic construct; antigen binding domain

<400> SEQUENCE: 242

Gln Val Gln Leu Val Glu Ser Gly Gly Gly Val Val Gln Pro Gly Arg
1               5                   10                  15

Ser Leu Arg Leu Ser Cys Ala Ala Ser Gly Thr Ile Phe Ser Thr His
                    20                  25                  30

Gly Met His Trp Val Arg Gln Ala Pro Gly Lys Gly Leu Glu Trp Val
            35                  40                  45

Ala Val Ile Ser Tyr Asp Gly Asn Lys Lys Tyr Tyr Ala Gly Ser Val
        50                  55                  60

Lys Gly Arg Phe Thr Ile Ser Arg Asp Asn Ser Lys Asn Thr Leu Tyr
65                  70                  75                  80

Leu Gln Met Asn Asp Val Arg Ser Glu Asp Thr Ala Val Tyr His Cys
                    85                  90                  95

Thr Thr Asp Ile Thr Gly Ile Thr Asp Tyr Trp Gly Gln Gly Thr Leu
                100                 105                 110

Val Thr Val Ser Ser
            115

<210> SEQ ID NO 243
<211> LENGTH: 106
<212> TYPE: PRT
<213> ORGANISM: Artificial Sequence
<220> FEATURE:
<223> OTHER INFORMATION: synthetic construct; antigen binding domain

<400> SEQUENCE: 243

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Asp
                    20                  25                  30

Leu Gly Trp Tyr Gln Gln Lys Leu Gly Lys Ala Pro Lys Arg Leu Ile
            35                  40                  45

Tyr Ala Ala Ser Ser Leu Glu Ser Gly Val Pro Ser Arg Phe Ser Gly
        50                  55                  60

Ser Gly Ser Gly Thr Glu Phe Ile Leu Thr Ile Ser Ser Leu Gln Ala
65                  70                  75                  80
```

Glu Asp Phe Ala Thr Tyr Tyr Cys Leu Gln His Asn Gly Phe Pro Thr
            85                  90                  95

Phe Gly Gln Gly Thr Lys Val Glu Ile Lys
            100                 105

<210> SEQ ID NO 244
<211> LENGTH: 121
<212> TYPE: PRT
<213> ORGANISM: Artificial Sequence
<220> FEATURE:
<223> OTHER INFORMATION: synthetic construct; antigen binding domain

<400> SEQUENCE: 244

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Pro Gly Gln Gly Leu Glu Trp Val
            35                  40                  45

Ala Val Ile Trp Tyr Ala Gly Ser Asn Lys Phe Tyr Ala Asp Ser Val
        50                  55                  60

Lys Gly Arg Phe Thr Ile Ser Arg Asp Asn Ser Lys Asn Ser Ala Tyr
65                  70                  75                  80

Leu Gln Met Asn Ser Leu Arg Ala Glu Asp Thr Ala Val Tyr Tyr Cys
                85                  90                  95

Ala Arg Ala Pro Leu Gly Tyr Tyr Tyr Gly Met Asp Val Trp Gly
            100                 105                 110

Gln Gly Thr Thr Val Thr Val Ser Ser
            115                 120

<210> SEQ ID NO 245
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 245

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 246
<211> LENGTH: 125
<212> TYPE: PRT
<213> ORGANISM: Artificial Sequence
<220> FEATURE:
<223> OTHER INFORMATION: synthetic construct; antigen binding domain

```
<400> SEQUENCE: 246

Gln Val Gln Leu Val Glu Ser Gly Gly Gly Val Val Gln Pro Gly Arg
1               5                   10                  15

Ser Leu Arg Leu Ser Cys Ala Ala Ser Gly Leu Thr Val Ser Ser Tyr
            20                  25                  30

Val Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Gly Asp Ser Val
    50                  55                  60

Lys Gly Arg Phe Thr Ile Ser Arg Asp Asn Ser Lys Lys Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Pro Leu Ser Ser Ser Ser Asp Tyr Tyr Gly Leu
            100                 105                 110

Asp Val Trp Gly Gln Gly Thr Thr Val Thr Val Ser Ser
        115                 120                 125

<210> SEQ ID NO 247
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 247

Ala Ile Gln Met Thr Gln Ser Pro Ser Ser Leu Ser Ala Ser Val Gly
1               5                   10                  15

Asp Arg Val Thr Ile Ile Cys Arg Ala Ser Gln Gly Ile Arg Asn Asp
            20                  25                  30

Leu Gly Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 248
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 248

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Glu Met Tyr Trp Val Arg Gln Ala Pro Gly Lys Gly Leu Glu Trp Val
        35                  40                  45

Ser Tyr Ile Ser Ser Ser Gly Thr Thr Ile Tyr Tyr Ala Asp Ser Val
    50                  55                  60
```

```
Lys Gly Arg Phe Ser Val Ser Arg Glu Asn Ala Arg Ser Ser Leu Tyr
65                  70                  75                  80

Leu Gln Met Asn Ser Leu Arg Val Glu Asp Ser Ala Val Tyr Phe Cys
                85                  90                  95

Ala Lys Tyr Asn Trp Asn Ser Phe Tyr Gly Leu Asp Val Trp Gly Gln
            100                 105                 110

Gly Thr Thr Val Thr Val Ser Ser
            115                 120

<210> SEQ ID NO 249
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 249

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Leu Leu Ile
        35                  40                  45

Ser Ala Ala Ser Ser Leu Gln Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Ala Asp Phe Ala Thr Tyr Tyr Cys Leu Gln Tyr Asn Tyr Ala Leu
                85                  90                  95

Thr Phe Gly Gly Gly Thr Lys Val Glu Ile Lys
            100                 105

<210> SEQ ID NO 250
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 250

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Val Tyr
            20                  25                  30

Glu Met Asn Trp Val Arg Gln Ala Pro Gly Lys Gly Leu Glu Trp Ile
        35                  40                  45

Ser Tyr Ile Gly Ser Ser Gly Phe Thr Ile Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Leu Asn Ser Leu Arg Ala Glu Asp Thr Ala Val Tyr Tyr Cys
                85                  90                  95

Ala Arg Gly Trp Asn Asp Gly Val Pro Asn Tyr Leu Gly Met Asp Val
            100                 105                 110

Trp Gly Gln Gly Thr Thr Val Thr Val Ser Ser
        115                 120

<210> SEQ ID NO 251
```

```
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 251

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Lys Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Arg Tyr His Cys Gln Gln Tyr Asp Lys Ile Pro Leu
                85                  90                  95

Thr Phe Gly Gly Gly Thr Lys Val Glu Ile Lys
            100                 105

<210> SEQ ID NO 252
<211> LENGTH: 123
<212> TYPE: PRT
<213> ORGANISM: Artificial Sequence
<220> FEATURE:
<223> OTHER INFORMATION: synthetic construct; antigen binding domain

<400> SEQUENCE: 252

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Val Gly Ser Asn Lys Tyr Tyr Gly Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Ile Tyr Tyr Cys
                85                  90                  95

Ala Arg Gly Gly Gln Leu Gly Ser Phe Tyr Tyr Tyr Met Asp Val
            100                 105                 110

Trp Gly Gln Gly Thr Thr Val Thr Val Ser Ser
        115                 120

<210> SEQ ID NO 253
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 253

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30
```

Leu Gly Trp Tyr Gln Gln Lys Pro Gly Lys Ala Pro Lys Arg Leu Ile
        35                  40                  45

Tyr Asp Val Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Leu Ala Thr Tyr Tyr Cys Leu Gln His Asn Ser Tyr Pro Trp
                 85                  90                  95

Thr Phe Gly Gln Gly Thr Lys Val Glu Ile Lys
            100                 105

<210> SEQ ID NO 254
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 254

Gln Val Gln Leu Val Glu Ser Gly Gly Gly Val Val Gln Pro Gly Arg
 1               5                  10                  15

Ser Leu Arg Ile Ser Cys Ala Ala Ser Gly Phe Thr Phe Asn Asn Tyr
            20                  25                  30

Gly Phe His Trp Val Arg Gln Ala Pro Gly Arg Gly Leu Glu Trp Val
        35                  40                  45

Ala Val Ile Trp Tyr Ser Gly Ser Asn Lys Tyr Tyr Gly Asp Ser Val
 50                  55                  60

Lys Gly Arg Phe Thr Ile Ser Arg Asp Asn Ser Lys Asn Ile Leu Tyr
 65                  70                  75                  80

Leu Gln Met Asn Ser Leu Arg Ala Glu Asp Thr Ala Ile Tyr Tyr Cys
                 85                  90                  95

Ala Arg Phe Pro Phe Ser Ser Ser Trp Leu Leu Asp Tyr Trp Gly Gln
            100                 105                 110

Gly Thr Leu Val Thr Val Ser Ser
        115                 120

<210> SEQ ID NO 255
<211> LENGTH: 107
<212> TYPE: PRT
<213> ORGANISM: Artificial Sequence
<220> FEATURE:
<223> OTHER INFORMATION: synthetic construct; antigen binding domain

<400> SEQUENCE: 255

Asp Ile Gln Leu Thr Gln Ser Pro Ser Phe Leu Ser Ala Ser Val Gly
 1               5                  10                  15

Asp Arg Val Thr Phe Thr Cys Trp Ala Ser Gln Gly Ile Ser Asp Tyr
            20                  25                  30

Leu Ala Trp Tyr Gln Gln Lys Pro Gly Lys Ala Pro Lys Leu Leu Ile
        35                  40                  45

Tyr Ala Ala Ser Ala Leu Gln Ser Gly Val Pro Ser Arg Phe Ser Gly
 50                  55                  60

Ser Gly Ser Gly Thr Glu Phe Thr Leu Thr Val Ser Ser Leu Gln Pro
 65                  70                  75                  80

Glu Asp Phe Ala Thr Tyr Tyr Cys Gln Gln Leu Asn Ser Tyr Pro Phe
                 85                  90                  95

Thr Phe Gly Pro Gly Thr Lys Val Asp Ile Lys
            100                 105

<210> SEQ ID NO 256
<211> LENGTH: 119
<212> TYPE: PRT
<213> ORGANISM: Artificial Sequence
<220> FEATURE:
<223> OTHER INFORMATION: synthetic construct; antigen binding domain

<400> SEQUENCE: 256

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Thr
            20                  25                  30

Asn His Tyr Trp Gly Trp Ile Arg Gln Pro Pro Gly Lys Gly Leu Glu
        35                  40                  45

Trp Ile Gly Asn Val Tyr Tyr Ile Gly Asn Ala Tyr Tyr Asn Pro Ser
    50                  55                  60

Leu Lys Thr Gly Val Thr Phe Ser Val Asp Thr Ser Lys Asn Gln Phe
65                  70                  75                  80

Ser Leu Asn Leu Arg Ser Val Thr Ala Ala Asp Thr Ala Met Tyr Tyr
                85                  90                  95

Cys Ala Arg Leu Ser Asn Trp Asn Phe Leu Asp Leu Trp Gly Gln Gly
            100                 105                 110

Thr Leu Val Thr Val Ser Ser
        115
```

<210> SEQ ID NO 257
<211> LENGTH: 106
<212> TYPE: PRT
<213> ORGANISM: Artificial Sequence
<220> FEATURE:
<223> OTHER INFORMATION: synthetic construct; antigen binding domain

<400> SEQUENCE: 257

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Phe Asn Asn Trp Leu Ser
                85                  90                  95

Phe Gly Gly Gly Thr Lys Val Glu Ile Lys
            100                 105
```

<210> SEQ ID NO 258
<211> LENGTH: 122
<212> TYPE: PRT
<213> ORGANISM: Artificial Sequence
<220> FEATURE:
<223> OTHER INFORMATION: synthetic construct; antigen binding domain

<400> SEQUENCE: 258

```
Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Val Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Gly Val Tyr His Cys
                85                  90                  95

Ala Arg Asp Ser Met Val Arg Pro Tyr Tyr Tyr Gly Met Asp Val Trp
            100                 105                 110

Gly Gln Gly Thr Thr Val Thr Val Ser Ser
            115                 120
```

<210> SEQ ID NO 259
<211> LENGTH: 108
<212> TYPE: PRT
<213> ORGANISM: Artificial Sequence
<220> FEATURE:
<223> OTHER INFORMATION: synthetic construct; antigen binding domain

<400> SEQUENCE: 259

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 260
<211> LENGTH: 125
<212> TYPE: PRT
<213> ORGANISM: Artificial Sequence
<220> FEATURE:
<223> OTHER INFORMATION: synthetic construct; antigen binding domain

<400> SEQUENCE: 260

```
Gln Val Gln Leu Val Glu Ser Gly Gly Gly Val Val Gln Pro Gly Arg
1               5                   10                  15

Ser Leu Arg Leu Ser Cys Ser Ala Ser Gly Phe Thr Leu Ser Asn Phe
            20                  25                  30

Val Met His Trp Val Arg Gln Ala Pro Gly Lys Gly Leu Glu Trp Val
        35                  40                  45

Ala Val Ile Leu Tyr Asp Gly Ser Asn Lys Tyr Tyr Ala Asp Ser Val
    50                  55                  60

Lys Gly Arg Phe Thr Ile Ser Arg Asp Asn Ser Asn Asn Arg Leu Tyr
65                  70                  75                  80

Leu Gln Met Asn Ser Leu Arg Ala Glu Asp Thr Ala Leu Tyr Tyr Cys
                85                  90                  95
```

```
Ala Arg Gly Glu Ser Leu Gly Ser Pro Ile Tyr Tyr Tyr Gly Leu
            100                 105                 110

Asp Val Trp Gly Gln Gly Thr Thr Val Thr Val Ser Ser
            115                 120                 125

<210> SEQ ID NO 261
<211> LENGTH: 120
<212> TYPE: PRT
<213> ORGANISM: Artificial Sequence
<220> FEATURE:
<223> OTHER INFORMATION: synthetic construct; antigen binding domain

<400> SEQUENCE: 261

Gln Val Gln Leu Gln Glu Ser Gly Pro Gly Leu Val Lys Pro Ser Glu
1               5                   10                  15

Thr Leu Ser Leu Thr Cys Ile Val Ser Gly Ser Ile Ser Gly Tyr
            20                  25                  30

Phe Trp Asn Trp Ile Arg Gln Pro Pro Gly Lys Gly Leu Glu Trp Ile
            35                  40                  45

Gly Tyr Ile Tyr Tyr Ser Gly Thr Thr Ile Tyr Asn Pro Ser Leu Lys
    50                  55                  60

Ser Arg Phe Thr Ile Ser Leu Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Glu Ser Tyr Asn Pro Ser Pro Arg Tyr Phe Asp His Trp Gly Gln
            100                 105                 110

Gly Thr Leu Val Thr Val Ser Ser
            115                 120

<210> SEQ ID NO 262
<211> LENGTH: 125
<212> TYPE: PRT
<213> ORGANISM: Artificial Sequence
<220> FEATURE:
<223> OTHER INFORMATION: synthetic construct; antigen binding domain

<400> SEQUENCE: 262

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Gly Met His Trp Val Arg Gln Ala Pro Gly Lys Gly Leu Glu Trp Met
            35                  40                  45

Ala Val Ile Trp Tyr Ala Gly Ser Asn Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Thr Ala Glu Asp Thr Ala Val Tyr Tyr Cys
                85                  90                  95

Ala Arg Gly Ser Ser Leu Ala Ala Pro Asp Leu Tyr Lys Tyr Gly Met
            100                 105                 110

Asp Val Trp Gly Gln Gly Thr Thr Val Thr Val Ser Ser
            115                 120                 125

<210> SEQ ID NO 263
<211> LENGTH: 117
<212> TYPE: PRT
```

```
<213> ORGANISM: Artificial Sequence
<220> FEATURE:
<223> OTHER INFORMATION: synthetic construct; antigen binding domain

<400> SEQUENCE: 263

Gln Val Gln Leu Gln Glu Ser Gly Pro Gly Leu Val Lys Pro Ser Glu
1               5                   10                  15

Thr Leu Ser Leu Thr Cys Thr Ile Ser Gly Gly Ser Ile Ser Asn Ser
            20                  25                  30

Phe Leu Thr Trp Ile Arg Gln Pro Pro Gly Lys Gly Leu Glu Trp Ile
        35                  40                  45

Gly Tyr Ile Tyr His Arg Gly Asn Thr Asp Ser Asn Pro Ser Leu Lys
    50                  55                  60

Ser Arg Val Thr Ile Ser Thr Asp Pro Ser Lys Asn Gln Phe Ser Leu
65                  70                  75                  80

Thr Leu His Ser Val Thr Ala Ala Asp Ser Ala Ile Tyr Tyr Cys Ala
                85                  90                  95

Arg Gly Gln Phe Met Glu Trp Phe Asp Phe Trp Gly Gly Thr Leu
            100                 105                 110

Val Thr Val Ser Ser
        115

<210> SEQ ID NO 264
<211> LENGTH: 125
<212> TYPE: PRT
<213> ORGANISM: Artificial Sequence
<220> FEATURE:
<223> OTHER INFORMATION: synthetic construct; antigen binding domain

<400> SEQUENCE: 264

Gln Val Gln Leu Val Glu Ser Gly Gly Gly Val Val Gln Pro Gly Arg
1               5                   10                  15

Ser Leu Arg Val Ser Cys Glu Ala Ser Gly Phe Thr Leu Ser Ser Tyr
            20                  25                  30

Gly Met Asn Trp Val Arg Gln Ala Pro Gly Lys Gly Leu Glu Trp Val
        35                  40                  45

Ala Val Ile Trp Tyr Asp Gly Ser Asn Lys Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Gly Leu Arg Asp Asp Thr Ala Val Tyr Tyr Cys
                85                  90                  95

Ala Arg Gly Glu Gln Leu Gly Ser His Val Tyr Tyr Tyr Gly Met
            100                 105                 110

Asp Val Trp Gly Gln Gly Thr Thr Val Thr Val Ser Ser
        115                 120                 125

<210> SEQ ID NO 265
<211> LENGTH: 125
<212> TYPE: PRT
<213> ORGANISM: Artificial Sequence
<220> FEATURE:
<223> OTHER INFORMATION: synthetic construct; antigen binding domain

<400> SEQUENCE: 265

Gln Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Ser Asn Tyr
            20                  25                  30
```

Val Met His Trp Val Arg Gln Thr Pro Gly Lys Gly Leu Glu Trp Val
         35                  40                  45

Ala Ile Ile Leu Phe Pro Gly Ser Asn Lys Tyr Tyr Val Asp Ser Val
     50                  55                  60

Gln Gly Arg Phe Thr Ile Ser Arg Asp Asn Ser Lys Asn Thr Leu Ser
65                   70                  75                  80

Leu Gln Met Asn Ser Leu Arg Ala Glu Asp Thr Ala Val Tyr Tyr Cys
                 85                  90                  95

Ala Arg Gly Ser Ser Leu Thr Ala Leu Asp Tyr Tyr Tyr Gly Leu
             100                 105                 110

Asp Val Trp Gly Gln Gly Thr Thr Val Thr Val Ser Ser
             115                 120                 125

<210> SEQ ID NO 266
<211> LENGTH: 125
<212> TYPE: PRT
<213> ORGANISM: Artificial Sequence
<220> FEATURE:
<223> OTHER INFORMATION: synthetic construct; antigen binding domain

<400> SEQUENCE: 266

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
             20                  25                  30

Val Met His Trp Val Arg Gln Ala Pro Gly Lys Gly Leu Glu Trp Val
         35                  40                  45

Ala Ile Ile Trp Tyr Asp Gly Thr Asn Glu Asp Tyr Ala Asp Ser Val
     50                  55                  60

Lys Val Arg Phe Thr Ile Ser Arg Asp Ile Ser Lys Asn Thr Leu Tyr
65                   70                  75                  80

Leu Gln Met Asn Ser Leu Arg Ala Glu Asp Thr Ala Val Tyr Tyr Cys
                 85                  90                  95

Ala Arg Asp Trp Phe Asp Cys Ser Ser Thr Ser Cys Tyr Arg Tyr Phe
             100                 105                 110

Asp Leu Trp Gly Arg Gly Thr Leu Val Thr Val Ser Ser
             115                 120                 125

<210> SEQ ID NO 267
<211> LENGTH: 109
<212> TYPE: PRT
<213> ORGANISM: Artificial Sequence
<220> FEATURE:
<223> OTHER INFORMATION: synthetic construct; antigen binding domain

<400> SEQUENCE: 267

Ser Leu Arg Leu Ser Cys Ala Ala Ser Gly Phe Thr Phe Ser Asn Asn
1               5                   10                  15

Asn Met His Trp Val Arg Gln Ala Pro Gly Lys Gly Leu Glu Trp Val
             20                  25                  30

Ala Val Ile Trp Tyr Asp Gly Ser Asn Lys Asp Tyr Val Asp Ser Val
         35                  40                  45

Lys Gly Arg Phe Thr Ile Ser Arg Asp Asn Ser Lys Asn Thr Leu Tyr
         50                  55                  60

Leu Gln Met Asn Ser Leu Arg Ala Glu Asp Thr Ala Val Tyr Tyr Cys
65                   70                  75                  80

Ala Arg Phe Val Val Ala Pro Ala Thr Tyr Ser Tyr Tyr Tyr Ile Ile

```
                    85                  90                  95

Asp Val Trp Gly Gln Gly Thr Thr Val Thr Val Ser Ser
            100                 105

<210> SEQ ID NO 268
<211> LENGTH: 126
<212> TYPE: PRT
<213> ORGANISM: Artificial Sequence
<220> FEATURE:
<223> OTHER INFORMATION: synthetic construct; antigen binding domain

<400> SEQUENCE: 268

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
                20                  25                  30

Gly Met His Trp Val Arg Gln Ala Pro Gly Lys Gly Leu Glu Trp Val
            35                  40                  45

Ala Val Ile Ser Tyr Asp Gly Arg Ile Lys Tyr Tyr Glu Asp Ser Val
        50                  55                  60

Lys Gly Arg Phe Ile Ile Ser Arg Asp Asn Ser Lys Asn Thr Leu Tyr
65                  70                  75                  80

Leu Gln Val Asn Thr Leu Arg Ala Glu Asp Thr Ala Val Tyr Tyr Cys
                85                  90                  95

Ala Lys Glu Arg Arg Tyr Cys Ser Asp Thr Asn Thr Cys Ser Asp Val
            100                 105                 110

Phe Asp Val Trp Gly Gln Gly Thr Met Val Thr Val Ser Ser
        115                 120                 125

<210> SEQ ID NO 269
<211> LENGTH: 11
<212> TYPE: PRT
<213> ORGANISM: Mus musculus

<400> SEQUENCE: 269

Cys Ala Ser Ser Arg Asn Thr Glu Val Phe Phe
1               5                   10

<210> SEQ ID NO 270
<211> LENGTH: 12
<212> TYPE: PRT
<213> ORGANISM: Mus musculus

<400> SEQUENCE: 270

Cys Ala Ser Ser Ile Gly Asn Thr Glu Val Phe Phe
1               5                   10

<210> SEQ ID NO 271
<211> LENGTH: 14
<212> TYPE: PRT
<213> ORGANISM: Mus musculus

<400> SEQUENCE: 271

Cys Ala Ser Ser Gln Pro Gly Lys Asn Thr Glu Val Phe Phe
1               5                   10

<210> SEQ ID NO 272
<211> LENGTH: 15
<212> TYPE: PRT
<213> ORGANISM: Mus musculus

<400> SEQUENCE: 272
```

```
Cys Ala Ser Ser Leu Gly Gln Gly Asn Asn Ser Pro Leu Tyr Phe
1               5                   10                  15

<210> SEQ ID NO 273
<211> LENGTH: 15
<212> TYPE: PRT
<213> ORGANISM: Mus musculus

<400> SEQUENCE: 273

Cys Ala Ser Ser Gln Gly Gln Gly Gly Ala Glu Thr Leu Tyr Phe
1               5                   10                  15

<210> SEQ ID NO 274
<211> LENGTH: 13
<212> TYPE: PRT
<213> ORGANISM: Mus musculus

<400> SEQUENCE: 274

Cys Ala Ser Ser Pro Pro Met Gly Gly Gln Leu Tyr Phe
1               5                   10

<210> SEQ ID NO 275
<211> LENGTH: 14
<212> TYPE: PRT
<213> ORGANISM: Mus musculus

<400> SEQUENCE: 275

Cys Ala Ser Ser Gln Glu Gly Ala Asn Thr Glu Val Phe Phe
1               5                   10

<210> SEQ ID NO 276
<211> LENGTH: 15
<212> TYPE: PRT
<213> ORGANISM: Mus musculus

<400> SEQUENCE: 276

Cys Ala Ser Ser Gln Val Gln Gly Thr Gly Asn Thr Leu Tyr Phe
1               5                   10                  15

<210> SEQ ID NO 277
<211> LENGTH: 14
<212> TYPE: PRT
<213> ORGANISM: Mus musculus

<400> SEQUENCE: 277

Cys Ala Ser Ser Gln Glu Gly Asp Gly Tyr Glu Gln Tyr Phe
1               5                   10

<210> SEQ ID NO 278
<211> LENGTH: 13
<212> TYPE: PRT
<213> ORGANISM: Mus musculus

<400> SEQUENCE: 278

Cys Thr Ser Ala Glu Gly Gly Gly Thr Glu Val Phe Phe
1               5                   10

<210> SEQ ID NO 279
<211> LENGTH: 14
<212> TYPE: PRT
<213> ORGANISM: Mus musculus

<400> SEQUENCE: 279

Cys Ala Ser Ser Pro Pro Gly Gly Gly Thr Glu Val Gly Gly
```

<210> SEQ ID NO 280
<211> LENGTH: 14
<212> TYPE: PRT
<213> ORGANISM: Mus musculus

<400> SEQUENCE: 280

Cys Ala Ser Ser Gly Thr Asp Asn Gln Asp Thr Gln Tyr Phe
1               5                   10

<210> SEQ ID NO 281
<211> LENGTH: 14
<212> TYPE: PRT
<213> ORGANISM: Mus musculus

<400> SEQUENCE: 281

Cys Ala Ser Ser Pro Gly Thr Gly Gly Tyr Glu Gln Tyr Phe
1               5                   10

<210> SEQ ID NO 282
<211> LENGTH: 14
<212> TYPE: PRT
<213> ORGANISM: Mus musculus

<400> SEQUENCE: 282

Cys Ala Ser Ser Leu Glu Leu Gly Phe Tyr Glu Gln Tyr Phe
1               5                   10

<210> SEQ ID NO 283
<211> LENGTH: 15
<212> TYPE: PRT
<213> ORGANISM: Mus musculus

<400> SEQUENCE: 283

Cys Ala Ser Ser Leu Gly Gly Ala Pro Asn Glu Arg Leu Phe Phe
1               5                   10                  15

<210> SEQ ID NO 284
<211> LENGTH: 14
<212> TYPE: PRT
<213> ORGANISM: Mus musculus

<400> SEQUENCE: 284

Cys Ala Ser Ser Gln Glu Gly Asp Ser Tyr Glu Gln Tyr Phe
1               5                   10

<210> SEQ ID NO 285
<211> LENGTH: 11
<212> TYPE: PRT
<213> ORGANISM: Mus musculus

<400> SEQUENCE: 285

Cys Ala Ser Ser Arg Asn Thr Glu Val Phe Phe
1               5                   10

<210> SEQ ID NO 286
<211> LENGTH: 16
<212> TYPE: PRT
<213> ORGANISM: Mus musculus

<400> SEQUENCE: 286

Cys Ala Ser Gly Asp Ala Met Gly Gly Arg Asp Tyr Ala Glu Gln Phe
1               5                   10                  15

<210> SEQ ID NO 287
<211> LENGTH: 12
<212> TYPE: PRT
<213> ORGANISM: Mus musculus

<400> SEQUENCE: 287

Cys Gly Ala Arg Glu Gly Gln Asp Thr Gln Tyr Phe
1               5                   10

<210> SEQ ID NO 288
<211> LENGTH: 11
<212> TYPE: PRT
<213> ORGANISM: Mus musculus

<400> SEQUENCE: 288

Cys Gly Ala Arg Thr Gly Gly Glu Gln Tyr Phe
1               5                   10

<210> SEQ ID NO 289
<211> LENGTH: 12
<212> TYPE: PRT
<213> ORGANISM: Mus musculus

<400> SEQUENCE: 289

Cys Thr Cys Ser Ala Gly Asn Gln Ala Pro Leu Phe
1               5                   10

<210> SEQ ID NO 290
<211> LENGTH: 14
<212> TYPE: PRT
<213> ORGANISM: Mus musculus

<400> SEQUENCE: 290

Cys Ala Ser Ser Gly Thr Gly Gly Gly Ala Glu Gln Phe Phe
1               5                   10

<210> SEQ ID NO 291
<211> LENGTH: 15
<212> TYPE: PRT
<213> ORGANISM: Mus musculus

<400> SEQUENCE: 291

Cys Ala Ser Ser Asp Glu Gly Gly Gly Thr Gly Gln Leu Tyr Phe
1               5                   10                  15

<210> SEQ ID NO 292
<211> LENGTH: 16
<212> TYPE: PRT
<213> ORGANISM: Mus musculus

<400> SEQUENCE: 292

Cys Ala Ser Ser Arg Asp Trp Gly Gly Ser Gln Asn Thr Leu Tyr Phe
1               5                   10                  15

<210> SEQ ID NO 293
<211> LENGTH: 14
<212> TYPE: PRT
<213> ORGANISM: Mus musculus

<400> SEQUENCE: 293

Cys Ala Ser Ser Pro Thr Gly Tyr Asn Ser Pro Leu Tyr Phe
1               5                   10

<210> SEQ ID NO 294

```
<211> LENGTH: 15
<212> TYPE: PRT
<213> ORGANISM: Mus musculus

<400> SEQUENCE: 294

Cys Ala Ser Ser Gln Val Gln Gly Ser Ala Glu Thr Leu Tyr Phe
1               5                   10                  15

<210> SEQ ID NO 295
<211> LENGTH: 15
<212> TYPE: PRT
<213> ORGANISM: Mus musculus

<400> SEQUENCE: 295

Cys Ala Ser Ser Gly Thr Gly Gly Asn Gln Asp Thr Gln Tyr Phe
1               5                   10                  15

<210> SEQ ID NO 296
<211> LENGTH: 16
<212> TYPE: PRT
<213> ORGANISM: Mus musculus

<400> SEQUENCE: 296

Cys Ala Ser Gly Asp Ala Gly Thr Gly Asn Tyr Ala Glu Gln Phe Phe
1               5                   10                  15

<210> SEQ ID NO 297
<211> LENGTH: 15
<212> TYPE: PRT
<213> ORGANISM: Mus musculus

<400> SEQUENCE: 297

Cys Ala Ser Ser Leu Arg Thr Gly Tyr Asn Ser Pro Leu Tyr Phe
1               5                   10                  15

<210> SEQ ID NO 298
<211> LENGTH: 14
<212> TYPE: PRT
<213> ORGANISM: Mus musculus

<400> SEQUENCE: 298

Cys Ala Ser Arg Leu Gly Gly Asp Gln Asn Thr Leu Tyr Phe
1               5                   10

<210> SEQ ID NO 299
<211> LENGTH: 12
<212> TYPE: PRT
<213> ORGANISM: Mus musculus

<400> SEQUENCE: 299

Cys Ala Ser Lys Thr Gly Gly Tyr Glu Gln Tyr Phe
1               5                   10

<210> SEQ ID NO 300
<211> LENGTH: 11
<212> TYPE: PRT
<213> ORGANISM: Mus musculus

<400> SEQUENCE: 300

Cys Ala Ser Ser Glu Gly Asp Thr Leu Tyr Phe
1               5                   10

<210> SEQ ID NO 301
<211> LENGTH: 15
<212> TYPE: PRT
```

-continued

<213> ORGANISM: Mus musculus

<400> SEQUENCE: 301

Cys Ala Ser Ser Pro Gly Thr Phe Asn Gln Asp Thr Gln Tyr Phe
1               5                   10                  15

<210> SEQ ID NO 302
<211> LENGTH: 13
<212> TYPE: PRT
<213> ORGANISM: Mus musculus

<400> SEQUENCE: 302

Cys Ala Ser Ala Ser Trp Thr Gly Asp Glu Gln Tyr Phe
1               5                   10

<210> SEQ ID NO 303
<211> LENGTH: 14
<212> TYPE: PRT
<213> ORGANISM: Mus musculus

<400> SEQUENCE: 303

Cys Ala Ser Ser Leu Pro Gly Ser Gln Asn Thr Leu Tyr Phe
1               5                   10

<210> SEQ ID NO 304
<211> LENGTH: 14
<212> TYPE: PRT
<213> ORGANISM: Mus musculus

<400> SEQUENCE: 304

Cys Ala Ser Ser Arg Asp Trp Ala Gln Asp Thr Gln Tyr Phe
1               5                   10

<210> SEQ ID NO 305
<211> LENGTH: 14
<212> TYPE: PRT
<213> ORGANISM: Mus musculus

<400> SEQUENCE: 305

Cys Ala Ser Ser Asp Asn Trp Gly Ala Gly Glu Gln Tyr Phe
1               5                   10

<210> SEQ ID NO 306
<211> LENGTH: 14
<212> TYPE: PRT
<213> ORGANISM: Mus musculus

<400> SEQUENCE: 306

Cys Ala Ser Ser Ser Gly Thr Ala Ser Asp Thr Gln Tyr Phe
1               5                   10

<210> SEQ ID NO 307
<211> LENGTH: 15
<212> TYPE: PRT
<213> ORGANISM: Mus musculus

<400> SEQUENCE: 307

Cys Ala Ser Ser Gln Thr Arg Asp Trp Gly Tyr Glu Gln Tyr Phe
1               5                   10                  15

<210> SEQ ID NO 308
<211> LENGTH: 14
<212> TYPE: PRT
<213> ORGANISM: Mus musculus

```
<400> SEQUENCE: 308

Cys Thr Cys Ser Gly Gly Leu Gly Gly Leu Glu Gln Tyr Phe
1               5                   10

<210> SEQ ID NO 309
<211> LENGTH: 14
<212> TYPE: PRT
<213> ORGANISM: Mus musculus

<400> SEQUENCE: 309

Cys Ala Ser Ser Leu Gly Thr Gly Gly Ile Glu Gln Tyr Phe
1               5                   10

<210> SEQ ID NO 310
<211> LENGTH: 15
<212> TYPE: PRT
<213> ORGANISM: Mus musculus

<400> SEQUENCE: 310

Cys Ala Ser Ser Leu Ser Asp Ser Asn Gln Asp Thr Gln Tyr Phe
1               5                   10                  15

<210> SEQ ID NO 311
<211> LENGTH: 14
<212> TYPE: PRT
<213> ORGANISM: Mus musculus

<400> SEQUENCE: 311

Cys Ala Ser Ser Glu Arg Gly Gly Arg Asp Thr Gln Tyr Phe
1               5                   10

<210> SEQ ID NO 312
<211> LENGTH: 15
<212> TYPE: PRT
<213> ORGANISM: Mus musculus

<400> SEQUENCE: 312

Cys Thr Cys Ser Ala Val Arg Glu Gly Asn Ser Pro Leu Tyr Phe
1               5                   10                  15

<210> SEQ ID NO 313
<211> LENGTH: 15
<212> TYPE: PRT
<213> ORGANISM: Mus musculus

<400> SEQUENCE: 313

Cys Ala Ser Ser Leu Thr Gly Val Ser Asn Glu Arg Leu Phe Phe
1               5                   10                  15

<210> SEQ ID NO 314
<211> LENGTH: 13
<212> TYPE: PRT
<213> ORGANISM: Mus musculus

<400> SEQUENCE: 314

Cys Ala Ser Ser Arg Gln Leu Asn Ser Asp Tyr Thr Phe
1               5                   10

<210> SEQ ID NO 315
<211> LENGTH: 15
<212> TYPE: PRT
<213> ORGANISM: Mus musculus

<400> SEQUENCE: 315
```

Cys Ala Ser Ser Leu Arg Gln Gly Ser Asn Thr Glu Val Phe Phe
1               5                   10                  15

<210> SEQ ID NO 316
<211> LENGTH: 16
<212> TYPE: PRT
<213> ORGANISM: Mus musculus

<400> SEQUENCE: 316

Cys Ala Ser Ser Gln Asn Arg Asp Ile Ser Ala Glu Thr Leu Tyr Phe
1               5                   10                  15

<210> SEQ ID NO 317
<211> LENGTH: 13
<212> TYPE: PRT
<213> ORGANISM: Mus musculus

<400> SEQUENCE: 317

Cys Ala Ser Ser Trp Thr Ala Asn Thr Glu Val Phe Phe
1               5                   10

<210> SEQ ID NO 318
<211> LENGTH: 15
<212> TYPE: PRT
<213> ORGANISM: Mus musculus

<400> SEQUENCE: 318

Cys Ala Ser Ser Leu Arg Asp Trp Gly Gln Asp Thr Gln Tyr Phe
1               5                   10                  15

<210> SEQ ID NO 319
<211> LENGTH: 15
<212> TYPE: PRT
<213> ORGANISM: Mus musculus

<400> SEQUENCE: 319

Cys Ala Ser Ser His Trp Gly Gly Thr Thr Gly Gln Leu Tyr Phe
1               5                   10                  15

<210> SEQ ID NO 320
<211> LENGTH: 15
<212> TYPE: PRT
<213> ORGANISM: Mus musculus

<400> SEQUENCE: 320

Cys Ala Ser Ser Tyr Ser Lys Gly Ser Ala Glu Thr Leu Tyr Phe
1               5                   10                  15

<210> SEQ ID NO 321
<211> LENGTH: 13
<212> TYPE: PRT
<213> ORGANISM: Mus musculus

<400> SEQUENCE: 321

Cys Ala Val Ser Met Ile Asn Tyr Asn Val Leu Tyr Phe
1               5                   10

<210> SEQ ID NO 322
<211> LENGTH: 12
<212> TYPE: PRT
<213> ORGANISM: Mus musculus

<400> SEQUENCE: 322

Cys Ala Ser Ser Asp Gly Gln Asn Thr Leu Tyr Phe
1               5                   10

```
<210> SEQ ID NO 323
<211> LENGTH: 13
<212> TYPE: PRT
<213> ORGANISM: Mus musculus

<400> SEQUENCE: 323

Cys Ala Ser Ser Gln Glu Gly Pro Gly Gln Leu Tyr Phe
1               5                   10

<210> SEQ ID NO 324
<211> LENGTH: 14
<212> TYPE: PRT
<213> ORGANISM: Mus musculus

<400> SEQUENCE: 324

Cys Ala Ser Thr Gly Gln Gly Tyr Asn Ser Pro Leu Tyr Phe
1               5                   10
```